US 8,877,760 B2

(12) United States Patent
Song et al.

(10) Patent No.: US 8,877,760 B2
(45) Date of Patent: Nov. 4, 2014

(54) SUBSTITUTED PYRAZINE-2-CARBOXAMIDE KINASE INHIBITORS

(71) Applicant: Portola Pharmaceuticals, Inc., South San Francisco, CA (US)

(72) Inventors: Yonghong Song, Foster City, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/684,462

(22) Filed: Nov. 23, 2012

(65) Prior Publication Data

US 2013/0131040 A1 May 23, 2013

Related U.S. Application Data

(60) Provisional application No. 61/563,466, filed on Nov. 23, 2011.

(51) Int. Cl.
| | | |
|---|---|---|
| A61K 31/427 | (2006.01) | |
| A61K 31/497 | (2006.01) | |
| C07D 241/20 | (2006.01) | |
| C07D 417/12 | (2006.01) | |

(52) U.S. Cl.
USPC ....... 514/255.06; 514/372; 544/407; 548/206

(58) Field of Classification Search
CPC . A61K 31/427; A61K 31/497; C07D 241/20; C07D 417/12
USPC .............. 514/255.06, 372; 544/407; 548/206
See application file for complete search history.

(56) References Cited

U.S. PATENT DOCUMENTS

| | | | |
|---|---|---|---|
| 5,691,364 A | 11/1997 | Buckman et al. | |
| 6,797,706 B1 * | 9/2004 | Hisamichi et al. | 514/183 |
| 7,122,542 B2 | 10/2006 | Singh et al. | |
| 7,517,886 B2 | 4/2009 | Singh et al. | |
| 7,557,210 B2 | 7/2009 | Singh et al. | |
| 8,178,671 B2 | 5/2012 | Singh et al. | |
| 2005/0272753 A1 | 12/2005 | Nagashima et al. | |
| 2009/0270418 A1 | 10/2009 | Sloss et al. | |
| 2010/0048567 A1 | 2/2010 | Jia et al. | |
| 2010/0190980 A1 | 7/2010 | Umemiya et al. | |
| 2011/0166161 A1 | 7/2011 | Terasawa et al. | |

FOREIGN PATENT DOCUMENTS

| | | |
|---|---|---|
| WO | WO 03/063794 | 8/2003 |
| WO | WO 2004/014382 | 2/2004 |
| WO | WO 2005/012294 | 2/2005 |
| WO | WO 2005/016893 | 2/2005 |
| WO | WO 2009/136995 A2 | 11/2009 |
| WO | WO 2009/145856 A1 | 12/2009 |
| WO | WO 2010/097248 A1 | 9/2010 |
| WO | WO 2012/061415 A1 | 5/2012 |

OTHER PUBLICATIONS

Berge, S.M. et al., "Pharmaceutical Salts," Journal of Pharmaceutical Science, 66:1-19, 1977.
Blaire et al., "Lack of Expression of Thy-1 (CD90) on Acute Myeloid Leukemia Cells With Long-Term Proliferative Ability In Vitro and In Vivo," 1997, Blood 89:3104-3112.
Braselmann et al., "R406, an Orally Available Spleen Tyrosine Kinase Inhibitor Blocks Fc Receptor Signaling and Reduces Immune Complex-Mediated Inflammation," J Pharmacol Exp Ther 319(3): 998-1008 (2006).
Burnett and Knapper, "Targenting Treatment in AML," Hematology Am Soc Hematol Educ Program 2007: 429-34 (2007).
Chen, L., et.al, "Protein tyrosine phosphatase receptor-type O truncated (PTPROt) regulates SYK phosphorylation, proximal B-cell-receptor signaling, and cellular proliferation," Blood, 2006; 108:3428-3433.
Chen, Monti et al., "SYK-dependent tonic B-cell receptor signaling is a rational treatment target in diffuse large B-cell lymphoma," Blood 111(4): 2230-7 (2008).
Chen, R. et al., "MicroRNA regulation in mantle cell lymphoma," Journal of Clinical Oncology, 2007 ASCO Annual Meeting Proceedings (Post-Meeting Edition).vol. 25, No. 18S (Jun. 20 Supplement), 2007: 8056.
Cheng, Rowley et al., "SYK tyrosine kinase required formouse viability and B-cell development," 1995; Turner, Mee et al. Nature 378(6554): 303-6 (1995).
Couture, C. et al., "Activation of p561ck by p72,k through Physical Association and N-Terminal Tyrosine Phosphorylationt," Mol. Cell. Biol., 14:5249-5258, 1994.
Couture, C. et al., "p56lck-independent activation and tyrosine phosphorylation of p72sYk by T-cell antigen receptor/CD3 stimulation," Proc. Natl. Acad. Sci. USA, 91:5301-5305, 1994.
Crow, A.R. et al., "Inhibition of Immune Thrombocytopenic Purpura (ITP) by an Orally Bioavailabl Inhibitor of Syk Kinase Activity," Blood, 106:abstract 2165, 2005.
Crowley, M.T. et al., "A Critical Role for Syk in Signal Transduction and Phagocytosis Mediated by Fc g Receptors on Macrophages," J. Exp. Med., 186:1027-1039, 1997.
Friedberg, JW et al, "Inhibition of Syk with fostamatinib disodium has significant clinical activity in non-Hodgkin lymphoma and chronic lymphocytic leukemia," Blood 2010; 115(13), 2578-2585.

(Continued)

*Primary Examiner* — Douglas M Willis
(74) *Attorney, Agent, or Firm* — Kilpatrick Townsend & Stockton LLP

(57) ABSTRACT

Provided are substituted pyrazine-2-carboxamide compounds of Formula I:

(I)

useful for inhibiting of Syk kinase, intermediates used in making such compounds, methods for their preparation, pharmaceutical compositions thereof, methods for inhibition Syk kinase activity, and methods for treating conditions mediated at least in part by Syk kinase activity.

5 Claims, No Drawings

(56) References Cited

OTHER PUBLICATIONS

Garcia-Bustos et al., "PIK1, an essential phosphatidylinositol 4-kinase associated with the yeast nucleus," (1994), EMBO J. 13:2352-2361.

Gobessi, Stefania et al., "Constitutive activation of the protein tyrosine kinase Syk in Chronic Lymphocytic Leukemia B-cells," Blood, 2007, 110, Abstract 1123.

Gururajan et al., "Spleen Tyrosine Kinase (Syk), a Novel Target of Curcumin, Is Required for B Lymphoma Growth," J Immunol 178(1): 111-21 (2007).

Gururajan et al., "Cutting Edge: Constitutive B Cell Receptor Signaling Is Critical for Basal Growth of B Lymphoma," 2006, 176:5715-5719.

Hahn, Cynthia K. et al., "Syk is a new target for AML differentiation," Blood, 2007, 110, Abstract 209.

Hanks & Hunter, "The eukaryotic protein kinase superfamily: kinase (catalytic) domain structure and classification," (1995), FASEB J. 9:576-596.

Heinrich, Griffith et al., "Inhibition of c-kit receptor tyrosine kinase activity by STI 571, a selective tyrosine kinase inhibitor," Blood 96(3): 925-32 (2000).

Hiles et al., "Phosphatidylinositol 3-Kinase: Structure and Expression of the 110 kd Catalytic Subunit," (1992), Cell 70:419-429.

Hutchcroft, J E. et al., "Association of the 72-kDa Protein-tyrosine Kinase PTK72 with the B Cell Antigen Receptor," J. Biol. Chem., 267:8613-8619, 1992.

Irish, Czerwinski et al., "Altered B-cell receptor signaling kinetics distinguish human follicular lymphoma B cells from tumor-infiltrating nonmalignant B cells," J Immunol 176(10): 5715-9 (2006).

Jumaa, Hendriks et al., "B cell signaling and tumorigenesis," Annu Rev Immunol 23: 415-45 (2005).

Knighton et al., "Crystal structure of the catalytic subunit of cyclic adenosine monophosphate-dependent protein kinase," (1991), Science 253:407-414.

Kraus et al., "Survival of Resting Mature B Lymphocytes Depends on BCR Signaling via the Igα/β Heterodimer," Cell 117(6): 787-800 (2004).

Kuno, Y. et.al., "Constitutive kinase activation of the *TEL-Syk* fusion gene in myelodysplastic syndrome with t(9;12)(q22;p12)," Blood, 2001; 97:1050-1055.

Kunz et al., "Target of Rapamycin in Yeast, TOR2, Is an Essential Phosphatidylinositol Kinase Homolog Required for G1 Progression," (1993), Cell 73:585-596.

Kuppers, R., "Mechanisms of B-Cell Lymphoma Pathogenesis," Nat Rev Cancer, 2005; 5:251-262.

Lam, Kuhn et al., "In Vivo Ablation of Surface Immunoglobulin on Mature B Cells by Inducible Gene Targeting Results in Rapid Cell Death," Cell 90(6): 1073-83 (1997).

Latour, S. et. al., "Regulation of T-Cell Antigen Receptor Signalling by Syk Tyrosine Protein Kinase," Mol Cell Biol., 17:4434-4441, 1997.

Law, D.A. et al., "Genetic and Pharmacological Analyses of Syk Function in allbb3 Signaling in Platelets," Blood, 93:2645-2652, 1999.

Leseux, L. et. al., "Syk-dependent mTOR activation in follicular lymphoma cells," Blood, 2006; 108:4156-4162.

Liddle et al., "Discovery of GSK143, a highly potent, selective and orally efficacious spleen tyrosine kinase inhibitor," Bioorg. Med. Chem. Lett,, 21(20):6188-6194 (Oct. 15, 2011).

Mocsai et al., "Syk is Required for Integrin Signaling in Neutrophils," (2002), Immunity 16:547-558.

Passegue et al., "Normal and leukemic hematopoiesis: Are leukemias a stem cell disorder or a reacquisition of stem cell characteristics?," Proc. Natl. Acad. Sci. USA, 2003, 100:11842-9.

Poole, A. et al., "The Fc receptor g-chain and the tyrosine kinase Syk are essential for activation of mouse platelets by collagen," EMBO J., 16:2333-2341, 1997.

Reilly, M.P., "Heparin-induced thrombocytopenia/thrombosis in a transgenic mouse model requires human platelet factor 4 and platelet activation through FcgRIIA," Blood, 98:2442-2447, 2001.

Rinaldi, A. et.al, "Genomic and expression profiling identifies the B-cell associated tyrosine kinase Syk as a possible therapeutic target in mantle cell lymphoma," Br. J. Haematol., 2006; 132:303-316.

Rolli, Gallwitz et al. "Amplification of B Cell Antigen Receptor Signaling by a Syk/ITAM Positive Feedback Loop," Mol Cell 10(5): 1057-69 (2002).

Rossi, A.B. et al., "Identification of the Syk kinase inhibitor R112 by a human mast cell screen," J Allergy Clin Immunol., 118:749-755, 2006.

Takata, M. et al., "Tyrosine kinases Lyn and Syk regulate B cell receptorcoupled Ca2+ mobilization through distinct pathways," EMBO J., 13:1341-1349, 1994.

Turhan et al., "Highly Purified Primitive Hematopoietic Stem Cells are PML-RARA Negative and Generate Nonclonal Progenitors in Acute Promyelocytic Leukemia," 1995, Blood 85:2154-2161.

Turner et al., "Tyrosine kinase SYK: essential functions for immunoreceptor signaling," Immunology Today, (2000) 21:148-154.

Wossning, T. et.al., "Deregulated Syk inhibits diff erentiation and induces growth factor—independent proliferation of pre-B cells," JEM, 2006; 203:2829-2840.

Yousefi, S. et al., "Requirement of Lyn and Syk Tyrosine Kinases for the Prevention of Apoptosis by Cytokinesin Human Eosinophils," J. E. Med., 183:1407-1414, 1996.

\* cited by examiner

SUBSTITUTED PYRAZINE-2-CARBOXAMIDE KINASE INHIBITORS

CROSS-REFERENCES TO RELATED APPLICATIONS

This application claims priority from U.S. Provisional Application 61/563,466 filed Nov. 23, 2011, which is incorporated by reference in its entirety herewith.

FIELD OF THE INVENTION

In one embodiment, provided are pyrazines compounds which act as inhibitors of Spleen tyrosine kinase (Syk). Pharmaceutical compositions containing these compounds, methods for their use to treat a condition mediated at least in part by syk activity, and methods for their preparation are also provided.

BACKGROUND OF THE INVENTION

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as Syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the Syk family of protein tyrosine kinases. The interaction of Syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via Syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of Syk (Rossi, A. B. et al., *J Allergy Clin Immunol.*, 118:749-755, 2006). In immune-thrombocytopenia, antibody bound platelets are cleared by the spleen by an Fc receptor/ITAM/Syk-mediated process (Crow, A. R. et al., *Blood*, 106:abstract 2165, 2005). Drug-induced thrombocytopenia, caused by heparin-platelet factor 4 immune complexes that activate platelet FcγRIIa, also involve Syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. Syk is activated during both phases of integrin signaling, and inhibition of Syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from Syk deficient mouse (Poole, A. et al., *EMBO J.*, 16:2333-2341, 1997). Thus Syk inhibitors may also possess anticoagulation action.

Because of the role Syk plays in Ig-induced platelet activation, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin α2β1.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of Syk. Activation of GPVI leads to induction of multiple platelet functions including: activation of integrins α2β1 to achieve firm platelet adhesion, and GP IIb-IIIa which mediates platelet aggregation and thrombosis growth; platelet secretion, allowing for the delivery of inflammatory proteins such as CD40L, RANTES and TGFβ to the vessel wall; and the expression of P-selectin which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from Syk deficient mouse (Crowley, M. T. et al., *J. Exp. Med.*, 186:1027-1039, 1997). This suggests that Syk has a markedly important role in the FcγR-mediated phagocytosis of macrophages.

It has also been reported that an antisense oligonucleotide of Syk suppresses the apoptosis inhibition of eosinophils induced by GM-CSF (Yousefi, S. et al., *J. E. Med.*, 183:1407-1414, 1996), showing that Syk is essential for the life extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA,* 91:5301-5305, 1994; and Couture, C. et al., *Mol. Cell. Biol.*, 14:5249-5258, 1994). Syk is present in mature T-cell populations, such as intraepithelial γδT-cells and naïve αβ T-cells, and has been reported to be capable of phosphorylation of multiple components of the TCR signaling cascade (Latour, S. et. al., *Mol Cell Biol.*, 17:4434-4441, 1997). As a consequence, Syk inhibitors may serve as agents for inhibiting cellular immunity mediated by T-cell antigen receptor.

Recent comparative genomic hybridization studies have identied Syk as another gene important in the pathogenesis of Mantle Cell Lymphoma (MCL) (Chen, R. et al. *Journal of Clinical Oncology,* 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, *Br. J. Haematol.,* 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, Blood, 2006; 108: 4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B cell and Syk-dependent survival of non-Hodgkins lymphoma cell lines in vitro (Chen, L., et. al, *Blood,* 2006; 108:3428-3433), Syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits Syk, may have significant clinical activity in CLL patients (Friedberg J W et al, Blood 2010; 115(13),).

The oncogenic potential of the spleen tyrosine kinase (Syk) has been described in a number of different settings. Clinically, Syk over-expression is reported in Mantle Cell Lymphoma (Rinaldi, A, et. al, *Br. J. Haematol.*, 2006; 132:303-316) and the TEL-Syk fusion protein (Translocated ETS Leukemia) generated by a chromosomal translocation (t(9; 12)(q22;p12)) leads to increased Syk activity and is associated with myelodysplastic syndrome (Kuno, Y., et. al, *Blood,* 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840). Additional recent studies also suggest that Syk-dependant survival signals may play a role in B-cell malignancies, including DLBCL, mantle cell lymphoma and follicular lymphoma (Gururajan, Jennings et al. 2006; Irish, Czerwinski et al. J Immunol 176(10): 5715-9 (2006). Given the role of tonic BCR signaling in normal B cells and Syk-dependent survival of NHL cell lines in vitro, the specific inhibition of Syk may prove promising for the treatment of certain B-cell lymphomas.

Interestingly, Syk signaling appears to be required for B-cell development and survival in humans and mouse. Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, *Blood*, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immuno-tyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378 (6554): 303-6 (1995). Inducible loss of the B cell receptor (Lam, Kuhn et al. Cell 90(6): 1073-83 (1997) or Igα (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B cells.

Recently, R406 (Rigel Pharmaceuticals) was reported to inhibit ITAM signaling in response to various stimuli, including FceR1 and BCR induced Syk activation (Braselmann, Taylor et al. J Pharmacol Exp Ther 319(3): 998-1008(2006). Interestingly, this ATP-competitive inhibitor of Syk was also active against Flt3, cKit, and JAK kinases, but not against Src kinsase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2010; 115(13)). Although the precise mechanism of action is unclear for R406, the data suggest that inhibition of kinases that mediate survival signaling in lymphocytes is clinically beneficial.

Additional recent studies also suggest that Syk-dependant survival signals may play a role in B-cell malignancies, including DLBCL, mantle cell lymphoma and follicular lymphoma (see e.g., S. Linfengshen et al. *Blood*, February 2008; 111: 2230-2237; J. M. Irish et al. *Blood*, 2006; 108: 3135-3142; A. Renaldi et al. *Brit J. Haematology*, 2006; 132: 303-316; M. Guruoajan et al. *J. Immunol*, 2006; 176: 5715-5719; L. Laseux et al. *Blood*, 2006; 108: 4156-4162.

While progress has been made in this field, there remains a need in the art for compounds that inhibit Syk kinase, as well as for methods for treating conditions in a patient, such as restenosis, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of Syk activity (also referred to herein as "Syk inhibitors") as well as to methods for their preparation and use, and to pharmaceutical compositions containing the same.

In another embodiment, provided is a compound of Formula (I):

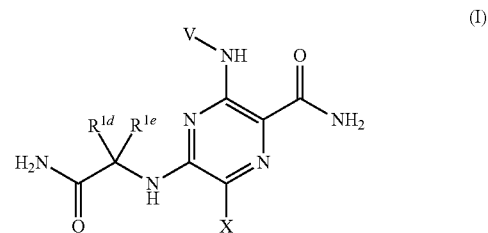

or a pharmaceutically acceptable salt thereof, wherein X, V, $R^{1d}$ and $R^{1e}$ are described below.

In one embodiment, provided is a compound of Formula (II):

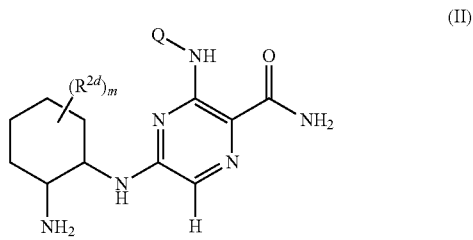

or a pharmaceutically acceptable salt thereof, wherein $R^{2d}$, m, and Q are described below.

In another embodiment, provided is a compound of Formula (III):

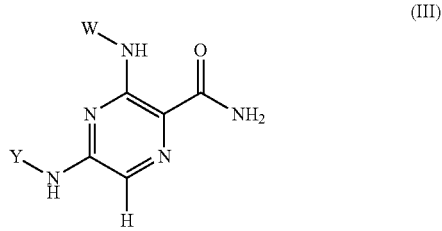

(III)

or a pharmaceutically acceptable salt thereof, wherein Y and W are described below.

The present invention also provides a pharmaceutical composition comprising a therapeutically effective amount of a compound provided herein, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by Syk activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: restenosis, inflammation, heparin induced thrombocytopenia, dilated cardiomyopathy, sickle cell disease, atherosclerosis, myocardial infarction, vascular inflammation, unstable angina, acute coronary syndromes, allergy, asthma, rheumatoid arthritis, B-cell mediated diseases such as Non Hodgkin's lymphoma, Crohn's disease, anti-phospholipid syndrome, lupus, psoriasis, multiple sclerosis, and chronic lymphocytic leukemia. Thus, in one embodiment, methods are disclosed which include the administration of an effective amount of a compound provided herein, typically in the form of a pharmaceutical composition, to a subject in need thereof.

The present invention also provides a method for inhibiting the Syk activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

DETAILED DESCRIPTION OF THE INVENTION

As used herein, the below terms have the following meanings unless specified otherwise:

1. Abbreviations and Definitions

The abbreviations used herein are conventional, unless otherwise defined. The following abbreviations are used: ACN=acetonitrile, AcOH=acetic acid, AIBN=azobisisobutyronitrile (also azobisisobutylonitrile), aq.=aqueous, Ar=argon, Boc=t-butylcarboxy, Bz—benzoyl, Bn=benzyl, BOP=benzotriazol-1-yloxytris(dimethylamino)-phosphonium hexafluorophosphate, BPO=benzoyl peroxide, nBuOH=n-butanol, ° C.=degrees celcius, $CBr_4$=tetrabromomethane, Cbz=benzyloxycarbonyl, mCPBA=m-chloroperoxybenzoic acid, $CH_2Cl_2$ or DCM=dichloromethane, $Cs_2CO_3$=cesium carbonate, $CuCl_2$=copper chloride; DIBAL=diisobutylaluminum hydride, DIEA=Hunig's base or diisopropyl ethylamine, DME=dimethoxy-ethane, DMF=dimethyl formamide, DMSO=dimethyl sulfoxide, DPPA=diphenyl phosphoryl azide, EDC=1-ethyl-3-(3-dimethylaminopropyl) carbodiimide, $Et_3N$=triethylamine, EtOAc=ethyl acetate, g=gram, HATU=2-(1H 7-azabenzotriazol-1-yl)-1,1,3,3-tetramethyl uronium hexafluorophosphate, HOBT=hydroxybenzotriazole, $H_2$=hydrogen; $H_2O$=water; HBr=hydrogen bromide; HCl=hydrogen chloride, HIV=human immunodeficiency virus, HPLC=high pressure liquid chromatography, h=hour, IgE=immunoglobulin E, $IC_{50}$=The concentration of an inhibitor that is required for 50% inhibition of an enzyme in vitro, IPA=isopropyl alcohol, kg=kilogram, KCN=potassium cyanide, KOH=potassium hydroxide, $K_2PO_4$=potassium phosphate, LDA=lithium diisopropylamide, $LiAlH_4$=lithium aluminum hydride=LiOH: lithium hydroxide; MeCN=acetonitrile; MS=Mass Spec, m/z=mass to charge ratio, Ms=methanesulfonyl, MHz=Mega Hertz, MeOH=methanol, MTBE=methyl tert-butyl ether, μM=micromolar, μL=microliter, mg=milligram, mm=millimeter, mM=millimolar, mmol=millimole, mL=milliliter, mOD/min=millioptical density units per minute, min=minute, M=molar, $Na_2CO_3$=sodium carbonate, ng=nanogram, $NaHCO_3$=sodium bicarbonate; $NaNO_2$=sodium nitrite; NaOH=sodium hydroxide; $Na_2S_2O_3$=sodium thiosulfate; $Na_2SO_4$=sodium sulfate; NBS=N-bromosuccinimide; $NH_4Cl$=ammonium chloride; $NH_4OAc$=ammonium acetate; NaSMe=sodium methylthiolate, NBS=N-bromosuccinamide, n-BuLi=n-butyl lithium, nm=nanometer, nM=nanomolar, N=Normal, NMP=N-methylpyrrolidone, NMR=nuclear magnetic resonance, Pd/C=palladium on carbon, $Pd(PPh_3)_4$=Tetrakis-(triphenyl-phosphine)-palladium, pM=picomolar, Pin=pinacolato, PEG=polyethylene glycol, PMB=paramethoxybenzyl, $PPh_3$ or $Ph_3P$=triphenyl phosphine, psi=pound per square inch, RLV=Raucher leukemia virus, Ra-Ni=Rainey Nickel, rp=reverse phase, sat=saturated, $SOCl_2$=thionyl chloride, RT=room temperature, TEA=triethylamine, THF=tetrahydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. Alkyl includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkylene" by itself or as part of another substituent means a divalent radical derived from an alkane, as exemplified by —CH$_2$CH$_2$CH$_2$CH$_2$—. Typically, an alkylene group will have from 1, 2, 3, 4, 5, 6, 7 or 8 carbon atoms that is derived by the removal of one hydrogen atom from a single carbon atom of a parent alkyl.

"Alkenyl" refers to a linear monovalent hydrocarbon radical or a branched monovalent hydrocarbon radical having the number of carbon atoms indicated in the prefix and containing at least one double bond, but no more than three double bonds. For example, (C$_2$-C$_6$)alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, (C$_2$-C$_6$)alkynyl is meant to include ethynyl, propynyl and the like.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in C$_{3-8}$cycloalkylC$_{3-8}$alkylene-, the cycloalkyl portion is meant to have the stated number of carbon atoms (e.g., from three to eight carbon atoms), while the alkylene portion has from one to eight carbon atoms. Examples of cycloalkyl include cyclopentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of aryl groups include phenyl, 1-naphthyl, 2-naphthyl and 4-biphenyl.

The terms "heterocycle", "heterocyclyl" or "heterocyclic" refer to a saturated or unsaturated non-aromatic cyclic group containing at least one heteroatom and optionally one or more oxo substituents. As used herein, the term "heteroatom" is meant to include oxygen (O), nitrogen (N), sulfur (S) and silicon (Si), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein.

"Bicyclic heteroaryl" refers to bicyclic aromatic radical that contain from one to five heteroatoms selected from N, O, and S, wherein the nitrogen and sulfur atoms are optionally oxidized, and the nitrogen atom(s) are optionally quaternized. A bicyclic heteroaryl group can be attached to the remainder of the molecule through a heteroatom or through a carbon atom and can contain 5 to 10 carbon atoms. Non-limiting examples of bicyclic heteroaryl groups include 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl and 6-quinolyl.

In each of the above embodiments designating a number of atoms e.g. "C$_{1-8}$" is meant to include all possible embodiments that have one fewer atom. Non-limiting examples include C$_{1-7}$, C$_{2-8}$, C$_{2-7}$, C$_{3-8}$, C$_{3-7}$ and the like.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "acyl" refers to the group —C(=O)R$^c$ where R$^c$ is alkyl, alkenyl, alkynyl, cycloalkyl, cycloalkenyl, aryl, heteroaryl or heterocyclyl. Acyl includes the "acetyl" group —C(=O)CH$_3$.

"Acylamino-" refers to the group —NR$^a$C(=O)R$^c$ where R$^c$ is alkyl, alkenyl, alkynyl, cycloalkyl, cycloalkenyl, aryl, heteroaryl or heterocyclyl.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Alkoxyalkylene" refers to -(alkoxy)(alkylene) wherein alkoxy and alkylene are defined herein.

"Alkoxycarbonylalkylene" refers to the group -alkylene-C(=O)OR$^d$ wherein R$^d$ is alkyl.

"Alkoxycarbonylamino" refers to to —NR$^a$C(=O)OR$^d$ wherein R$^a$ is H or alkyl and R$^d$ is alkyl.

"Alkoxycarbonylaminoalkylene" refers to to -alkylene-NR$^a$C(=O)OR$^d$ wherein R$^a$ is H or alkyl R$^d$ is alkyl.

"Alkylaminoalkylene" refers to the group -alkyleneNR$^a$R$^d$ wherein R$^a$ is H or alkyl and R$^d$ is alkyl.

"Alkylcarbonyl" refers to the group —C(=O)R$^c$ where R$^c$ is alkyl.

"Alkylcycloalkyl" refers to the group -cycloalkyl-R$^d$ where R$^d$ is alkyl.

"Alkylheterocyclyl" refers to the group -heterocyclyl-$R^d$ where $R^d$ is alkyl.

"Alkylsulfonyl" refers to —$S(=O)_2R^e$ where $R^e$ is alkyl. Alkylsulfonyl groups employed in compounds of the present invention are typically $C_{1-6}$alkylsulfonyl groups.

"Alkylsulfonylalkylene" refers to -alkylene-$S(=O)_2R^e$ where $R^e$ is alkyl. Alkylsulfonyl groups employed in compounds of the present invention are typically $C_{1-6}$alkylsulfonyl groups.

"Alkylthio" refers to —$SR^e$ where $R^e$ is alkyl.

"Alkylthioalkylene" refers to -(alkylene)$SR^e$ where $R^e$ is alkyl and alkylene is as defined herein.

"Amino" refers to a monovalent radical —$NR^aR^b$ or divalent radical —$NR^a$-. The term includes "alkylamino" which refers to the group —$NR^aR^b$ where $R^a$ is alkyl and $R^b$ is H or alkyl. The term also includes "arylamino" which refers to the group —$NR^aR^b$ where at least one $R^a$ or $R^b$ is aryl. The term also includes "(alkyl)(aryl)amino" which refers to the group —$NR^aR^b$ where $R^a$ is alkyl and $R^b$ is aryl. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

"Aminoalkylene" refers to -alkylene-amino wherein alkylene and amino are as defined herein.

"Aminoalkylenecarbonyl" refers to —$C(=O)$-alkylene-amino wherein alkylene and amino are as defined herein.

"Aminoalkyleneaminocarbonyl" refers to —$C(=O)NR^a$-alkylene-amino wherein $R^a$ is H or alkyl and alkylene and amino are as defined herein.

"Aminocarbonyl" or "aminoacyl" refers to the amide —$C(=O)$amino wherein amino is as defined herein. The term "alkylaminocarbonyl" refers herein to the group —$C(=O)$—$NR^aR^b$ where $R^a$ is alkyl and $R^b$ is H or alkyl. The term "arylaminocarbonyl" refers herein to the group —$C(=O)$—$NR^aR^b$ where $R^a$ or $R^b$ is aryl.

"Aminocycloalkyl" refers to the group -cycloalkyl-amino, wherein cycloalkyl and amino are as defined herein.

"Aminosulfonyl" refers to —$S(O)_2$amino where amino is as defined herein.

"Arylalkoxycarbonylamino" refers to the group —$NR^aC(=O)O$-alkylene-$R^c$ wherein $R^a$ is H or alkyl and $R^c$ is aryl.

"Arylcarbonyl" refers to the group —$C(=O)R^c$ where $R^c$ is aryl.

"Arylalkylenecarbonyl" refers to the group —$C(=O)$-alkylene-$R^c$ where $R^c$ is aryl.

"Arylcarbonylamino" refers to —$NR^aC(=O)R^c$ wherein $R^c$ is aryl.

"Aryloxy" refers to —$OR^d$ where $R^d$ is aryl. Representative examples of aryloxy groups include phenoxy, naphthoxy, and the like.

"Aryloxyalkylene" refers to —O-alkylene-$R^d$ where $R^d$ is aryl.

"Azido" refers to the group —$N_3$.

"Bond" when used a element in a Markush group means that the corresponding group does not exist, and the groups of both sides are directly linked.

"Carbonyl" refers to the divalent group —$C(=O)$—.

"Carboxy" or "carboxyl" refers to the group —$CO_2H$.

"Carboxyalkylene" refers to the group -alkylene-$CO_2H$.

"Cycloalkylalkylene" refers to a radical —$R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl, and the like.

"Ester" refers to —$C(=O)OR^d$ wherein $R^d$ is alkyl, cycloalkyl, aryl, heteroaryl, or heterocyclyl.

"Halo" or "halogen" by themselves or as part of another substituent, mean, unless otherwise stated, a fluorine, chlorine, bromine, or iodine atom. Additionally, terms such as "haloalkylene", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "halo$C_{1-8}$alkylene" is meant to include trifluoromethyl, 2,2,2-trifluoroethyl, 4-chlorobutyl, 3-bromopropyl, and the like. The term "perhaloalkylene" means, unless otherwise stated, alkyl substituted with (2m'+1) halogen atoms, where m' is the total number of carbon atoms in the alkyl group. For example, the term "perhalo$C_{1-8}$alkylene", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heterocyclylalkylene" refers to the -alkylene-$R^c$ where $R^c$ is heterocyclyl.

"Heteroarylalkylene" refers to the -alkylene-$R^c$ where $R^c$ is aryl.

"Hydroxy" or "hydroxyl" refers to the group —OH.

"Hydroxycarbonylamino" refers to to —$NR^aC(=O)OH$.

"Hydroxyalkoxy" refers to to -alkoxy-OH wherein alkoxy is as defined herein.

"Hydroxyalkylene" refers to to -alkylene-OH wherein alkylene is as defined herein.

"Nitro" refers to —$NO_2$.

"Nitroso" refers to the group —NO.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Oxo" refers to the divalent atom =O.

"Heteroarylsulfinyl" refers to the group —$S(=O)$—$R^e$ where $R^e$ is as defined heteroaryl.

"Sulfonyl" refers to the group —$S(O)_2$—$R^e$.

"Sulfonylamino" refers to —$NR^aS(=O)_2$—$R^e$ where $R^a$ is selected from the group consisting of hydrogen, alkyl, alkenyl, alkynyl, aryl, cycloalkyl, cycloalkenyl, heteroaryl and heterocyclyl and $R^e$ is selected from the group consisting of hydrogen, alkyl, alkenyl, alkynyl, aryl, cycloalkyl, cycloalkenyl, heteroaryl and heterocyclyl.

"Thiol" refers to the group —SH.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers".

When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Tautomer" refers to alternate forms of a molecule that differ in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active Syk selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatagraphic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of Syk" and related terms and phrases refer to a condition or disorder associated with inappropriate, e.g., less than or greater than normal, activity of Syk and at least partially responsive to or affected by modulation of Syk (e.g., Syk antagonist or agonist results in some improvement in patient well-being in at least some patients). Inappropriate functional activity of Syk might arise as the result of expression of Syk in cells which normally do not express the receptor, greater than normal production of Syk, or slower than normal metabolic inactivation or elimination of Syk or its active metabolites, increased expression of Syk or degree of intracellular activation (leading to, e.g., inflammatory and immune-related disorders and conditions) or decreased expression of Syk. A condition or disorder associated with Syk may include a "Syk-mediated condition or disorder".

As used herein, the phrases "a condition or disorder mediated at least in part by Syk kinase activity", and related phrases and terms refer to a condition or disorder characterized by inappropriate, e.g., greater than normal, Syk activity. Inappropriate Syk functional activity might arise as the result of Syk expression in cells which normally do not express Syk or increased Syk expression or degree of intracellular activation (leading to, e.g., inflammatory and immune-related disorders and conditions). A condition or disorder mediated at least in part by Syk or JAK kinase activity may be completely or partially mediated by inappropriate Syk functional activity. However, a condition or disorder mediated at least in part by Syk kinase activity is one in which modulation of Syk results in some effect on the underlying condition or disorder (e.g., an Syk antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of Syk, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Syk, either directly or indirectly, and/or the upregulation or downregulation of the expression of Syk, either directly or indirectly. In a preferred embodiment, the modulation is direct Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Syk can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100% Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "platelet" refers to a minute, nonnucleated, dislike cell found in the blood plasma of mammals that functions to promote blood clotting.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reaquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The phrase "selectively" or "specifically" when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

As used herein, the term "Sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "Sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "Syk" refers to a spleen tyrosine kinase (RefSeq Accession No. P-043405) or a variant thereof that is capable of mediating a cellular response to T-cell receptors in vitro or in vivo. Syk variants include proteins substantially homologous to native Syk, i.e., proteins having one or more naturally or non-naturally occurring amino acid deletions, insertions or substitutions (e.g., Syk derivatives, homologs and fragments). The amino acid sequence of Syk variant preferably is at least about 80% identical to a native Syk, more preferably at least about 90% identical, and most preferably at least about 95% identical.

The term "Syk inhibitor" refers to any agent that inhibits the catalytic activity of spleen tyrosine kinase.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. Embodiments of the Invention a. Compounds

In one embodiment, provided is a compound of Formula (I) or a pharmaceutically acceptable salt thereof:

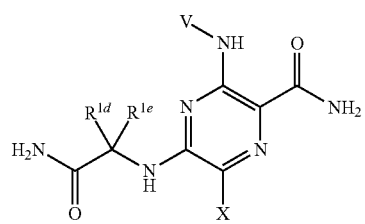

(I)

wherein
X is H or halo;
V is selected from the group consisting of:
  a) heteroaryl optionally substituted with one to five $R^{1a}$ groups;
  b) cycloalkyl optionally substituted with one to five $R^{1a}$ groups;
  c) heterocyclyl optionally substituted with one to five $R^{1a}$ groups; and
  d) aryl substituted with $R^{1b}$ and optionally substituted with one to four $R^{1a}$ groups;

$R^{1b}$ is selected from the group consisting of $C_{1-8}$ alkyl, $C_{3-8}$ cycloalkyl$C_{1-8}$ alkyl, $C_{1-8}$ alkoxy, $C_{3-8}$ cycloalkoxy, hydroxy$C_{1-8}$alkyl, $C_{1-8}$ alkoxyalkyl, halo$C_{1-8}$ alkyl, halo$C_{1-8}$ alkoxy, amino, $C_{1-8}$ alkylamino, di$C_{1-8}$ alkylamino, halo, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, morpholinyl, phenyl, and heteroaryl optionally substituted with one to three $R^{1c}$ groups;

$R^{1a}$ and $R^{1c}$ are independently selected from the group consisting of $C_{1-8}$ alkyl, $C_{2-8}$ alkenyl, $C_{2-8}$alkynyl, $C_{3-8}$ cycloalkyl$C_{1-8}$ alkylene, $C_{1-8}$ alkoxy, $C_{3-8}$ cycloalkoxy, hydroxy$C_{1-8}$ alkylene, $C_{1-8}$ alkoxyalkylene, halo$C_{1-8}$ alkylene, halo$C_{1-8}$ alkoxy, amino, hydroxyl, $C_{1-8}$ alkylamino, di$C_{1-8}$ alkylamino, $C_{1-8}$alkylthio, oxo, halo, cyano, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, heterocyclyl, phenyl, heteroaryl, heteroarylsulfinyl; $C_{1-8}$arylalkylene, amino$C_{1-8}$alkylene, amino$C_{3-8}$cycloalkyl, and heterocyclyl$C_{1-8}$alkylene;

$R^{1d}$ is selected from the group consisting of hydrogen, $C_{3-8}$cycloalkyl, $C_{3-8}$cycloalkyl$C_{1-8}$ alkylene, $C_{1-8}$alkyl, aryl, $C_{1-8}$alkoxy$C_{1-8}$alkylene, halo$C_{1-8}$alkyl, $C_{1-8}$alkylsulfinyl$C_{1-8}$alkylene, and $C_{1-8}$alkylsulfonyl$C_{1-8}$alkylene aryl$C_{1-8}$alkylene, heteroaryl, and heteroaryl$C_{1-8}$alkylene wherein $R^{1d}$ is optionally substituted with one to five groups independently selected from halo, $C_{1-8}$alkyl, amino, $C_{1-8}$alkoxy, $C_{1-8}$alkylthio, and hydroxyl;

$R^{1e}$ is hydrogen or together with $R^{1d}$ and the carbon atom to which they are attached to form a $C_{3-8}$cycloalkyl ring.

In some embodiments, X is H. In some embodiments, X is halogen.

In some embodiments, $R^{1e}$ is H. In some embodiments, $R^{1d}$ and the carbon atom to which they are attached to form a $C_{3-8}$cycloalkyl ring.

In some embodiments, $R^{1d}$ is hydrogen. In some embodiments, $R^{1d}$ is $C_{3-8}$cycloalkyl. In some embodiments, $R^{1d}$ is $C_{3-8}$cycloalkyl$C_{1-8}$alkylene. In some embodiments, $R^{1d}$ is $C_{1-8}$alkyl In some embodiments, $R^{1d}$ is aryl. In some embodiments, $R^{1d}$ is $C_{1-8}$alkoxy$C_{1-8}$alkylene. In some embodiments, $R^{1d}$ is halo$C_{1-8}$alkyl. In some embodiments, $R^{1d}$ is $C_{1-8}$alkylsulfinyl$C_{1-8}$alkylene. In some embodiments, $R^{1d}$ is $C_{1-8}$alkylsulfonyl$C_{1-8}$alkylene. In some embodiments, $R^{1d}$ is aryl$C_{1-8}$alkylene. In some embodiments, $R^{1d}$ is heteroaryl. In some embodiments, $R^{1d}$ is heteroaryl$C_{1-8}$alkylene. In any of the above embodiments, $R^{1d}$ is optionally substituted with one, or two, or three or four or five groups independently selected from halo, $C_{1-8}$alkyl, amino, $C_{1-8}$alkoxy, $C_{1-8}$alkylthio, and hydroxyl. In some embodiments, $R^{1d}$ is selected from the group consisting of hydrogen, isopropyl, sec-butyl, tert-butyl, methyl, ethyl, $CF_3CH_2$—, $CHF_2CH_2$—, methoxymethylene, methylsulfinylethylene, and methylsulfonylethylene. In some embodiments, $R^{1d}$ is cycloalkyl, cycloalkyl$C_{1-8}$alkyl, or heteroaryl$C_{1-8}$alkyl. In some embodiments, $R^{1d}$ is optionally substituted with one or two or three or four or five groups independently selected from halo, $C_1$-$C_6$alkyl, and amino. In some embodiments, $R^{1d}$ is selected from the group consisting of cyclopropyl, cyclopropylmethylene, phenyl and benzyl.

In some embodiments, $R^{1a}$ is $C_{1-8}$ alkyl. In some embodiments, $R^{1a}$ is $C_{2-8}$ alkenyl. In some embodiments, $R^{1a}$ is $C_{2-8}$alkynyl. In some embodiments, $R^{1a}$ is $C_{3-8}$ cycloalkyl$C_{1-8}$ alkylene. In some embodiments, $R^{1a}$ is $C_{1-8}$ alkoxy. In some embodiments, $R^{1a}$ is $C_{3-8}$ cycloalkoxy. In some embodiments, $R^{1a}$ is hydroxy$C_{1-8}$ alkylene. In some embodiments, $R^{1a}$ is $C_{1-8}$ alkoxyalkylene. In some embodiments, $R^{1a}$ is halo$C_{1-8}$ alkylene. In some embodiments, $R^{1a}$ is halo$C_{1-8}$ alkoxy. In some embodiments, $R^{1a}$ is amino. In some embodiments, $R^{1a}$ is hydroxyl. In some embodiments, $R^{1a}$ is $C_{1-8}$ alkylamino. In some embodiments, $R^{1a}$ is di$C_{1-8}$ alkylamino. In some embodiments, $R^{1a}$ is $C_{1-8}$alkylthio. In some embodiments, $R^{1a}$ is oxo. In some embodiments, $R^{1a}$ is halo. In some embodiments, $R^{1a}$ is cyano. In some embodiments, $R^{1a}$ is halo$C_{1-8}$ alkylaminocarbonyl. In some embodiments, $R^{1a}$ is $C_{1-8}$alkylaminocarbonyl. In some embodiments, $R^{1a}$ is di$C_{1-8}$ alkylaminocarbonyl. In some embodiments, $R^{1a}$ is aminocarbonyl, heterocyclylcarbonyl. In some embodiments, $R^{1a}$ is $C_{1-8}$ alkylcarbonylamino. In some embodiments, $R^{1a}$ is $C_{1-8}$ alkylsulfonyl. In some embodiments, $R^{1a}$ is aminosulfonyl. In some embodiments, $R^{1a}$ is $C_{3-8}$ cycloalkyl. In some embodiments, $R^{1a}$ is $C_{1-8}$ alkylcarbonylpiperadinyl. In some embodiments, $R^{1a}$ is heterocyclyl. In some embodiments, $R^{1a}$ is phenyl. In some embodiments, $R^{1a}$ is heteroaryl. In some embodiments, $R^{1a}$ is heteroarylsulfinyl. In some embodiments, $R^{1a}$ is $C_{1-8}$arylalkylene. In some embodiments, $R^{1a}$ is amino$C_{1-8}$alkylene. In some embodiments, $R^{1a}$ is amino$C_{3-8}$cycloalkyl. In some embodiments, $R^{1a}$ is heterocyclyl$C_{1-8}$alkylene.

In some embodiments, $R^{1c}$ is $C_{1-8}$ alkyl. In some embodiments, $R^{1c}$ is $C_{2-8}$ alkenyl. In some embodiments, $R^{1c}$ is $C_{2-8}$alkynyl. In some embodiments, $R^{1c}$ is $C_{3-8}$ cycloalkyl$C_{1-8}$ alkylene. In some embodiments, $R^{1c}$ is $C_{1-8}$ alkoxy. In some embodiments, $R^{1c}$ is $C_{3-8}$ cycloalkoxy. In some embodiments, $R^{1c}$ is hydroxy$C_{1-8}$ alkylene. In some embodiments, $R^{1c}$ is $C_{1-8}$ alkoxyalkylene. In some embodiments, $R^{1c}$ is halo$C_{1-8}$ alkylene. In some embodiments, $R^{1c}$ is halo$C_{1-8}$ alkoxy. In some embodiments, $R^{1c}$ is amino. In some embodiments, $R^{1c}$ is hydroxyl. In some embodiments, $R^{1c}$ is $C_{1-8}$ alkylamino. In some embodiments, $R^{1c}$ is di$C_{1-8}$ alkylamino. In some embodiments, $R^{1c}$ is $C_{1-8}$alkylthio. In some embodiments, $R^{1c}$ is oxo. In some embodiments, $R^{1c}$ is halo. In some embodiments, $R^{1c}$ is cyano. In some embodiments, $R^{1c}$ is halo$C_{1-8}$ alkylaminocarbonyl. In some embodiments, $R^{1c}$ is $C_{1-8}$alkylaminocarbonyl. In some embodiments, $R^{1c}$ is di$C_{1-8}$ alkylaminocarbonyl. In some embodiments, $R^{1c}$ is aminocarbonyl, heterocyclylcarbonyl. In some embodiments, $R^{1c}$ is $C_{1-8}$ alkylcarbonylamino. In some embodiments, $R^{1c}$ is $C_{1-8}$ alkylsulfonyl. In some embodiments, $R^{1c}$ is aminosulfonyl. In some embodiments, $R^{1c}$ is $C_{3-8}$ cycloalkyl. In some embodiments, $R^{1c}$ is $C_{1-8}$ alkylcarbonylpiperadinyl. In some embodiments, $R^{1c}$ is heterocyclyl. In some embodiments, $R^{1c}$ is phenyl. In some embodiments, $R^{1c}$ is heteroaryl. In some embodiments, $R^{1c}$ is heteroarylsulfinyl. In some embodiments, $R^{1c}$ is $C_{1-8}$arylalkylene. In some embodiments, $R^{1c}$ is amino$C_{1-8}$alkylene. In some embodiments, $R^{1c}$ is amino$C_{3-8}$cycloalkyl. In some embodiments, $R^{1c}$ is heterocyclyl$C_{1-8}$alkylene.

In some embodiments, V is heteroaryl optionally substituted with one or two or three or four or five $R^{1a}$ groups. In some embodiments, V is cycloalkyl optionally substituted with one or two or three or four or five $R^{1a}$ groups. In some embodiments, V is heterocyclyl optionally substituted with one or two or three or four or five $R^{1a}$ groups. In some embodiments, V is phenyl substituted with $R^{1b}$ and optionally substituted with one or two or three or four $R^{1a}$ groups. In some embodiments, V is phenyl substituted with heteroaryl optionally substituted with one or two or three $R^{1c}$ groups.

In some embodiments, V is phenyl. In some embodiments, V is

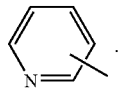

In some embodiments, V is

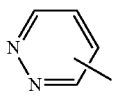

In some embodiments, V is

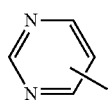

In some embodiments, W is

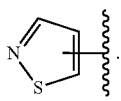

In some embodiments, V is

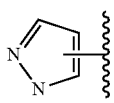

In some embodiments, V is

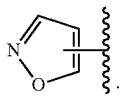

In some embodiments, V is

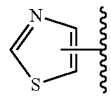

In some embodiments, V is

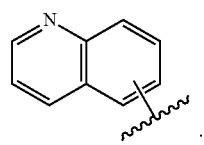

In some embodiments, V is
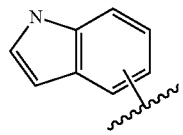
In some embodiments, V is
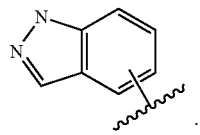
In some embodiments, V is
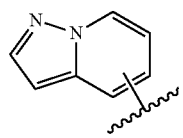
In some embodiments, V is
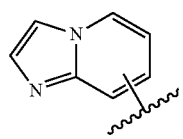
In some embodiments, V is
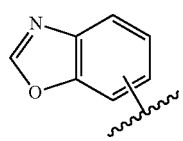
In some embodiments, V is
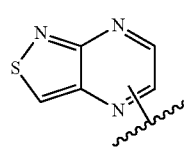
In some embodiments, V is
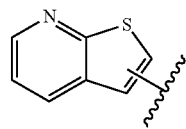
In some embodiments, V is
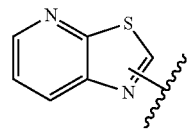
In some embodiments, V is
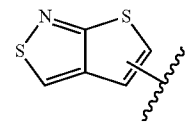
In some embodiments, V is
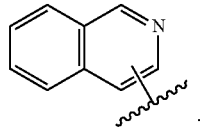
In some embodiments, V is
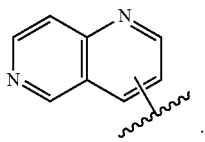
In some embodiments, V is
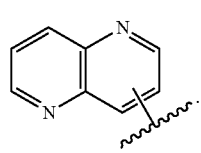
In some embodiments, V is
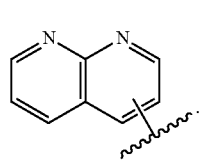
In some embodiments, V is
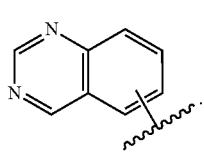

In some embodiments, V is
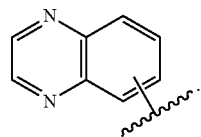
In some embodiments, V is
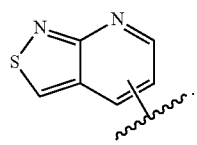
In some embodiments, V is
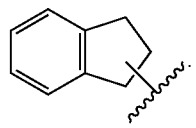
In some embodiments, V is
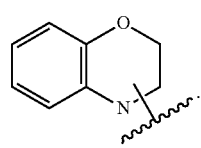
In some embodiments, V is
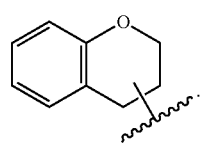
In some embodiments, V is
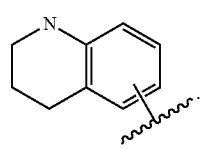
In some embodiments, V is
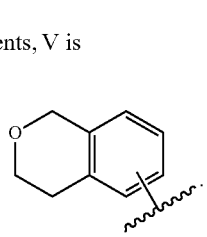
In some embodiments, V is
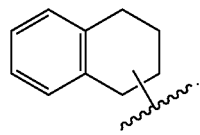
In some embodiments V W is
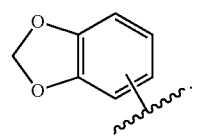
In some embodiments, V is
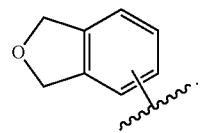
In some embodiments, W is
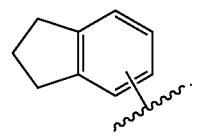
In some embodiments, V is
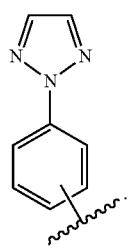
In some embodiments, V is
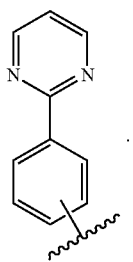

In some embodiments, V is
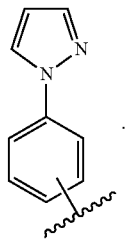
In some embodiments, V is
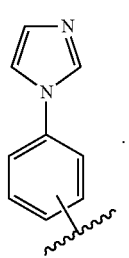
In some embodiments, V is
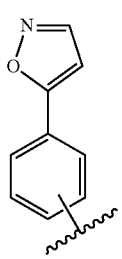
In some embodiments, V is
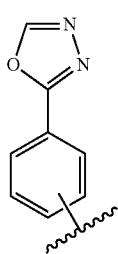
In some embodiments, V is
In some embodiments, V is
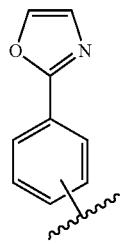
In some embodiments, V is
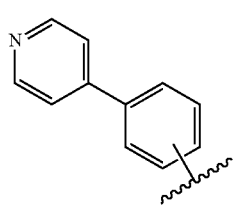
In some embodiments, V is
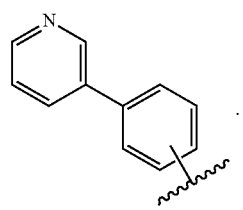
In some embodiments, V is
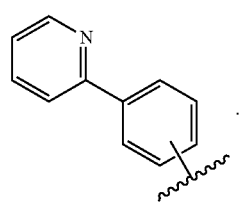
In some embodiments, V is
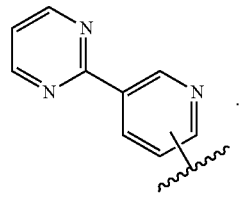
In some embodiments, V is
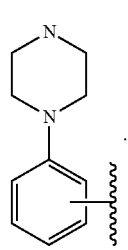

In some embodiments, V is
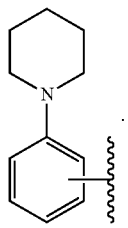
In some embodiments, V is
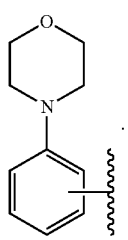
In some embodiments, V is
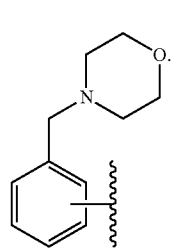
In some embodiments, V is
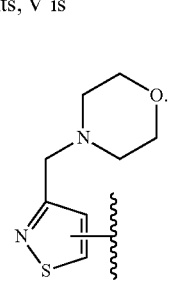
In some embodiments, V is
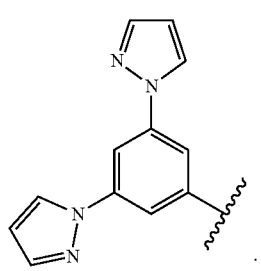 [SMILES: *c1cc(-n2cccn2)cc(-n2cccn2)c1]
In some embodiments, V is
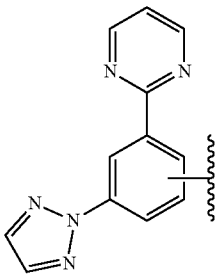
In some embodiments, V is
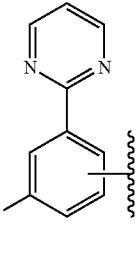
In some embodiments, V is
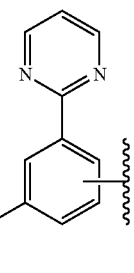
In some embodiments, V is
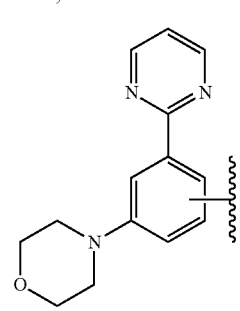
In some embodiments, V is
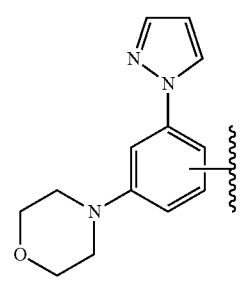

In some embodiments, V is

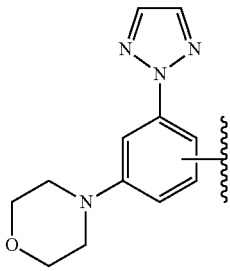

In some embodiments, V is

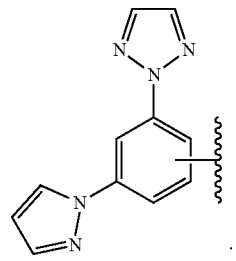

In some embodiments, V is

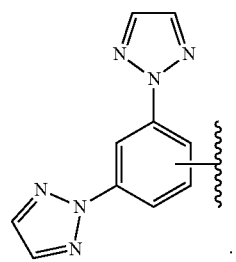

In some embodiments, V is

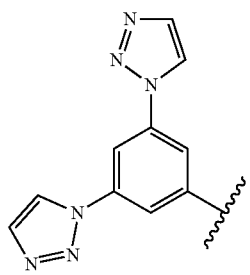

In some embodiments, V is

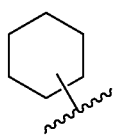

In some embodiments, V is

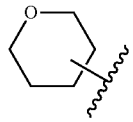

In some embodiments, V is

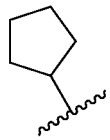

Within any of the embodiments, herein, V is optionally substituted with one or two or three substituents independently selected from the group consisting of $C_{1-8}$ alkyl, $C_{3-8}$ cycloalkyl$C_{1-8}$ alkyl, $C_{1-8}$ alkoxy, $C_{3-8}$ cycloalkoxy, hydroxy$C_{1-8}$ alkyl, $C_{1-8}$ alkoxyalkyl, halo$C_{1-8}$ alkyl, halo$C_{1-8}$ alkoxy, amino, $C_{1-8}$ alkylamino, di$C_{1-8}$ alkylamino, oxo, halo, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, morpholinyl, phenyl, pyridyl, and pyrimidyl.

In one embodiment, provided is a compound of Formula (II) or a pharmaceutically acceptable salt thereof:

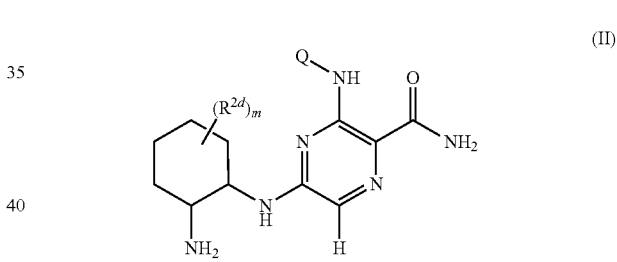

(II)

wherein
Q is selected from the group consisting of:
a) heteroaryl optionally substituted with one to five $R^{2a}$ groups;
b) cycloalkyl optionally substituted with one to five $R^{2a}$ groups;
c) heterocyclyl optionally substituted with one to five $R^{2a}$ groups; and
d) aryl substituted with $R^{2b}$ and optionally substituted with one to four $R^{2a}$ groups;

$R^{2b}$ is selected from the group consisting of $C_{1-8}$ alkyl, $C_{3-8}$ cycloalkyl$C_{1-8}$ alkyl, $C_{1-8}$ alkoxy, $C_{3-8}$ cycloalkoxy, hydroxy$C_{1-8}$ alkyl, $C_{1-8}$ alkoxyalkyl, halo$C_{1-8}$ alkyl, halo$C_{1-8}$ alkoxy, amino, $C_{1-8}$ alkylamino, di$C_{1-8}$ alkylamino, halo, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, morpholinyl, phenyl, and heteroaryl optionally substituted with one to three $R^{2c}$ groups;

$R^{2a}$ and $R^{2c}$ are independently selected from the group consisting of $C_{1-8}$ alkyl, $C_{2-8}$ alkenyl, $C_{2-8}$alkynyl, $C_{3-8}$ cycloalkyl$C_{1-8}$ alkylene, $C_{1-8}$ alkoxy, $C_{3-8}$ cycloalkoxy, hydroxy$C_{1-8}$ alkylene, $C_{1-8}$ alkoxyalkylene, halo$C_{1-8}$ alkylene, haloC$_{1-8}$ alkoxy, amino, hydroxyl, C$_{1-8}$ alkylamino, diC$_{1-8}$ alkylamino, C$_{1-8}$alkylthio, oxo, halo, cyano, haloC$_{1-8}$ alkylaminocarbonyl, C$_{1-8}$alkylaminocarbonyl, diC$_{1-8}$ alkylaminocarbonyl, aminocarbonyl, heterocyclylcarbonyl, C$_{1-8}$ alkylcarbonylamino, C$_{1-8}$ alkylsulfonyl, aminosulfonyl, C$_{3-8}$ cycloalkyl, C$_{1-8}$ alkylcarbonylpiperadinyl, heterocyclyl, phenyl, heteroaryl, heteroarylsulfinyl; C$_{1-8}$arylalkylene, aminoC$_{1-8}$alkylene, aminoC$_{3-8}$cycloalkyl, and heterocyclylC$_{1-8}$alkylene;

R$^{2d}$ is halo; and m is 1, 2, 3, 4, or 5.

In some embodiments, m is 1. In some embodiments, m is 2. In some embodiments, m is 3. In some embodiments, m is 4. In some embodiments, m is 5.

In some embodiments, wherein R$^{2d}$ is fluoro.

In some embodiments, Q is heteroaryl optionally substituted with one or two or three or four or five R$^{2a}$ groups. In some embodiments, Q is cycloalkyl optionally substituted with one or two or three or four or five R$^{2a}$ groups. In some embodiments, Q is heterocyclyl optionally substituted with one or two or three or four or five R$^{2a}$ groups. In some embodiments, Q is phenyl substituted with R$^{2b}$ and optionally substituted with one or two or three or four R$^{2a}$ groups.

In some embodiments, R$^{2b}$ is C$_{1-8}$ alkyl. In some embodiments, R$^{2b}$ is C$_{3-8}$ cycloalkylC$_{1-8}$ alkyl. In some embodiments, R$^{2b}$ is C$_{1-8}$ alkoxy. In some embodiments, R$^{2b}$ is C$_{3-8}$ cycloalkoxy. In some embodiments, R$^{2b}$ is hydroxyC$_{1-8}$ alkyl. In some embodiments, R$^{2b}$ is C$_{1-8}$ alkoxyalkyl. In some embodiments, R$^{2b}$ is haloC$_{1-8}$ alkyl. In some embodiments, R$^{2b}$ is haloC$_{1-8}$ alkoxy. In some embodiments, R$^{2b}$ is amino. In some embodiments, R$^{2b}$ is C$_{1-8}$ alkylamino. In some embodiments, R$^{2b}$ is diC$_{1-8}$ alkylamino. In some embodiments, R$^{2b}$ is halo. In some embodiments, R$^{2b}$ is haloC$_{1-8}$ alkylaminocarbonyl. In some embodiments, R$^{2b}$ is C$_{1-8}$alkylaminocarbonyl. In some embodiments, R$^{2b}$ is diC$_{1-8}$ alkylaminocarbonyl. In some embodiments, R$^{2b}$ is aminocarbonyl. In some embodiments, R$^{2b}$ is heterocyclylcarbonyl. In some embodiments, R$^{2b}$ is C$_{1-8}$ alkylcarbonylamino. In some embodiments, R$^{2b}$ is C$_{1-8}$ alkylsulfonyl. In some embodiments, R$^{2b}$ is aminosulfonyl. In some embodiments, R$^{2b}$ is C$_{3-8}$ cycloalkyl. In some embodiments, R$^{2b}$ is C$_{1-8}$ alkylcarbonylpiperadinyl. In some embodiments, R$^{2b}$ is morpholinyl. In some embodiments, R$^{2b}$ is phenyl. In some embodiments, R$^{2b}$ is heteroaryl. In some embodiments, R$^{2b}$ is optionally substituted with one or two or three R$^{2c}$ groups.

In some embodiments, R$^{2a}$ is C$_{1-8}$ alkyl. In some embodiments, R$^{2a}$ is C$_{2-8}$ alkenyl. In some embodiments, R$^{2a}$ is C$_{2-8}$alkynyl. In some embodiments, R$^{2a}$ is C$_{3-8}$ cycloalkylC$_{1-8}$ alkylene. In some embodiments, R$^{2a}$ is C$_{1-8}$ alkoxy. In some embodiments, R$^{2a}$ is C$_{3-8}$ cycloalkoxy. In some embodiments, R$^{2a}$ is hydroxyC$_{1-8}$ alkylene. In some embodiments, R$^{2a}$ is C$_{1-8}$ alkoxyalkylene. In some embodiments, R$^{2a}$ is haloC$_{1-8}$ alkylene. In some embodiments, R$^{2a}$ is haloC$_{1-8}$ alkoxy. In some embodiments, R$^{2a}$ is amino. In some embodiments, R$^{2a}$ is hydroxyl. In some embodiments, R$^{2a}$ is C$_{1-8}$ alkylamino. In some embodiments, R$^{2a}$ is diC$_{1-8}$ alkylamino. In some embodiments, R$^{2a}$ is C$_{1-8}$alkylthio. In some embodiments, R$^{2a}$ is oxo. In some embodiments, R$^{2a}$ is halo. In some embodiments, R$^{2a}$ is cyano. In some embodiments, R$^{2a}$ is haloC$_{1-8}$ alkylaminocarbonyl. In some embodiments, R$^{2a}$ is C$_{1-8}$alkylaminocarbonyl. In some embodiments, R$^{2a}$ is diC$_{1-8}$ alkylaminocarbonyl. In some embodiments, R$^{2a}$ is aminocarbonyl, heterocyclylcarbonyl. In some embodiments, R$^{2a}$ is C$_{1-8}$ alkylcarbonylamino. In some embodiments, R$^{2a}$ is C$_{1-8}$ alkylsulfonyl. In some embodiments, R$^{2a}$ is aminosulfonyl. In some embodiments, R$^{2a}$ is C$_{3-8}$ cycloalkyl. In some embodiments, R$^{2a}$ is C$_{1-8}$ alkylcarbonylpiperadinyl. In some embodiments, R$^{2a}$ is heterocyclyl. In some embodiments, R$^{2a}$ is phenyl. In some embodiments, R$^{2a}$ is heteroaryl. In some embodiments, R$^{2a}$ is heteroarylsulfinyl. In some embodiments, R$^{2a}$ is C$_{1-8}$arylalkylene. In some embodiments, R$^{2a}$ is aminoC$_{1-8}$alkylene. In some embodiments, R$^{2a}$ is aminoC$_{3-8}$cycloalkyl. In some embodiments, R$^{2a}$ is heterocyclylC$_{1-8}$alkylene.

In some embodiments, R$^{2c}$ is C$_{1-8}$ alkyl. In some embodiments, R$^{2c}$ is C$_{2-8}$ alkenyl. In some embodiments, R$^{2c}$ is C$_{2-8}$alkynyl. In some embodiments, R$^{2c}$ is C$_{3-8}$ cycloalkylC$_{1-8}$ alkylene. In some embodiments, R$^{2c}$ is C$_{1-8}$ alkoxy. In some embodiments, R$^{2c}$ is C$_{3-8}$ cycloalkoxy. In some embodiments, R$^{2c}$ is hydroxyC$_{1-8}$ alkylene. In some embodiments, R$^{2c}$ is C$_{1-8}$ alkoxyalkylene. In some embodiments, R$^{2c}$ is haloC$_{1-8}$ alkylene. In some embodiments, R$^{2c}$ is haloC$_{1-8}$ alkoxy. In some embodiments, R$^{2c}$ is amino. In some embodiments, R$^{2c}$ is hydroxyl. In some embodiments, R$^{2c}$ is C$_{1-8}$ alkylamino. In some embodiments, R$^{2c}$ is diC$_{1-8}$ alkylamino. In some embodiments, R$^{2c}$ is C$_{1-8}$alkylthio. In some embodiments, R$^{2c}$ is oxo. In some embodiments, R$^{2c}$ is halo. In some embodiments, R$^{2c}$ is cyano. In some embodiments, R$^{2c}$ is haloC$_{1-8}$ alkylaminocarbonyl. In some embodiments, R$^{2c}$ is C$_{1-8}$alkylaminocarbonyl. In some embodiments, R$^{2c}$ is diC$_{1-8}$ alkylaminocarbonyl. In some embodiments, R$^{2c}$ is aminocarbonyl, heterocyclylcarbonyl. In some embodiments, R$^{2c}$ is C$_{1-8}$ alkylcarbonylamino. In some embodiments, R$^{2c}$ is C$_{1-8}$ alkylsulfonyl. In some embodiments, R$^{2c}$ is aminosulfonyl. In some embodiments, R$^{2c}$ is C$_{3-8}$ cycloalkyl. In some embodiments, R$^{2c}$ is C$_{1-8}$ alkylcarbonylpiperadinyl. In some embodiments, R$^{2c}$ is heterocyclyl. In some embodiments, R$^{2c}$ is phenyl. In some embodiments, R$^{2c}$ is heteroaryl. In some embodiments, R$^{2c}$ is heteroarylsulfinyl. In some embodiments, R$^{2c}$ is C$_{1-8}$arylalkylene. In some embodiments, R$^{2c}$ is aminoC$_{1-8}$alkylene. In some embodiments, R$^{2c}$ is aminoC$_{3-8}$cycloalkyl. In some embodiments, R$^{2c}$ is heterocyclylC$_{1-8}$alkylene.

In some embodiments, the compound of Formula (II) has the formula:

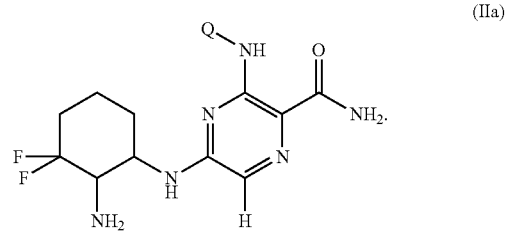

(IIa)

In some embodiments, R$^{2a}$ is C$_{1-8}$ alkyl. In some embodiments, R$^{2a}$ is C$_{2-8}$ alkenyl. In some embodiments, R$^{2a}$ is C$_{2-8}$alkynyl. In some embodiments, R$^{2a}$ is C$_{3-8}$ cycloalkylC$_{1-8}$ alkylene. In some embodiments, R$^{2a}$ is C$_{1-8}$ alkoxy. In some embodiments, R$^{2a}$ is C$_{3-8}$ cycloalkoxy. In some embodiments, R$^{2a}$ is hydroxyC$_{1-8}$ alkylene. In some embodiments, R$^{2a}$ is C$_{1-8}$ alkoxyalkylene. In some embodiments, R$^{2a}$ is haloC$_{1-8}$ alkylene. In some embodiments, R$^{2a}$ is haloC$_{1-8}$ alkoxy. In some embodiments, R$^{2a}$ is amino. In some embodiments, R$^{2a}$ is hydroxyl. In some embodiments, R$^{2a}$ is C$_{1-8}$ alkylamino. In some embodiments, R$^{2a}$ is diC$_{1-8}$ alkylamino. In some embodiments, R$^{2a}$ is C$_{1-8}$alkylthio. In some embodiments, R$^{2a}$ is oxo. In some embodiments, R$^{2a}$ is halo. In some embodiments, R$^{2a}$ is cyano. In some embodiments, R$^{2a}$ is haloC$_{1-8}$ alkylaminocarbonyl. In some embodiments, $R^{2a}$ is $C_{1-8}$alkylaminocarbonyl. In some embodiments, $R^{2a}$ is $diC_{1-8}$ alkylaminocarbonyl. In some embodiments, $R^{2a}$ is aminocarbonyl, heterocyclylcarbonyl. In some embodiments, $R^{2a}$ is $C_{1-8}$ alkylcarbonylamino. In some embodiments, $R^{2a}$ is $C_{1-8}$ alkylsulfonyl. In some embodiments, $R^{2a}$ is aminosulfonyl. In some embodiments, $R^{2a}$ is $C_{3-8}$ cycloalkyl. In some embodiments, $R^{2a}$ is $C_{1-8}$ alkylcarbonylpiperadinyl. In some embodiments, $R^{2a}$ is heterocyclyl. In some embodiments, $R^{2a}$ is phenyl. In some embodiments, $R^{2a}$ is heteroaryl. In some embodiments, $R^{2a}$ is heteroarylsulfinyl. In some embodiments, $R^{2a}$ is $C_{1-8}$arylalkylene. In some embodiments, $R^{2a}$ is amino$C_{1-8}$alkylene. In some embodiments, $R^{2a}$ is amino$C_{3-8}$cycloalkyl. In some embodiments, $R^{2a}$ is heterocyclyl$C_{1-8}$alkylene.

In some embodiments, $R^{2c}$ is $C_{1-8}$ alkyl. In some embodiments, $R^{2c}$ is $C_{2-8}$ alkenyl. In some embodiments, $R^{2c}$ is $C_{2-8}$alkynyl. In some embodiments, $R^{2c}$ is $C_{3-8}$ cycloalkyl$C_{1-8}$ alkylene. In some embodiments, $R^{2c}$ is $C_{1-8}$ alkoxy. In some embodiments, $R^{2c}$ is $C_{3-8}$ cycloalkoxy. In some embodiments, $R^{2c}$ is hydroxy$C_{1-8}$ alkylene. In some embodiments, $R^{2c}$ is $C_{1-8}$ alkoxyalkylene. In some embodiments, $R^{2c}$ is halo$C_{1-8}$ alkylene. In some embodiments, $R^{2c}$ is halo$C_{1-8}$ alkoxy. In some embodiments, $R^{2c}$ is amino. In some embodiments, $R^{2c}$ is hydroxyl. In some embodiments, $R^{2c}$ is $C_{1-8}$ alkylamino. In some embodiments, $R^{2c}$ is di$C_{1-8}$ alkylamino. In some embodiments, $R^{2c}$ is $C_{1-8}$alkylthio. In some embodiments, $R^{2c}$ is oxo. In some embodiments, $R^{2c}$ is halo. In some embodiments, $R^{2c}$ is cyano. In some embodiments, $R^{2c}$ is halo$C_{1-8}$ alkylaminocarbonyl. In some embodiments, $R^{2c}$ is $C_{1-8}$alkylaminocarbonyl. In some embodiments, $R^{2c}$ is di$C_{1-8}$ alkylaminocarbonyl. In some embodiments, $R^{2c}$ is aminocarbonyl, heterocyclylcarbonyl. In some embodiments, $R^{2c}$ is $C_{1-8}$ alkylcarbonylamino. In some embodiments, $R^{2c}$ is $C_{1-8}$ alkylsulfonyl. In some embodiments, $R^{2c}$ is aminosulfonyl. In some embodiments, $R^{2c}$ is $C_{3-8}$ cycloalkyl. In some embodiments, $R^{2c}$ is $C_{1-8}$ alkylcarbonylpiperadinyl. In some embodiments, $R^{2c}$ is heterocyclyl. In some embodiments, $R^{2c}$ is phenyl. In some embodiments, $R^{2c}$ is heteroaryl. In some embodiments, $R^{2c}$ is heteroarylsulfinyl. In some embodiments, $R^{2C}$ is $C_{1-8}$arylalkylene. In some embodiments, $R^{2C}$ is amino$C_{1-8}$alkylene. In some embodiments, $R^{2C}$ is amino$C_{3-8}$cycloalkyl. In some embodiments, $R^{2c}$ is heterocyclyl$C_{1-8}$alkylene.

In some embodiments, Q is heteroaryl optionally substituted with one or two or three or four or five $R^{2a}$ groups. In some embodiments, Q is cycloalkyl optionally substituted with one or two or three or four or five $R^{2a}$ groups. In some embodiments, Q is heterocyclyl optionally substituted with one or two or three or four or five $R^{2a}$ groups. In some embodiments, Q is phenyl substituted with $R^{2b}$ and optionally substituted with one or two or three or four $R^{2a}$ groups. In some embodiments, Q is phenyl substituted with heteroaryl optionally substituted with one or two or three $R^{2C}$ groups.

In some embodiments, Q is phenyl. In some embodiments, Q is

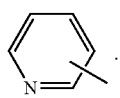

In some embodiments, Q is

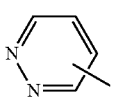

In some embodiments, V is

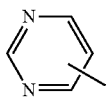

In some embodiments, Q is

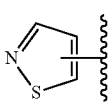

In some embodiments, Q is

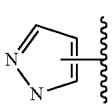

In some embodiments, Q is

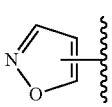

In some embodiments, Q is

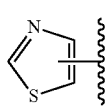

In some embodiments, Q is

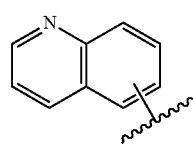

In some embodiments, Q is

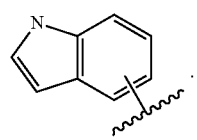

In some embodiments, Q is

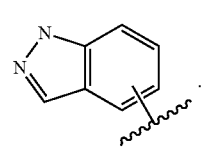

In some embodiments, Q is
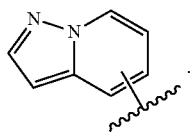
In some embodiments, Q is
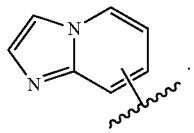
In some embodiments, Q is
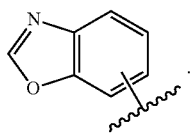
In some embodiments, V is
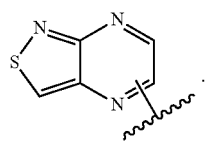
In some embodiments, Q is
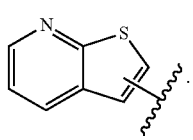
In some embodiments, Q is
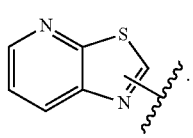
In some embodiments, Q is
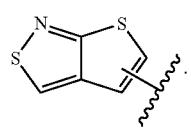
In some embodiments, V is
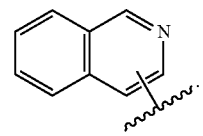
In some embodiments, Q is
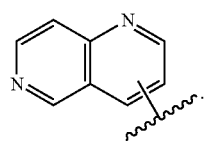
In some embodiments, Q is
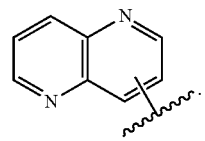
In some embodiments, Q is
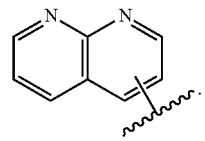
In some embodiments, Q is
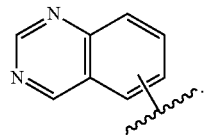
In some embodiments, Q is
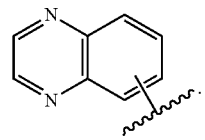
In some embodiments, Q is
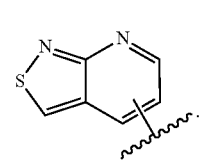

In some embodiments, Q is
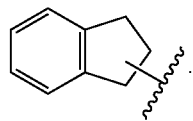
In some embodiments, Q is
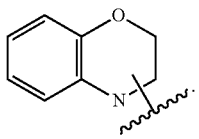
In some embodiments, Q is
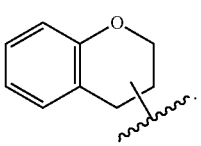
In some embodiments, Q is
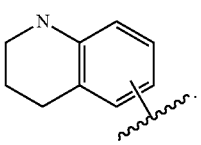
In some embodiments, Q is
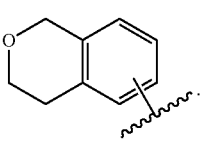
In some embodiments, Q is
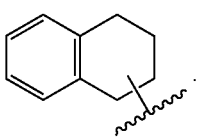
In some embodiments V W is
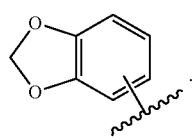
In some embodiments, Q is
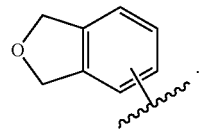
In some embodiments, Q is
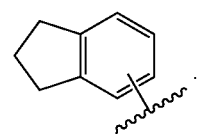
In some embodiments, Q is
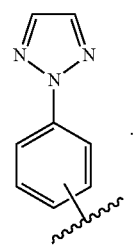
In some embodiments, Q is
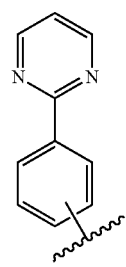
In some embodiments, Q is
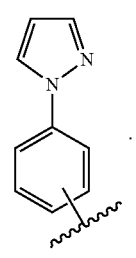
In some embodiments, Q is
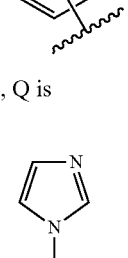
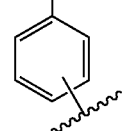

In some embodiments, Q is
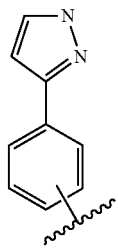
In some embodiments, Q is
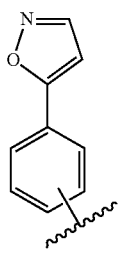
In some embodiments, Q is
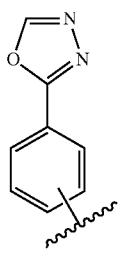
In some embodiments, Q is
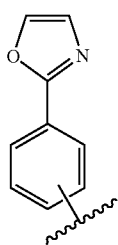
In some embodiments, Q is
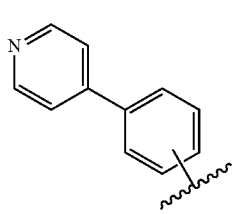
In some embodiments, Q is
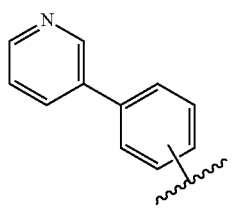
In some embodiments, Q is
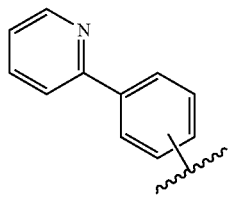
In some embodiments, Q is
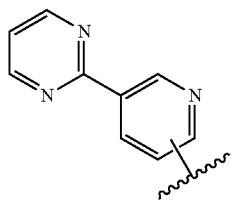
In some embodiments, Q is
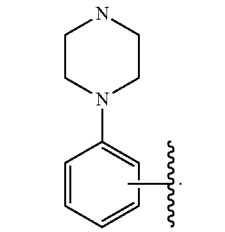
In some embodiments, Q is
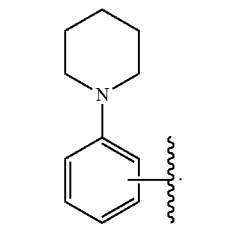

In some embodiments, Q is
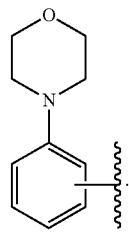
In some embodiments, Q is
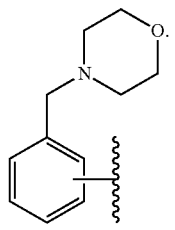
In some embodiments, Q is
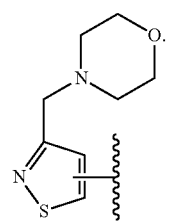
In some embodiments, Q is
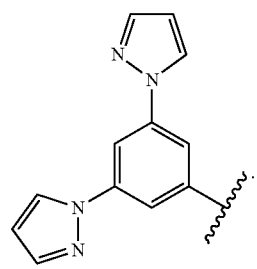 [SMILES: *c1cc(-n2cccn2)cc(-n2cccn2)c1]
In some embodiments, Q is
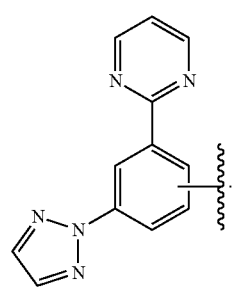
In some embodiments, Q is
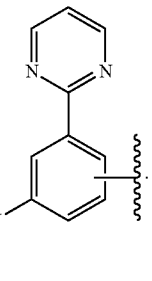
In some embodiments, Q is
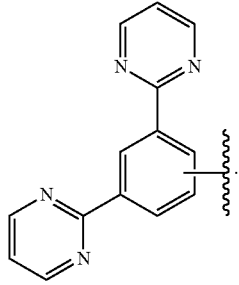
In some embodiments, Q is
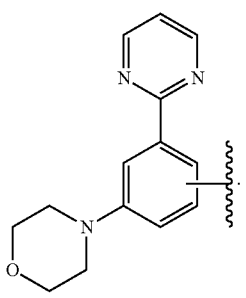
In some embodiments, Q is
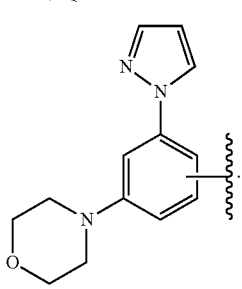
In some embodiments, Q is
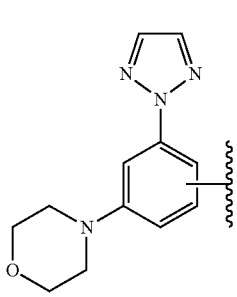

In some embodiments, Q is

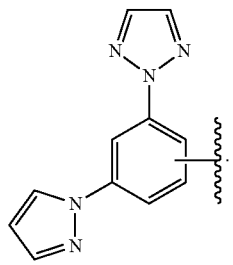

In some embodiments, Q is

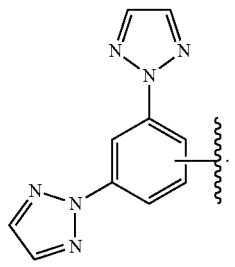

In some embodiments, Q is

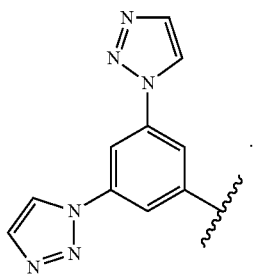 [SMILES: *c1cc(-n2ccnn2)cc(-n2ccnn2)c1]

In some embodiments, Q is

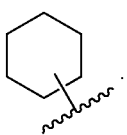

In some embodiments, Q is

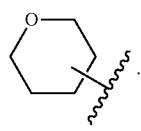

In some embodiments, V is

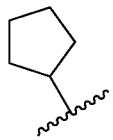

In one embodiment, provided is a compound of Formula (III) or a pharmaceutically acceptable salt thereof:

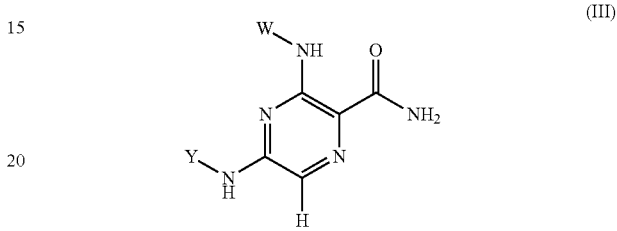

(III)

wherein
W is selected from the group consisting of:
  a) heteroaryl optionally substituted with one to five $R^{3a}$ groups;
  b) cycloalkyl optionally substituted with one to five $R^{3a}$ groups;
  c) heterocyclyl optionally substituted with one to five $R^{3a}$ groups; and
  d) aryl substituted with $R^{3b}$ and optionally substituted with one to four $R^{3a}$ groups;
$R^{3b}$ is -is selected from the group consisting of $C_{1-8}$ alkyl, $C_{3-8}$ cycloalkyl$C_{1-8}$ alkyl, $C_{1-8}$ alkoxy, $C_{3-8}$ cycloalkoxy, hydroxy$C_{1-8}$ alkyl, $C_{1-8}$ alkoxyalkyl, halo$C_{1-8}$ alkyl, halo$C_{1-8}$ alkoxy, amino, $C_{1-8}$ alkylamino, di$C_{1-8}$ alkylamino, halo, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, morpholinyl, phenyl, and heteroaryl optionally substituted with one to three $R^{3c}$ groups;
$R^{3a}$ and $R^{3c}$ are independently selected from the group consisting of $C_{1-8}$ alkyl, $C_{2-8}$ alkenyl, $C_{2-8}$alkynyl, $C_{3-8}$ cycloalkyl$C_{1-8}$ alkylene, $C_{1-8}$ alkoxy, $C_{3-8}$ cycloalkoxy, hydroxy$C_{1-8}$ alkylene, $C_{1-8}$ alkoxyalkylene, halo$C_{1-8}$ alkylene, halo$C_{1-8}$ alkoxy, amino, hydroxyl, $C_{1-8}$ alkylamino, di$C_{1-8}$ alkylamino, $C_{1-8}$alkylthio, oxo, halo, cyano, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, heterocyclyl, phenyl, heteroaryl, heteroarylsulfinyl; $C_{1-8}$arylalkylene, amino$C_{1-8}$alkylene;
Y is selected from the group consisting of a)

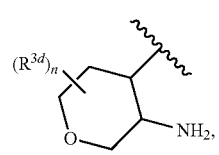

-continued b) 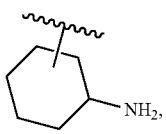

c) 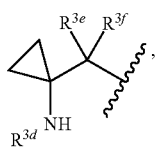

d) 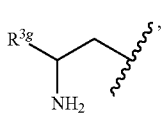

e) 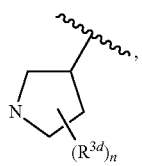

f) 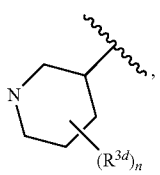

g) 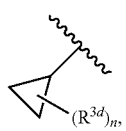

h) phenyl substituted with heteroaryl, optionally substituted with $R^{3b}$;

$R^{3d}$ is independently selected from the group consisting of $C_{1-8}$alkyl, $C_{1-8}$alkylcarbonyl, cyano$C_{1-8}$alkylene, hydroxy$C_{1-8}$alkylene, halo$C_{1-8}$alkylene, halo, and amino, and n is 0, 1, 2, 3, 4, or 5;

$R^{3e}$ is selected from the group consisting of hydrogen, cycloalkyl, cycloalkyl$C_{1-8}$alkyl, and $C_{1-8}$alkyl, wherein $R^{3e}$ is optionally substituted with one to five groups independently selected from halo, $C_{1-8}$alkyl, and amino;

$R^{if}$ is hydrogen or together with $R^{3e}$ and the carbon atom to which they are attached to form a cycloalkyl ring;

$R^{3g}$ is $C_{1-8}$alkyl optionally substituted with one to three halo substituents; and $R^{3h}$ is selected from the group consisting of halo, amino, $C_{1-8}$alkylcarbonyl and $C_{1-8}$alkyl.

In some embodiments, Y is

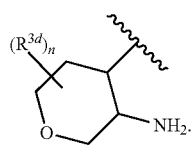

In some embodiments, Y is:

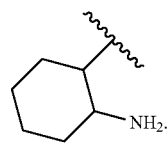

In some embodiments, Y is:

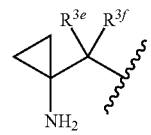

In some embodiments, Y is

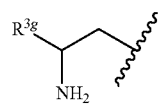

In some embodiments, Y is:

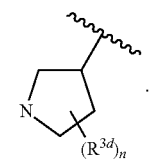

In some embodiments, Y is:

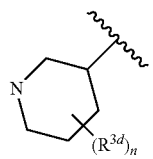

In some embodiments, Y is:

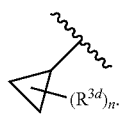

In some embodiments, wherein Y is phenyl substituted with heteroaryl, optionally substituted with $R^{3h}$.

In some embodiments, W is heteroaryl optionally substituted with one or two or three or four or five $R^{3a}$ groups. In some embodiments, W is cycloalkyl optionally substituted with one or two or three or four or five $R^{3a}$ groups. In some embodiments, W is heterocyclyl optionally substituted with one or two or three or four or five $R^{3a}$ groups. In some embodiments, W is phenyl substituted with $R^{3b}$ and optionally substituted with one or two or three or four $R^{3a}$ groups. In some embodiments, W is phenyl substituted with heteroaryl optionally substituted with one or two or three $R^{3c}$ groups.

In some embodiments, $R^{3b}$ is $C_{1-8}$ alkyl. In some embodiments, $R^{3b}$ is $C_{3-8}$ cycloalkyl$C_{1-8}$ alkyl. In some embodiments, $R^{3b}$ is $C_{1-8}$ alkoxy, $C_{3-8}$ cycloalkoxy. In some embodiments, $R^{3b}$ is hydroxy$C_{1-8}$ alkyl. In some embodiments, $R^{3b}$ is $C_{1-8}$ alkoxyalkyl. In some embodiments, $R^{3b}$ is halo$C_{1-8}$ alkyl. In some embodiments, $R^{3b}$ is halo$C_{1-8}$ alkoxy. In some embodiments, $R^{3b}$ is amino. In some embodiments, $R^{3b}$ is $C_{1-8}$ alkylamino. In some embodiments, $R^{3b}$ is di$C_{1-8}$ alkylamino. In some embodiments, $R^{3b}$ is halo. In some embodiments, $R^{3b}$ is halo$C_{1-8}$ alkylaminocarbonyl. In some embodiments, $R^{3b}$ is $C_{1-8}$alkylaminocarbonyl. In some embodiments, $R^{3b}$ is di$C_{1-8}$ alkylaminocarbonyl. In some embodiments, $R^{3b}$ is aminocarbonyl. In some embodiments, $R^{3b}$ is heterocyclylcarbonyl. In some embodiments, $R^{3b}$ is $C_{1-8}$ alkylcarbonylamino. In some embodiments, $R^{3b}$ is $C_{1-8}$ alkylsulfonyl. In some embodiments, $R^{3b}$ is aminosulfonyl. In some embodiments, $R^{3b}$ is $C_{3-8}$ cycloalkyl. In some embodiments, $R^{3b}$ is $C_{1-8}$ alkylcarbonylpiperadinyl. In some embodiments, $R^{3b}$ is morpholinyl. In some embodiments, $R^{3b}$ is phenyl. In some embodiments, $R^{3b}$ is heteroaryl. In some embodiments, $R^{3b}$ is optionally substituted with one or two or three $R^{3'}$ groups.

In some embodiments, $R^{3a}$ is $C_{1-8}$ alkyl. In some embodiments, $R^{3a}$ is $C_{2-8}$ alkenyl. In some embodiments, $R^{3a}$ is $C_{2-8}$alkynyl. In some embodiments, $R^{3a}$ is $C_{3-8}$ cycloalkyl$C_{1-8}$ alkylene. In some embodiments, $R^{3a}$ is $C_{1-8}$ alkoxy. In some embodiments, $R^{3a}$ is $C_{3-8}$ cycloalkoxy. In some embodiments, $R^{3a}$ is hydroxy$C_{1-8}$ alkylene. In some embodiments, $R^{3a}$ is $C_{1-8}$ alkoxyalkylene. In some embodiments, $R^{3a}$ is halo$C_{1-8}$ alkylene. In some embodiments, $R^{3a}$ is halo$C_{1-8}$ alkoxy. In some embodiments, $R^{3a}$ is amino. In some embodiments, $R^{3a}$ is hydroxyl. In some embodiments, $R^{3a}$ is $C_{1-8}$ alkylamino. In some embodiments, $R^{3a}$ is di$C_{1-8}$ alkylamino. In some embodiments, $R^{3a}$ is $C_{1-8}$alkylthio. In some embodiments, $R^{3a}$ is oxo. In some embodiments, $R^{3a}$ is halo. In some embodiments, $R^{3a}$ is cyano. In some embodiments, $R^{3a}$ is halo$C_{1-8}$ alkylaminocarbonyl. In some embodiments, $R^{3a}$ is $C_{1-8}$alkylaminocarbonyl. In some embodiments, $R^{3a}$ is di$C_{1-8}$ alkylaminocarbonyl. In some embodiments, $R^{3a}$ is aminocarbonyl, heterocyclylcarbonyl. In some embodiments, $R^{3a}$ is $C_{1-8}$ alkylcarbonylamino. In some embodiments, $R^{3a}$ is $C_{1-8}$ alkylsulfonyl. In some embodiments, $R^{3a}$ is aminosulfonyl. In some embodiments, $R^{3a}$ is $C_{3-8}$ cycloalkyl. In some embodiments, $R^{3a}$ is $C_{1-8}$ alkylcarbonylpiperadinyl. In some embodiments, $R^{3a}$ is heterocyclyl. In some embodiments, $R^{3a}$ is phenyl. In some embodiments, $R^{3a}$ is heteroaryl. In some embodiments, $R^{3a}$ is heteroarylsulfinyl. In some embodiments, $R^{3a}$ is $C_{1-8}$arylalkylene. In some embodiments, $R^{3a}$ is amino$C_{1-8}$alkylene. In some embodiments, $R^{3a}$ is amino$C_{3-8}$cycloalkyl. In some embodiments, $R^{3a}$ is heterocyclyl$C_{1-8}$alkylene.

In some embodiments, $R^{3c}$ is $C_{1-8}$ alkyl. In some embodiments, $R^{3c}$ is $C_{2-8}$ alkenyl. In some embodiments, $R^{3c}$ is $C_{2-8}$alkynyl. In some embodiments, $R^{3c}$ is $C_{3-8}$ cycloalkyl$C_{1-8}$ alkylene. In some embodiments, $R^{3c}$ is $C_{1-8}$ alkoxy. In some embodiments, $R^{3c}$ is $C_{3-8}$ cycloalkoxy. In some embodiments, $R^{3c}$ is hydroxy$C_{1-8}$ alkylene. In some embodiments, $R^{3c}$ is $C_{1-8}$ alkoxyalkylene. In some embodiments, $R^{3c}$ is halo$C_{1-8}$ alkylene. In some embodiments, $R^{3c}$ is halo$C_{1-8}$ alkoxy. In some embodiments, $R^{3c}$ is amino. In some embodiments, $R^{2c}$ is hydroxyl. In some embodiments, $R^{3c}$ is $C_{1-8}$ alkylamino. In some embodiments, $R^{3c}$ is di$C_{1-8}$ alkylamino. In some embodiments, $R^{3c}$ is $C_{1-8}$alkylthio. In some embodiments, $R^{3c}$ is oxo. In some embodiments, $R^{3c}$ is halo. In some embodiments, $R^{3c}$ is cyano. In some embodiments, $R^{3c}$ is halo$C_{1-8}$ alkylaminocarbonyl. In some embodiments, $R^{3c}$ is $C_{1-8}$alkylaminocarbonyl. In some embodiments, $R^{3c}$ is di$C_{1-8}$ alkylaminocarbonyl. In some embodiments, $R^{3c}$ is aminocarbonyl, heterocyclylcarbonyl. In some embodiments, $R^{3c}$ is $C_{1-8}$ alkylcarbonylamino. In some embodiments, $R^{3c}$ is $C_{1-8}$ alkylsulfonyl. In some embodiments, $R^{3c}$ is aminosulfonyl. In some embodiments, $R^{3c}$ is $C_{3-8}$ cycloalkyl. In some embodiments, $R^{3c}$ is $C_{1-8}$ alkylcarbonylpiperadinyl. In some embodiments, $R^{3c}$ is heterocyclyl. In some embodiments, $R^{3c}$ is phenyl. In some embodiments, $R^{3c}$ is heteroaryl. In some embodiments, $R^{3c}$ is heteroarylsulfinyl. In some embodiments, $R^{3c}$ is $C_{1-8}$arylalkylene. In some embodiments, $R^{3c}$ is amino$C_{1-8}$alkylene. In some embodiments, $R^{3c}$ is amino$C_{3-8}$cycloalkyl. In some embodiments, $R^{3c}$ is heterocyclyl$C_{1-8}$alkylene.

In some embodiments, W is phenyl. In some embodiments, W is

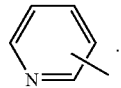

In some embodiments, W is

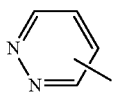

In some embodiments, W is

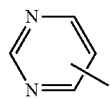

In some embodiments, W is

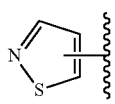

In some embodiments, W is

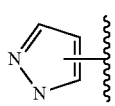

In some embodiments, W is

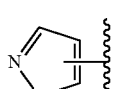

In some embodiments, W is
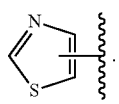
In some embodiments, W is
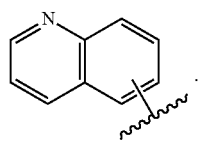
In some embodiments, W is
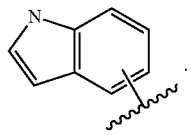
In some embodiments, W is
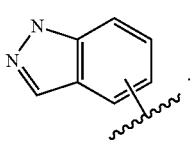
In some embodiments, W is
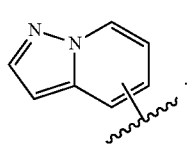
In some embodiments, W is
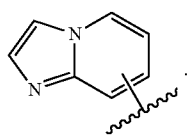
In some embodiments, W is
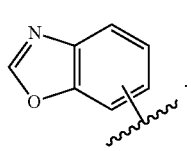
In some embodiments, W is
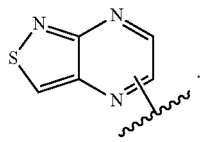
In some embodiments, W is
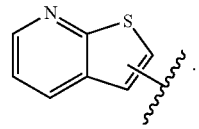
In some embodiments, W is
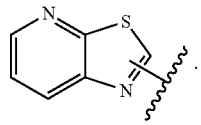
In some embodiments, W is
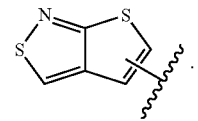
In some embodiments, W is
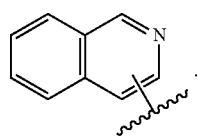
In some embodiments, W is
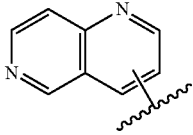
In some embodiments, W is
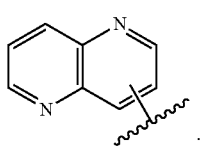

In some embodiments, W is
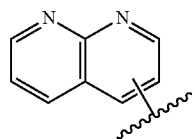
In some embodiments, W is
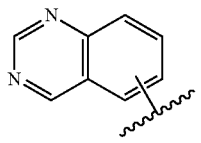
In some embodiments, W is
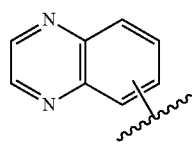
In some embodiments, W is
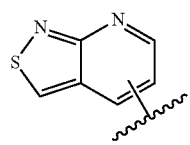
In some embodiments, W is
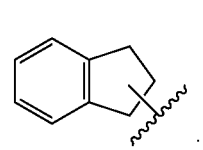
In some embodiments, W is
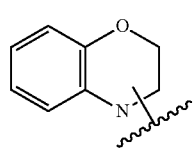
In some embodiments, W is
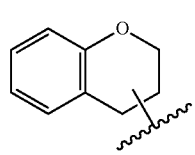
In some embodiments, W is
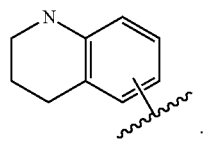
In some embodiments, W is
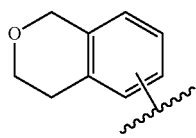
In some embodiments, W is
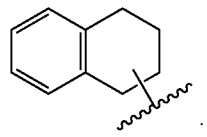
In some embodiments, W is
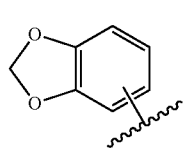
In some embodiments, W is
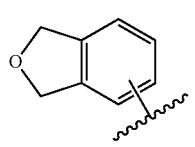
In some embodiments, W is
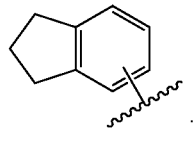
In some embodiments, W is
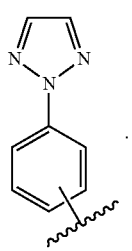

In some embodiments, W is
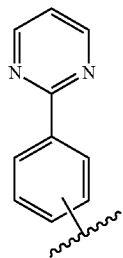
In some embodiments, W is
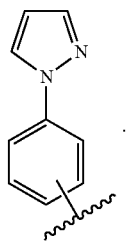
In some embodiments, W is
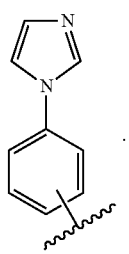
In some embodiments, W is
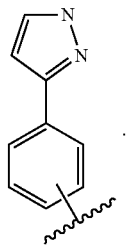
In some embodiments, W is
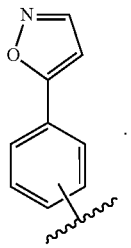
In some embodiments, W is
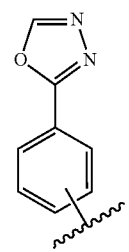
In some embodiments, W is
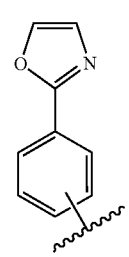
In some embodiments, W is
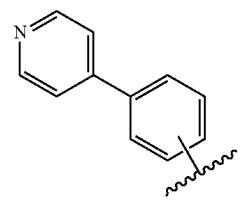
In some embodiments, W is
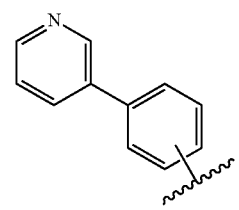
In some embodiments, W is
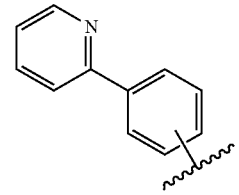

In some embodiments, W is
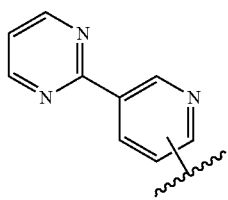
In some embodiments, W is
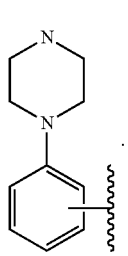
In some embodiments, W is
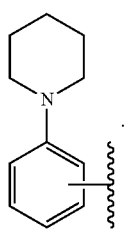
In some embodiments, W is
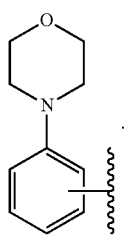
In some embodiments, W is
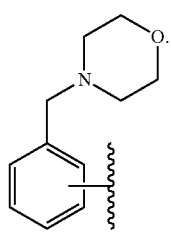
In some embodiments, W is
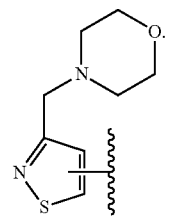
In some embodiments, W is
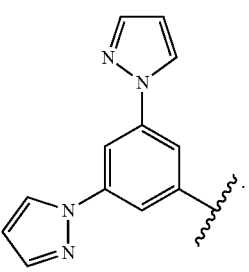 [SMILES: *c1cc(-n2cccn2)cc(-n2cccn2)c1]
In some embodiments, W is
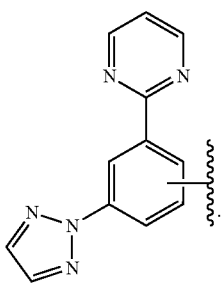
In some embodiments, W is
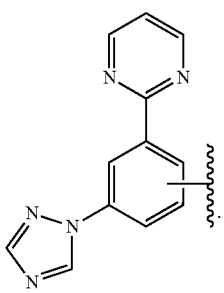
In some embodiments, W is
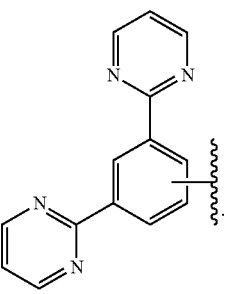

In some embodiments, W is

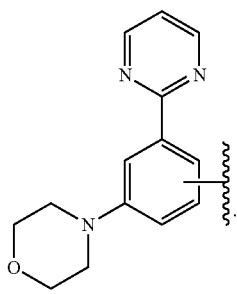

In some embodiments, W is

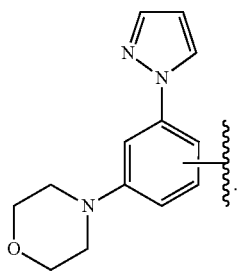

In some embodiments, W is

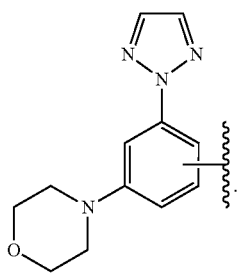

In some embodiments, W is

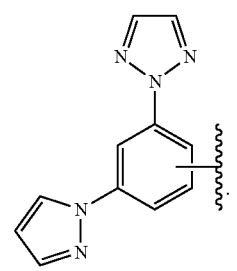

In some embodiments, W is

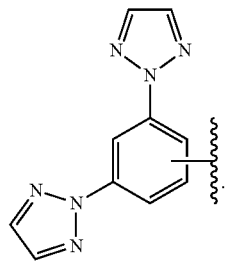

In some embodiments, W is

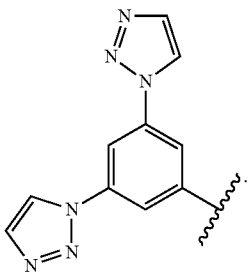 [SMILES: *c1cc(-n2ccnn2)cc(-n2ccnn2)c1]

In some embodiments, W is

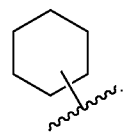

In some embodiments, W is

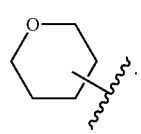

In some embodiments, W is

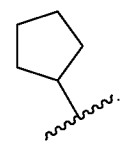

Within any of the embodiments herein, W is optionally substituted with one or two or three substituents independently selected from the group consisting of $C_{1-8}$ alkyl, $C_{3-8}$ cycloalkyl$C_{1-8}$ alkylene, $C_{1-8}$ alkoxy, $C_{3-8}$ cycloalkoxy, hydroxy$C_{1-8}$ alkylene, $C_{1-8}$ alkoxyalkyl, halo$C_{1-8}$ alkyl, halo$C_{1-8}$ alkoxy, amino, $C_{1-8}$ alkylamino, di$C_{1-8}$ alkylamino, oxo, halo, halo$C_{1-8}$ alkylaminocarbonyl, $C_{1-8}$alkylaminocarbonyl, di$C_{1-8}$ alkylaminocarbonyl, aminocarbonyl, heterocyclylcarbonyl, $C_{1-8}$ alkylcarbonylamino, $C_{1-8}$ alkylsulfonyl, aminosulfonyl, $C_{3-8}$ cycloalkyl, $C_{1-8}$ alkylcarbonylpiperadinyl, morpholinyl, phenyl, pyridyl, and pyrimidyl.

In some embodiments, W is

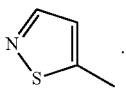

In some embodiments, W is

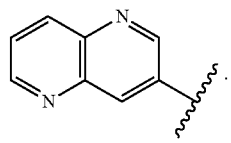 [SMILES: *c1cnc2cccnc2c1]

In some embodiments, W is

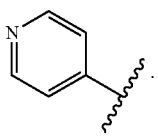

In some embodiments, W L

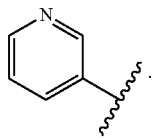 [SMILES: *c1cccnc1]

The present invention provides in another embodiment, a compound of the examples or a pharmaceutically acceptable salt thereof.

The present invention provides in another embodiment, a compound of any one of Table 1 or a pharmaceutically acceptable salt thereof.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

b. Methods of Synthesis

The compounds of the present invention may be prepared by known organic synthesis techniques, including the methods described in more detail in the Examples.

One skilled in the art will recognize that in certain embodiments it may be advantageous to use a protecting group strategy. The protecting group can be removed using methods known to those skilled in the art.

The compounds of the present invention may generally be utilized as the free base. Alternatively, the compounds of this invention may be used in the form of acid addition salts as described below.

c. Inhibition of Syk Kinases

The activity of a specified compound as an inhibitor of a Syk kinase may be assessed in vitro or in vivo. In some embodiments, the activity of a specified compound can be tested in a cellular assay. Selectivity could also be ascertained in biochemical assays with isolated kinases. Exemplary assays of this type are described in greater detail in the Examples.

d. Compositions and Methods of Administration

The present invention further provides compositions comprising one or more compounds provided herein or a pharmaceutically acceptable salt, ester or prodrug thereof, and a pharmaceutically acceptable carrier or diluent. It will be appreciated that the compounds provided herein in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds provided herein, similar to metabolically labile esters or carbamates, which are capable of producing the parent compounds provided herein in vivo, are within the scope of this invention.

As used herein, the term "pharmaceutically acceptable salts" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more Syk inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the Syk inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more Syk inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more Syk inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more Syk inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more Syk inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the Syk inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered Syk inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more Syk inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more Syk inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more Syk inhibitors can be in the form of emulsions, lotions, gels, foams, creams, jellies, solutions, suspensions, ointments, and transdermal patches.

Topical application for the lower intestinal tract may be effected in a rectal suppository formulation or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing Syk activity as well as treating or ameliorating a Syk associated state, symptom, condition, disorder or disease in a patient in need thereof (e.g., human or non-human). In one embodiment, the Syk associated state, symptom, condition, disorder or disease is mediated, at least in part by Syk kinase activity. In more specific embodiments, the present invention provides a method for treating a condition or disorder mediated at least in part by Syk kinase activity is cardiovascular disease, inflammatory disease or autoimmune disease.

In one embodiment, the invention provides methods for preventing or treating a condition in a mammal mediated at least in part by syk activity comprising the step of administering to the mammal a therapeutically effective amount of a compound of the present invention. Such conditions include, but are not limited, to restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purura, heparin induced thrombocytopenia, dilated cardiomypathy, sickle cell disease, atherosclerosis, myocardial infarction, vacular inflammation, unstable angina or acute coronary syndromes.

In another embodiment, the present invention also provides a method for treating allergy, asthma, theumatoid arthritis, B Cell mediated disease such as Non-Hodgkin's Lymphoma, anti phospholipids syndrome, lupus, psoriasis, multiple sclerosis, end stage renal disease or chronic lymphocytic leukemia.

In another embodiment, the present invention provides a method for treating hemolytic anemia or immune thrombocytopenic purpura.

In another embodiment, the present invention provides a method for treating vasculitis, including but not limited to: Large vessel vasculitis, such as Giant cell arteritis and Takayasu's arteritis; Medium vessel vasculitis, such as Polyarteritis nodosa (PAN) and Kawasaki Disease; Small vessel vasculitis, such as Wegener's granulomatosis, Churg-Strauss syndrome, Microscopic polyangiitis, Henoch-Schonlein purpura, Cryoglobulinaemic vasculitis, and Cutaneous leucocytoclastic angiitis.

In another embodiment, the present invention provides a method for treating a Auto-immune blistering skin disease including but not limited to: *Pemphigus*, such as *Pemphigus vulgaris*, *Pemphigus foliaceus*, *Paraneoplastic pemphigus*, and IgA *pemphigus*; and Subepidermal autoimmune blistering skin disease, such as Bullous pemphigoid, Pemphigoid gestationis, Linear IgA dermatosis, Mucous membrane pemphigoid, Lichen planus pemphigoides, Anti-laminin g1/p200 pemphigoid, Epidermolysis bullosa acquisita and Dermatitis herpetiformis.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a Syk kinase. Syk kinase is a tyrosine kinase known to play a critical role in Fcγ receptor signaling, as well as in other signaling cascades, such as those involving B-cell receptor signaling (Turner et al., (2000), Immunology Today 21:148-154) and integrins beta(1), beta (2), and beta (3) in neutrophils (Mocsai et al., (2002), Immunity 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004, the disclosures of which are incorporated herein by reference. The described herein and Syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a Syk inhibitory compound or one of the other current treatments for the particular disease. The compounds could also be used in combination with Syk inhibitory compounds in patients that are Syk-compound resistant or non-responsive. Suitable Syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits Syk kinase with an $IC_{50}$ in the range of at least 10 µM.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

Active compounds of the invention typically inhibit the Syk and/or JAK/Stat pathway. The activity of a specified compound as an inhibitor of a Syk kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) (Cynthia K. Hahn, Kenneth N. Ross, Rose M. Kakoza, Steven Karr, Jinyan Du, Shao-E Ong, Todd R. Golub, Kimberly Stegmaier, Syk is a new target for AML differentiation, Blood, 2007, 110, Abstract 209) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant Syk activity can be treated with the Syk inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant Syk activity can be treated with the Syk inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

The inventive methods comprise administering an effective amount of a compound or composition described herein to a mammal or non-human animal. As used herein, "effective amount" of a compound or composition of the invention includes those amounts that antagonize or inhibit Syk. An amount which antagonizes or inhibits Syk is detectable, for example, by any assay capable of determining Syk activity, including the one described below as an illustrative testing method. Effective amounts may also include those amounts which alleviate symptoms of a Syk associated disorder treatable by inhibiting Syk. Accordingly, "antagonists of Syk" or include compounds which interact with the Syk and modulate, e g., inhibit or decrease, the ability of a second compound, e.g., another Syk ligand, to interact with the Syk. The Syk binding compounds are preferably antagonists. The language "Syk binding compound" and (e.g., exhibits binding affinity to the receptor) includes those compounds which interact with Syk resulting in modulation of the activity of Syk or JAK, respectively. Syk binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of Syk modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

In one embodiment, provided is a method of using one or more of the compounds provided herein to treat a variety of disorders, symptoms and diseases (e.g., inflammatory, autoimmune, neurological, neurodegenerative, oncology and cardiovascular). In certain groups of embodiments the inflammatory disease and autoimmune disease is selected from the group consisting of organ transplants, osteoarthritis, irritable bowel disease (IBD), asthma, chronic obstructive pulmonary disease (COPD), systemic lupus erythematosus, multiple sclerosis, rheumatoid arthritis (RA), Crohn's disease, Type I diabetes, conjunctivitis, uveitis, vasculitis and psoriasis. In certain groups of embodiments the inflammatory disease is selected from the group consisting of allergy, asthma, rheumatoid arthritis, B Cell mediated diseases such as Non Hodgkin's Lymphoma, anti phospholipid syndrome, lupus, psoriasis, multiple sclerosis and end stage renal disease. In certain groups of embodiments the cardiovascular disease is selected from the group consisting of immune thrombocytopenic purpura, hemolytic anemia and heparin induced thrombocytopenia. In certain groups of embodiments the inflammatory disease is rheumatoid arthritis. In certain groups of embodiments the sickle cell disease is selected from the group consisting of sickle cell anemia, sickle-hemoglobin C disease, sickle beta-plus thalassemia, and sickle beta-zero thalassemia. In certain groups of embodiments the autoimmune disease is selected from the group consisting of organ transplants, chronic obstructive pulmonary disease (COPD), hemolytic anemia, immune thrombocytopenic purpura (ITP), multiple sclerosis, Sjogren's syndrome Type I diabetes, rheumatoid arthritis, lupus (including systemic lupus erythematosus(SLE), vasculitis, glomerular nephritis (GN), auto-immune-blistering disease, atopic dermatitis(eczema), atherosclerosis, autoimmune neutropenia and psoriasis. In certain groups of embodiments the cell proliferative disorder is leukemia, a lymphoma, myeloproliferative disorders, hematological malignancies, and chronic idiopathic myelofibrosis. In certain groups of embodiments the disorder is acute myeloid leukemia (AML), chronic lymphocytic leukemia (CLL), acute lymphoblastic leukemia (ALL) or non-Hodgkin's lymphoma.

The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are potent inhibitors of Syk kinases, exhibiting $IC_{50}$s in the respective assay in the range of less than 5 µM, with most being in the nanomolar, and several in the sub-nanomolar, range.

f. Kits

Still another aspect of this invention is to provide a kit comprising separate containers in a single package, wherein the inventive pharmaceutical compounds, compositions and/ or salts thereof are used in combination with pharmaceutically acceptable carriers to treat states, disorders, symptoms and diseases where Syk plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (UPLC) system with Waters Acquity UPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/ water as the mobile phase. One system may use TFA as the modifier and measure in positive ion mode [reported as MH+, (M+1) or (M+H)+] and the other may use either formic acid or ammonium acetate and measure in both positive [reported as MH⁺, (M+1) or (M+H)⁺] and negative [reported as M−, (M−1) or (M−H)⁻] ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices Mel-Temp apparatus (Holliston, Mass.).

Preparative separations may be carried out as needed, using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Example 1

(R)-5-(1-amino-4-methyl-1-oxopentan-2-ylamino)-3-(quinolin-3-ylamino)pyrazine-2-carboxamide

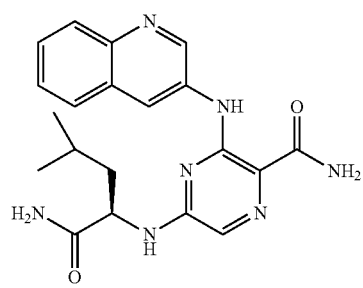 [SMILES: CC(C)C[C@@H](Nc1cnc(C(N)=O)c(Nc2cnc3ccccc3c2)n1)C(N)=O]

Scheme 1

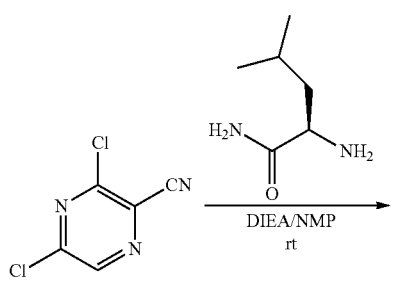

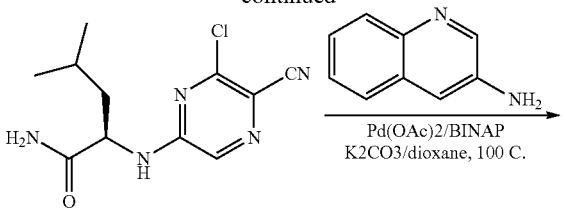

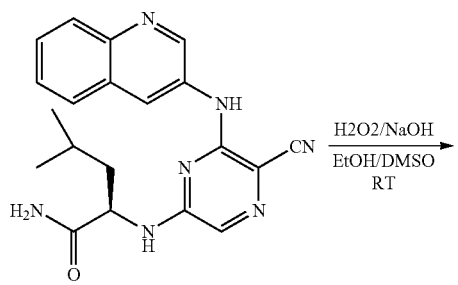

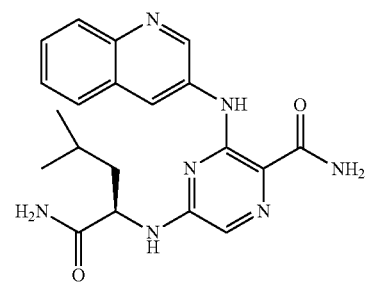

A solution of 3,5-dichloropyrazine-2-carbonitrile (348 mg, 2.00 mmol), D-leucinamide hydrochloride (333 mg, 2.00 mmol) and DIEA (1.00 mL, 5.75 mmol) in NMP (8 mL) was stirred at room temperature for 20 h. Water and EtOAc were added. Organic phase was separated, dried over Na₂SO₄, concentrated in vacuo to give (R)-2-(6-chloro-5-cyanopyrazin-2-ylamino)-4-methylpentanamide as an oil (535 mg).

A mixture of (R)-2-(6-chloro-5-cyanopyrazin-2-ylamino)-4-methylpentanamide (70 mg, 0.261 mmol), 3-aminoquinoline (60 mg, 0.416 mmol), K₂CO₃ (60 mg, 0.434 mmol), BINAP (25 mg, 0.040 mmol) and Pd(OAc)₂ (10 mg, 0.044 mmol) in dioxane (2 mL) was degassed with Ar, then was stirred at 100 C for 20 h. Water and EtOAc were added. Organic phase was separated, dried over Na₂SO₄, concentrated in vacuo to give (R)-2-(5-cyano-6-(quinolin-3-ylamino)pyrazin-2-ylamino)-4-methylpentanamide as a crude residue (131 mg). The crude (R)-2-(5-cyano-6-(quinolin-3-ylamino)pyrazin-2-ylamino)-4-methylpentanamide (131 mg) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (30 mg). MS 394.4 (M+H); UV 201.1, 247.4, 297.8, 352.3 nm; t 0.476 min.

Example 2

(R)-5-(1-amino-4-methyl-1-oxopentan-2-ylamino)-3-(quinolin-6-ylamino)pyrazine-2-carboxamide

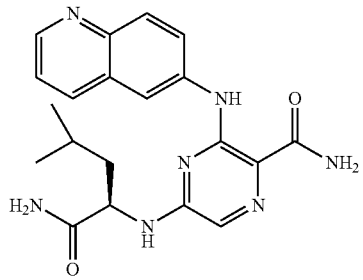 [SMILES: CC(C)C[C@@H](Nc1cnc(C(N)=O)c(Nc2ccc3ncccc3c2)n1)C(N)=O]

A mixture of (R)-2-(6-chloro-5-cyanopyrazin-2-ylamino)-4-methylpentanamide (80 mg, 0.299 mmol), 6-aminoquinoline (60 mg, 0.416 mmol), K₂CO₃ (65 mg, 0.471 mmol), BINAP (25 mg, 0.040 mmol) and Pd(OAc)2 (10 mg, 0.044 mmol) in dioxane (2 mL) was degassed with Ar, then was stirred at 100 C for 20 h. Water and EtOAc were added. Organic phase was separated, dried over Na₂SO₄, concentrated in vacuo to give (R)-2-(5-cyano-6-(quinolin-6-ylamino)pyrazin-2-ylamino)-4-methylpentanamide as a crude residue (151 mg). The crude (R)-2-(5-cyano-6-(quinolin-6-ylamino)pyrazin-2-ylamino)-4-methylpentanamide (151 mg) was dissolved in EtOH (2 mL) and DMSO (1 mL), aq. 1N NaOH (1.0 mL) and aq. H2O2 (50%, 1.0 mL) were added. The mixture was stirred at room temperature for 60 min. HOAc (0.5 mL) was added. The mixture was then concentrated in vacuo. The residue was purified by HPLC to give the titled compound (21 mg). MS 394.2 (M+H); UV 201.1, 265.8, 297.2, 358.5 nm; t 0.451 min.

Example 3

(R)-5-(1-amino-4-methyl-1-oxopentan-2-ylamino)-3-(1-methyl-1H-indol-4-ylamino)pyrazine-2-carboxamide

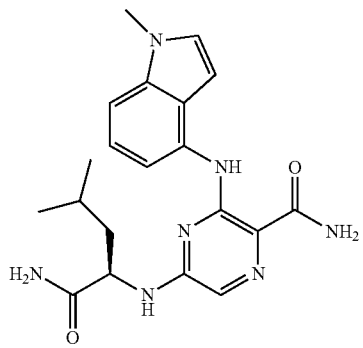 [SMILES: CC(C)C[C@@H](Nc1cnc(C(N)=O)c(Nc2cccc3c2ccn3C)n1)C(N)=O]

A mixture of (R)-2-(6-chloro-5-cyanopyrazin-2-ylamino)-4-methylpentanamide (80 mg, 0.299 mmol), 4-amino-N-methyl-indole (62 mg, 0.424 mmol), K₂CO₃ (65 mg, 0.471 mmol), BINAP (25 mg, 0.040 mmol) and Pd(OAc)2 (10 mg, 0.044 mmol) in dioxane (2 mL) was degassed with Ar, then was stirred at 100 C for 20 h. Water and EtOAc were added. Organic phase was separated, dried over Na₂SO₄, concentrated in vacuo to give (R)-2-(5-cyano-6-(1-methyl-1H-indol-4-ylamino)pyrazin-2-ylamino)-4-methylpentanamide as a crude residue (151 mg).

The crude (R)-2-(5-cyano-6-(1-methyl-1H-indol-4-ylamino)pyrazin-2-ylamino)-4-methylpentanamide (151 mg) was dissolved in EtOH (2 mL) and DMSO (1 mL), aq. 1N NaOH (1.0 mL) and aq. H2O2 (50%, 1.0 mL) were added. The mixture was stirred at room temperature for 60 min. HOAc (0.5 mL) was added. The mixture was then concentrated in vacuo. The residue was purified by HPLC to give the titled compound (9 mg). MS 396.4 (M+H); UV 202.2, 273.1, 324.8 nm; t 0.613 min.

Example 4

(R)-5-(1-amino-1-oxopropan-2-ylamino)-3-(quinolin-6-ylamino)pyrazine-2-carboxamide

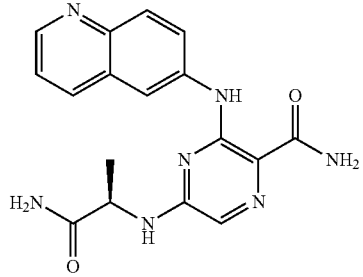 [SMILES: C[C@@H](Nc1cnc(C(N)=O)c(Nc2ccc3ncccc3c2)n1)C(N)=O]

A solution of 3,5-dichloropyrazine-2-carbonitrile (150 mg, 0.862 mmol), D-alaninamide hydrochloride (107 mg, 0.858 mmol) and DIEA (0.400 mL, 2.30 mmol) in NMP (4 mL) was stirred at room temperature for 20 h. Water and EtOAc were added. Organic phase was separated, dried over Na₂SO₄, concentrated in vacuo to give (R)-2-(6-chloro-5-cyanopyrazin-2-ylamino)propanamide as an oil (194 mg).

A mixture of (R)-2-(6-chloro-5-cyanopyrazin-2-ylamino) propanamide (97 mg, 0.430 mmol), 6-aminoquinoline (62 mg, 0.430 mmol), K₂CO₃ (100 mg, 0.724 mmol), BINAP (30 mg, 0.048 mmol) and Pd(OAc)2 (15 mg, 0.066 mmol) in dioxane (2 mL) was degassed with Ar, then was stirred at 110 C for 20 h. The mixture was concentrated in vacuo. The residue was purified by HPLC to give (R)-2-(5-cyano-6-(quinolin-6-ylamino)pyrazin-2-ylamino)propanamide (15 mg). The compound (R)-2-(5-cyano-6-(quinolin-6-ylamino) pyrazin-2-ylamino)propanamide (15 mg, 0.045 mmol) was dissolved in EtOH (1 mL) and DMSO (0.5 mL), aq. 1N NaOH (0.5 mL) and aq. H2O2 (50%, 0.5 mL) were added. The mixture was stirred at room temperature for 90 min. HOAc (0.5 mL) was added. The mixture was then concentrated in vacuo. The residue was purified by HPLC to give the titled compound (14 mg). MS 352.58 (M+H); UV 202.9, 265.2, 297.2, 357.9 nm; t 0.335 min.

Example 5

(R)-5-(1-amino-1-oxopropan-2-ylamino)-3-(quinolin-3-ylamino)pyrazine-2-carboxamide

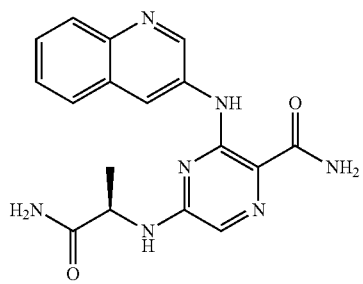 [SMILES: C[C@@H](Nc1cnc(C(N)=O)c(Nc2cnc3ccccc3c2)n1)C(N)=O]

A mixture of (R)-2-(6-chloro-5-cyanopyrazin-2-ylamino)propanamide (97 mg, 0.430 mmol), 3-aminoquinoline (62 mg, 0.430 mmol), $K_2CO_3$ (100 mg, 0.724 mmol), BINAP (30 mg, 0.048 mmol) and Pd(OAc)2 (15 mg, 0.066 mmol) in dioxane (2 mL) was degassed with Ar, then was stirred at 110 C for 20 h. The mixture was concentrated in vacuo. The residue was purified by HPLC to give (R)-2-(5-cyano-6-(quinolin-3-ylamino)pyrazin-2-ylamino)propanamide (74 mg).

The compound (R)-2-(5-cyano-6-(quinolin-3-ylamino)pyrazin-2-ylamino)propanamide (74 mg, 0.222 mmol) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (63 mg). MS 352.3 (M+H); UV 206.6, 223.0, 245.6, 295.3, 351.1 nm; t 0.360 min.

Example 6

5-(1-amino-4,4,4-trifluoro-1-oxobutan-2-ylamino)-3-(quinolin-6-ylamino)pyrazine-2-carboxamide

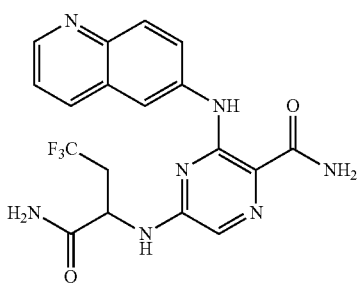 [SMILES: NC(=O)c1ncc(NC(CC(F)(F)F)C(N)=O)nc1Nc1ccc2ncccc2c1]

A solution of 3,5-dichloropyrazine-2-carbonitrile (50 mg, 0.287 mmol), 2-amino-4,4,4-trifluorobutanamide hydrochloride (50 mg, 0.259 mmol) and DIEA (0.150 mL, 0.862 mmol) in NMP (1 mL) was stirred at room temperature for 20 h. Water and EtOAc were added. Organic phase was separated, dried over $Na_2SO_4$, concentrated in vacuo to give 2-(6-chloro-5-cyanopyrazin-2-ylamino)-4,4,4-trifluorobutanamide (67 mg).

A mixture of 2-(6-chloro-5-cyanopyrazin-2-ylamino)-4,4,4-trifluorobutanamide (67 mg, 0.228 mmol), 6-aminoquinoline (48 mg, 0.333 mmol), $K_2CO_3$ (100 mg, 0.724 mmol), BINAP (25 mg, 0.040 mmol) and Pd(OAc)2 (10 mg, 0.044 mmol) in dioxane (2 mL) was degassed with Ar, then was stirred at 110 C for 20 h. The mixture was concentrated in vacuo. The residue was purified by HPLC to give 2-(5-cyano-6-(quinolin-6-ylamino)pyrazin-2-ylamino)-4,4,4-trifluorobutanamide (5 mg).

The compound 2-(5-cyano-6-(quinolin-6-ylamino)pyrazin-2-ylamino)-4,4,4-trifluorobutanamide (5 mg, 0.012 mmol) was dissolved in EtOH (1 mL) and DMSO (0.5 mL), aq. 1N NaOH (0.5 mL) and aq. H2O2 (50%, 0.5 mL) were added. The mixture was stirred at room temperature for 30 min. HOAc (0.5 mL) was added. The mixture was then concentrated in vacuo. The residue was purified by HPLC to give the titled compound (4 mg). MS 420.3 (M+H); UV 204.7, 263.3, 297.7 nm; t 0.417 min.

Example 7

(R)-5-(1-amino-3-cyclopropyl-1-oxopropan-2-ylamino)-3-(quinolin-3-ylamino)pyrazine-2-carboxamide

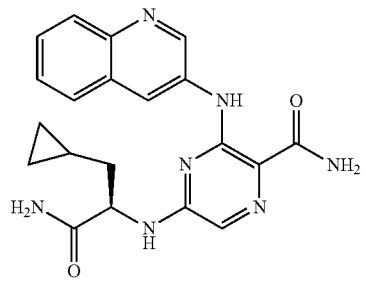 [SMILES: NC(=O)c1ncc(N[C@H](CC2CC2)C(N)=O)nc1Nc1cnc2ccccc2c1]

A solution of 3,5-dichloropyrazine-2-carbonitrile (158 mg, 0.908 mmol), (R)-2-amino-3-cyclopropylpropanamide hydrochloride (150 mg, 0.911 mmol) and DIEA (0.400 mL, 2.30 mmol) in NMP (5 mL) was stirred at room temperature for 20 h. Water and EtOAc were added. Organic phase was separated, dried over $Na_2SO_4$, concentrated in vacuo to give (R)-2-(6-chloro-5-cyanopyrazin-2-ylamino)-3-cyclopropylpropanamide (240 mg).

A mixture of (R)-2-(6-chloro-5-cyanopyrazin-2-ylamino)-3-cyclopropylpropanamide (78 mg, 0.293 mmol), 3-aminoquinoline (60 mg, 0.416 mmol), $K_2CO_3$ (70 mg, 0.507 mmol), BINAP (25 mg, 0.040 mmol) and Pd(OAc)2 (10 mg, 0.044 mmol) in dioxane (2 mL) was degassed with Ar, then was stirred at 110 C for 3 h. The mixture was concentrated in vacuo. The residue was purified by HPLC to give (R)-2-(5-cyano-6-(quinolin-3-ylamino)pyrazin-2-ylamino)-3-cyclopropylpropanamide (48 mg).

The compound (R)-2-(5-cyano-6-(quinolin-3-ylamino)pyrazin-2-ylamino)-3-cyclopropylpropanamide (48 mg, 0.128 mmol) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (35 mg). MS 392.3 (M+H); UV 202.9, 223.0, 246.8, 296.0, 351.7 nm; t 0.437 min.

Example 8

(R)-5-(1-amino-3-cyclopropyl-1-oxopropan-2-ylamino)-3-(quinolin-6-ylamino)pyrazine-2-carboxamide

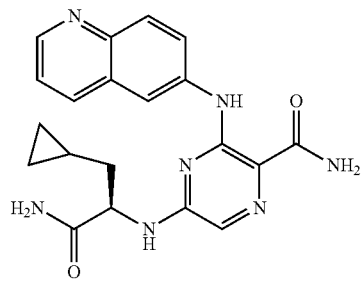 [SMILES: NC(=O)c1ncc(N[C@H](CC2CC2)C(N)=O)nc1Nc1ccc2ncccc2c1]

A mixture of (R)-2-(6-chloro-5-cyanopyrazin-2-ylamino)-3-cyclopropylpropanamide (80 mg, 0.301 mmol), 6-aminoquinoline (60 mg, 0.416 mmol), K₂CO₃ (65 mg, 0.471 mmol), BINAP (25 mg, 0.040 mmol) and Pd(OAc)2 (10 mg, 0.044 mmol) in dioxane (2 mL) was degassed with Ar, then was stirred at 110 C for 20 h. Water and EtOAc were added. Organic phase was separated, dried over Na₂SO₄, concentrated in vacuo to give a crude (R)-2-(5-cyano-6-(quinolin-6-ylamino)pyrazin-2-ylamino)-3-cyclopropylpropanamide (130 mg). The crude (R)-2-(5-cyano-6-(quinolin-6-ylamino)pyrazin-2-ylamino)-3-cyclopropylpropanamide (130 mg) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (35 mg). MS 392.2 (M+H); UV 203.6, 266.4, 299.0, 358.5 nm; t 0.406 min.

Example 9

(R)-5-(1-amino-3-cyclopropyl-1-oxopropan-2-ylamino)-3-(thieno[2,3-b]pyridin-3-ylamino)pyrazine-2-carboxamide

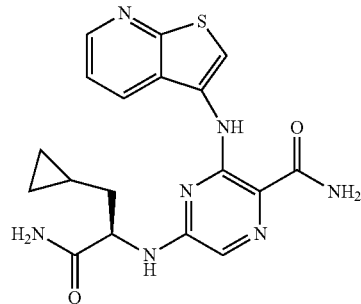 [SMILES: NC(=O)c1ncc(N[C@H](CC2CC2)C(N)=O)nc1Nc1csc2ncccc12]

A mixture of (R)-2-(6-chloro-5-cyanopyrazin-2-ylamino)-3-cyclopropylpropanamide (78 mg, 0.293 mmol), thieno[2,3-b]pyridin-3-amine (60 mg, 0.400 mmol), K₂CO₃ (70 mg, 0.507 mmol), BINAP (25 mg, 0.040 mmol) and Pd(OAc)2 (10 mg, 0.044 mmol) in dioxane (2 mL) was degassed with Ar, then was stirred at 110 C for 3 h. The mixture was concentrated in vacuo. The residue was purified by HPLC to give (R)-2-(5-cyano-6-(thieno[2,3-b]pyridin-3-ylamino)pyrazin-2-ylamino)-3-cyclopropylpropanamide (33 mg). The compound (R)-2-(5-cyano-6-(thieno[2,3-b]pyridin-3-ylamino)pyrazin-2-ylamino)-3-cyclopropylpropanamide (33 mg, 0.087 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (34 mg). MS 398.2 (M+H); UV 203.6, 224.8, 262.1, 294.1, 357.3 nm; t 0.532 min.

Example 10

3-(3-(2H-1,2,3-triazol-2-yl)phenylamino)-5-((1R,2S)-2-aminocyclohexylamino)pyrazine-2-carboxamide

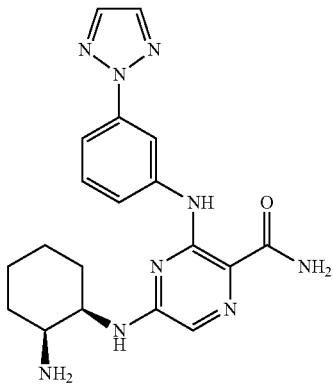 [SMILES: NC(=O)c1ncc(N[C@@H]2CCCC[C@@H]2N)nc1Nc1cccc(-n2nccn2)c1]

Scheme 2

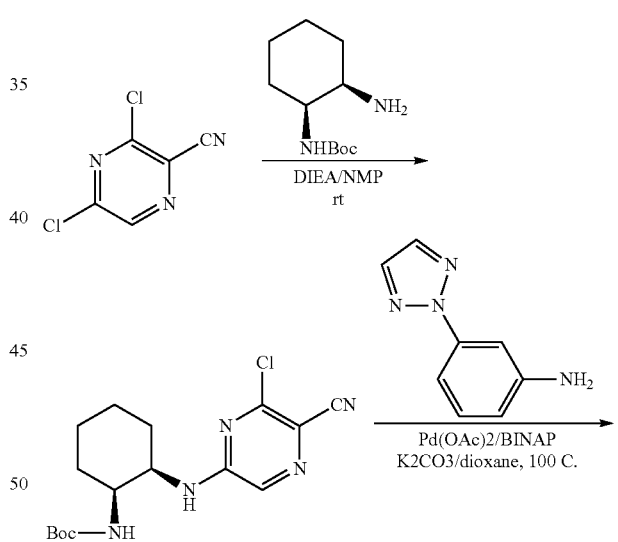

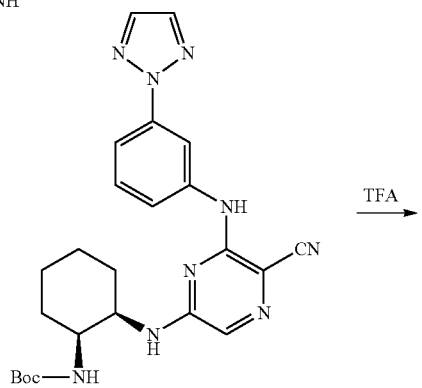

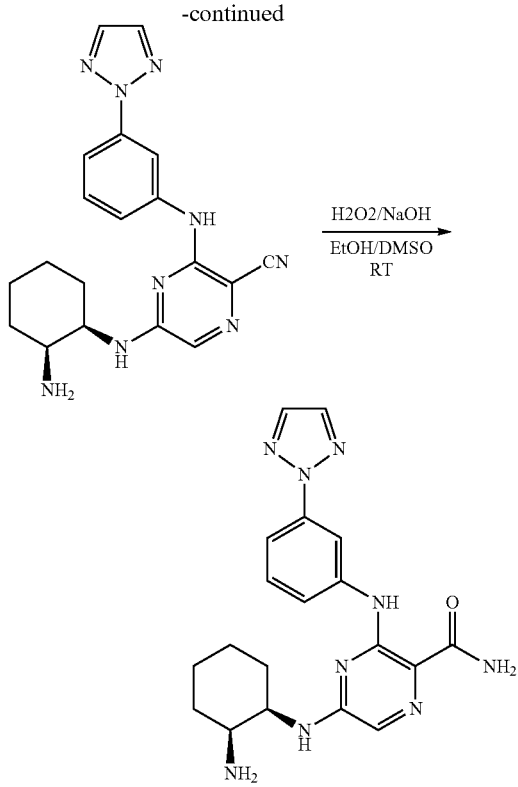

A solution of 3,5-dichloropyrazine-2-carbonitrile (100 mg, 0.574 mmol), tert-butyl (1S,2R)-2-aminocyclohexylcarbamate (123 mg, 0.574 mmol) and DIEA (0.150 mL, 0.862 mmol) in NMP (3 mL) was stirred at room temperature for 20 h. HOAc (0.3 mL) was added. Then, water was added to induce precipitation. The precipitate was collected, dried on vacuum to give tert-butyl (1S,2R)-2-(6-chloro-5-cyanopyrazin-2-ylamino)cyclohexylcarbamate (165 mg). A mixture of tert-butyl (1S,2R)-2-(6-chloro-5-cyanopyrazin-2-ylamino)cyclohexylcarbamate (80 mg, 0.227 mmol), 3-(2H-1,2,3-triazol-2-yl)aniline (50 mg, 0.312 mmol), K$_2$CO$_3$ (60 mg, 0.434 mmol), BINAP (20 mg, 0.032 mmol) and Pd(OAc)2 (10 mg, 0.044 mmol) in dioxane (2 mL) was degassed with Ar, then was stirred at 100 C for 20 h. Water and EtOAc were added. Organic phase was separated. The aqueous phase was extracted with EtOAc again. The combined organic phases were dried over Na$_2$SO$_4$, concentrated in vacuo to give a crude tert-butyl (1S,2R)-2-(6-(3-(2H-1,2,3-triazol-2-yl)phenylamino)-5-cyanopyrazin-2-ylamino)cyclohexylcarbamate (170 mg). The crude tert-butyl (1S,2R)-2-(6-(3-(2H-1,2,3-triazol-2-yl)phenylamino)-5-cyanopyrazin-2-ylamino)cyclohexylcarbamate (170 mg) was dissolved in TFA (4 mL). After being stirred at room temperature for 2 h, the mixture was concentrated in vacuo. The residue was purified by HPLC to give 3-(3-(2H-1,2,3-triazol-2-yl)phenylamino)-5-((1R,2S)-2-aminocyclohexylamino)pyrazine-2-carbonitrile (28 mg).

The compound 3-(3-(2H-1,2,3-triazol-2-yl)phenylamino)-5-((1R,2S)-2-aminocyclohexylamino)pyrazine-2-carbonitrile (28 mg) was dissolved in EtOH (2 mL) and DMSO (1 mL), aq. 1N NaOH (1.0 mL) and aq. H2O2 (50%, 1.0 mL) were added. The mixture was stirred at room temperature for 20 min. HOAc (0.5 mL) was added. The mixture was then concentrated in vacuo. The residue was purified by HPLC to give the titled compound (26 mg). MS 394.4 (M+H); UV 201.7, 262.8, 304.6, 359.2 nm; t 0.520 min.

Example 11

5-((1R,2S)-2-aminocyclohexylamino)-3-(1-methyl-1H-indol-4-ylamino)pyrazine-2-carboxamide

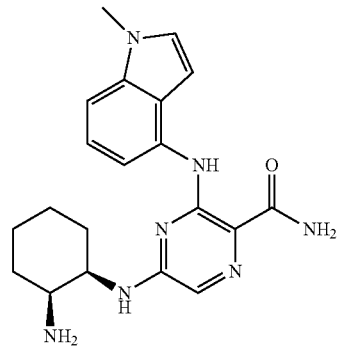 [SMILES: Cn1ccc2c(Nc3nc(N[C@@H]4CCCC[C@@H]4N)cnc3C(N)=O)cccc21]

A mixture of tert-butyl (1S,2R)-2-(6-chloro-5-cyanopyrazin-2-ylamino)cyclohexylcarbamate (80 mg, 0.227 mmol), 1-methyl-1H-indol-4-amine (50 mg, 0.342 mmol), K$_2$CO$_3$ (65 mg, 0.471 mmol), BINAP (25 mg, 0.040 mmol) and Pd(OAc)2 (10 mg, 0.044 mmol) in dioxane (2 mL) was degassed with Ar, then was stirred at 100 C for 20 h. Water and EtOAc were added. Organic phase was separated. The aqueous phase was extracted with EtOAc again. The combined organic phases were dried over Na$_2$SO$_4$, concentrated in vacuo to give a crude tert-butyl (1S,2R)-2-(5-cyano-6-(1-methyl-1H-indol-4-ylamino)pyrazin-2-ylamino)cyclohexylcarbamate (153 mg).

The crude tert-butyl (1S,2R)-2-(5-cyano-6-(1-methyl-1H-indol-4-ylamino)pyrazin-2-ylamino)cyclohexylcarbamate (153 mg) was dissolved in TFA (4 mL). After being stirred at room temperature for 2 h, the mixture was concentrated in vacuo. The residue was purified by HPLC to give 5-((1R,2S)-2-aminocyclohexylamino)-3-(1-methyl-1H-indol-4-ylamino)pyrazine-2-carbonitrile (18 mg).

The compound 5-((1R,2S)-2-aminocyclohexylamino)-3-(1-methyl-1H-indol-4-ylamino)pyrazine-2-carbonitrile (18 mg) was dissolved in EtOH (2 mL) and DMSO (1 mL), aq. 1N NaOH (1.0 mL) and aq. H2O2 (50%, 1.0 mL) were added. The mixture was stirred at room temperature for 20 min. HOAc (0.5 mL) was added. The mixture was then concentrated in vacuo. The residue was purified by HPLC to give the titled compound (9 mg). MS 380.5 (M+H); UV 221.2, 273.8, 322.5 nm; t 0.518 min.

Example 12

5-((1R,2S)-2-aminocyclohexylamino)-3-(3-(pyrimidin-2-yl)phenylamino)pyrazine-2-carboxamide

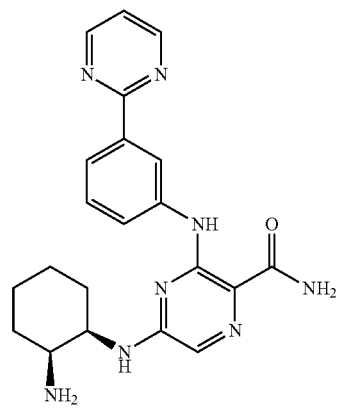 [SMILES: NC(=O)c1ncc(N[C@@H]2CCCC[C@@H]2N)nc1Nc1cccc(-c2ncccn2)c1]

A mixture of tert-butyl (1S,2R)-2-(6-chloro-5-cyanopyrazin-2-ylamino)cyclohexylcarbamate (100 mg, 0.284 mmol), 3-(pyrimidin-2-yl)aniline (100 mg, 0.584 mmol), K₂CO₃ (118 mg, 0.855 mmol), BINAP (30 mg, 0.048 mmol) and Pd(OAc)2 (15 mg, 0.066 mmol) in dioxane (2 mL) was degassed with Ar, then was stirred at 110 C for 20 h. Water and EtOAc were added. Organic phase was separated, dried over Na₂SO₄, concentrated in vacuo to give a crude tert-butyl (1S,2R)-2-(5-cyano-6-(3-(pyrimidin-2-yl)phenylamino)pyrazin-2-ylamino)cyclohexylcarbamate.

The crude tert-butyl (1S,2R)-2-(5-cyano-6-(3-(pyrimidin-2-yl)phenylamino)pyrazin-2-ylamino)cyclohexylcarbamate was dissolved in TFA (3 mL). After being stirred at room temperature for 1 h, the mixture was concentrated in vacuo. The residue was purified by HPLC to give 5-((1R,2S)-2-aminocyclohexylamino)-3-(3-(pyrimidin-2-yl)phenylamino)pyrazine-2-carbonitrile (60 mg).

The compound 5-((1R,2S)-2-aminocyclohexylamino)-3-(3-(pyrimidin-2-yl)phenylamino)pyrazine-2-carbonitrile (60 mg) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (47 mg). MS 405.3 (M+H); UV 202.9, 254.8, 304.6 nm; t 0.471 min.

Example 13

5-((1R,2S)-2-aminocyclohexylamino)-3-(4-carbamoylphenylamino)pyrazine-2-carboxamide

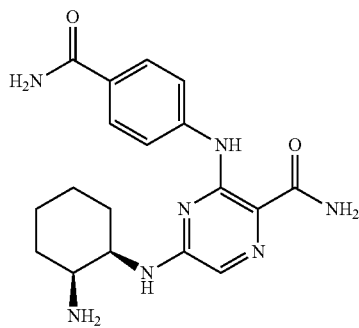 [SMILES: NC(=O)c1ccc(Nc2nc(N[C@@H]3CCCC[C@@H]3N)cnc2C(N)=O)cc1]

A mixture of tert-butyl (1S,2R)-2-(6-chloro-5-cyanopyrazin-2-ylamino)cyclohexylcarbamate (90 mg, 0.256 mmol), 4-aminobenzonitrile (42 mg, 0.355 mmol), K₂CO₃ (100 mg, 0.724 mmol), BINAP (30 mg, 0.048 mmol) and Pd(OAc)2 (15 mg, 0.066 mmol) in dioxane (2 mL) was degassed with Ar, then was stirred at 110 C for 20 h. Water and EtOAc were added. Organic phase was separated, dried over Na₂SO₄, concentrated in vacuo to give a crude tert-butyl (1S,2R)-2-(5-cyano-6-(4-cyanophenylamino)pyrazin-2-ylamino)cyclohexylcarbamate (166 mg).

The crude tert-butyl (1S,2R)-2-(5-cyano-6-(4-cyanophenylamino)pyrazin-2-ylamino)cyclohexylcarbamate (166 mg) was dissolved in TFA (5 mL). After being stirred at room temperature for 30 min, the mixture was concentrated in vacuo. The residue was purified by HPLC to give 5-((1R,2S)-2-aminocyclohexylamino)-3-(4-cyanophenylamino)pyrazine-2-carbonitrile (40 mg).

The compound 5-((1R,2S)-2-aminocyclohexylamino)-3-(4-cyanophenylamino)pyrazine-2-carbonitrile (40 mg) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (41 mg). MS 370.2 (M+H); UV 204.2, 269.5, 320.0 nm; t 0.375 min.

Example 14

5-((1R,2R)-2-amino-3,3-difluorocyclohexylamino)-3-(quinolin-6-ylamino)pyrazine-2-carboxamide

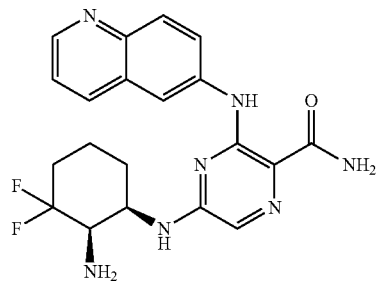 [SMILES: NC(=O)c1ncc(N[C@@H]2CCCC(F)(F)[C@@H]2N)nc1Nc1ccc2ncccc2c1]

Scheme 3

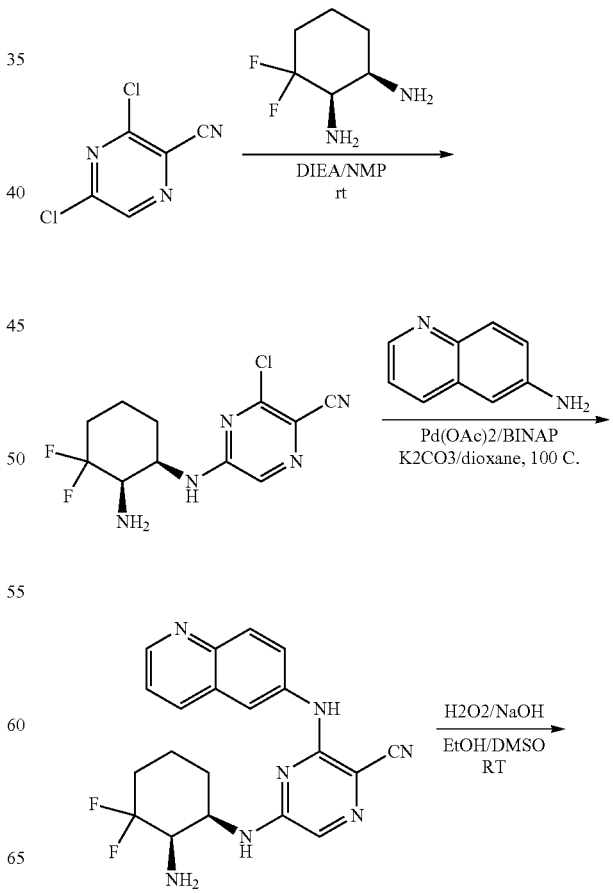

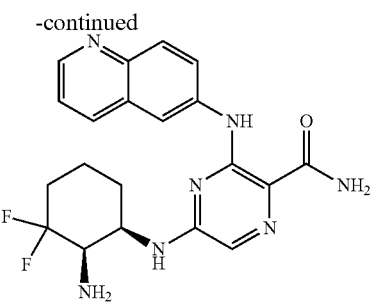

A solution of 3,5-dichloropyrazine-2-carbonitrile (102 mg, 0.586 mmol), (1R,2R)-3,3-difluorocyclohexane-1,2-diamine dihydrochloride (132 mg, 0.591 mmol) and DIEA (0.400 mL, 2.30 mmol) in DMF (2 mL) was stirred at room temperature for 20 h. Water and EtOAc were added. Organic phase was separated, washed with water, dried over $Na_2SO_4$, concentrated in vacuo to give 5-((1R,2R)-2-amino-3,3-difluorocyclohexylamino)-3-chloropyrazine-2-carbonitrile (153 mg).

A mixture of 5-((1R,2R)-2-amino-3,3-difluorocyclohexylamino)-3-chloropyrazine-2-carbonitrile (97 mg, 0.241 mmol), 6-aminoquinoline (50 mg, 0.347 mmol), $K_2CO_3$ (100 mg, 0.724 mmol), BINAP (25 mg, 0.040 mmol) and $Pd(OAc)_2$ (10 mg, 0.044 mmol) in dioxane (2 mL) was degassed with Ar, then was stirred at 110 C for 20 h. Water was added to induce precipitation. The precipitate was collected, and dried on vacuum to give 5-((1R,2R)-2-amino-3,3-difluorocyclohexylamino)-3-(quinolin-6-ylamino)pyrazine-2-carbonitrile as a solid. The solid 5-((1R,2R)-2-amino-3,3-difluorocyclohexylamino)-3-(quinolin-6-ylamino) pyrazine-2-carbonitrile was dissolved in EtOH (4 mL) and DMSO (2 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (26 mg). MS 414.2 (M+H); UV 200.0, 263.4, 296.0, 356.1 nm; t 0.335 min.

Example 15

3-(3-(2H-1,2,3-triazol-2-yl)phenylamino)-5-((1R,2R)-2-amino-3,3-difluorocyclohexylamino)pyrazine-2-carboxamide

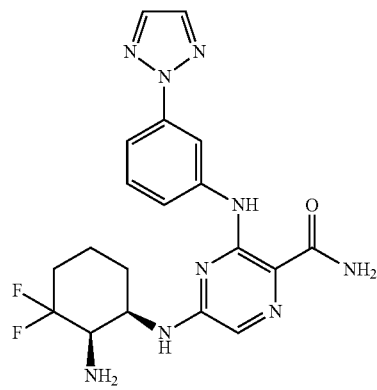 [SMILES: NC(=O)c1ncc(N[C@@H]2CCCC(F)(F)[C@@H]2N)nc1Nc1cccc(-n2nccn2)c1]

A mixture of 5-((1R,2R)-2-amino-3,3-difluorocyclohexylamino)-3-chloropyrazine-2-carbonitrile (76 mg, 0.264 mmol), 3-(2H-1,2,3-triazol-2-yl)aniline (60 mg, 0.375 mmol), $K_2CO_3$ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 3 h. The mixture was concentrated in vacuo. The residue was purified by HPLC to give 3-(3-(2H-1,2,3-triazol-2-yl)phenylamino)-5-((1R,2R)-2-amino-3,3-difluorocyclohexylamino)pyrazine-2-carbonitrile (41 mg).

The compound 3-(3-(2H-1,2,3-triazol-2-yl)phenylamino)-5-((1R,2R)-2-amino-3,3-difluorocyclohexylamino)pyrazine-2-carbonitrile (41 mg) was dissolved in EtOH (2 mL) and DMSO (1 mL), aq. 1N NaOH (1.0 mL) and aq. H2O2 (50%, 1.0 mL) were added. The mixture was stirred at room temperature for 30 min. HOAc (0.5 mL) was added. The mixture was then concentrated in vacuo. The residue was purified by HPLC to give the titled compound (38 mg). MS 430.3 (M+H); UV 202.3, 262.1, 299.7, 358.5 nm; t 0.488 min.

Example 16

5-((1R,2R)-2-amino-3,3-difluorocyclohexylamino)-3-(3-(pyrimidin-2-yl)phenylamino)pyrazine-2-carboxamide

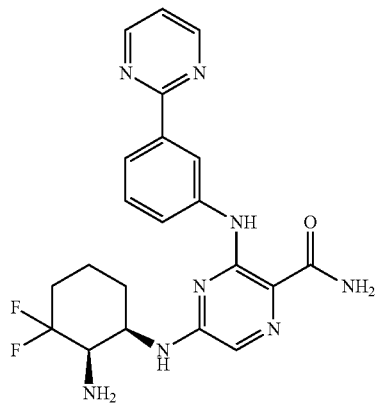 [SMILES: NC(=O)c1ncc(N[C@@H]2CCCC(F)(F)[C@@H]2N)nc1Nc1cccc(-c2ncccn2)c1]

A mixture of 5-((1R,2R)-2-amino-3,3-difluorocyclohexylamino)-3-chloropyrazine-2-carbonitrile (76 mg, 0.264 mmol), 3-(pyrimidin-2-yl)aniline (64 mg, 0.375 mmol), $K_2CO_3$ (90 mg, 0.652 mmol), BINAP (30 mg, 0.048 mmol) and Pd(OAc)2 (10 mg, 0.044 mmol) in dioxane (2 mL) was degassed with Ar, then was stirred at 110 C for 3 h. The mixture was concentrated in vacuo. The residue was purified by HPLC to give 5-((1R,2R)-2-amino-3,3-difluorocyclohexylamino)-3-(3-(pyrimidin-2-yl)phenylamino)pyrazine-2-carbonitrile (58 mg). The compound 5-((1R,2R)-2-amino-3,3-difluorocyclohexylamino)-3-(3-(pyrimidin-2-yl)phenylamino)pyrazine-2-carbonitrile (58 mg, 0.131 mmol) was dissolved in EtOH (2 mL) and DMSO (1 mL), aq. 1N NaOH (1.0 mL) and aq. H2O2 (30%, 1.0 mL) were added. The mixture was stirred at room temperature for 90 min. HOAc (0.5 mL) was added. The mixture was then concen-

Example 17

5-((1R,2R)-2-amino-3,3-difluorocyclohexylamino)-3-(phenylamino)pyrazine-2-carboxamide

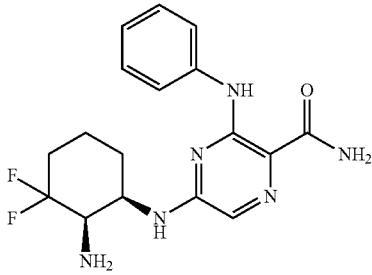 [SMILES: NC(=O)c1ncc(N[C@@H]2CCCC(F)(F)[C@@H]2N)nc1Nc1ccccc1]

A mixture of 5-((1R,2R)-2-amino-3,3-difluorocyclohexylamino)-3-chloropyrazine-2-carbonitrile (74 mg, 0.257 mmol), aniline (0.040 mL, 0.439 mmol), $K_2CO_3$ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 3 h. The mixture was concentrated in vacuo. The residue was purified by HPLC to give 5-((1R,2R)-2-amino-3,3-difluorocyclohexylamino)-3-(phenylamino)pyrazine-2-carbonitrile (47 mg).

The compound 5-((1R,2R)-2-amino-3,3-difluorocyclohexylamino)-3-(phenylamino)pyrazine-2-carbonitrile (47 mg, 0.136 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (31 mg). MS 363.3 (M+H); UV 203.6, 248.7, 301.5 nm; t 0.477 min.

Example 18

5-((1R,2R)-2-amino-3,3-difluorocyclohexylamino)-3-(4-(isoxazol-5-yl)phenylamino)pyrazine-2-carboxamide

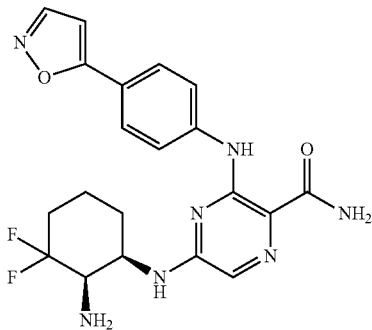 [SMILES: NC(=O)c1ncc(N[C@@H]2CCCC(F)(F)[C@@H]2N)nc1Nc1ccc(-c2ccno2)cc1]

A mixture of 5-((1R,2R)-2-amino-3,3-difluorocyclohexylamino)-3-chloropyrazine-2-carbonitrile (74 mg, 0.257 mmol), 4-(isoxazol-5-yl)aniline (60 mg, 0.375 mmol), $K_2CO_3$ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 20 h. The mixture was concentrated in vacuo. The residue was purified by HPLC to give 5-((1R,2R)-2-amino-3,3-difluorocyclohexylamino)-3-(4-(isoxazol-5-yl)phenylamino)pyrazine-2-carbonitrile (4 mg). The compound 5-((1R,2R)-2-amino-3,3-difluorocyclohexylamino)-3-(4-(isoxazol-5-yl)phenylamino)pyrazine-2-carbonitrile (4 mg, 0.010 mmol) was dissolved in EtOH (1 mL) and DMSO (0.5 mL), aq. 1N NaOH (0.50 mL) and aq. H2O2 (30%, 0.50 mL) were added. The mixture was stirred at room temperature for 60 min. HOAc (0.25 mL) was added. The mixture was then concentrated in vacuo. The residue was purified by HPLC to give the titled compound (3 mg). MS 430.4 (M+H); UV 202.3, 234.0, 274.4, 331.8 nm; t 0.483 min.

Example 19

5-((1R,2R)-2-amino-3,3-difluorocyclohexylamino)-3-(4-carbamoylphenylamino)pyrazine-2-carboxamide

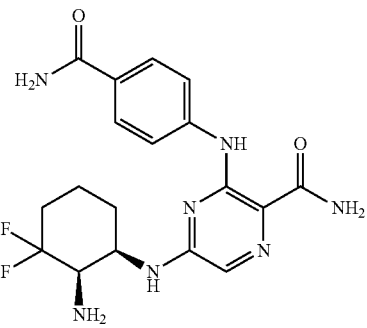 [SMILES: NC(=O)c1ccc(Nc2nc(N[C@@H]3CCCC(F)(F)[C@@H]3N)cnc2C(N)=O)cc1]

A mixture of 5-((1R,2R)-2-amino-3,3-difluorocyclohexylamino)-3-chloropyrazine-2-carbonitrile (74 mg, 0.257 mmol), 4-cyanoaniline (40 mg, 0.339 mmol), $K_2CO_3$ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 4 h. The mixture was concentrated in vacuo. The residue was purified by HPLC to give 5-((1R,2R)-2-amino-3,3-difluorocyclohexylamino)-3-(4-cyanophenylamino)pyrazine-2-carbonitrile (36 mg).

The compound 5-((1R,2R)-2-amino-3,3-difluorocyclohexylamino)-3-(4-cyanophenylamino)pyrazine-2-carbonitrile (36 mg, 0.100 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (40 mg). MS 406.0 (M+H); UV 204.2, 267.1, 320.0 nm; t 0.365 min.

Example 20

(R)-5-(1-amino-4-methyl-1-oxopentan-2-ylamino)-3-(4-carbamoylphenylamino)pyrazine-2-carboxamide

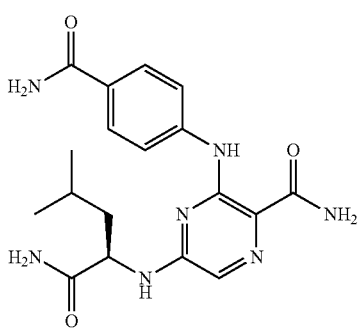 [SMILES: CC(C)C[C@@H](Nc1cnc(C(N)=O)c(Nc2ccc(C(N)=O)cc2)n1)C(N)=O]

A mixture of (R)-2-(6-chloro-5-cyanopyrazin-2-ylamino)-4-methylpentanamide (75 mg, 0.280 mmol), 4-cyanoaniline (40 mg, 0.339 mmol), K₂CO₃ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 2 h. The mixture was concentrated in vacuo. The residue was purified by HPLC to give (R)-2-(5-cyano-6-(4-cyanophenylamino)pyrazin-2-ylamino)-4-methylpentanamide (57 mg).

The compound (R)-2-(5-cyano-6-(4-cyanophenylamino)pyrazin-2-ylamino)-4-methylpentanamide (57 mg, 0.163 mmol) was dissolved in EtOH (2 mL) and DMSO (1 mL), aq. 1N NaOH (1.0 mL) and aq. H2O2 (30%, 1.0 mL) were added. The mixture was stirred at room temperature for 60 min. HOAc (0.5 mL) was added. The mixture was then concentrated in vacuo. The residue was purified by HPLC to give the titled compound (46 mg). MS 386.4 (M+H); UV 206.0, 269.5, 325.6 nm; t 0.475 min.

Example 21

(R)-5-(1-amino-4-methyl-1-oxopentan-2-ylamino)-3-(4-(isoxazol-5-yl)phenylamino)pyrazine-2-carboxamide

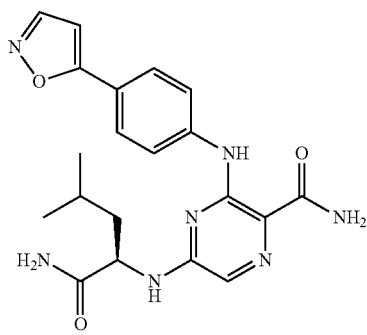 [SMILES: CC(C)C[C@@H](Nc1cnc(C(N)=O)c(Nc2ccc(-c3ccno3)cc2)n1)C(N)=O]

A mixture of (R)-2-(6-chloro-5-cyanopyrazin-2-ylamino)-4-methylpentanamide (68 mg, 0.254 mmol), 4-(isoxazol-5-yl)aniline (60 mg, 0.375 mmol), K₂CO₃ (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 20 h. The mixture was concentrated in vacuo. The residue was purified by HPLC to give (R)-2-(5-cyano-6-(4-(isoxazol-5-yl)phenylamino)pyrazin-2-ylamino)-4-methylpentanamide (5 mg).

The compound (R)-2-(5-cyano-6-(4-(isoxazol-5-yl)phenylamino)pyrazin-2-ylamino)-4-methylpentanamide (5 mg, 0.012 mmol) was dissolved in EtOH (1 mL) and DMSO (0.5 mL), aq. 1N NaOH (0.50 mL) and aq. H2O2 (30%, 0.50 mL) were added. The mixture was stirred at room temperature for 30 min. HOAc (0.2 mL) was added. The mixture was then concentrated in vacuo. The residue was purified by HPLC to give the titled compound (3 mg). MS 410.3 (M+H); UV 202.3, 235.2, 276.9, 331.2 nm; t 0.627 min.

Example 22

(R)-5-(1-amino-4-methyl-1-oxopentan-2-ylamino)-3-(3-methylisothiazol-5-ylamino)pyrazine-2-carboxamide

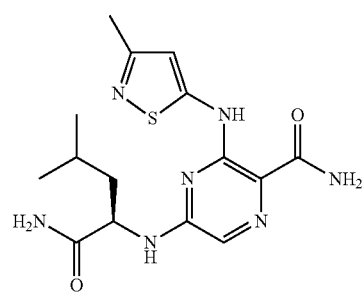 [SMILES: Cc1cc(Nc2nc(N[C@H](CC(C)C)C(N)=O)cnc2C(N)=O)sn1]

A mixture of (R)-2-(6-chloro-5-cyanopyrazin-2-ylamino)-4-methylpentanamide (75 mg, 0.280 mmol), 3-methylisothiazol-5-amine hydrochloride (50 mg, 0.332 mmol), K₂CO₃ (100 mg, 0.724 mmol), BINAP (25 mg, 0.040 mmol) and Pd(OAc)2 (15 mg, 0.066 mmol) in dioxane (3 mL) was degassed with Ar, then was stirred at 110 C for 20 h. The mixture was concentrated in vacuo. The residue was purified by HPLC to give (R)-2-(5-cyano-6-(3-methylisothiazol-5-ylamino)pyrazin-2-ylamino)-4-methylpentanamide (17 mg).

The compound (R)-2-(5-cyano-6-(3-methylisothiazol-5-ylamino)pyrazin-2-ylamino)-4-methylpentanamide (17 mg, 0.049 mmol) was dissolved in EtOH (1 mL) and DMSO (0.5 mL), aq. 1N NaOH (0.50 mL) and aq. H2O2 (30%, 0.50 mL) were added. The mixture was stirred at room temperature for 60 min. HOAc (0.1 mL) was added. The mixture was then concentrated in vacuo. The residue was purified by HPLC to give the titled compound (7 mg). MS 364.3 (M+H); UV 210.2, 275.0, 323.7 nm; t 0.458 min.

Example 23

5-((1R,2R)-2-amino-3,3-difluorocyclohexylamino)-3-(3-methylisothiazol-5-ylamino)pyrazine-2-carboxamide

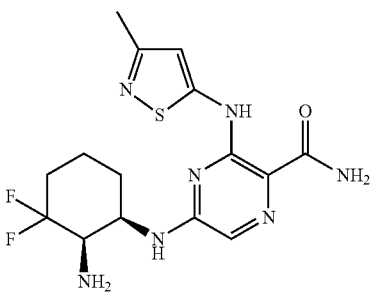 [SMILES: Cc1cc(Nc2nc(N[C@@H]3CCCC(F)(F)[C@@H]3N)cnc2C(N)=O)sn1]

A mixture of 5-((1R,2R)-2-amino-3,3-difluorocyclohexylamino)-3-chloropyrazine-2-carbonitrile (74 mg, 0.257 mmol), 3-methylisothiazol-5-amine hydrochloride (50 mg, 0.332 mmol), K₂CO₃ (100 mg, 0.724 mmol), BINAP (25 mg, 0.040 mmol) and Pd(OAc)2 (10 mg, 0.044 mmol) in dioxane (2 mL) was degassed with Ar, then was stirred at 110 C for 5 h. The mixture was concentrated in vacuo. The residue was purified by HPLC to give 5-((1R,2R)-2-amino-3,3-difluoro-cyclohexylamino)-3-(3-methylisothiazol-5-ylamino)pyrazine-2-carbonitrile (80 mg). The compound 5-((1R,2R)-2-amino-3,3-difluorocyclohexylamino)-3-(3-methylisothiazol-5-ylamino)pyrazine-2-carbonitrile (80 mg, 0.219 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (44 mg). MS 384.2 (M+H); UV 209.0, 270.7, 321.3 nm; t 0.362 min.

Example 24

5-((1R,2R)-2-amino-3,3-difluorocyclohexylamino)-3-(4-methoxyphenylamino)pyrazine-2-carboxamide

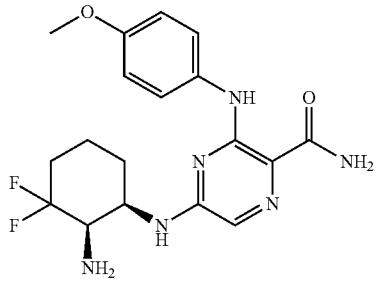 [SMILES: COc1ccc(Nc2nc(N[C@@H]3CCCC(F)(F)[C@@H]3N)cnc2C(N)=O)cc1]

A mixture of 5-((1R,2R)-2-amino-3,3-difluorocyclohexylamino)-3-chloropyrazine-2-carbonitrile (74 mg, 0.257 mmol), p-anisidine (42 mg, 0.341 mmol), K2CO3 (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 4 h. The mixture was concentrated in vacuo. The residue was purified by HPLC to give 5-((1R,2R)-2-amino-3,3-difluorocyclohexylamino)-3-(4-methoxyphenylamino)pyrazine-2-carbonitrile (43 mg).

The compound 5-((1R,2R)-2-amino-3,3-difluorocyclohexylamino)-3-(4-methoxyphenylamino)pyrazine-2-carbonitrile (43 mg, 0.115 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (32 mg). MS 393.3 (M+H); UV 206.0, 251.1, 297.8 nm; t 0.471 min.

Example 25

5-((1R,2R)-2-amino-3,3-difluorocyclohexylamino)-3-(2-oxo-1,2,3,4-tetrahydroquinolin-6-ylamino)pyrazine-2-carboxamide

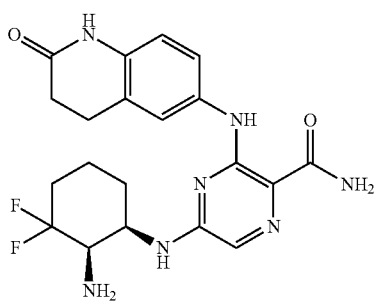 [SMILES: NC(=O)c1ncc(N[C@@H]2CCCC(F)(F)[C@@H]2N)nc1Nc1ccc2c(c1)CCC(=O)N2]

A mixture of 5-((1R,2R)-2-amino-3,3-difluorocyclohexylamino)-3-chloropyrazine-2-carbonitrile (74 mg, 0.257 mmol), 6-amino-3,4-dihydroquinolin-2(1H)-one (50 mg, 0.308 mmol), K2CO3 (80 mg, 0.579 mmol), BINAP (25 mg, 0.040 mmol) and Pd(OAc)2 (15 mg, 0.066 mmol) in dioxane (2 mL) was degassed with Ar, then was stirred at 110 C for 4 h. The mixture was concentrated in vacuo. The residue was purified by HPLC to give 5-((1R,2R)-2-amino-3,3-difluorocyclohexylamino)-3-(2-oxo-1,2,3,4-tetrahydroquinolin-6-ylamino)pyrazine-2-carbonitrile (45 mg).

The compound 5-((1R,2R)-2-amino-3,3-difluorocyclohexylamino)-3-(2-oxo-1,2,3,4-tetrahydroquinolin-6-ylamino)pyrazine-2-carbonitrile (45 mg, 0.108 mmol) was dissolved in EtOH (2 mL) and DMSO (1 mL), aq. 1N NaOH (1.0 mL) and aq. H2O2 (30%, 1.0 mL) were added. The mixture was stirred at room temperature for 20 min. HOAc (0.1 mL) was added. The mixture was then concentrated in vacuo. The residue was purified by HPLC to give the titled compound (24 mg). MS 432.3 (M+H); UV 209.6, 308.9 nm; t 0.422 min.

Example 26

5-((1R,2R)-2-amino-3,3-difluorocyclohexylamino)-3-(4-(pyridin-4-yl)phenylamino)pyrazine-2-carboxamide

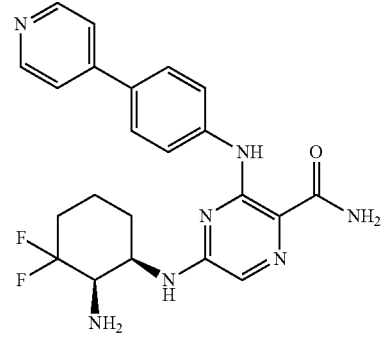 [SMILES: NC(=O)c1ncc(N[C@@H]2CCCC(F)(F)[C@@H]2N)nc1Nc1ccc(-c2ccncc2)cc1]

To a mixture of 4-pyridylboronic acid (500 mg, 4.06 mmol), 1-iodo-4-nitrobenzene (1.01 g, 4.06 mmol) and Pd(Ph3P)2Cl2 (140 mg, 0.199 mmol) in dioxane (15 mL), a solution of Na2CO3 (1.00 g, 9.43 mmol) in H2O (10 mL) was added. The mixture was stirred at 100 C for 20 h. Water and EtOAc were added. Organic phase was separated, washed with 5% NaHCO3, dried over Na2SO4, concentrated in vacuo. The residue was purified by a silica gel column on ISCO, eluted with 20-100% EtOAc in hexanes to give 4-(4-nitrophenyl)pyridine as a solid (342 mg).

A mixture of 4-(4-nitrophenyl)pyridine (274 mg, 1.37 mmol) and Pd—C(10%, 80 mg) in MeOH (10 mL) was hydrogenated under balloon H2 for 20 h. The mixture was then filtered through celite. The filtrate was concentrated in vacuo to give 4-(pyridin-4-yl)aniline as a solid (211 mg).

A mixture of 5-((1R,2R)-2-amino-3,3-difluorocyclohexylamino)-3-chloropyrazine-2-carbonitrile (74 mg, 0.257 mmol), 4-(pyridin-4-yl)aniline (60 mg, 0.352 mmol), K2CO3 (100 mg, 0.724 mmol), BINAP (25 mg, 0.040 mmol) and Pd(OAc)2 (15 mg, 0.066 mmol) in dioxane (4 mL) was degassed with Ar, then was stirred at 110 C for 20 h. The mixture was concentrated in vacuo. The residue was purified by HPLC to give 5-((1R,2R)-2-amino-3,3-difluorocyclohexylamino)-3-(4-(pyridin-4-yl)phenylamino)pyrazine-2-carbonitrile (41 mg).

The compound 5-((1R,2R)-2-amino-3,3-difluorocyclohexylamino)-3-(4-(pyridin-4-yl)phenylamino)pyrazine-2-carbonitrile (41 mg, 0.097 mmol) was dissolved in EtOH (2 mL) and DMSO (1 mL), aq. 1N NaOH (1.0 mL) and aq. H2O2 (30%, 1.0 mL) were added. The mixture was stirred at room temperature for 15 min. HOAc (0.1 mL) was added. The mixture was then concentrated in vacuo. The residue was purified by HPLC to give the titled compound (32 mg). MS 440.3 (M+H); UV 201.7, 242.5, 278.7 nm; t 0.384 min.

Example 27

(R)-3-(4-(1,3,4-oxadiazol-2-yl)phenylamino)-5-(1-amino-1-oxobutan-2-ylamino)pyrazine-2-carboxamide

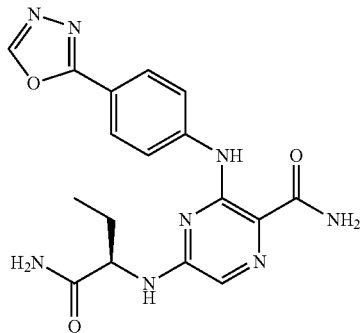 [SMILES: CC[C@@H](Nc1cnc(C(N)=O)c(Nc2ccc(-c3nnco3)cc2)n1)C(N)=O]

A solution of 3,5-dichloropyrazine-2-carbonitrile (628 mg, 3.60 mmol), 2-(R)-amino-butanamide hydrochloride (500 mg, 3.60 mmol) and DIEA (1.60 mL, 9.20 mmol) in DMF (10 mL) was stirred at room temperature for 4 h. Water and EtOAc were added. Organic phase was separated, washed with water, dried over Na2SO4, concentrated in vacuo to give (R)-2-(6-chloro-5-cyanopyrazin-2-ylamino)butanamide (843 mg) as a semi-solid.

A mixture of (R)-2-(6-chloro-5-cyanopyrazin-2-ylamino) butanamide (70 mg, 0.292 mmol), 4-(1,3,4-oxadiazol-2-yl)aniline (60 mg, 0.372 mmol), K2CO3 (80 mg, 0.579 mmol), BINAP (25 mg, 0.040 mmol) and Pd(OAc)2 (10 mg, 0.044 mmol) in dioxane (2 mL) was degassed with Ar, then was stirred at 110 C for 20 h. The mixture was concentrated in vacuo. The residue was purified by HPLC to give (R)-2-(6-(4-(1,3,4-oxadiazol-2-yl)phenylamino)-5-cyanopyrazin-2-ylamino)butanamide (57 mg).

The compound (R)-2-(6-(4-(1,3,4-oxadiazol-2-yl)phenylamino)-5-cyanopyrazin-2-ylamino)butanamide (57 mg, 0.156 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.5 mL) was added. The mixture was then concentrated in vacuo. The residue was purified by HPLC to give the titled compound (3 mg). MS 383.3 (M+H); UV 204.7, 275.5, 329.8 nm; t 0.449 min.

Example 28

(R)-5-(1-amino-1-oxobutan-2-ylamino)-3-(4-(pyridin-4-yl)phenylamino)pyrazine-2-carboxamide

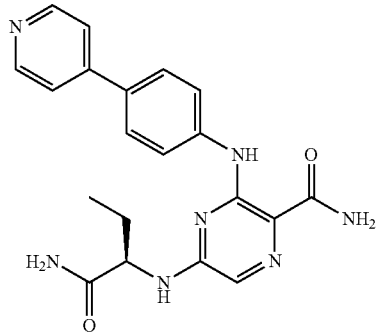 [SMILES: CC[C@@H](Nc1cnc(C(N)=O)c(Nc2ccc(-c3ccncc3)cc2)n1)C(N)=O]

A mixture of (R)-2-(6-chloro-5-cyanopyrazin-2-ylamino) butanamide (80 mg, 0.334 mmol), 4-(pyridin-4-yl)aniline (56 mg, 0.329 mmol), K2CO3 (110 mg, 0.797 mmol), BINAP (30 mg, 0.048 mmol) and Pd(OAc)2 (15 mg, 0.066 mmol) in dioxane (3 mL) was degassed with Ar, then was stirred at 110 C for 4 h. The mixture was concentrated in vacuo. The residue was purified by HPLC to give (R)-2-(5-cyano-6-(4-(pyridin-4-yl)phenylamino)pyrazin-2-ylamino)butanamide (57 mg).

The compound (R)-2-(5-cyano-6-(4-(pyridin-4-yl)phenylamino)pyrazin-2-ylamino)butanamide (57 mg, 0.152 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.1 mL) was added. The mixture was then concentrated in vacuo. The residue was purified by HPLC to give the titled compound (31 mg). MS 392.3 (M+H); UV 204.2, 244.4, 281.2, 360.0 nm; t 0.404 min.

Example 29

(R)-5-(1-amino-1-oxobutan-2-ylamino)-3-(4-(pyridin-3-yl)phenylamino)pyrazine-2-carboxamide

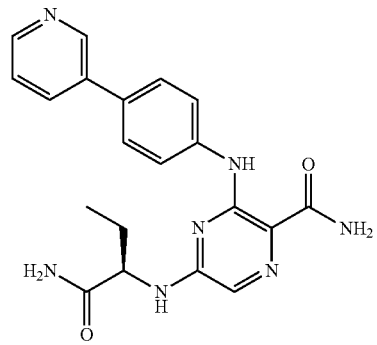 [SMILES: CC[C@@H](Nc1cnc(C(N)=O)c(Nc2ccc(-c3cccnc3)cc2)n1)C(N)=O]

To a mixture of 3-pyridylboronic acid (500 mg, 4.06 mmol), 1-iodo-4-nitrobenzene (1.01 g, 4.06 mmol) and Pd(Ph3P)2Cl2 (140 mg, 0.199 mmol) in dioxane (15 mL), a solution of Na2CO3 (1.00 g, 9.43 mmol) in H2O (10 mL) was added. The mixture was stirred at 100 C for 2 h. Water and EtOAc were added. Organic phase was separated, washed with 5% NaHCO₃, dried over Na₂SO₄, concentrated in vacuo. The residue was purified by a silica gel column on ISCO, eluted with 20-100% EtOAc in hexanes to give 3-(4-nitrophenyl)pyridine as a solid (487 mg). A mixture of 3-(4-nitrophenyl)pyridine (487 mg, 2.43 mmol) and Pd—C(10%, 80 mg) in MeOH (25 mL) and EtOAc (5 mL) was hydrogenated under balloon H2 for 5 h. The mixture was then filtered through celite. The filtrate was concentrated in vacuo to give 4-(pyridin-3-yl)aniline as a solid (403 mg).

A mixture of (R)-2-(6-chloro-5-cyanopyrazin-2-ylamino)butanamide (100 mg, 0.417 mmol), 4-(pyridin-3-yl)aniline (77 mg, 0.452 mmol), K₂CO₃ (100 mg, 0.724 mmol), BINAP (30 mg, 0.048 mmol) and Pd(OAc)2 (15 mg, 0.066 mmol) in dioxane (3 mL) was degassed with Ar, then was stirred at 110 C for 20 h. The mixture was concentrated in vacuo. The residue was purified by HPLC to give (R)-2-(5-cyano-6-(4-(pyridin-3-yl)phenylamino)pyrazin-2-ylamino)butanamide (90 mg).

The compound (R)-2-(5-cyano-6-(4-(pyridin-3-yl)phenylamino)pyrazin-2-ylamino)butanamide (90 mg, 0.241 mmol) was dissolved in EtOH (2 mL) and DMSO (1 mL), aq. 1N NaOH (1.0 mL) and aq. H2O2 (30%, 1.0 mL) were added. The mixture was stirred at room temperature for 20 min. HOAc (0.1 mL) was added. The mixture was then concentrated in vacuo. To the residue, CH3CN (6 mL) and H₂O (8 mL) were added to induce precipitation. The precipitate was collected by filtration, and dried on vacuum to give the titled compound (40 mg). The filtrate was purified by HPLC to give additional titled compound (11 mg). MS 392.3 (M+H); UV 202.3, 235.8, 274.4, 336.1 nm; t 0.404 min.

Example 30

(R)-5-(1-amino-1-oxobutan-2-ylamino)-3-(2-oxo-1,2,3,4-tetrahydroquinolin-6-ylamino)pyrazine-2-carboxamide

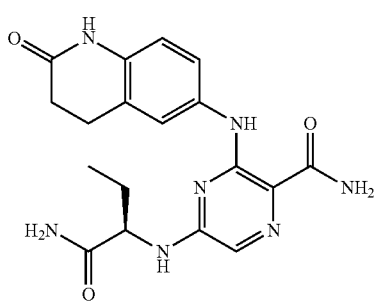 [SMILES: CC[C@@H](Nc1cnc(C(N)=O)c(Nc2ccc3c(c2)CCC(=O)N3)n1)C(N)=O]

A mixture of (R)-2-(6-chloro-5-cyanopyrazin-2-ylamino)butanamide (80 mg, 0.334 mmol), 6-amino-3,4-dihydroquinolin-2(1H)-one (60 mg, 0.370 mmol), K₂CO₃ (100 mg, 0.724 mmol), BINAP (25 mg, 0.040 mmol) and Pd(OAc)2 (10 mg, 0.044 mmol) in dioxane (2 mL) was degassed with Ar, then was stirred at 110 C for 4 h. The mixture was concentrated in vacuo. The residue was purified by HPLC to give (R)-2-(5-cyano-6-(2-oxo-1,2,3,4-tetrahydroquinolin-6-ylamino)pyrazin-2-ylamino)butanamide (72 mg).

The compound (R)-2-(5-cyano-6-(2-oxo-1,2,3,4-tetrahydroquinolin-6-ylamino)pyrazin-2-ylamino)butanamide (72 mg, 0.197 mmol) was dissolved in EtOH (2 mL) and DMSO (1 mL), aq. 1N NaOH (1.0 mL) and aq. H2O2 (30%, 1.0 mL) were added. The mixture was stirred at room temperature for 15 min. HOAc (0.1 mL) was added. The mixture was then concentrated in vacuo. The residue was purified by HPLC to give the titled compound (48 mg). MS 384.3 (M+H); UV 207.8, 308.9 nm; t 0.465 min.

Example 31

(R)-5-(1-amino-1-oxo-3-phenylpropan-2-ylamino)-3-(quinolin-6-ylamino)pyrazine-2-carboxamide

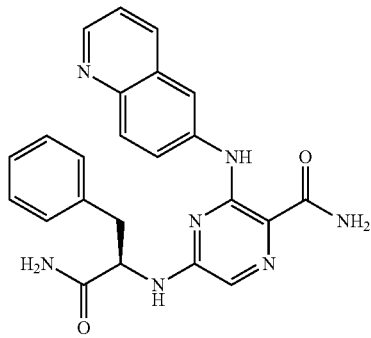 [SMILES: NC(=O)c1ncc(N[C@H](Cc2ccccc2)C(N)=O)nc1Nc1ccc2ncccc2c1]

A solution of 3,5-dichloropyrazine-2-carbonitrile (86 mg, 0.494 mmol), D-phenylalaninamide (81 mg, 0.494 mmol) and DIEA (0.130 mL, 0.747 mmol) in DMF (2 mL) was stirred at room temperature for 20 h. Water and EtOAc were added. Organic phase was separated, washed with 1N HCl, then with 5% NaHCO₃, dried over Na₂SO₄, concentrated in vacuo to give (R)-2-(6-chloro-5-cyanopyrazin-2-ylamino)-3-phenylpropanamide (128 mg) as an oil.

A mixture of (R)-2-(6-chloro-5-cyanopyrazin-2-ylamino)-3-phenylpropanamide (128 mg, 0.424 mmol), 6-aminoquinoline (80 mg, 0.555 mmol), K₂CO₃ (100 mg, 0.724 mmol), BINAP (30 mg, 0.048 mmol) and Pd(OAc)2 (15 mg, 0.066 mmol) in dioxane (3 mL) was degassed with Ar, then was stirred at 110 C for 20 h. The mixture was concentrated in vacuo. The residue was purified by HPLC to give (R)-2-(5-cyano-6-(quinolin-6-ylamino)pyrazin-2-ylamino)-3-phenylpropanamide (21 mg).

The compound (R)-2-(5-cyano-6-(quinolin-6-ylamino)pyrazin-2-ylamino)-3-phenylpropanamide (21 mg, 0.051 mmol) was dissolved in EtOH (2 mL) and DMSO (1 mL), aq. 1N NaOH (1.0 mL) and aq. H2O2 (30%, 1.0 mL) were added. The mixture was stirred at room temperature for 60 min. HOAc (0.1 mL) was added. The mixture was then concentrated in vacuo. The residue was purified by HPLC to give the titled compound (17 mg). MS 428.3 (M+H); UV 204.7, 265.7, 297.7 nm; t 0.465 min.

Example 32

(R)-5-(1-amino-1-oxo-3-(thiophen-2-yl)propan-2-ylamino)-3-(quinolin-6-ylamino)pyrazine-2-carboxamide

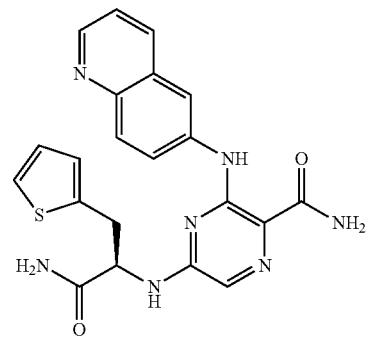 [SMILES: NC(=O)c1ncc(N[C@H](Cc2cccs2)C(N)=O)nc1Nc1ccc2ncccc2c1]

A solution of Boc-β-(2-thienyl)-D-alanine (504 mg, 1.86 mmol), HOBt hydrate (340 mg, 2.22 mmol) and EDC (460 mg, 2.39 mmol) in DMF (8 mL) was stirred at room temperature for 30 min. Conc. NH4OH (0.800 mL) was added. The mixture was stirred at room temperature for 20 h. Water and EtOAc were added. Organic phase was separated, washed with 5% NaHCO₃, dried over Na₂SO₄, concentrated in vacuo to give (R)-tert-butyl 1-amino-1-oxo-3-(thiophen-2-yl)propan-2-ylcarbamate as a solid (448 mg).

The solid (R)-tert-butyl 1-amino-1-oxo-3-(thiophen-2-yl)propan-2-ylcarbamate (448 mg) was dissolved in dioxane (4 mL), aq. 6N HCl (5 mL) was added. After being stirred at room temperature for 1 h, the mixture was concentrated in vacuo to give (R)-2-amino-3-(thiophen-2-yl)propanamide hydrochloride as a solid (337 mg).

A solution of 3,5-dichloropyrazine-2-carbonitrile (137 mg, 0.787 mmol), (R)-2-amino-3-(thiophen-2-yl)propanamide hydrochloride (163 mg, 0.789 mmol) and DIEA (0.350 mL, 2.01 mmol) in DMF (4 mL) was stirred at room temperature for 4 h. Water and EtOAc were added. Organic phase was separated, washed with 1N HCl, then with 5% NaHCO₃, dried over Na₂SO₄, concentrated in vacuo to give (R)-2-(6-chloro-5-cyanopyrazin-2-ylamino)-3-(thiophen-2-yl)propanamide (185 mg).

A mixture of (R)-2-(6-chloro-5-cyanopyrazin-2-ylamino)-3-(thiophen-2-yl)propanamide (92 mg, 0.299 mmol), 6-aminoquinoline (60 mg, 0.416 mmol), K₂CO₃ (80 mg, 0.579 mmol), BINAP (25 mg, 0.040 mmol) and Pd(OAc)2 (15 mg, 0.066 mmol) in dioxane (2 mL) was degassed with Ar, then was stirred at 110 C for 6 h. The mixture was concentrated in vacuo. The residue was purified by HPLC to give (R)-2-(5-cyano-6-(quinolin-6-ylamino)pyrazin-2-ylamino)-3-(thiophen-2-yl)propanamide (40 mg).

The compound (R)-2-(5-cyano-6-(quinolin-6-ylamino)pyrazin-2-ylamino)-3-(thiophen-2-yl)propanamide (40 mg, 0.096 mmol) was dissolved in EtOH (2 mL) and DMSO (1 mL), aq. 1N NaOH (1.0 mL) and aq. H2O2 (30%, 1.0 mL) were added. The mixture was stirred at room temperature for 30 min. HOAc (0.1 mL) was added. The mixture was then concentrated in vacuo. The residue was purified by HPLC to give the titled compound (11 mg). MS 434.3 (M+H); UV 204.2, 265.8, 298.4, 357.9 nm; t 0.453 min.

Example 33

(R)-5-(2-amino-2-oxo-1-phenylethylamino)-3-(quinolin-6-ylamino)pyrazine-2-carboxamide

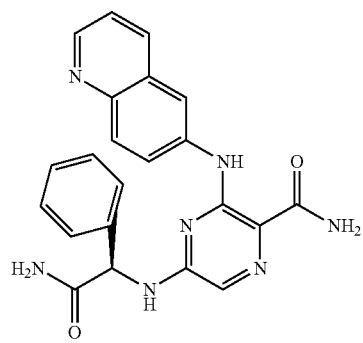 [SMILES: NC(=O)c1ncc(N[C@@H](C(N)=O)c2ccccc2)nc1Nc1ccc2ncccc2c1]

A solution of Boc-D-phenylglycine (500 mg, 1.99 mmol), HOBt hydrate (370 mg, 2.41 mmol) and EDC (500 mg, 2.60 mmol) in DMF (8 mL) was stirred at room temperature for 30 min. Conc. NH4OH (1.00 mL) was added. The mixture was stirred at room temperature for 20 h. Water and EtOAc were added. Organic phase was separated, washed with 5% NaHCO₃, dried over Na₂SO₄, concentrated in vacuo to give (R)-tert-butyl 2-amino-2-oxo-1-phenylethylcarbamate as a solid (446 mg).

The solid (R)-tert-butyl 2-amino-2-oxo-1-phenylethylcarbamate (446 mg) was dissolved in dioxane (5 mL), aq. 6N HCl (8 mL) was added. After being stirred at room temperature for 20 h, the mixture was concentrated in vacuo to give (R)-2-amino-2-phenylacetamide hydrochloride as a solid (329 mg).

A solution of 3,5-dichloropyrazine-2-carbonitrile (150 mg, 0.862 mmol), (R)-2-amino-2-phenylacetamide hydrochloride (160 mg, 0.858 mmol) and DIEA (0.400 mL, 2.30 mmol) in DMF (5 mL) was stirred at room temperature for 6 h. Water and EtOAc were added. Organic phase was separated, washed with 1N HCl, then with 5% NaHCO₃, dried over Na₂SO₄, concentrated in vacuo to give (R)-2-(6-chloro-5-cyanopyrazin-2-ylamino)-2-phenylacetamide (245 mg).

A mixture of (R)-2-(6-chloro-5-cyanopyrazin-2-ylamino)-2-phenylacetamide (81 mg, 0.281 mmol), 6-aminoquinoline (60 mg, 0.416 mmol), K₂CO₃ (100 mg, 0.724 mmol), BINAP (25 mg, 0.040 mmol) and Pd(OAc)2 (15 mg, 0.066 mmol) in dioxane (2 mL) was degassed with Ar, then was stirred at 110 C for 20 h. The mixture was concentrated in vacuo. The residue was purified by HPLC to give (R)-2-(5-cyano-6-(quinolin-6-ylamino)pyrazin-2-ylamino)-2-phenylacetamide (15 mg).

The compound (R)-2-(5-cyano-6-(quinolin-6-ylamino)pyrazin-2-ylamino)-2-phenylacetamide (15 mg, 0.037 mmol) was dissolved in EtOH (2 mL) and DMSO (1 mL), aq. 1N NaOH (1.0 mL) and aq. H2O2 (30%, 1.0 mL) were added. The mixture was stirred at room temperature for 20 min. HOAc (0.1 mL) was added. The mixture was then concentrated in vacuo. The residue was purified by HPLC to give the titled compound (9 mg). MS 414.3 (M+H); UV 201.1, 265.8, 297.2, 358.5 nm; t 0.445 min.

Example 34

5-(1-carbamoylcyclobutylamino)-3-(quinolin-6-ylamino)pyrazine-2-carboxamide

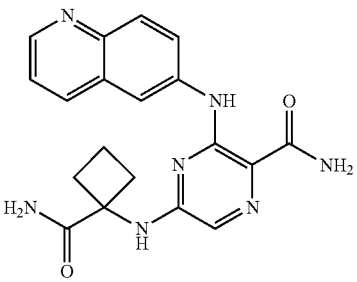 [SMILES: NC(=O)c1ncc(NC2(C(N)=O)CCC2)nc1Nc1ccc2ncccc2c1]

A solution of 3,5-dichloropyrazine-2-carbonitrile (100 mg, 0.574 mmol), 1-aminocyclobutanecarboxamide hydrochloride (108 mg, 0.717 mmol) and DIEA (0.350 mL, 2.01 mmol) in DMF (4 mL) was stirred at room temperature for 70 h. Water and EtOAc were added. Organic phase was separated, washed with 1N HCl, then with 5% NaHCO₃, dried over Na₂SO₄, concentrated in vacuo. The residue was purified by HPLC to give 1-(6-chloro-5-cyanopyrazin-2-ylamino)cyclobutanecarboxamide (22 mg).

A mixture of 1-(6-chloro-5-cyanopyrazin-2-ylamino)cyclobutanecarboxamide (22 mg, 0.087 mmol), 6-aminoquinoline (30 mg, 0.208 mmol), K₂CO₃ (90 mg, 0.652 mmol), BINAP (25 mg, 0.040 mmol) and Pd(OAc)2 (15 mg, 0.066 mmol) in dioxane (2 mL) was degassed with Ar, then was stirred at 110 C for 5 h. The mixture was concentrated in vacuo. The residue was purified by HPLC to give 1-(5-cyano-6-(quinolin-6-ylamino)pyrazin-2-ylamino)cyclobutanecarboxamide (10 mg).

The compound 1-(5-cyano-6-(quinolin-6-ylamino)pyrazin-2-ylamino)cyclobutanecarboxamide (10 mg, 0.028 mmol) was dissolved in EtOH (1 mL) and DMSO (0.5 mL), aq. 1N NaOH (0.50 mL) and aq. H2O2 (30%, 0.50 mL) were added. The mixture was stirred at room temperature for 15 min. HOAc (0.1 mL) was added. The mixture was then concentrated in vacuo. The residue was purified by HPLC to give the titled compound (7 mg). MS378.2 (M+H); UV 204.8, 267.7, 297.8, 358.5 nm; t 0.423 min.

Example 35

Preparation of 5-((1R,2S)-2-aminocyclohexylamino)-3-(tetrahydro-2H-pyran-4-ylamino)pyrazine-2-carboxamide

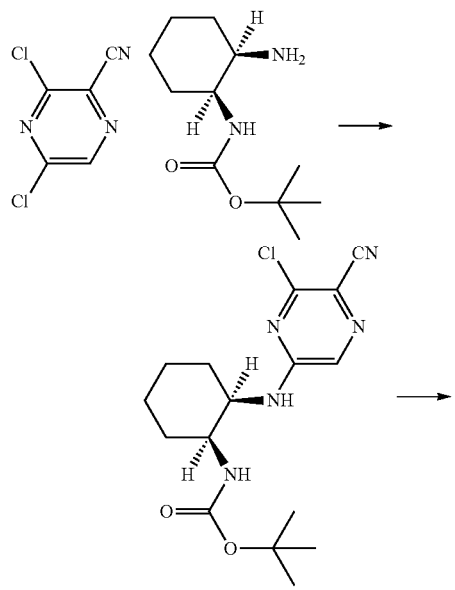

The title compound was prepared according to the synthetic scheme illustrated below:

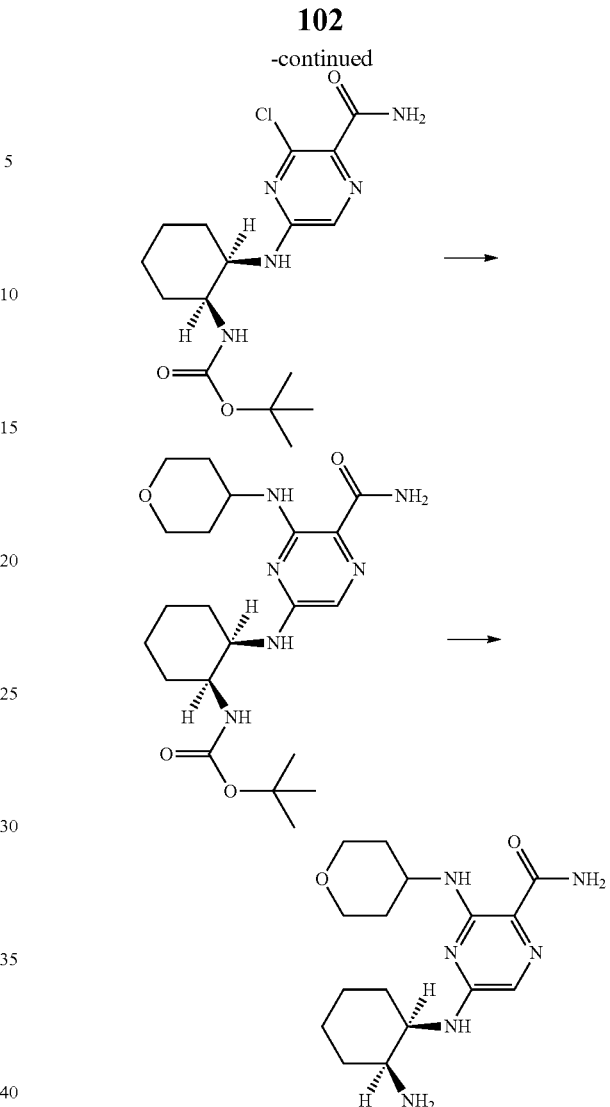

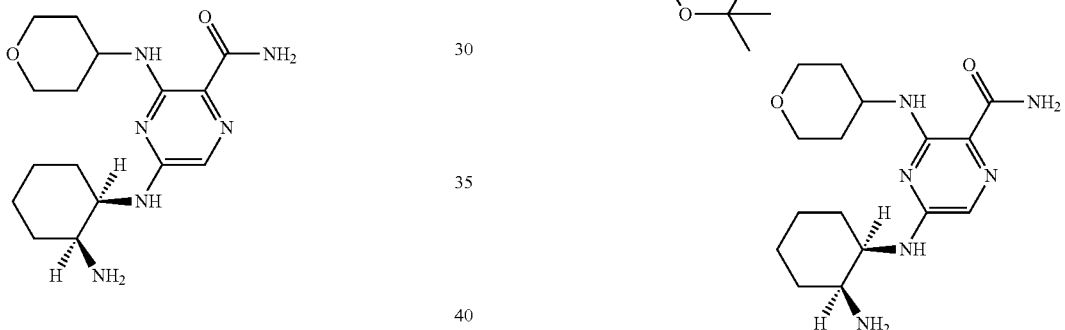

To the solution of 3,5-dichloropyrazine-2-carbonitrile (2.00 g, 11.5 mmol) in 30 mL NMP were added tert-butyl (1S,2R)-2-aminocyclohexylcarbamate (2.71 g, 12.6 mmol) and DIEA (4.07 mL, 13.8 mmol). The mixture was stirred at RT for 1.5 h. To it was poured 300 mL water. After stirring vigorously for 2 h, the solid was isolated by filtration, washed with water and dried in vacuum oven for overnight to afford tert-butyl (1S,2R)-2-(6-chloro-5-cyanopyrazin-2-ylamino)cyclohexylcarbamate in quantitative yield.

Tert-butyl (1S,2R)-2-(6-chloro-5-cyanopyrazin-2-ylamino)cyclohexylcarbamate (300 mg) was dissolved in 20 mL methanol and 10 mL DMSO. To it were added K₂CO₃ powder (300 mg) and then 3 mL H₂O₂ (50% solution). The mixture was stirred at 40° C. for 1 h. To it was poured 200 mL EtOAc. The mixture was then washed with water and brine. The organic phase was dried over MgSO₄, concentrated in vacuo and pumped to dryness to afford tert-butyl (1S,2R)-2-(5-carbamoyl-6-chloropyrazin-2-ylamino)cyclohexylcarbamate in quantitative yield. Tert-butyl (1S,2R)-2-(5-carbamoyl-6-chloropyrazin-2-ylamino)cyclohexylcarbamate (60 mg, 0.16 mmol) was dissolved in 3 mL NMP. To it were added 4-aminoterahydropyran (100 mg, 0.96 mmol) and DIEA (55 µL, 0.32 mmol). The mixture was stirred at 100° C. for overnight in a sealed tube. It was cooled to RT, diluted with EtOAc, washed with sat. NH₄Cl solution, dried over MgSO₄, concentrated in vacuo to afford crude tert-butyl (1S, 2R)-2-(5-carbamoyl-6-(tetrahydro-2H-pyran-4-ylamino) pyrazin-2-ylamino)cyclohexylcarbamate. It was treated with 1:1 DCM and TFA at RT for 1.5 h. It was concentrated and subjected to reverse phase preparative HPLC to isolate the title compound as HCl salt (57 mg). MS found for C16H26N6O2 as (M+H)⁺ 335.5. UV: λ=282 nm.

Example 36

Preparation of 5-((1R,2S)-2-aminocyclohexylamino)-3-(cyclopentylamino)pyrazine-2-carboxamide

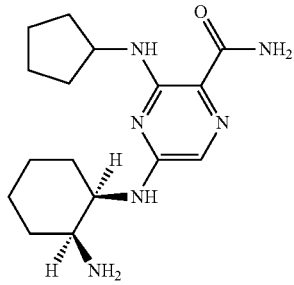 [SMILES: NC(=O)c1ncc(N[C@@H]2CCCC[C@@H]2N)nc1NC1CCCC1]

The title compound was synthesized using a procedure similar to that described in Example 35. MS found for C16H26N6O as (M+H)⁺ 319.5. UV: λ=282 nm.

Example 37

Preparation of 5-((1R,2S)-2-aminocyclohexylamino)-3-(2,3-dihydro-1H-inden-2-ylamino)pyrazine-2-carboxamide

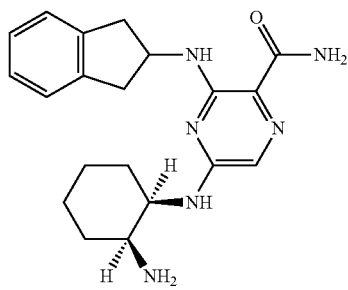 [SMILES: NC(=O)c1ncc(N[C@@H]2CCCC[C@@H]2N)nc1NC1Cc2ccccc2C1]

The title compound was synthesized using a procedure similar to that described in Example 35. MS found for C20H26N6O as (M+H)⁺ 367.5. UV: λ=278 nm.

Example 38

Preparation of 5-((1R,2S)-2-aminocyclohexylamino)-3-((R)-2,3-dihydro-1H-inden-1-ylamino) pyrazine-2-carboxamide

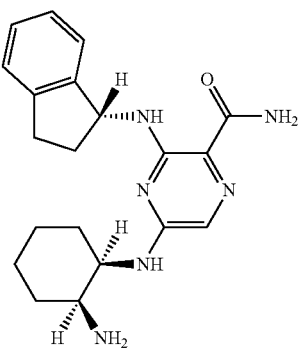 [SMILES: NC(=O)c1ncc(N[C@@H]2CCCC[C@@H]2N)nc1N[C@@H]1CCc2ccccc21]

The title compound was synthesized using a procedure similar to that described in Example 35. The final deprotection step was accomplished using the mixture of 9:1 DCM and TFA. MS found for C20H26N6O as (M+H)⁺ 367.6. UV: λ=282 nm.

Example 39

Preparation of 5-((1R,2S)-2-aminocyclohexylamino)-3-((S)-2,3-dihydro-1H-inden-1-ylamino) pyrazine-2-carboxamide

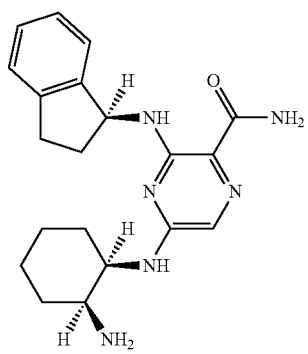 [SMILES: NC(=O)c1ncc(N[C@@H]2CCCC[C@@H]2N)nc1N[C@H]1CCc2ccccc21]

The title compound was synthesized using a procedure similar to that described in Example 35. The final deprotection step was accomplished using the mixture of 9:1 DCM and TFA. MS found for C20H26N6O as (M+H)⁺ 367.6. UV: λ=273 nm.

The following compounds can be made using the similar procedure:

Example 40

5-((1R,2S)-2-aminocyclohexylamino)-3-(chroman-4-ylamino)pyrazine-2-carboxamide

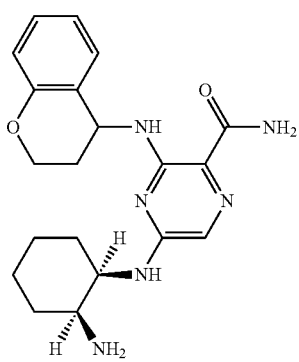 [SMILES: NC(=O)c1ncc(N[C@@H]2CCCC[C@@H]2N)nc1NC1CCOc2ccccc21]

Example 41

5-((1R,2S)-2-aminocyclohexylamino)-3-(1,2,3,4-tetrahydronaphthalen-1-ylamino)pyrazine-2-carboxamide

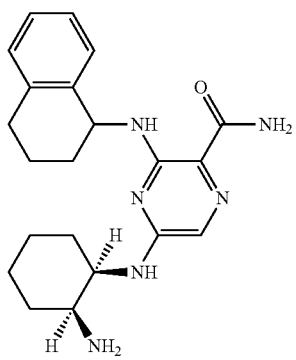 [SMILES: NC(=O)c1ncc(N[C@@H]2CCCC[C@@H]2N)nc1NC1CCCc2ccccc21]

Example 42

5-((1R,2S)-2-aminocyclohexylamino)-3-(chroman-3-ylamino)pyrazine-2-carboxamide

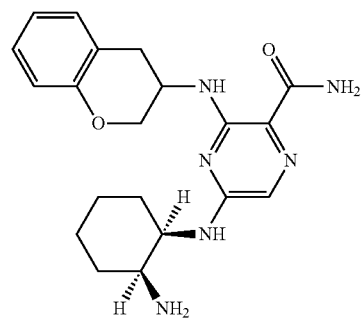 [SMILES: NC(=O)c1ncc(N[C@@H]2CCCC[C@@H]2N)nc1NC1COc2ccccc2C1]

Example 43

5-((1R,2S)-2-aminocyclohexylamino)-3-(1,2,3,4-tetrahydronaphthalen-2-ylamino)pyrazine-2-carboxamide

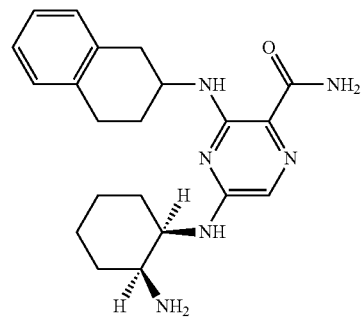 [SMILES: NC(=O)c1ncc(N[C@@H]2CCCC[C@@H]2N)nc1NC1CCc2ccccc2C1]

For the title compound, MS found for C21H28N6O as (M+H)+ 381.6. UV: λ=278 nm.

Example 44

Preparation of 5-((1R,2S)-2-aminocyclohexylamino)-3-(3,5-di(1H-pyrazol-1-yl)phenylamino)pyrazine-2-carboxamide

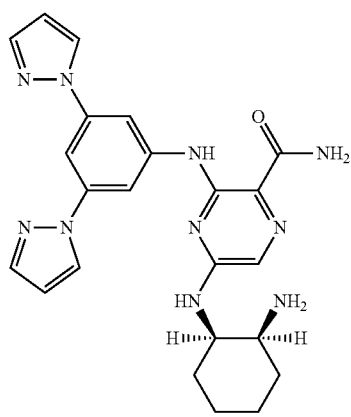 [SMILES: NC(=O)c1ncc(N[C@@H]2CCCC[C@@H]2N)nc1Nc1cc(-n2cccn2)cc(-n2cccn2)c1]

The title compound was prepared according to the synthetic scheme illustrated below:

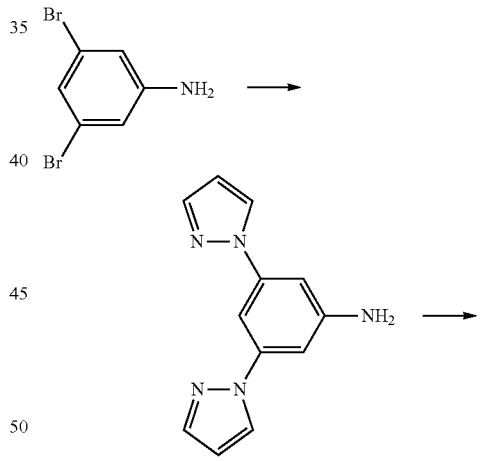

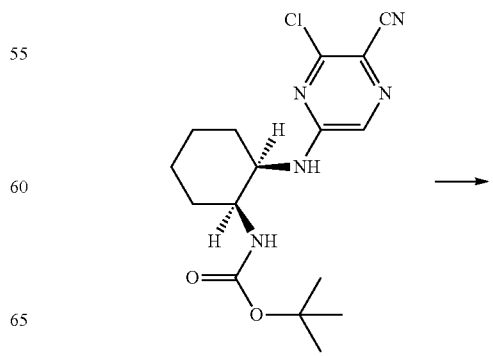

-continued

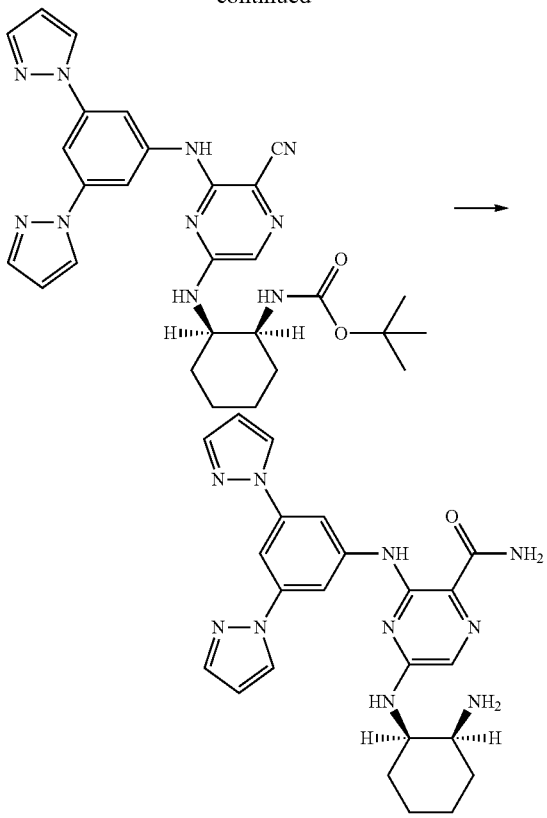

The mixture of 3,5-dibromoaniline (1.16 g, 4.6 mmol), pyrazole (1.88 g, 27.6 mmol), K₃PO₄ (3.90 g, 18.4 mmol), CuI (176 mg, 0.92 mmol), ethylenediamine (61 μL, 0.92 mmol) in 20 mL dioxane and 5 mL DMSO in a sealed tube were stirred at 120° C. for two days. The mixture was cooled to RT and diluted with 300 mL chloroform. The slurry was vigorously stirred and filtered through celite. The filtrate was washed with brine three times, dried over MgSO₄, concentrated in vacuo and subjected to flash column to isolate major product, 3,5-di(1H-pyrazol-1-yl)aniline (720 mg), and minor product, 3-bromo-5-(1H-pyrazol-1-yl)aniline (400 mg).

The mixture of tert-butyl (1S,2R)-2-(6-chloro-5-cyanopyrazin-2-ylamino)cyclohexylcarbamate (170 mg, 0.50 mmol), 3,5-di(1H-pyrazol-1-yl)aniline (150 mg, 1.0 mmol), fine powder Cs₂CO₃ (650 mg, 2.0 mmol), BINAP (62 mg, 0.1 mmol) and Pd(OAc)₂ (23 mg, 0.1 mmol) in 20 mL dioxane was degassed using argon stream and stirred at 110° C. under argon atmosphere for overnight. The mixture was cooled to RT, diluted with 200 mL EtOAc, vigorously stirred for 15 m, filtered through celite. The filtrate was concentrated in vacuo and subjected to flash column to isolate the coupling product.

The coupling product was treated with neat TFA at RT for 30 m. It was concentrated in vacuo. The residue was diluted with 50 mL hexane and concentrated in vacuo to completely get rid of TFA. The residue was then dissolved in 2 mL DMSO and 10 mL methanol. To this solution were added KOH (100 mg) and then 1 mL H₂O₂ (50%). The mixture was stirred at RT for 1 h and quenched with 5 mL acetonitrile. It was then acidified with 0.5 mL TFA. The mixture was concentrated in vacuo and then subjected to reverse phase preparative HPLC to isolate the title compound. MS found for C23H26N10O as (M+H)⁺ 459.6. UV: λ=254, 306 nm. ¹H NMR: (CD₃OD) δ 8.37 (2H, d, J=2.4 Hz), 8.15 (2H, d, J=2.0 Hz), 7.79 (2H, d, J=2.0 Hz), 7.70 (1H, t, J=2.0 Hz), 7.59 (1H, s), 6.58 (2H, m), 4.70 (1H, m), 3.72 (1H, m), 1.84-1.50 (8H, m) ppm.

Example 45

Preparation of 3-(3-(1H-pyrazol-1-yl)-5-(pyrimidin-2-yl)phenylamino)-5-((1R,2S)-2-aminocyclohexylamino)pyrazine-2-carboxamide

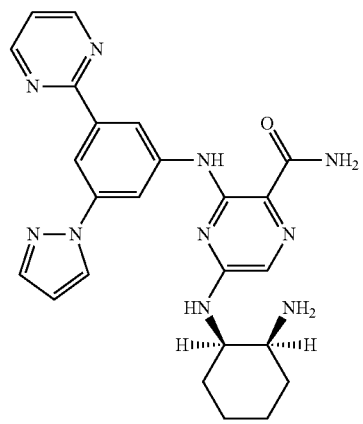 [SMILES: NC(=O)c1ncc(N[C@@H]2CCCC[C@@H]2N)nc1Nc1cc(-c2ncccn2)cc(-n2cccn2)c1]

The title compound was synthesized using a procedure similar to that described in Example 53. To prepare 3-(1H-pyrazol-1-yl)-5-(pyrimidin-2-yl)aniline, the mixture of 3-bromo-5-(1H-pyrazol-1-yl)aniline (400 mg, 1.69 mmol), 2-tributylstannylpyrimidine (820 μL, 2.54 mmol), Pd(Ph₃P)₄ (300 mg, 0.25 mmol) in 20 mL toluene was degassed using argon stream and stirred at 100° C. under argon atmosphere for overnight. The mixture was concentrated in vacuo and subjected to flash column to isolate the aniline (190 mg). For the title compound, MS found for C24H26N10O as (M+H)⁺ 471.6. UV: λ=249, 306 nm. ¹H NMR: (CD₃OD) δ 8.93-8.89 (2H, m), 8.59 (1H, m), 8.45 (1H, m), 8.35 (2H, m), 7.81 (1H, s), 7.58 (1H, s), 7.43 (1H, m), 6.60 (1H, s), 4.75 (1H, m), 3.72 (1H, m), 1.87-1.50 (8H, m) ppm.

The following compounds can be made using the similar procedure above.

Example 46

5-((1R,2S)-2-aminocyclohexylamino)-3-(3-(pyrimidin-2-yl)-5-(2H-1,2,3-triazol-2-yl)phenylamino)pyrazine-2-carboxamide

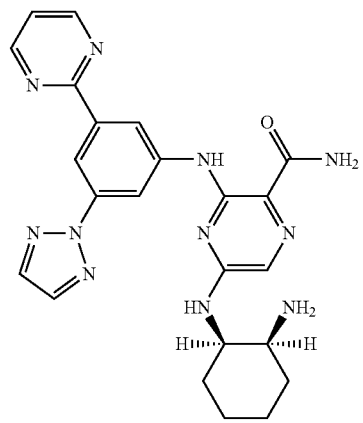 [SMILES: NC(=O)c1ncc(N[C@@H]2CCCC[C@@H]2N)nc1Nc1cc(-c2ncccn2)cc(-n2nccn2)c1]

Example 47

5-((1R,2S)-2-aminocyclohexylamino)-3-(3-(pyrimidin-2-yl)-5-(1H-1,2,4-triazol-1-yl)phenylamino)pyrazine-2-carboxamide

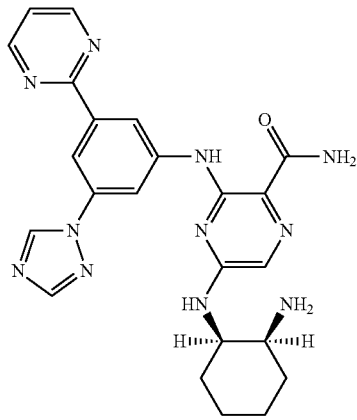 [SMILES: NC(=O)c1ncc(N[C@@H]2CCCC[C@@H]2N)nc1Nc1cc(-c2ncccn2)cc(-n2cncn2)c1]

Example 48

5-((1R,2S)-2-aminocyclohexylamino)-3-(3,5-di(pyrimidin-2-yl)phenylamino)pyrazine-2-carboxamide

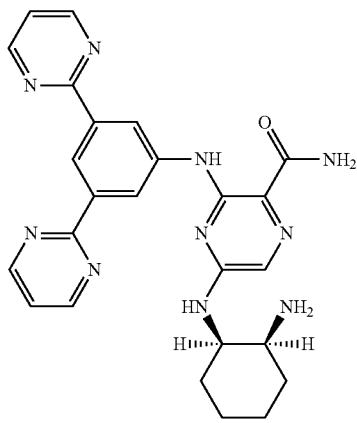 [SMILES: NC(=O)c1ncc(N[C@@H]2CCCC[C@@H]2N)nc1Nc1cc(-c2ncccn2)cc(-c2ncccn2)c1]

For the title compound, MS found for C25H26N10O as (M+H)+ 483.5. UV: λ=254, 315 nm.

Example 49

5-((1R,2S)-2-aminocyclohexylamino)-3-(3-morpholino-5-(pyrimidin-2-yl)phenylamino)pyrazine-2-carboxamide

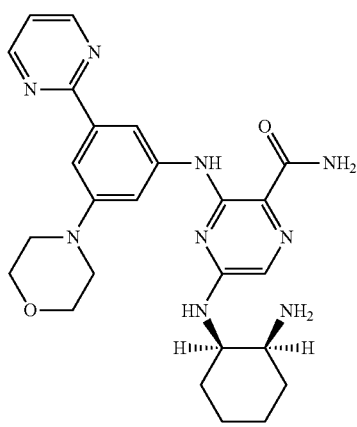 [SMILES: NC(=O)c1ncc(N[C@@H]2CCCC[C@@H]2N)nc1Nc1cc(-c2ncccn2)cc(N2CCOCC2)c1]

Example 50

5-((1R,2S)-2-aminocyclohexylamino)-3-(3-morpholino-5-(1H-pyrazol-1-yl)phenylamino)pyrazine-2-carboxamide

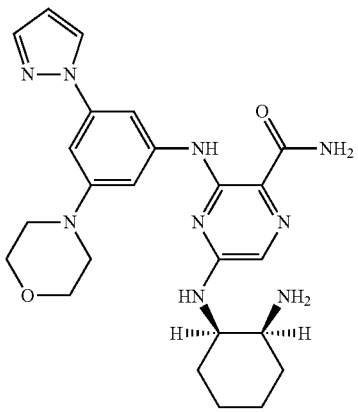 [SMILES: NC(=O)c1ncc(N[C@@H]2CCCC[C@@H]2N)nc1Nc1cc(N2CCOCC2)cc(-n2cccn2)c1]

For the title compound, MS found C24H31N9O2 as (M+H)+ 478.6. UV: λ=254, 306 nm.

Example 51

5-((1R,2S)-2-aminocyclohexylamino)-3-(3-morpholino-5-(2H-1,2,3-triazol-2-yl)phenylamino)pyrazine-2-carboxamide

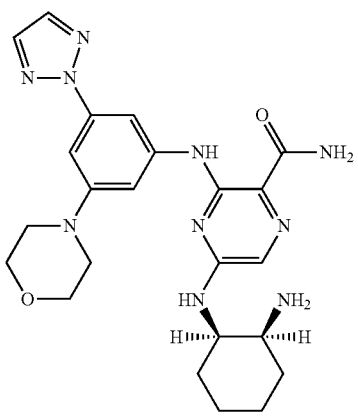 [SMILES: NC(=O)c1ncc(N[C@@H]2CCCC[C@@H]2N)nc1Nc1cc(N2CCOCC2)cc(-n2nccn2)c1]

Example 52

3-(3-(1H-pyrazol-1-yl)-5-(2H-1,2,3-triazol-2-yl)phenylamino)-5-((1R,2S)-2-aminocyclohexylamino)pyrazine-2-carboxamide

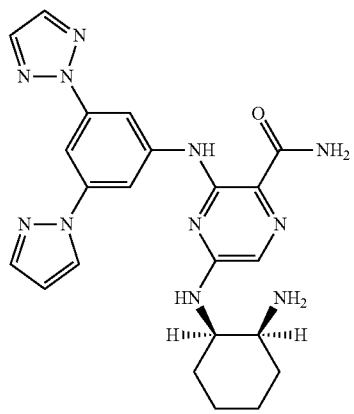 [SMILES: NC(=O)c1ncc(N[C@@H]2CCCC[C@@H]2N)nc1Nc1cc(-n2cccn2)cc(-n2nccn2)c1]

Example 53

5-((1R,2S)-2-aminocyclohexylamino)-3-(3,5-di(2H-1,2,3-triazol-2-yl)phenylamino)pyrazine-2-carboxamide

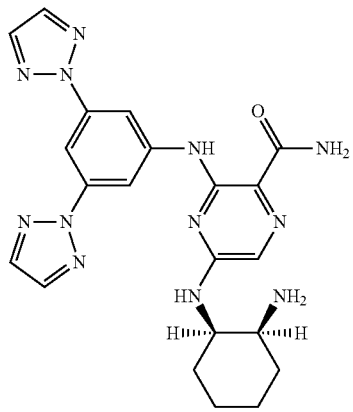 [SMILES: NC(=O)c1ncc(N[C@@H]2CCCC[C@@H]2N)nc1Nc1cc(-n2nccn2)cc(-n2nccn2)c1]

For the title compound, MS found for C21H24N12O as (M+H)+ 461.5. UV: λ=259, 311 nm.

Example 54

Preparation of cis-3-(1H-indazol-5-ylamino)-5-(2-aminocyclohexylamino)pyrazine-2-carboxamide

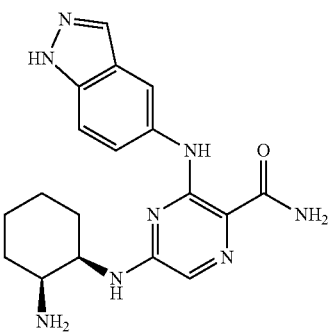

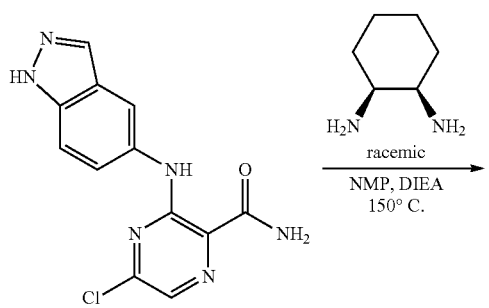

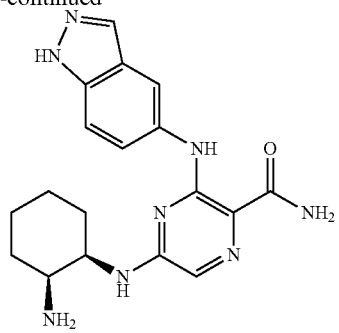

To 3-(1H-indazol-5-ylamino)-5-chloropyrazine-2-carboxamide (~100 mg) in ~3 mL NMP was added 6 equivalents of DIEA and 20 equivalents of racemic cis-1,2-cyclohexanediamine. The mixture was heated at 150° C. in a sealed tube overnight. The reaction mixture was cooled, acidified with TFA, diluted with water and prepped via rpHPLC to give the title compound. MS found for $C_{18}H_{22}N_8O$ as (M+H)+ 367.2.

Example 55

Preparation of (R)-5-(pyrrolidin-3-ylamino)-3-(quinolin-3-ylamino)pyrazine-2-carboxamide

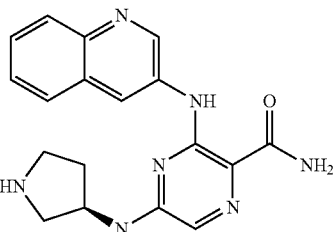

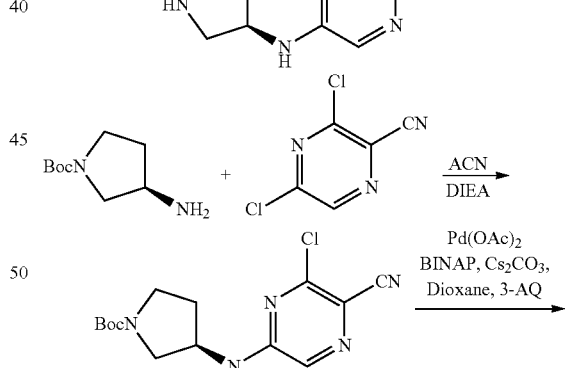

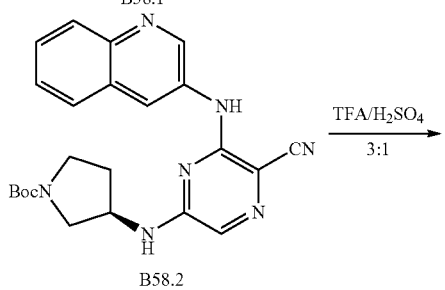

-continued

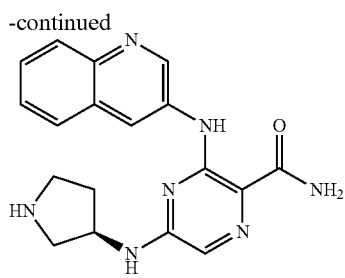

Commercially available (R)-(+)-N-Boc-3-aminopyrrolidine (1.0 g, 5.3 mmol) and 3,5-dichloropyrazine-2-carbonitrile (928 mg, 5.1 mmol) were dissolved in ~25 mL ACN. To this was added 1.4 mL DIEA. The reaction mixture was stirred at room temperature for 30 minutes. Water was added, solid precipitated and was filtered and dried to give crude B58.1 (1.56 g, 93% yield). To 120 mg B58.1 was added 100 mg 3-aminoquinoline (3-AQ), 375 mg $Cs_2CO_3$, 60 mg rac-BINAP, and 16 mg $Pd(OAc)_2$. These solids were mixed with 10 mL dioxane and the subsequent suspension was degassed with argon for 5 minutes. The reaction mixture was heated at 100° C. for 3 hours and then cooled down to approximately 60° C. The mixture was filtered and the filtrate was concentrated to give crude B58.2. This crude product was dissolved in 3 mL TFA and 1 mL $H_2SO_4$. The mixture was heated at 70° C. for 30 minutes. Volatiles were removed and 5 mL $H_2O$ and 1 mL ACN was added to the resulting residue. Precipitate was filtered and the filtrate was subjected to rpHPLC to give the title compound. MS found for $C_{18}H_{19}N_7O$ as $(M+H)^+$ 350.2.

Example 56

Preparation of (R)-5-(pyrrolidin-3-ylamino)-3-(quinolin-6-ylamino)pyrazine-2-carboxamide

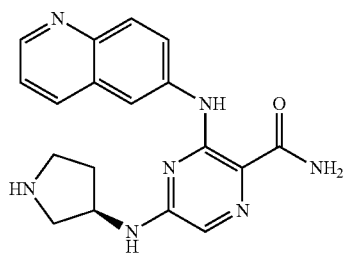 [SMILES: NC(=O)c1ncc(N[C@@H]2CCNC2)nc1Nc1ccc2ncccc2c1]

The title compound was prepared as described in Scheme B58 utilizing 6-aminoquinoline instead of 3-aminoquinoline. MS found for $C_{18}H_{19}N_7O$ as $(M+H)^+$ 350.2.

Example 57

Preparation of (S)-5-(piperidin-3-ylamino)-3-(quinolin-3-ylamino)pyrazine-2-carboxamide

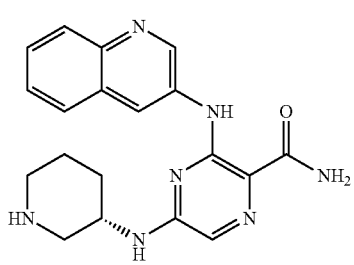 [SMILES: NC(=O)c1ncc(N[C@H]2CCCNC2)nc1Nc1cnc2ccccc2c1]

The title compound was prepared as described in Scheme B58 utilizing (S)—N—Boc-3-aminopiperidine instead of (R)-(+)-N-Boc-3-aminopyrrolidine. MS found for $C_{19}H_{21}N_7O$ as $(M+H)^+$ 364.2.

Example 58

Preparation of (S)-5-(piperidin-3-ylamino)-3-(quinolin-6-ylamino)pyrazine-2-carboxamide

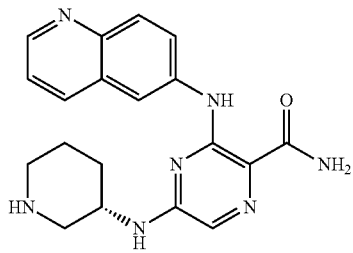 [SMILES: NC(=O)c1ncc(N[C@H]2CCCNC2)nc1Nc1ccc2ncccc2c1]

The title compound was prepared as described in Scheme B58 utilizing (S)—N—Boc-3-aminopiperidine instead of (R)-(+)-N-Boc-3-aminopyrrolidine and 6-aminoquinoline instead of 3-aminoquinoline. MS found for $C_{19}H_{21}N_7O$ as $(M+H)^+$ 364.2.

Example 59

3-(4-(4-acetylpiperazin-1-yl)phenylamino)-5-(cyclopropylamino)pyrazine-2-carboxamide

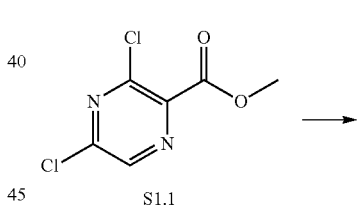
S1.1

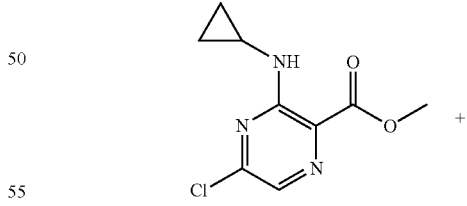
S1.2

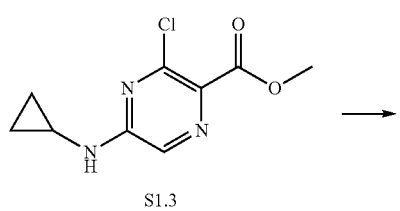
S1.3

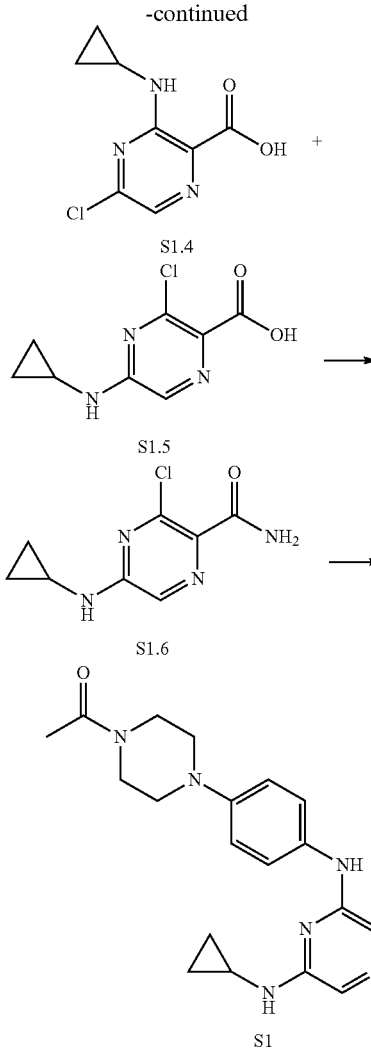

Step 1:

Dichloropyrazine S1.1 (synthesized as described in Yamada, K.; Mastuki, K.; Omori, K.; Kikkawa, K. US Patent Application 2004/0142930A1) (0.46 g, 2.7 mmol) was diluted with 10 mL of acetonitrile. To this was then added DIPEA (0.52 mL, 3.0 mmol) and cyclopropylamine (0.19 mL, 2.7 mmol) and the reactions stirred at rt overnight. The following day the reaction was concentrated by rotary evaporation and the resulting syrup diluted with water and stirred until a filterable precipitate formed. The solid was isolated by filtration and washed with water affording the desired product as a bright yellow solid containing regioisomers S1.2 and S1.3.

Step 2:

The mixture of regioisomers S1.2 and S1.3 (0.42 g, 1.9 mmol) were diluted with 20 mL of dioxane and 2.0 mL of 1M LiOH. The reaction was stirred at rt until all starting material had been consumed. The reaction was then acidified to pH=2 with 1M HCl and diluted with water to a total volume of 70 mL. The resulting solid was isolated by filtration affording the major isomer, S1.4, as a yellow solid (107 mg, 26%). Upon sitting, a precipitate formed in the filtrate which was then isolated and identified as regioisomer S1.5 (0.17 g, 42%).

Step 3:

Carboxylic acid S1.5 (0.17 g, 0.73 mmol) was diluted with 5 mL of DMF. To this was added HOBt (0.14 g, 1.0 mmol) and EDC (0.19 g, 1.0 mmol) and the resulting mixture stirred at rt for 10 min at which time all of the carboxylic acid had been consumed and the activated species formed. Ammonaid (0.5M in 1,4-dioxane, 3 mL, 1.5 mmol) was then added to the stirring solution and the reaction stirred at rt overnight. The reaction was concentrated to remove the 1,4-dioxane, then diluted with water and extracted with dichloromethane twice. The combined organic phases were washed once with saturated NaHCO₃ then concentrated affording the desired amide, S1.6, as a bright yellow solid.

Step 4:

Chloropyrazine S1.6 (25 mg, 0.12 mmol) was diluted with NMP (5 mL) and treated with 1-(4-(4-aminophenyl)piperazin-1-yl)ethanone (52 mg, 0.24 mmol) and DIPEA (42 uL, 0.24 mmol) and the resulting solution stirred at 150° C. for three days. The reaction mixture was diluted with water and acidified with a small amount of TFA, then purified by preparative HPLC affording the desired product (10 mg) after lyophilization. MS found for C20H25N7O2 as (M+H)+ 396.0. UV: λ=203, 262, 309 nm.

Example 60

5-(4-(4-acetylpiperazin-1-yl)phenylamino)-3-(cyclopropylamino)pyrazine-2-carboxamide

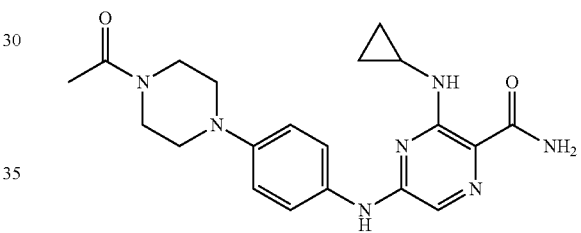

The titled compound was synthesized using a procedure similar to that described in Example S1, using intermediate S1.2. MS found for C20H25N7O2 as (M+H)+396.2. UV: λ=201, 284 nm.

Example 61

5-((1R,2S)-2-aminocyclohexylamino)-3-(m-tolylamino)pyrazine-2-carboxamide

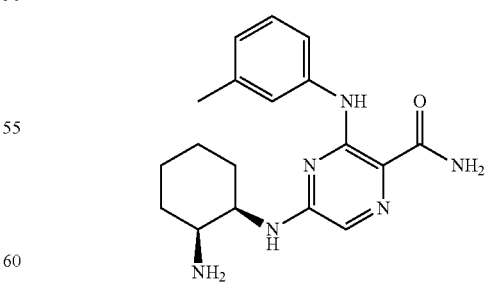

The titled compound was synthesized using a procedure similar to that described in Example S1, using m-toluidine in place of cyclopropylamine and Boc(1S,2R)-cyclohexanediamine in place of the aniline in Step 4. The Boc group was removed using 4M HCl in dioxane before purification by preparative HPLC. MS found for C18H24N6O as (M+H)+ 341.4. UV: λ=201, 284 nm. 1H NMR (400 MHz, MeOH-d4) δ 7.48 (s, 1H), 7.42 (m, 2H), 7.23 (t, 1H), 6.88 (d, 1H), 4.58 (m, 1H), 2.38 (s, 3H), 1.91 (m, 2H), 1.77 (m, 3H), 1.51-1.70 (m, 3H).

Example 62

3-(4-(1H-pyrazol-1-yl)phenylamino)-5-((1R,2S)-2-aminocyclohexylamino)pyrazine-2-carboxamide

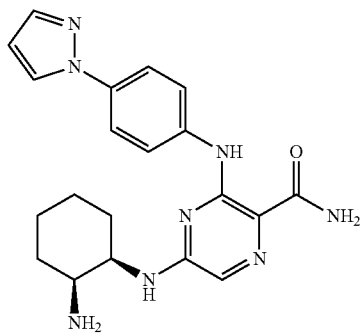

The titled compound was synthesized using a procedure similar to that described in Example S1, using 4-(1H-pyrazol-1-yl)aniline in place of cyclopropylamine and Boc(1S,2R)-cyclohexanediamine in place of the aniline in Step 4. The Boc group was removed using 4M HCl in dioxane before purification by preparative HPLC. MS found for C20H24N8O as (M+H)+393.4. UV: λ=203, 232, 291 nm. 1H NMR (400 MHz, MeOH-d4) δ 8.16 (s, 1H), 7.78 (d, 2H), 7.72 (s, 1H), 7.70 (d, 2H), (7.48 (s, 1H), 6.51 (s, 1H), 3.68 (m, 1H), 1.91 (m, 2H), 1.52-1.87 (m, 4H).

Example 63

(R)-5-(1-amino-4-methyl-1-oxopentan-2-ylamino)-3-(m-tolylamino)pyrazine-2-carboxamide

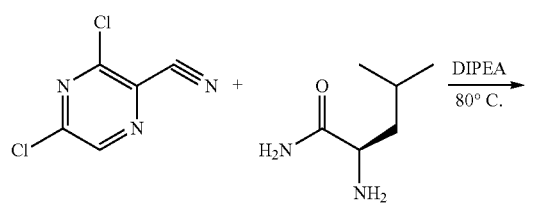

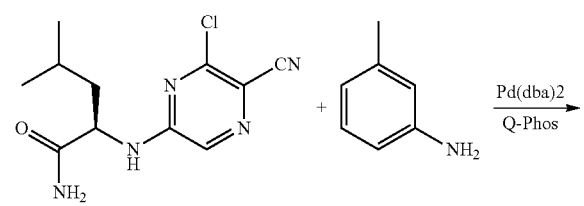

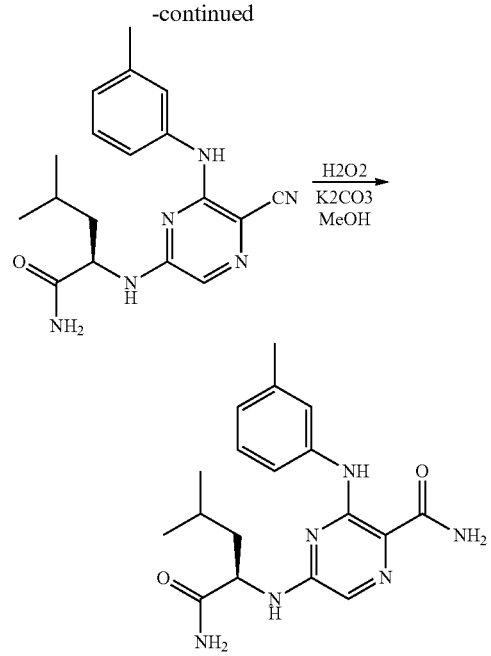

Step 1: To a mixture of 3,5-dichloropyrazine-2-carbonitrile (100 mg, 0.57 mmol) and D-leucinamide HCl salt (104 mg, 0.625 mmol) in AcCN (2 mL) was added DIPEA (0.223 mL, 1.254 mmol). After stirring at room temperature for 4 h, it was diluted with EtOAc, washed with sat. NaHCO₃, organic layer was separated and washed with brine, dried and concentrated to give (R)-2-(6-chloro-5-cyanopyrazin-2-ylamino)-4-methylpentanamide (150 mg).

Step 2: To a mixture of (R)-2-(6-chloro-5-cyanopyrazin-2-ylamino)-4-methylpentanamide (75 mg, 0.28 mmol) in toluene (1.5 mL) and dioxane (0.5 mL) was added m-toluidine (45 mg, 0.42 mmol), Pd(dba)2 (16 mg, 0.028 mmoL), Q-Phos (30 mg, 0.042 mmol) and Cs₂CO₃ (274 mg, 0.84 mmol). After heating at 95° C. for 15 h, the mixture was filtered, the filtrate was concentrated and purified by column chromatography to give (R)-2-(5-cyano-6-(m-tolylamino)pyrazin-2-ylamino)-4-methylpentanamide.

Step 3: To a mixture of (R)-2-(5-cyano-6-(m-tolylamino)pyrazin-2-ylamino)-4-methylpentanamide in methanol (1 ml) was added K₂CO₃ (excess)) and H₂O₂ (50%, a few drops). After completion, it was concentrated and purified by preparative HPLC to give (R)-5-(1-amino-4-methyl-1-oxopentan-2-ylamino)-3-(m-tolylamino)pyrazine-2-carboxamide (6 mg). MS found for C₁₈H₂₄N₆O₂ as (M+H)⁺ 357.3, UV: λ=253.4, 304.5.

Example 64

(R)-3-(3-(2H-1,2,3-triazol-2-yl)phenylamino)-5-(1-amino-4-methyl-1-oxopentan-2-ylamino)pyrazine-2-carboxamide

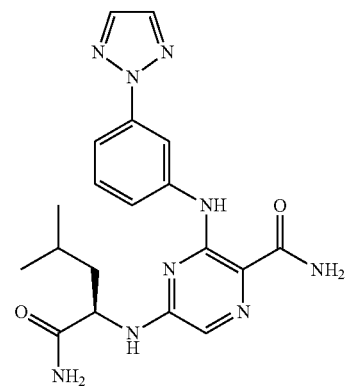 [SMILES: CC(C)C[C@@H](Nc1cnc(C(N)=O)c(Nc2cccc(-n3nccn3)c2)n1)C(N)=O]

The title compound was synthesized similar to Example 63. MS found for $C_{19}H_{23}N_9O_2$ as $(M+H)^+$ 410.3, UV: λ=261.7, 305.6.

Example 65

(R)-3-(3-(2H-1,2,3-triazol-2-yl)phenylamino)-5-(1-amino-3-methyl-1-oxobutan-2-ylamino)pyrazine-2-carboxamide

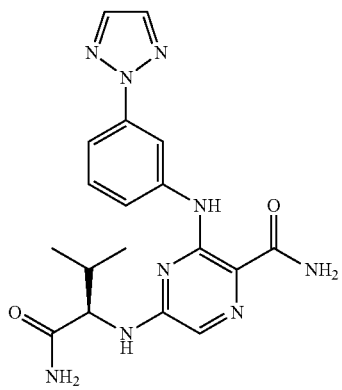 [SMILES: CC(C)[C@@H](Nc1cnc(C(N)=O)c(Nc2cccc(-n3nccn3)c2)n1)C(N)=O]

The title compound was synthesized similar to Example 63. MS found for $C_{18}H_{21}N_9O_2$ as $(M+H)^+$ 396.3, UV: λ=262.9, 306.8.

Example 66

(R)-5-(1-amino-3-methyl-1-oxobutan-2-ylamino)-3-(quinolin-3-ylamino)pyrazine-2-carboxamide

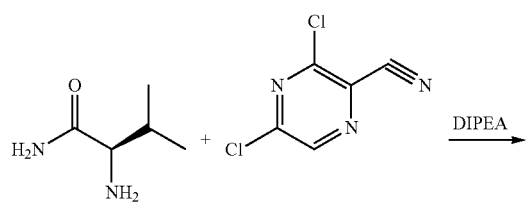

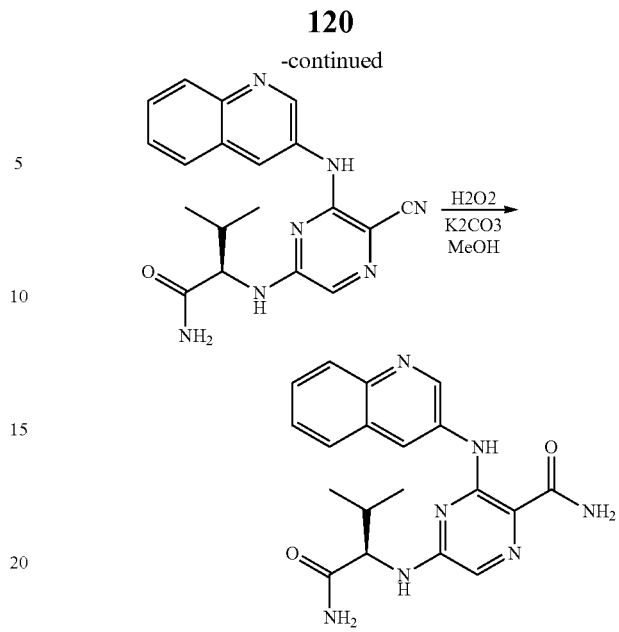

Step 1: To a mixture of 3,5-dichloropyrazine-2-carbonitrile (500 mg, 2.84 mmol) and D-valinamide HCl salt (476 mg, 3.12 mmol) in AcCN (10 mL) was added DIPEA (1.11 mL, 6.25 mmol). After stirring at room temperature for 4 h, it was diluted with EtOAc, washed with sat. NaHCO₃, organic layer was separated and washed with brine, dried and concentrated to give (R)-2-(6-chloro-5-cyanopyrazin-2-ylamino)-3-methylbutanamide (740 mg). Step 2: To a mixture of (R)-2-(6-chloro-5-cyanopyrazin-2-ylamino)-3-methylbutanamide (100 mg, 0.394 mmol) in Dioxane (2 mL) was added 3-aminoquinoline (71 mg, 0.492 mmol), Pd(OAc)₂ (18 mg, 0.079 mmol), BINAP (49 mg, 0.079 mmol) and K₂CO₃ (163 mg, 1.18 mmol). After heating at 95° C. for 5 h, the mixture was filtered, the filtrate was concentrated and purified by preparative HPLC to give (R)-2-(5-cyano-6-(quinolin-3-yl)pyrazin-2-ylamino)-3-methylbutanamide (113 mg).

Step 3: To a mixture of (R)-2-(5-cyano-6-(quinolin-3-yl)pyrazin-2-ylamino)-3-methylbutanamide (113 mg) in methanol (2 ml) was added K₂CO₃ (excess) and H₂O₂ (50%, a few drops). After completion, it was concentrated and purified by preparative HPLC to give (R)-5-(1-amino-3-methyl-1-oxobutan-2-ylamino)-3-(quinolin-3-ylamino)pyrazine-2-carboxamide (31 mg). MS found for $C_{19}H_{21}N_7O_2$ as $(M+H)^+$ 380.3, UV: λ=292.6.

Example 67

(R)-5-(1-amino-3-methyl-1-oxobutan-2-ylamino)-3-(quinolin-6-ylamino)pyrazine-2-carboxamide

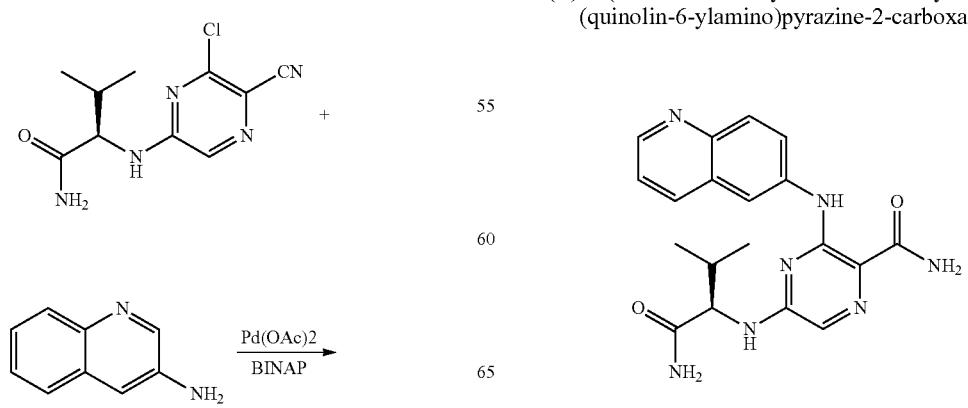

The title compound was synthesized similar to Example 66. MS found for $C_{19}H_{21}N_7O_2$ as (M+H)$^+$ 380.3, UV: λ=265.3, 292.6.

Example 68

(R)-5-(2-amino-1-cyclopropyl-2-oxoethylamino)-3-(quinolin-3-ylamino)pyrazine-2-carboxamide

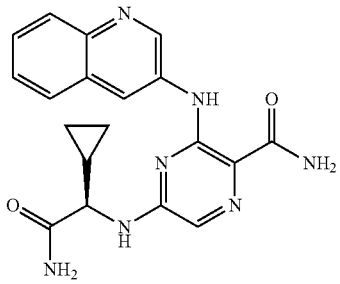 [SMILES: NC(=O)c1ncc(N[C@@H](C(N)=O)C2CC2)nc1Nc1cnc2ccccc2c1]

The title compound was synthesized similar to Example 66. MS found for $C_{19}H_{19}N_7O_2$ as (M+H)$^+$ 378.3. λ=246.3, 296.1.

Example 69

(R)-5-(1-amino-4-methyl-1-oxopentan-2-ylamino)-3-(p-tolylamino)pyrazine-2-carboxamide

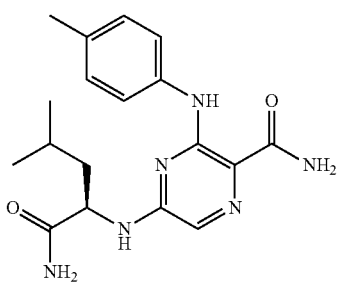 [SMILES: Cc1ccc(Nc2nc(N[C@H](CC(C)C)C(N)=O)cnc2C(N)=O)cc1]

The title compound was synthesized similar to Example 66. MS found for $C_{18}H_{24}N_6O_2$ as (M+H)$^+$ 357.3, UV: λ=253.4, 302.1.

Example 70

(R)-5-(1-amino-4-methyl-1-oxopentan-2-ylamino)-3-(5-fluoropyridin-3-ylamino)pyrazine-2-carboxamide

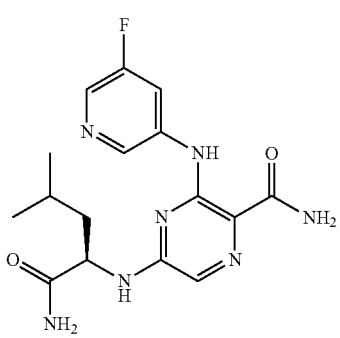 [SMILES: CC(C)C[C@@H](Nc1cnc(C(N)=O)c(Nc2cncc(F)c2)n1)C(N)=O]

The title compound was synthesized similar to Example 66. MS found for $C_{16}H_{20}FN_7O_2$ as (M+H)$^+$ 362.3, UV: λ=232.2, 259.4, 300.9.

Example 71

(R)-3-(4-(1H-pyrazol-1-yl)phenylamino)-5-(1-amino-3-methyl-1-oxobutan-2-ylamino)pyrazine-2-carboxamide

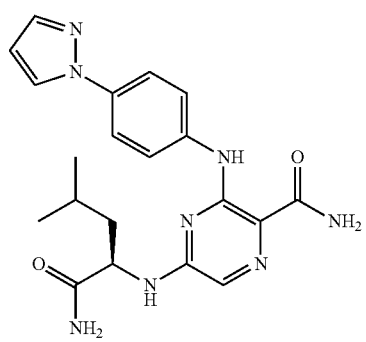 [SMILES: CC(C)C[C@@H](Nc1cnc(C(N)=O)c(Nc2ccc(-n3cccn3)cc2)n1)C(N)=O]

The title compound was synthesized similar to Example 66. MS found for $C_{20}H_{24}N_8O_2$ as (M+H)$^+$ 409.4, UV: λ=205.1, 268.8, 316.4.

Example 72

(R)-5-((1-aminocyclopropyl)(cyclopropyl)methylamino)-3-(3-(pyrimidin-2-yl)phenylamino)pyrazine-2-carboxamide

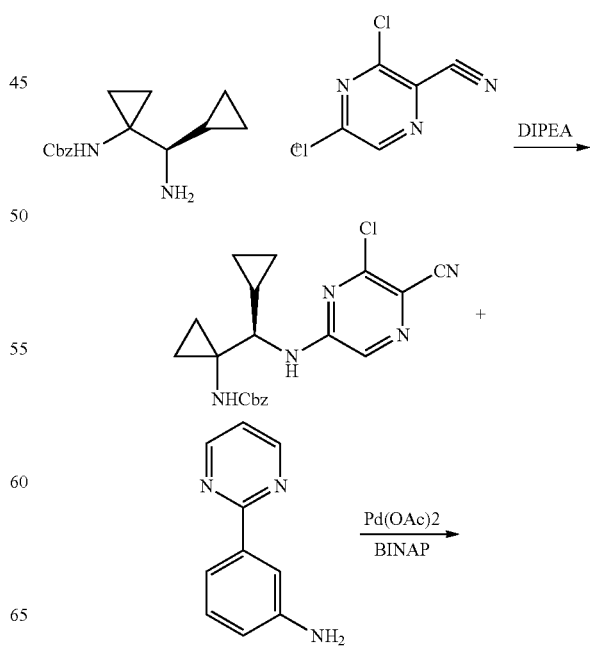

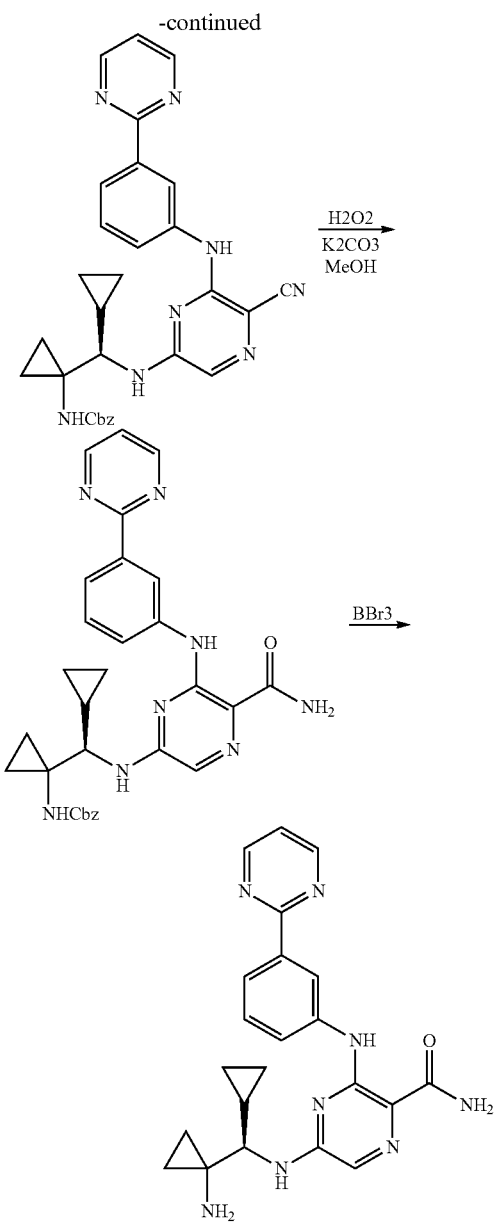

Step 1: To a mixture of 3,5-dichloropyrazine-2-carbonitrile (208 mg, 1.19 mmol) and (R)-benzyl 1-(amino(cyclopropyl)methyl)cyclopropylcarbamate HCl salt (350 mg, 1.19 mmol) in AcCN (2 mL) was added DIPEA (0.467 mL, 2.62 mmol). After stirring at room temperature for 3 h, it was diluted with EtOAc, washed with sat. NaHCO₃, organic layer was separated and washed with brine, dried and concentrated to give (R)-benzyl-1-((6-chloro-5-cyanopyrazin-2-ylamino)(cyclopropyl)methyl)cyclopropylcarbamate (480 mg).

Step 2: To a mixture of (R)-benzyl-1-((6-chloro-5-cyanopyrazin-2-ylamino)(cyclopropyl)methyl)cyclopropylcarbamate (80 mg, 0.20 mmol) in Dioxane (2 mL) was added 3-(pyrimidin-2-yl)aniline (41 mg, 0.24 mmol), Pd(OAc)2 (9 mg, 0.04 mmol), BINAP (25 mg, 0.04 mmol) and K₂CO₃ (83 mg, 0.6 mmol). After heating at 95° C. for 2 h, the mixture was filtered, the filtrate was concentrated and purified by preparative HPLC to give (R)-benzyl-1-((5-cyano-6-(3-(pyrimidin-2-yl)phenylamino)pyrazin-2-ylamino)(cyclopropyl)methyl)cyclopropylcarbamate.

Step 3: To a mixture of (R)-benzyl-1-((5-cyano-6-(3-(pyrimidin-2-yl)phenylamino)pyrazin-2-ylamino)(cyclopropyl)methyl)cyclopropylcarbamate in methanol (2 ml) was added K₂CO₃ (excess) and H₂O₂ (50%, a few drops). After completion, it was concentrated to give (R)-benzyl-1-((5-carbamoyl-6-(3-(pyrimidin-2-yl)phenylamino)pyrazin-2-ylamino)(cyclopropyl)methyl)cyclopropylcarbamate.

Step 4: to a suspension of (R)-benzyl-1-((5-carbamoyl-6-(3-(pyrimidin-2-yl)phenylamino)pyrazin-2-ylamino)(cyclopropyl)methyl)cyclopropylcarbamate in DCM was added BBr3 (excess), after completion, the solution was concentrated and purified by preparative HPLC to give (R)-5-((1-aminocyclopropyl)(cyclopropyl)methylamino)-3-(3-(pyrimidin-2-yl)phenylamino)pyrazine-2-carboxamide. MS found for $C_{22}H_{24}N_8O$ as $(M+H)^+$ 417.4, UV: $\lambda=257.0, 303.3$.

Example 73

(R)-5-(1-amino-1-oxobutan-2-ylamino)-3-(quinolin-3-ylamino)pyrazine-2-carboxamide

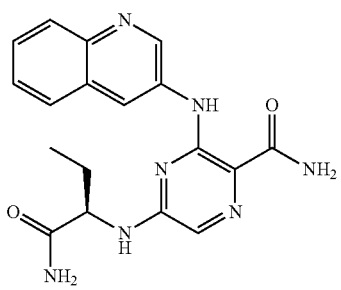 [SMILES: CC[C@@H](Nc1cnc(C(N)=O)c(Nc2cnc3ccccc3c2)n1)C(N)=O]

The title compound was synthesized similar to Example 66. MS found for $C_{18}H_{19}N_7O_2$ as $(M+H)^+$ 366.3, UV: $\lambda=246.3, 294.9$.

Example 74

(R)-5-(1-amino-1-oxobutan-2-ylamino)-3-(quinolin-6-ylamino)pyrazine-2-carboxamide

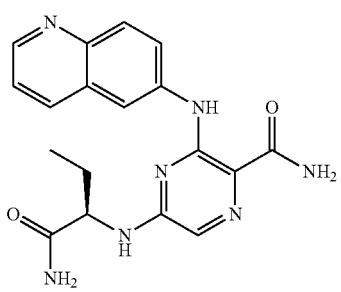 [SMILES: CC[C@@H](Nc1cnc(C(N)=O)c(Nc2ccc3ncccc3c2)n1)C(N)=O]

The title compound was synthesized similar to Example 66. MS found for $C_{18}H_{19}N_7O_2$ as $(M+H)^+$ 366.3, UV: $\lambda=202.8, 265.3, 298.5$.

Example 75

(R)-5-(1-amino-1-oxobutan-2-ylamino)-3-(thieno[2,3-b]pyridin-3-ylamino)pyrazine-2-carboxamide

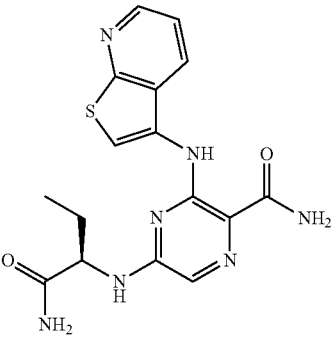 [SMILES: CC[C@@H](Nc1cnc(C(N)=O)c(Nc2csc3ncccc23)n1)C(N)=O]

The title compound was synthesized similar to Example 66. MS found for $C_{16}H_{17}N_7O_2S$ as $(M+H)^+$ 372.2, UV: λ=246.3, 294.9.

Example 76

(R)-5-(2-amino-1-cyclopropyl-2-oxoethylamino)-3-(quinolin-6-ylamino)pyrazine-2-carboxamide

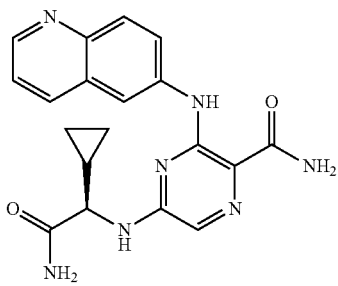 [SMILES: NC(=O)c1ncc(N[C@@H](C(N)=O)C2CC2)nc1Nc1ccc2ncccc2c1]

The title compound was synthesized similar to Example 66. MS found for $C_{19}H_{19}N_7O_2S$ as $(M+H)^+$ 378.3, UV: λ=265.3, 298.5.

Example 77

(R)-5-(1-amino-1-oxobutan-2-ylamino)-3-(3,5-dimethylphenylamino)pyrazine-2-carboxamide

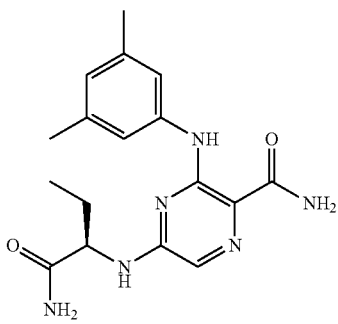 [SMILES: CC[C@@H](Nc1cnc(C(N)=O)c(Nc2cc(C)cc(C)c2)n1)C(N)=O]

The title compound was synthesized similar to Example 66. MS found for $C_{17}H_{22}N_6O_2$ as $(M+H)^+$ 343.3, UV: λ=297.3.

Example 78

5-((3R,4R)-3-aminotetrahydro-2H-pyran-4-ylamino)-3-(p-tolylamino)pyrazine-2-carboxamide

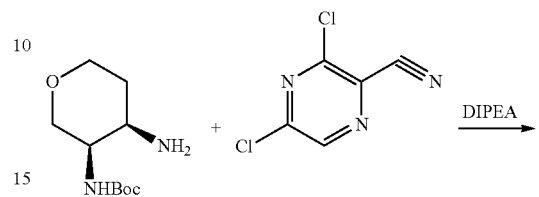

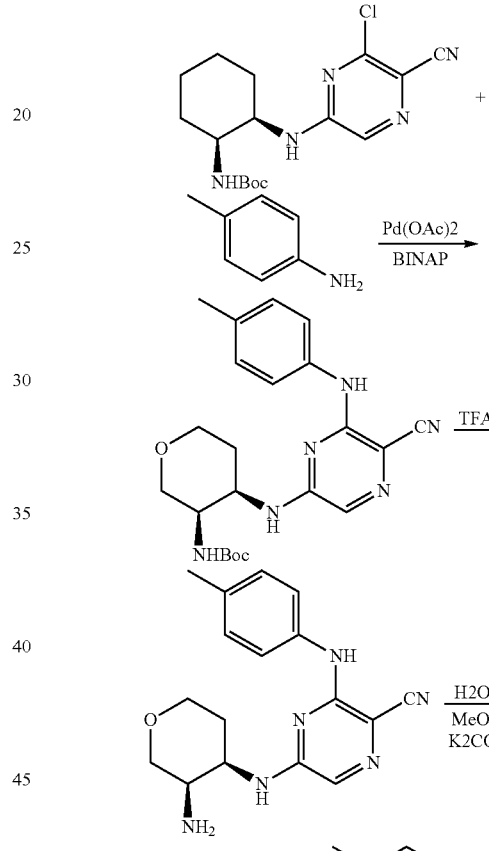

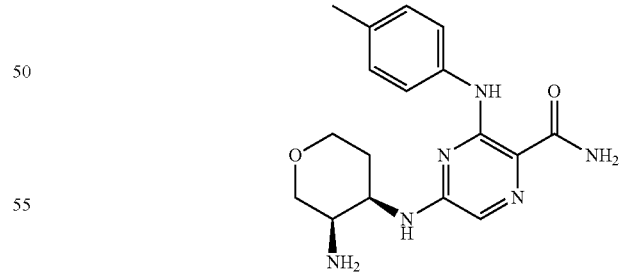

Step 1: To a mixture of 3,5-dichloropyrazine-2-carbonitrile (369 mg, 2.09 mmol) and tert-butyl (3R,4R)-4-aminotetrahydro-2H-pyran-3-ylcarbamate (500 mg, 2.3 mmol) in AcCN (7.5 mL) was added DIPEA (0.41 mL, 2.3 mmol). After stirring at room temperature for 5 h, it was diluted with EtOAc, washed with sat. NaHCO₃, organic layer was separated and washed with brine, dried and concentrated to give tert-butyl (3R,4R)-4-(6-chloro-5-cyanopyrazin-2-ylamino)tetrahydro-2H-pyran-3-ylcarbamate (880 mg).

Step 2: To a mixture of tert-butyl (3R,4R)-4-(6-chloro-5-cyanopyrazin-2-ylamino)tetrahydro-2H-pyran-3-ylcarbamate (100 mg, 0.28 mmol) in Dioxane (2 mL) was added p-toluidine (37 mg, 0.35 mmol), Pd(OAc)$_2$ (13 mg, 0.056 mmol), BINAP (35 mg, 0.056 mmol) and K$_2$CO$_3$ (116 mg, 0.84 mmol). After heating at 95° C. for 4 h, the mixture was filtered, the filtrate was concentrated and purified by preparative HPLC to give tert-butyl (3R,4R)-4-(5-cyano-6-(p-tolylamino)pyrazin-2-ylamino)tetrahydro-2H-pyran-3-ylcarbamate (53 mg).

Step 3: To a suspension of tert-butyl (3R,4R)-4-(5-cyano-6-(p-tolylamino)pyrazin-2-ylamino)tetrahydro-2H-pyran-3-ylcarbamate in DCM (1 mL) was added TFA (1 ml), after completion, the solution was concentrated to give 5-((3R,4R)-3-aminotetrahydro-2H-pyran-4-ylamino)-3-(p-tolylamino)pyrazine-2-carbonitrile as crude residue.

Step 4: To a solution of 5-((3R,4R)-3-aminotetrahydro-2H-pyran-4-ylamino)-3-(p-tolylamino)pyrazine-2-carbonitrile in methanol (1 ml) was added K$_2$CO$_3$ (excess) and H$_2$O$_2$ (50%, a few drops). After completion, it was concentrated and purified by preparative HPLC to give 5-((3R,4R)-3-aminotetrahydro-2H-pyran-4-ylamino)-3-(p-tolylamino)pyrazine-2-carboxamide. MS found for C$_{17}$H$_{22}$N$_6$O$_2$ as (M+H)$^+$ 343.3, UV: λ=251.2, 302.9.

Example 79

5-((3R,4R)-3-aminotetrahydro-2H-pyran-4-ylamino)-3-(quinolin-3-ylamino)pyrazine-2-carboxamide

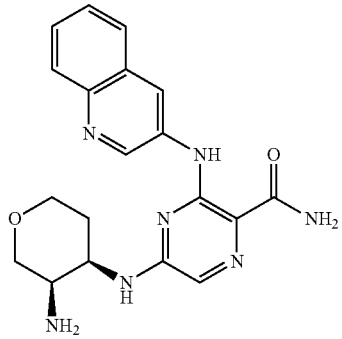 [SMILES: NC(=O)c1ncc(N[C@@H]2CCOC[C@@H]2N)nc1Nc1cnc2ccccc2c1]

The title compound was synthesized similar to Example 78. MS found for C$_{19}$H$_{21}$N$_7$O$_2$ as (M+H)$^+$ 380.3, UV: λ=242.8, 292.6.

Example 80

(R)-3-(4-(1H-imidazol-1-yl)phenylamino)-5-(1-amino-1-oxobutan-2-ylamino)-pyrazine-2-carboxamide

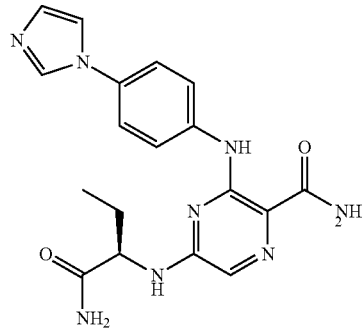 [SMILES: CC[C@@H](Nc1cnc(C(N)=O)c(Nc2ccc(-n3ccnc3)cc2)n1)C(N)=O]

The title compound was synthesized similar to Example 66. MS found for C$_{18}$H$_{20}$N$_8$O$_2$ as (M+H)$^+$ 381.3, UV: λ=262.9, 316.4.

Example 81

3-(3-(2H-1,2,3-triazol-2-yl)phenylamino)-5-((3R,4R)-3-aminotetrahydro-2H-pyran-4-ylamino)pyrazine-2-carboxamide

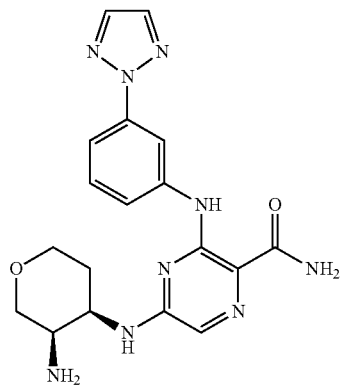 [SMILES: NC(=O)c1ncc(N[C@@H]2CCOC[C@@H]2N)nc1Nc1cccc(-n2nccn2)c1]

The title compound was synthesized similar to Example 78. MS found for C$_{18}$H$_{21}$N$_9$O$_2$ as (M+H)$^+$ 396.4, UV: λ=262.9, 306.6.

Example 82

5-((3R,4R)-3-aminotetrahydro-2H-pyran-4-ylamino)-3-(3-(pyrimidin-2-yl)phenylamino)pyrazine-2-carboxamide

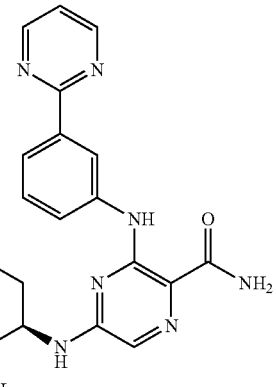

The title compound was synthesized similar to Example 78. MS found for C$_{20}$H$_{22}$N$_8$O$_2$ as (M+H)$^+$ 407.4, UV: λ=249.9, 302.1.

Example 83

(R)-5-(1-amino-4-methyl-1-oxopentan-2-ylamino)-3-(5-methylpyridin-3-ylamino)pyrazine-2-carboxamide

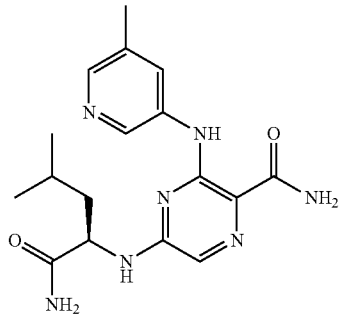 [SMILES: Cc1cncc(Nc2nc(N[C@H](CC(C)C)C(N)=O)cnc2C(N)=O)c1]

The title compound was synthesized similar to Example 66. MS found for $C_{17}H_{23}N_7O_2$ as $(M+H)^+$ 358.3, UV: $\lambda$=234.5, 261.7, 300.9.

Example 84

(R)-5-(1-amino-4-methyl-1-oxopentan-2-ylamino)-3-(2-methylpyridin-4-ylamino)pyrazine-2-carboxamide

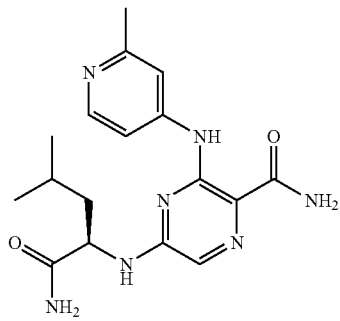 [SMILES: Cc1cc(Nc2nc(N[C@H](CC(C)C)C(N)=O)cnc2C(N)=O)ccn1]

The title compound was synthesized similar to Example 66. MS found for $C_{17}H_{23}N_7O_2$ as $(M+H)^+$ 358.6, UV: $\lambda$=273.6, 318.8.

Example 85

(R)-5-(1-amino-4-methyl-1-oxopentan-2-ylamino)-3-(6-(trifluoromethyl)pyridin-3-ylamino)pyrazine-2-carboxamide

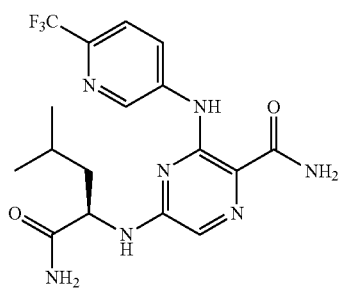 [SMILES: CC(C)C[C@@H](Nc1cnc(C(N)=O)c(Nc2ccc(C(F)(F)F)nc2)n1)C(N)=O]

The title compound was synthesized similar to Example 66. MS found for $C_{17}H_{20}F_3N_7O_2$ as $(M+H)^+$ 412.4, UV: $\lambda$=258.2, 302.1.

Example 86

(R)-5-(1-amino-4-methyl-1-oxopentan-2-ylamino)-3-(6-methylpyridin-3-ylamino)pyrazine-2-carboxamide

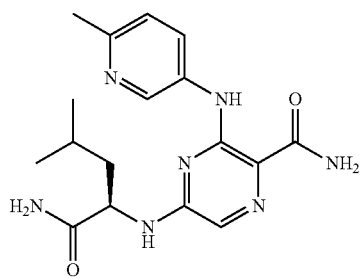 [SMILES: Cc1ccc(Nc2nc(N[C@H](CC(C)C)C(N)=O)cnc2C(N)=O)cn1]

The title compound was synthesized similar to Example 66. MS found for $C_{17}H_{23}N_7O_2$ as $(M+H)^+$ 358.3, UV: $\lambda$=259.4, 300.9.

Example 87

(R)-5-(1-amino-4-methyl-1-oxopentan-2-ylamino)-3-(3-(pyridin-4-yl)phenylamino)pyrazine-2-carboxamide

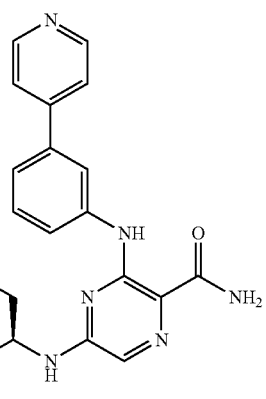

The title compound was synthesized similar to Example 66. MS found for $C_{22}H_{25}N_7O_2$ as $(M+H)^+$ 420.3, UV: $\lambda$=261.7, 300.9.

Example 88

(R)-5-(1-amino-4-methyl-1-oxopentan-2-ylamino)-3-(4-(pyridin-2-yl)phenylamino)pyrazine-2-carboxamide

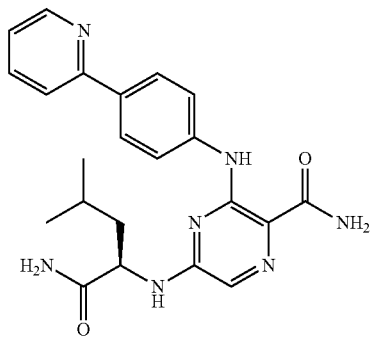 [SMILES: CC(C)C[C@@H](Nc1cnc(C(N)=O)c(Nc2ccc(-c3ccccn3)cc2)n1)C(N)=O]

The title compound was synthesized similar to Example 66. MS found for $C_{22}H_{25}N_7O_2$ as $(M+H)^+$ 420.3, UV: $\lambda$=277.1.

Example 89

(R)-5-(1-amino-4-methyl-1-oxopentan-2-ylamino)-3-(1-methyl-2-oxo-1,2,3,4-tetrahydroquinolin-6-ylamino)pyrazine-2-carboxamide

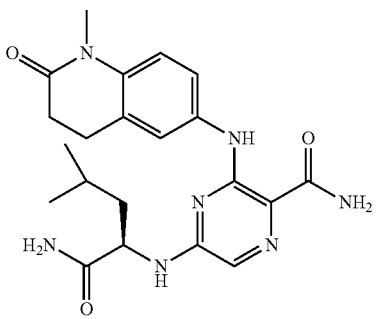 [SMILES: CC(C)C[C@@H](Nc1cnc(C(N)=O)c(Nc2ccc3c(c2)CCC(=O)N3C)n1)C(N)=O]

The title compound was synthesized similar to Example 66. MS found for $C_{21}H_{27}N_7O_3$ as $(M+H)^+$ 426.3, UV: $\lambda$=312.8.

Example 90

5-((1R,2S)-2-aminocyclohexylamino)-3-(1-methyl-2-oxo-1,2,3,4-tetrahydroquinolin-6-ylamino)pyrazine-2-carboxamide

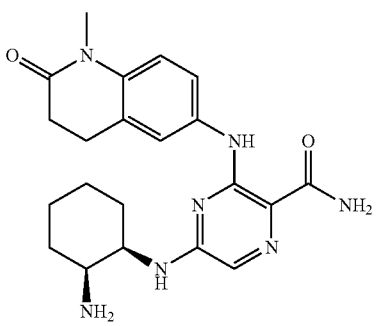 [SMILES: CN1C(=O)CCc2cc(Nc3nc(N[C@@H]4CCCC[C@@H]4N)cnc3C(N)=O)ccc21]

The title compound was synthesized similar to Example 78. MS found for $C_{21}H_{27}N_7O_2$ as $(M+H)^+$ 410.3, UV: $\lambda$=314.0.

Example 91

5-((2-aminocyclohexyl)amino)-3-(m-tolylamino)pyrazine-2-carboxamide

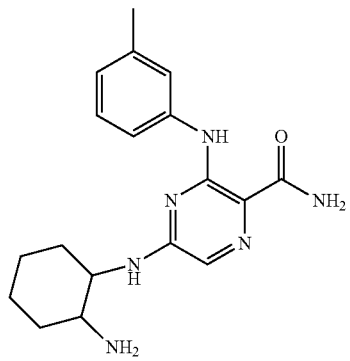 [SMILES: Cc1cccc(Nc2nc(NC3CCCCC3N)cnc2C(N)=O)c1]

The title compound was synthesized in a manner similar to that described above.

Example 92

(S)-5-((2-aminopropyl)amino)-3-(m-tolylamino)pyrazine-2-carboxamide

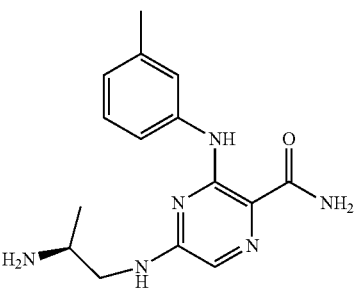 [SMILES: Cc1cccc(Nc2nc(NC[C@H](C)N)cnc2C(N)=O)c1]

The title compound was synthesized in a manner similar to that described above.

Example 93

5-(((1S,2S)-2-aminocyclohexyl)amino)-3-((3,5-dimethoxyphenyl)amino)pyrazine-2-carboxamide

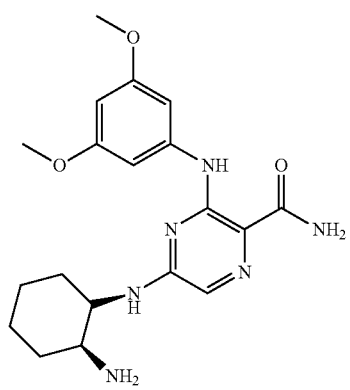

The title compound was synthesized in a manner similar to that described above.

Example 94

(S)-5-((l-amino-1-oxobutan-2-yl)amino)-3-((3,5-di(1H-pyrazol-1-yl)phenyl)amino)pyrazine-2-carboxamide

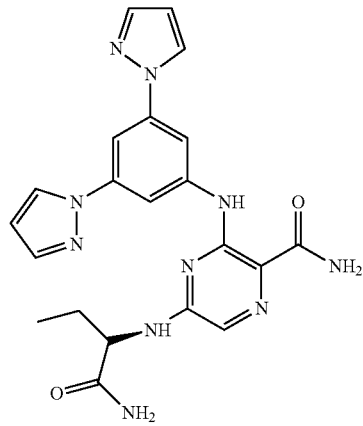

Example 95

(R)-3-(1-amino-4-methyl-1-oxopentan-2-ylamino)-5-(quinolin-3-ylamino)pyrazine-2-carboxamide

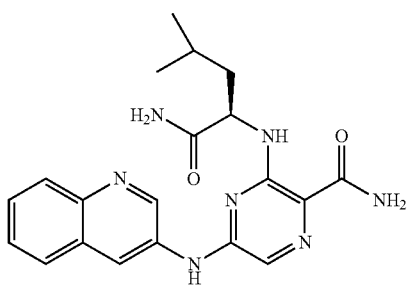 [SMILES: CC(C)C[C@@H](Nc1nc(Nc2cnc3ccccc3c2)cnc1C(N)=O)C(N)=O]

The title compound was synthesized in a manner similar to that described above. MS 394.4 (M+H); UV 201.7, 284.9 nm.

Example 96

5-(3-(2H-1,2,3-triazol-2-yl)phenylamino)-3-((1R,2S)-2-aminocyclohexylamino)pyrazine-2-carboxamide

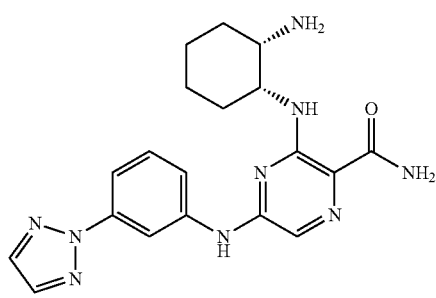 [SMILES: NC(=O)c1ncc(Nc2cccc(-n3nccn3)c2)nc1N[C@@H]1CCCC[C@@H]1N]

The title compound was synthesized in a manner similar to that described above. MS 394.3 (M+H); UV 206.6, 280.6 nm.

Example 97

(R)-5-(1-amino-1-oxobutan-2-ylamino)-3-(4-(4-aminophenyl)-1H-imidazol-1-yl)pyrazine-2-carboxamide

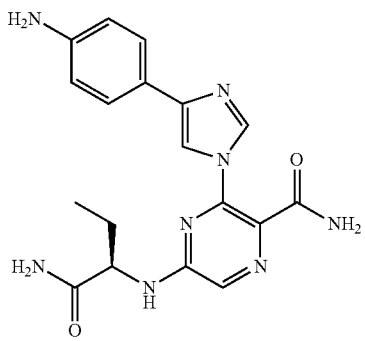 [SMILES: CC[C@@H](Nc1cnc(C(N)=O)c(-n2cnc(-c3ccc(N)cc3)c2)n1)C(N)=O]

The title compound was synthesized in a manner similar to that described above. MS 381.4 (M+H); UV 206.6, 259.1 nm.

Example 98

(R)-5-(1-amino-4-methyl-1-oxopentan-2-ylamino)-3-(3-(pyridin-2-yl)phenylamino)pyrazine-2-carboxamide

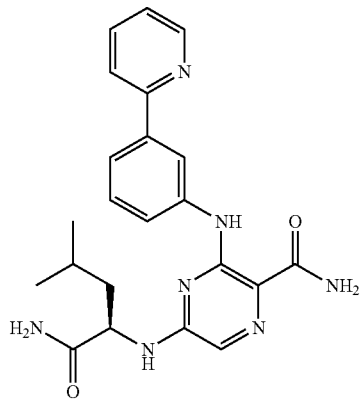 [SMILES: CC(C)C[C@@H](Nc1cnc(C(N)=O)c(Nc2cccc(-c3ccccn3)c2)n1)C(N)=O]

The title compound was synthesized in a manner similar to that described in Example 66. MS found for C22H25N7O2 as (M+H)$^+$ 420.3. UV: λ=241.6, 302.1.

Example 99

(R)-5-(1-amino-3-cyclopropyl-1-oxopropan-2-ylamino)-3-(5-methylpyridin-3-ylamino)pyrazine-2-carboxamide

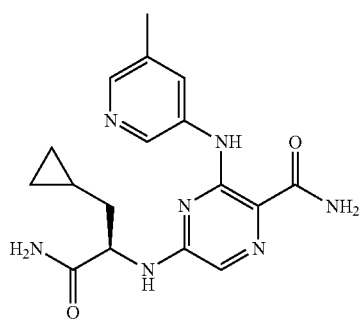 [SMILES: Cc1cncc(Nc2nc(N[C@H](CC3CC3)C(N)=O)cnc2C(N)=O)c1]

The title compound was synthesized in a manner similar to that described in Example 66. MS found for C17H21N7O2 as (M+H)+ 356.2. UV: λ=234.5, 259.4, 305.6.

Example 100

(R)-3-(6-(1-amino-3-cyclopropyl-1-oxopropan-2-ylamino)-3-carbamoylpyrazin-2-ylamino)-5-methylpyridine 1-oxide

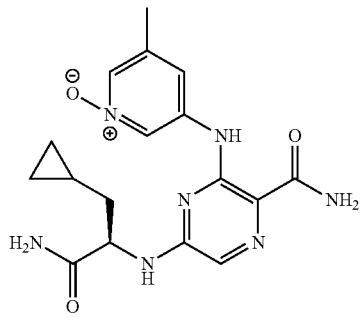 [SMILES: Cc1cc(Nc2nc(N[C@H](CC3CC3)C(N)=O)cnc2C(N)=O)c[n+]([O-])c1]

The title compound was synthesized in a manner similar to that described in Example 66. MS found for C17H21N7O3 as (M+H)+ 372.2. UV: λ=260.5, 303.3.

Example 101

(R)-5-(1-amino-3-cyclopropyl-1-oxopropan-2-ylamino)-3-(2-methylpyridin-4-ylamino)pyrazine-2-carboxamide

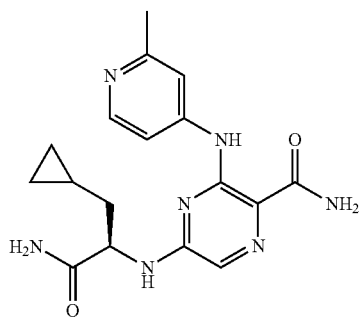 [SMILES: Cc1cc(Nc2nc(N[C@H](CC3CC3)C(N)=O)cnc2C(N)=O)ccn1]

The title compound was synthesized in a manner similar to that described in Example 66. MS found for C17H21N7O2 as (M+H)+ 356.2. UV: λ=273.6, 317.6.

Example 102

5-((1R,2R)-2-amino-3,3-difluorocyclohexylamino)-3-(quinolin-3-ylamino)pyrazine-2-carboxamide

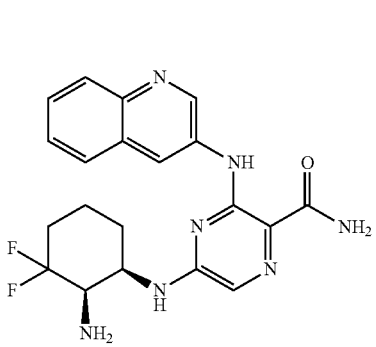 [SMILES: NC(=O)c1ncc(N[C@@H]2CCCC(F)(F)[C@@H]2N)nc1Nc1cnc2ccccc2c1]

The title compound was synthesized in a manner similar to that described in Example 14. MS 414.2 (M+H); UV 201.1, 241.9, 293.5, 349.2 nm.

Example 103

5-((1R,2R)-2-amino-3,3-difluorocyclohexylamino)-3-(m-tolylamino)pyrazine-2-carboxamide

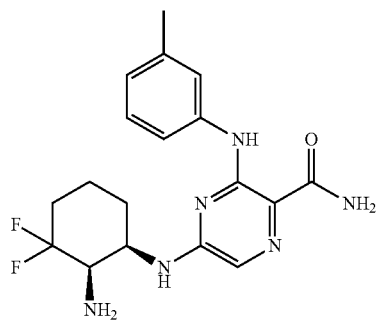 [SMILES: Cc1cccc(Nc2nc(N[C@@H]3CCCC(F)(F)[C@@H]3N)cnc2C(N)=O)c1]

The title compound was synthesized in a manner similar to that described in Example 14. MS 377.2 (M+H); UV 200.5, 249.3, 301.5 nm.

Example 104

5-((1R,2R)-2-amino-3,3-difluorocyclohexylamino)-3-(p-tolylamino)pyrazine-2-carboxamide

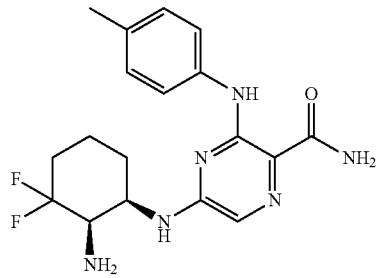 [SMILES: Cc1ccc(Nc2nc(N[C@@H]3CCCC(F)(F)[C@@H]3N)cnc2C(N)=O)cc1]

The title compound was synthesized in a manner similar to that described in Example 14. MS 377.3 (M+H); UV 205.4, 249.3, 299.7 nm.

Example 105

Preparation of (R)-3-((3-(2H-1,2,3-triazol-2-yl)phenyl)amino)-5-(pyrrolidin-3-ylamino)pyrazine-2-carboxamide

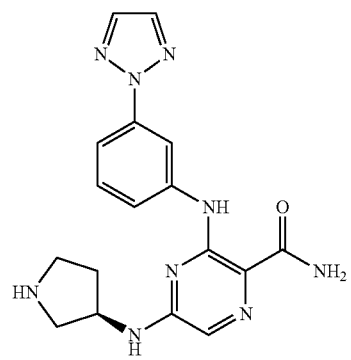 [SMILES: NC(=O)c1ncc(N[C@@H]2CCNC2)nc1Nc1cccc(-n2nccn2)c1]

The title compound was synthesized in a manner similar to that described in Example 11. MS found for C17H19N9O as (M+H)+ 366.3. UV: λ=262, 305 nm. ¹H NMR: (CD₃OD) δ 8.97 (1H, t, J=2.0 Hz), 7.86 (2H, s), 7.63 (1H, m), 7.35 (2H, m), 7.12 (1H, m), 4.80 (1H, m), 3.66 (1H, m), 3.47-3.30 (3H, m), 2.49-2.38 (1H, m), 2.14-2.05 (1H, m) ppm.

Example 106

Preparation of (R)-5-(pyrrolidin-3-ylamino)-3-(thieno[2,3-b]pyridin-3-ylamino)pyrazine-2-carboxamide

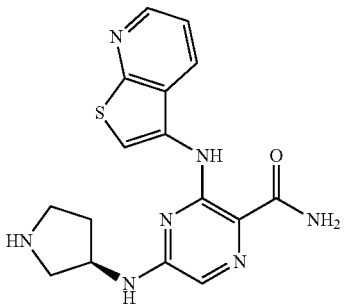 [SMILES: NC(=O)c1ncc(N[C@@H]2CCNC2)nc1Nc1csc2ncccc12]

The title compound was synthesized in a manner similar to that described in Example 11. MS found for C16H17N7OS as (M+H)+ 356.2. UV: λ=225, 262, 293, 357 nm. ¹H NMR: (CD₃OD) δ 8.60 (1H, dd, J=1.2 Hz, 4.4 Hz), 8.24 (1H, dd, J=1.6 Hz, 7.6 Hz), 7.98 (1H, s), 7.52 (1H, dd, J=4.8 Hz, 8.4 Hz), 7.46 (1H, s), 4.76 (1H, m), 3.63 (1H, m), 3.47-3.34 (3H, m), 2.52-2.42 (1H, m), 2.21-2.12 (1H, m) ppm.

Example 107

Preparation of (R)-3-(pyrazolo[1,5-a]pyridin-3-ylamino)-5-(pyrrolidin-3-ylamino)pyrazine-2-carboxamide

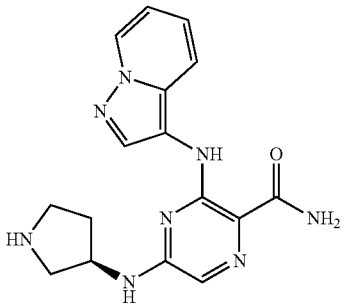 [SMILES: NC(=O)c1ncc(N[C@@H]2CCNC2)nc1Nc1cnn2ccccc12]

The title compound was synthesized in a manner similar to that described in Example 11. MS found for C16H18N8O as (M+H)+ 339.2. UV: λ=216, 293 nm. ¹H NMR: (CD₃OD) δ 8.46 (1H, dd, J=1.2 Hz, 6.0 Hz), 8.29 (1H, s), 7.56 (1H, dt, J=1.2 Hz, 8.4 Hz), 7.34 (1H, s), 7.20 (1H, m), 6.88 (1H, td, J=1.6 Hz, 6.4 Hz), 4.45 (1H, m), 3.44-3.20 (3H, m), 2.37-2.27 (1H, m), 2.13-2.04 (1H, m) ppm.

Example 108

Preparation of (S)-5-(pyrrolidin-3-ylamino)-3-(quinolin-6-ylamino)pyrazine-2-carboxamide

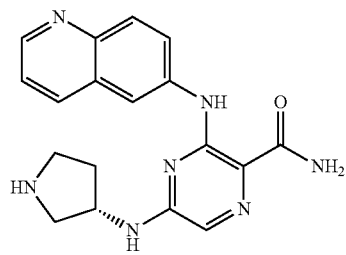 [SMILES: NC(=O)c1ncc(N[C@H]2CCNC2)nc1Nc1ccc2ncccc2c1]

The title compound was synthesized in a manner similar to that described in Example 11. MS found for C18H19N7O as (M+H)+ 350.2. UV: λ=204, 265, 297, 357 nm.

Example 109

Preparation of (S)-5-((1-acetylpiperidin-3-yl)amino)-3-(quinolin-3-ylamino)pyrazine-2-carboxamide

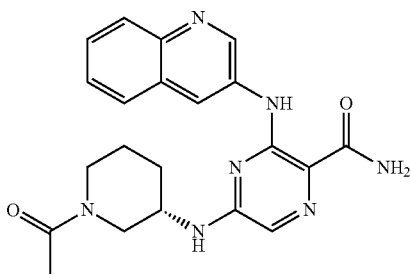 [SMILES: CC(=O)N1CCC[C@H](Nc2cnc(C(N)=O)c(Nc3cnc4ccccc4c3)n2)C1]

The title compound was synthesized in a manner similar to that described in Example 11 and utilized material from Example 57 for starting material as seen below.

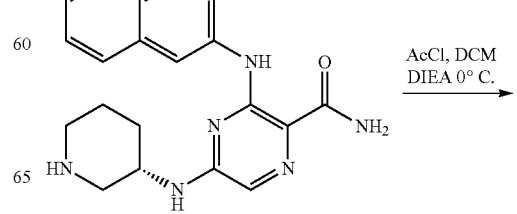

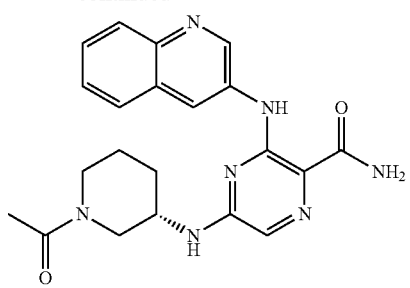

MS found for C21H23N7O2 as (M+H)⁺ 406.3. UV: λ=204, 250, 297, 353 nm.

Example 110

Preparation of (R)-5-((1-acetylpyrrolidin-3-yl)amino)-3-(quinolin-3-ylamino)pyrazine-2-carboxamide

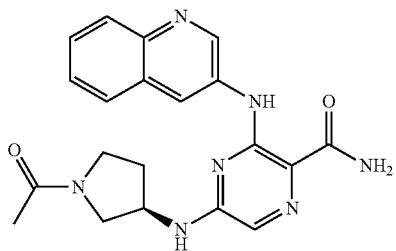 [SMILES: CC(=O)N1CC[C@@H](Nc2cnc(C(N)=O)c(Nc3cnc4ccccc4c3)n2)C1]

The title compound was synthesized in a manner similar to that described in Example 11 and 109. MS found for C20H21N7O2 as (M+H)⁺ 392.4. UV: λ=203, 249, 296, 352 nm.

Example 111

Preparation of (R)-5-((1-acetylpyrrolidin-3-yl)amino)-3-(quinolin-6-ylamino)pyrazine-2-carboxamide

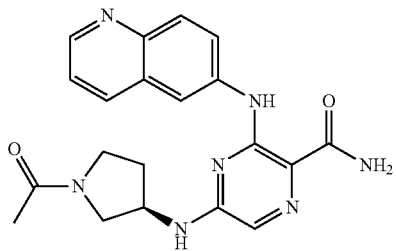 [SMILES: CC(=O)N1CC[C@@H](Nc2cnc(C(N)=O)c(Nc3ccc4ncccc4c3)n2)C1]

The title compound was synthesized in a manner similar to that described in Example 11 and 109. MS found for C20H21N7O2 as (M+H)⁺ 392.3. UV: λ=203, 267, 298, 358 nm.

Example 112

Preparation of (R)-5-(pyrrolidin-3-ylamino)-3-(p-tolylamino)pyrazine-2-carboxamide

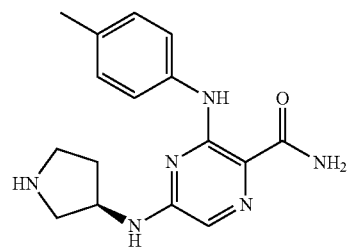 [SMILES: Cc1ccc(Nc2nc(N[C@@H]3CCNC3)cnc2C(N)=O)cc1]

The title compound was synthesized in a manner similar to that described in Example 11. MS found for C16H20N6O as (M+H)⁺ 313.2. UV: λ=205, 253, 302 nm.

Example 113

Preparation of (R)-3-(pyridin-3-ylamino)-5-(pyrrolidin-3-ylamino)pyrazine-2-carboxamide

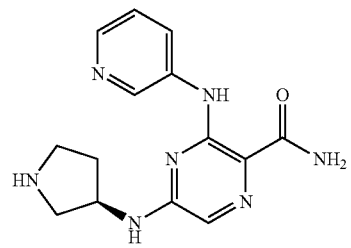 [SMILES: NC(=O)c1ncc(N[C@@H]2CCNC2)nc1Nc1cccnc1]

The title compound was synthesized in a manner similar to that described in Example 11. MS found for C14H17N7O as (M+H)⁺ 300.2. UV: λ=230, 259, 301 nm. ¹H NMR: (CD₃OD) δ 9.40 (1H, br), 8.42 (2H, m), 7.95 (1H, br), 7.58 (1H, s), 4.76 (1H, m), 3.69 (1H, dd), 3.53 (1H, dd), 3.36 (1H, m), 2.30 (1H, m), 2.19 (1H, m) ppm.

Example 114

Preparation of (R)-3-((3-(pyrimidin-2-yl)phenyl)amino)-5-(pyrrolidin-3-ylamino)pyrazine-2-carboxamide

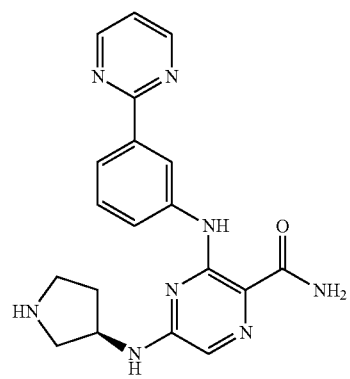 [SMILES: NC(=O)c1ncc(N[C@@H]2CCNC2)nc1Nc1cccc(-c2ncccn2)c1]

The title compound was synthesized in a manner similar to that described in Example 11. MS found for C19H20N8O as (M+H)⁺ 377.3. UV: λ=208, 250, 302 nm.

Example 115

Preparation of (R)-3-((5-fluoropyridin-3-yl)amino)-5-(pyrrolidin-3-ylamino)pyrazine-2-carboxamide

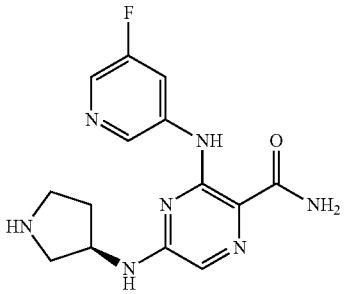 [SMILES: NC(=O)c1ncc(N[C@@H]2CCNC2)nc1Nc1cncc(F)c1]

The title compound was synthesized in a manner similar to that described in Example 11. MS found for C14H16FN7O as (M+H)+ 318.2. UV: λ=230, 259, 302 nm. $^1$H NMR: (CD$_3$OD) δ 8.81 (1H, br), 8.16-8.08 (3H, m), 7.51 (1H, s), 4.65 (1H, m), 3.61 (1H, dd), 3.52-3.36 (3H, m), 2.47 (1H, m), 2.19 (1H, m) ppm.

Example 116

Preparation of (R)-5-(pyrrolidin-3-ylamino)-3-(m-tolylamino)pyrazine-2-carboxamide

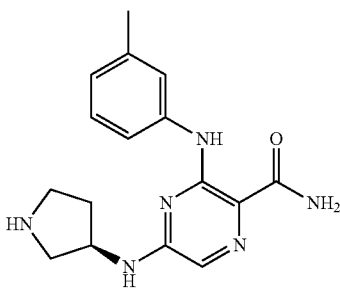 [SMILES: Cc1cccc(Nc2nc(N[C@@H]3CCNC3)cnc2C(N)=O)c1]

The title compound was synthesized in a manner similar to that described in Example 11. MS found for C16H20N6O as (M+H)+ 313.2. UV: λ=207, 253, 292. $^1$H NMR: (CD$_3$OD) δ 7.45 (1H, d, J=8.4 Hz), 7.39-7.35 (2H, m), 7.20 (1H, t, J=8.0 Hz), 6.86 (1H, m), 4.60 (1H, m), 3.58 (1H, dd), 3.50-3.34 (3H, m), 2.47 (1H, m), 2.37 (3H, s), 2.19 (1H, m) ppm.

Example 117

Preparation of (R)-3-((1,6-naphthyridin-3-yl)amino)-5-(pyrrolidin-3-ylamino)pyrazine-2-carboxamide

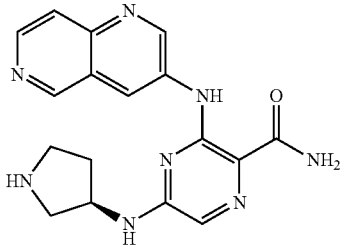 [SMILES: NC(=O)c1ncc(N[C@@H]2CCNC2)nc1Nc1cnc2ccncc2c1]

The title compound was synthesized in a manner similar to that described above. MS found for C17H18N8O as (M+H)+ 351.3. UV: λ=. $^1$H NMR: (CD$_3$OD) δ 9.42 (2H, dd), 8.96 (1H, dd), 8.62 (1H, dd), 8.16 (1H, dd), 7.58 (1H, s), 4.80 (1H, m), 3.68 (1H, dd), 3.50-3.39 (3H, m), 2.52 (1H, m), 2.23 (1H, m) ppm.

Example 118

Preparation of (R)-3-((1,6-naphthyridin-3-yl)amino)-5-((1-(cyanomethyl)pyrrolidin-3-yl)amino)pyrazine-2-carboxamide

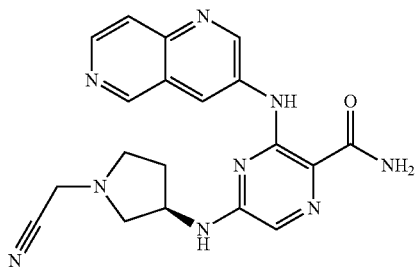 [SMILES: N#CCN1CC[C@@H](Nc2cnc(C(N)=O)c(Nc3cnc4ccncc4c3)n2)C1]

The title compound was synthesized in a manner similar to that described in Example 11. MS found for C19H19N9O as (M+H)+ 390.2. UV: λ=212, 267, 323. $^1$H NMR: (CD$_3$OD) δ 9.62 (1H, s), 9.35 (1H, d, J=2.4 Hz), 9.25 (1H, br), 8.61 (1H, d, J=6.8 Hz), 8.30 (1H, d, J=6.0 Hz), 7.52 (1H, s), 4.70 (1H, m), 3.98 (2H, d, J=4.4 Hz), 3.38 (1H, m), 3.14 (1H, m), 3.03-2.91 (2H, m), 2.56 (1H, m), 2.03 (1H, m) ppm.

Example 119

Preparation of (R)-5-((1-amino-4,4-difluoro-1-oxobutan-2-yl)amino)-3-((3-methylisothiazol-5-yl)amino)pyrazine-2-carboxamide

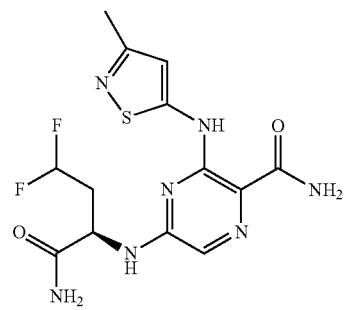 [SMILES: Cc1cc(Nc2nc(N[C@H](CC(F)F)C(N)=O)cnc2C(N)=O)sn1]

The title compound was synthesized in a manner similar to that described in Example 29. MS found for C13H15F2N7O2S as (M+H)+ 372.2. UV: λ=208, 272, 321 nm. $^1$H NMR: (CD$_3$OD) δ 7.69 (1H, s), 6.90 (1H, s), 6.17 (1H, tt), 4.80 (1H, m), 2.63 (1H, m), 2.47-2.32 (4H, m) ppm.

Example 120

Preparation of 5-(((1R,2S)-2-aminocyclohexyl)amino)-3-((3-methyl-4-phenylisothiazol-5-yl)amino)pyrazine-2-carboxamide

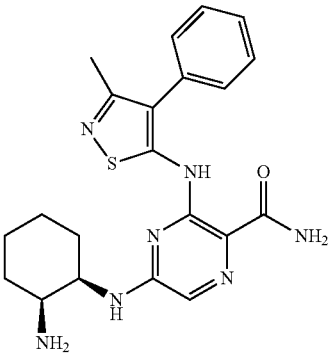

The title compound was synthesized in a manner similar to that described in Example 11. MS found for C21H25N7OS as (M+H)+ 424.4. UV: λ=269, 325 nm.

Example 121

Preparation of 5-(((1R,2S)-2-aminocyclohexyl)amino)-3-((3-methyl-4-(pyridin-3-yl)isothiazol-5-yl)amino)pyrazine-2-carboxamide

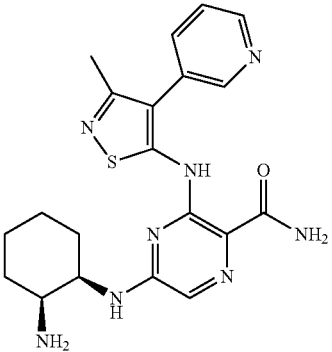 [SMILES: Cc1nsc(Nc2nc(N[C@@H]3CCCC[C@@H]3N)cnc2C(N)=O)c1-c1ccccc1]

The title compound was synthesized in a manner similar to that described in Example 11. MS found for C20H24N8OS as (M+H)+ 425.3. UV: λ=207, 241, 274, 329, 355 nm.

Example 122

Preparation of (R)-5-((1-amino-4,4-difluoro-1-oxobutan-2-yl)amino)-3-((3,4-dimethylphenyl)amino)pyrazine-2-carboxamide

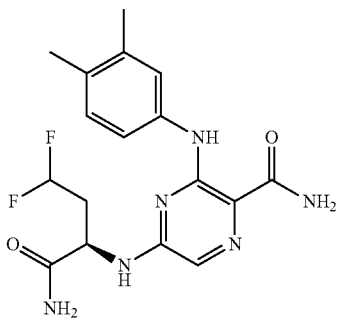 [SMILES: Cc1ccc(Nc2nc(N[C@H](CC(F)F)C(N)=O)cnc2C(N)=O)cc1C]

The title compound was synthesized in a manner similar to that described in Example 29. MS found for C17H20F2N6O2 as (M+H)+ 379.3. UV: λ=210, 253, 302 nm. 1H NMR: (DMSOd6) δ 11.36 (1H, s), 7.93 (1H, d, 7.6 Hz), 7.74 (1H, d, J=2.4 Hz), 7.57 (1H, br), 7.39-7.36 (2H, m), 7.28 (1H, br), 7.01 (1H, d, 8.0 Hz), 6.15 (1H, tdd), 4.51 (1H, m), 2.49-2.20 (2H, m), 2.19 (3H, s), 2.15 (3H, s) ppm.

Example 123

Preparation of (R)-5-((1-amino-4,4-difluoro-1-oxobutan-2-yl)amino)-3-(p-tolylamino)pyrazine-2-carboxamide

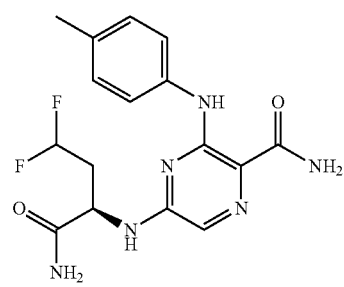 [SMILES: Cc1ccc(Nc2nc(N[C@H](CC(F)F)C(N)=O)cnc2C(N)=O)cc1]

The title compound was synthesized in a manner similar to that described in Example 29. MS found for C16H18F2N6O2 as (M+H)+ 365.3. UV: λ=213, 252, 303 nm.

Example 124

Preparation of (S)-5-((2-amino-4,4-difluorobutyl)amino)-3-((2,3-dibromo-4-methylphenyl)amino)pyrazine-2-carboxamide

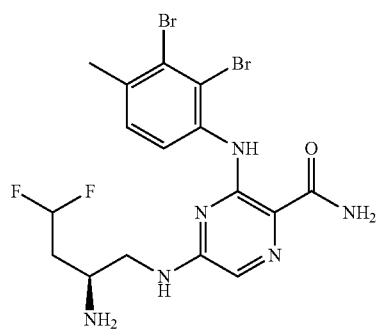 [SMILES: Cc1ccc(Nc2nc(NC[C@@H](N)CC(F)F)cnc2C(N)=O)c(Br)c1Br]

The title compound was synthesized in a manner similar to that described in Example 11. MS found for C16H18Br2F2N6O as (M+H)+ 506, 508, 510. UV: λ=204, 252, 302 nm.

Example 125

Preparation of 5-(((1R,2S)-2-aminocyclohexyl)amino)-3-((3-methyl-4-(pyrimidin-5-yl)isothiazol-5-yl)amino)pyrazine-2-carboxamide

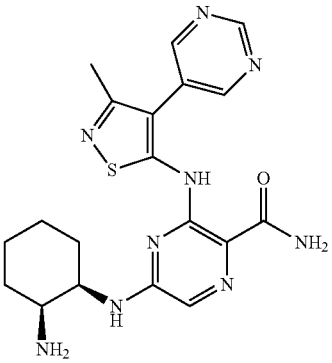 [SMILES: Cc1nsc(Nc2nc(N[C@@H]3CCCC[C@@H]3N)cnc2C(N)=O)c1-c1cncnc1]

The title compound was synthesized in a manner similar to that described in Example 11. MS found for C19H23N9OS as (M+H)+ 426.3. UV: λ=210, 240, 271, 326.

Example 126

Preparation of (R)-3-((1,5-naphthyridin-3-yl)amino)-5-((1-amino-4,4,4-trifluoro-1-oxobutan-2-yl)amino)pyrazine-2-carboxamide

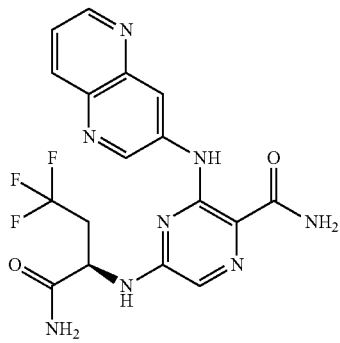 [SMILES: NC(=O)c1ncc(N[C@H](CC(F)(F)F)C(N)=O)nc1Nc1cnc2cccnc2c1]

The title compound was synthesized in a manner similar to that described above. MS found for C17H15F3N8O2 as (M+H)+ 421.3. UV: λ=213, 250, 303, 352.

Example 127

Preparation of (R)-3-((1,5-naphthyridin-3-yl)amino)-5-((1-amino-4,4-difluoro-1-oxobutan-2-yl)amino)pyrazine-2-carboxamide

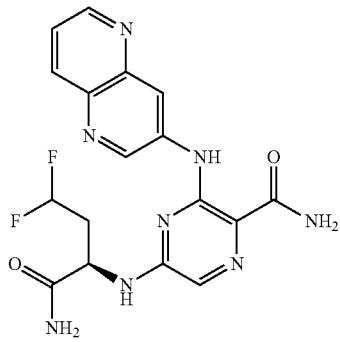

The title compound was synthesized in a manner similar to that described above. MS found for C17H16F2N8O2 as (M+H)+ 403.3. UV: λ=213, 250, 304, 352.

Example 128

Preparation of 5-(((1-aminocyclopropyl)methyl)amino)-3-(quinolin-6-ylamino)pyrazine-2-carboxamide

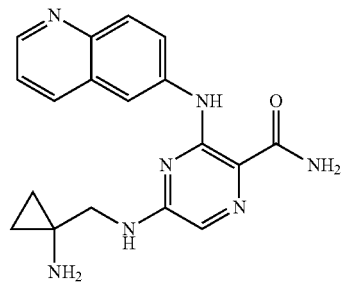 [SMILES: NC(=O)c1ncc(NCC2(N)CC2)nc1Nc1ccc2ncccc2c1]

The title compound was synthesized in a manner similar to that described above. MS found for C18H19N7O as (M+H)+ 350.3. UV: λ=266, 298.

Example 129

Preparation of 5-(((1-(methylamino)cyclopropyl)methyl)amino)-3-(quinolin-6-ylamino)pyrazine-2-carboxamide

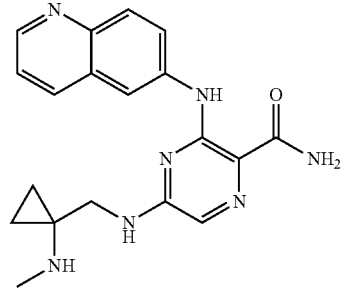 [SMILES: CNC1(CNc2cnc(C(N)=O)c(Nc3ccc4ncccc4c3)n2)CC1]

The title compound was synthesized in a manner similar to that described above. MS found for C19H21N7O as (M+H)+ 364.3. UV: λ=266, 298.

Example 130

Preparation of 5-(((1R,2S)-2-aminocyclohexyl)amino)-3-((4-ethyl-3-methylisothiazol-5-yl)amino)pyrazine-2-carboxamide

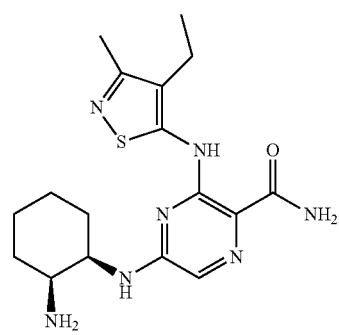 [SMILES: CCc1c(C)nsc1Nc1nc(N[C@@H]2CCCC[C@@H]2N)cnc1C(N)=O]

The title compound was synthesized in a manner similar to that described above. MS found for C17H25N7OS as (M+H)+ 376.3. UV: λ=212, 280, 327.

Example 131

Preparation of 5-(((1R,2S)-2-aminocyclohexyl)amino)-3-((3,4-dimethylisothiazol-5-yl)amino)pyrazine-2-carboxamide

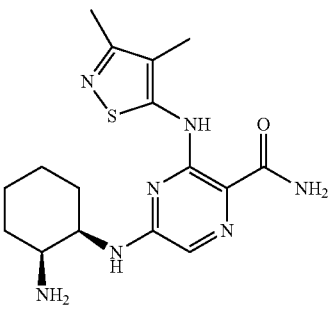

The title compound was synthesized in a manner similar to that described in Example 11. The isothiazole intermediate that was utilized was synthesized as described below.

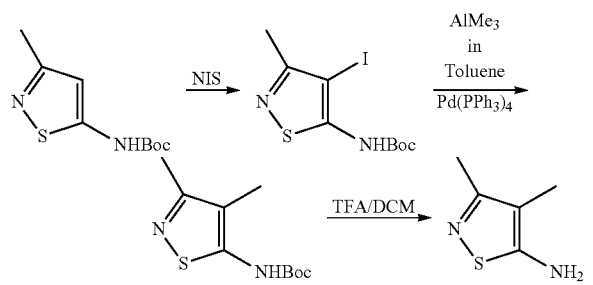

MS found for C16H23N7OS as (M+H)+ 362.4. UV: λ=212, 281, 327.

Example 132

Preparation of (R)-5-((1-amino-1-oxobutan-2-yl)amino)-3-((4-bromo-3-methylisothiazol-5-yl)amino)pyrazine-2-carboxamide

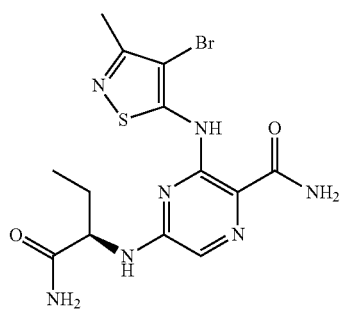 [SMILES: CC[C@@H](Nc1cnc(C(N)=O)c(Nc2snc(C)c2Br)n1)C(N)=O]

The title compound was synthesized utilizing the non-brominated intermediate seen below (precursor prepared as described in Example 22).

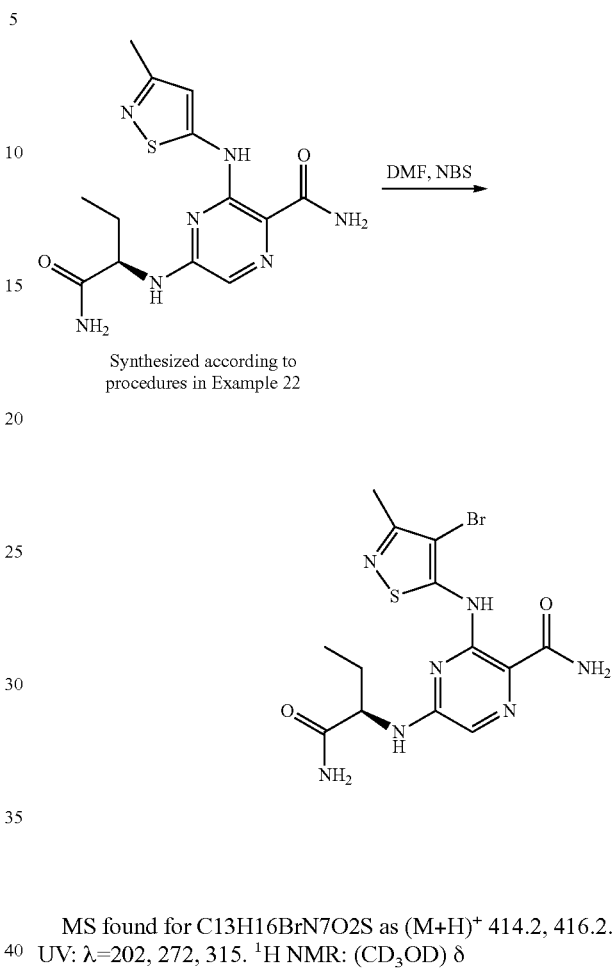

Synthesized according to procedures in Example 22

MS found for C13H16BrN7O2S as (M+H)+ 414.2, 416.2. UV: λ=202, 272, 315. 1H NMR: (CD3OD) δ

Example 133

Preparation of (R)-5-((1-amino-1-oxobutan-2-yl)amino)-3-((4-iodo-3-methylisothiazol-5-yl)amino)pyrazine-2-carboxamide

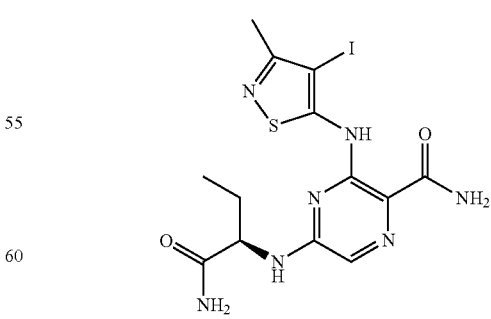

The title compound was synthesized in a manner similar to that described above.

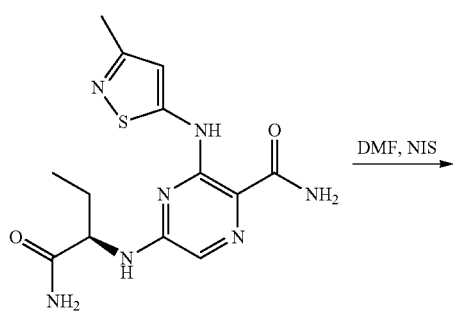

Synthesized according to procedures in Example 22

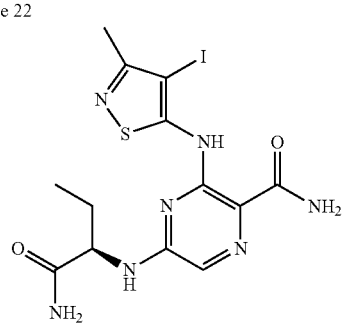

MS found for C13H16IN7O2S as (M+H)+ 462.2. UV: λ=202, 272, 315.

Example 134

Preparation of (R)-5-((1-amino-1-oxobutan-2-yl)amino)-6-iodo-3-((4-iodo-3-methylisothiazol-5-yl)amino)pyrazine-2-carboxamide

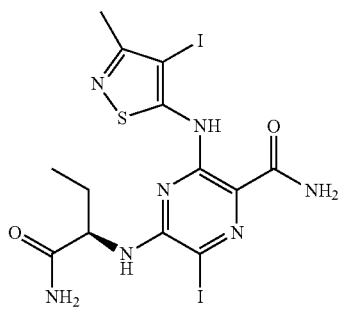 [SMILES: CC[C@@H](Nc1nc(Nc2snc(C)c2I)c(C(N)=O)nc1I)C(N)=O]

The title compound was synthesized in a manner similar to that described above.

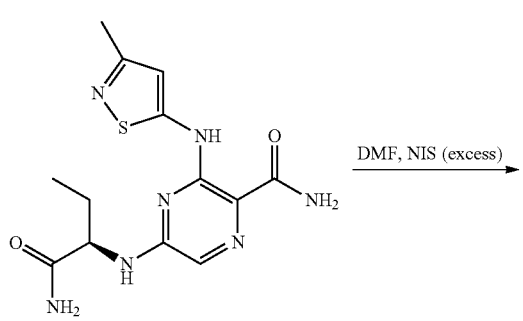

Synthesized according to procedures in Example 22

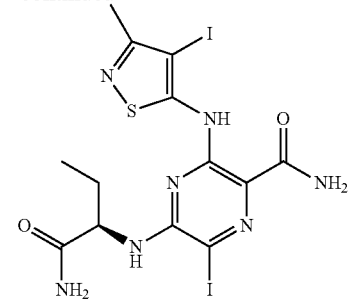

MS found for C13H15I2N7O2S as (M+H)+ 588.2. UV: λ=204, 273, 315.

Example 135

Preparation of (R)-5-((1-amino-1-oxobutan-2-yl)amino)-3-((4-chloro-3-methylisothiazol-5-yl)amino)pyrazine-2-carboxamide

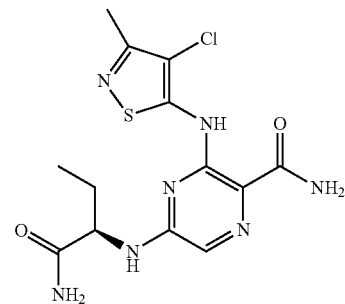 [SMILES: CC[C@@H](Nc1cnc(C(N)=O)c(Nc2snc(C)c2Cl)n1)C(N)=O]

The title compound was synthesized as described below.

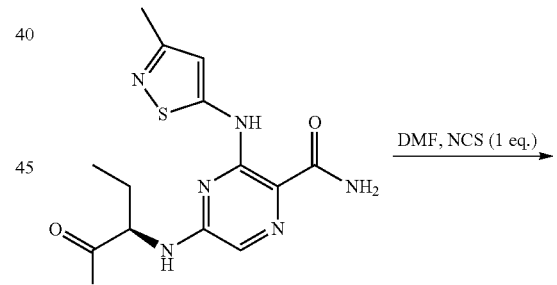

Synthesized according to procedures in Example 22

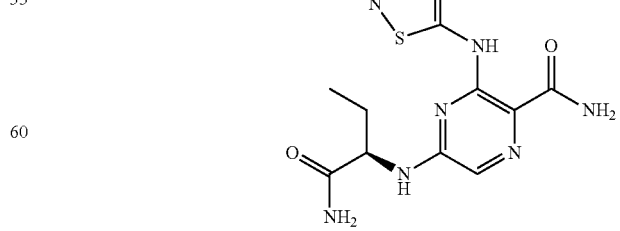

MS found for C13H16ClN7O2S as (M+H)+ 370.3, 372.2. UV: λ=203, 271, 315.

Example 136

Preparation of (R)-5-((1-amino-3-cyclopropyl-1-oxo-propan-2-yl)amino)-6-chloro-3-((3-methylisothiazol-5-yl)amino)pyrazine-2-carboxamide

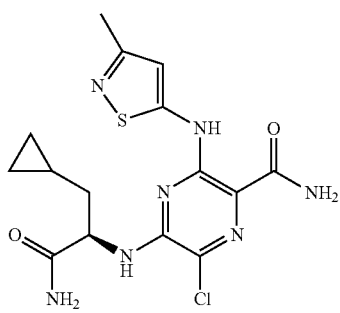 [SMILES: Cc1cc(Nc2nc(N[C@H](CC3CC3)C(N)=O)c(Cl)nc2C(N)=O)sn1]

The title compound was synthesized as described below.

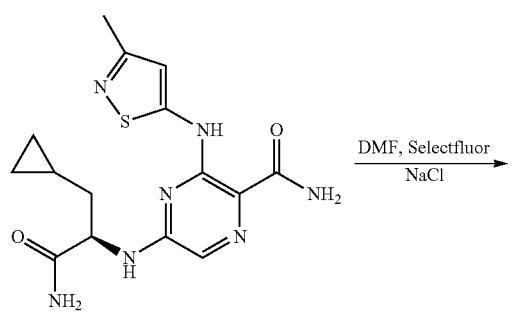

Synthesized according to procedures in Example 22

MS found for C15H18ClN7O2S as (M+H)+ 396.3, 398.4. UV: λ=208, 273, 321.

Example 137

Preparation of (R)-5-((1-amino-1-oxobutan-2-yl)amino)-6-chloro-3-((3-methylisothiazol-5-yl)amino)pyrazine-2-carboxamide

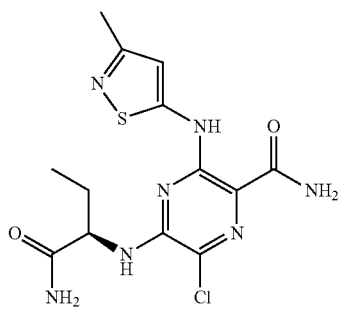 [SMILES: CC[C@@H](Nc1nc(Nc2cc(C)ns2)c(C(N)=O)nc1Cl)C(N)=O]

The title compound was synthesized as described below.

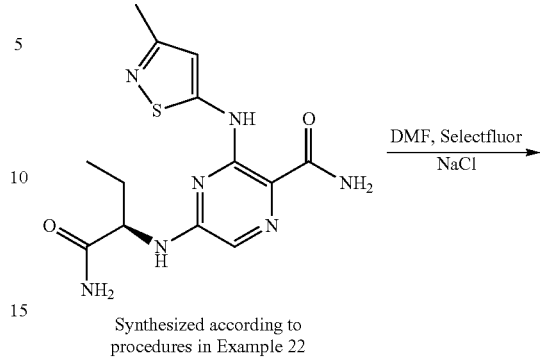

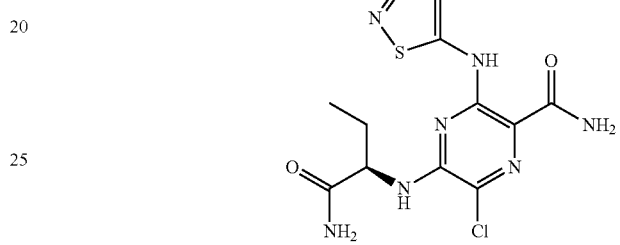

MS found for C13H16ClN7O2S as (M+H)+ 370.3, 372.3. UV: λ=207, 273, 322.

Example 138

Preparation of 5-(((1R,2S)-2-aminocyclohexyl)amino)-3-((4-fluoro-3-methylisothiazol-5-yl)amino)pyrazine-2-carboxamide

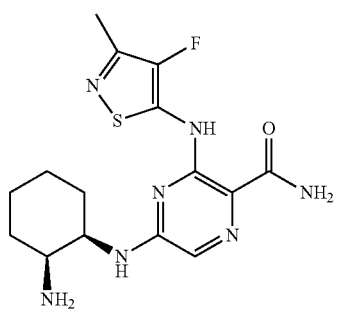 [SMILES: Cc1nsc(Nc2nc(N[C@@H]3CCCC[C@@H]3N)cnc2C(N)=O)c1F]

The title compound was synthesized in a manner similar to that described above. The fluoro-containing intermediate was synthesized as shown below.

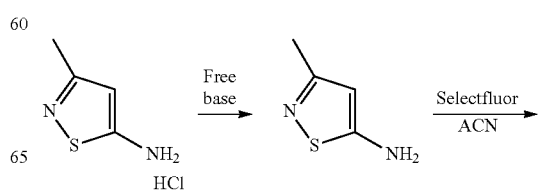

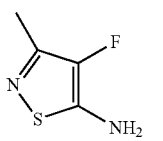

MS found for C15H20FN7OS as (M+H)+ 366.3. UV: λ=207, 270, 313.

Example 139

Preparation of 5-(((3R,5R)-5-(hydroxymethyl)pyrrolidin-3-yl)amino)-3-((3-methylisothiazol-5-yl)amino)pyrazine-2-carboxamide

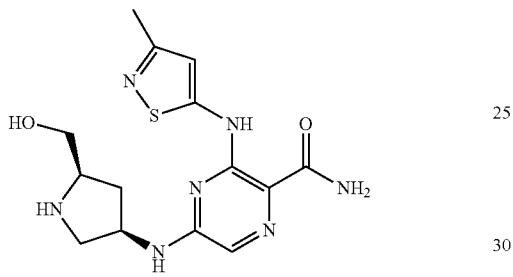

The title compound was synthesized in a manner similar to that described above. MS found for C14H19N7O2S as (M+H)+ 350.3. UV: λ=209, 275, 323.

Example 140

Preparation of 3-((6-fluoroquinolin-3-yl)amino)-5-(((3R,5R)-5-(hydroxymethyl)pyrrolidin-3-yl)amino)pyrazine-2-carboxamide

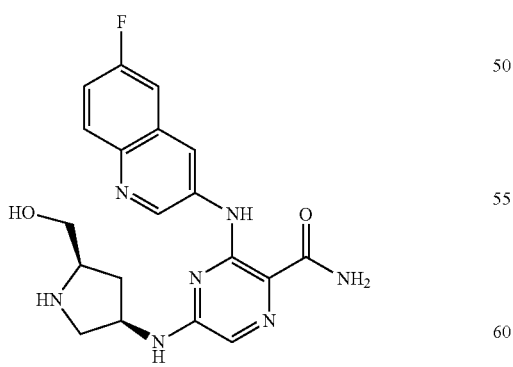

The title compound was synthesized in a manner similar to that described above. MS found for C19H20FN7O2 as (M+H)+ 398.4. UV: λ=205, 246, 297, 352.

Example 141

(R)-5-(1-amino-3-methyl-1-oxobutan-2-ylamino)-3-(3,4-dimethoxyphenylamino)pyrazine-2-carboxamide

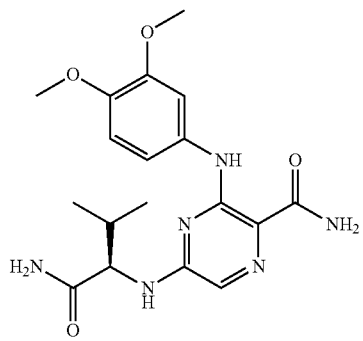 [SMILES: COc1ccc(Nc2nc(N[C@@H](C(N)=O)C(C)C)cnc2C(N)=O)cc1OC]

The title compound was synthesized in a manner similar to that described in Example 66. MS found for C18H24N6O4 as (M+H)+ 389.4. UV: λ=216.9, 259.4, 304.5.

Example 142

5-((1R,2S)-2-aminocyclohexylamino)-3-(3,4-dimethoxyphenylamino)pyrazine-2-carboxamide

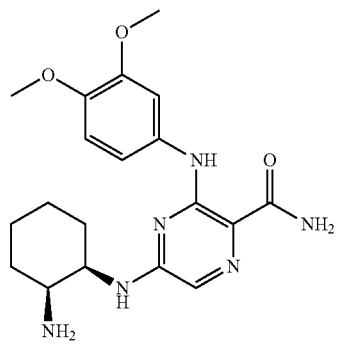 [SMILES: COc1ccc(Nc2nc(N[C@@H]3CCCC[C@@H]3N)cnc2C(N)=O)cc1OC]

The title compound was synthesized in a manner similar to that described in Example 78. MS found for C19H26N6O3 as (M+H)+ 387.6. UV: λ=216.9, 258.2, 302.1.

Example 143

5-((1R,2S)-2-aminocyclohexylamino)-3-(3-methyl-4-morpholinophenylamino)pyrazine-2-carboxamide

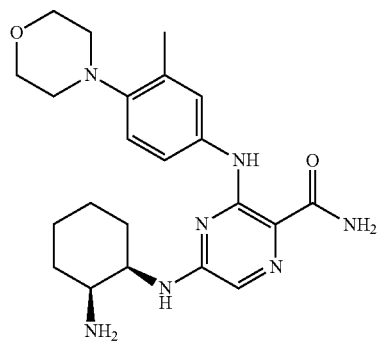 [SMILES: Cc1cc(Nc2nc(N[C@@H]3CCCC[C@@H]3N)cnc2C(N)=O)ccc1N1CCOCC1]

The title compound was synthesized in a manner similar to that described in Example 78. MS found for C22H31N7O2 as (M+H)+ 426.6. UV: λ=258.2, 308.0.

Example 144

(R)-5-(1-amino-3-methyl-1-oxobutan-2-ylamino)-3-(3-(morpholinomethyl)phenylamino)pyrazine-2-carboxamide

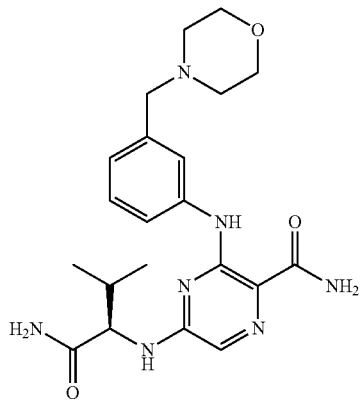 [SMILES: CC(C)[C@@H](Nc1cnc(C(N)=O)c(Nc2cccc(CN3CCOCC3)c2)n1)C(N)=O]

The title compound was synthesized in a manner similar to that described in Example 66. MS found for C21H29N7O3 as (M+H)+ 428.4. UV: λ=255.8, 305.6.

Example 145

5-((1R,2S)-2-aminocyclohexylamino)-3-(4-(methylsulfonylmethyl)phenylamino)pyrazine-2-carboxamide

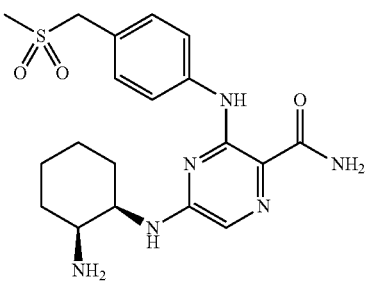 [SMILES: CS(=O)(=O)Cc1ccc(Nc2nc(N[C@@H]3CCCC[C@@H]3N)cnc2C(N)=O)cc1]

The title compound was synthesized in a manner similar to that described in Example 78. MS found for C19H26N6O3S as (M+H)+ 419.5. UV: λ=258.4, 308.2.

Example 146

(R)-5-(1-amino-3-methyl-1-oxobutan-2-ylamino)-3-(benzo[d][1,3]dioxol-5-ylamino)pyrazine-2-carboxamide

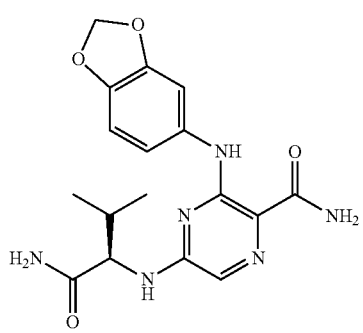 [SMILES: CC(C)[C@@H](Nc1cnc(C(N)=O)c(Nc2ccc3c(c2)OCO3)n1)C(N)=O]

The title compound was synthesized in a manner similar to that described in Example 66. MS found for C17H20N6O4 as (M+H)+ 373.5. UV: λ=260.5, 304.5.

Example 147

(R)-5-(1-amino-3-methyl-1-oxobutan-2-ylamino)-3-(3-(trifluoromethoxy)phenylamino)pyrazine-2-carboxamide

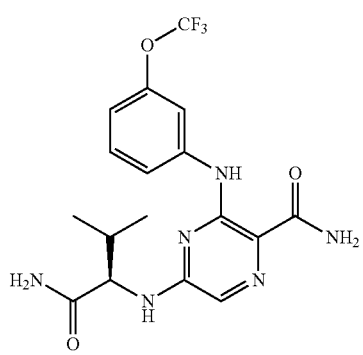 [SMILES: CC(C)[C@@H](Nc1cnc(C(N)=O)c(Nc2cccc(OC(F)(F)F)c2)n1)C(N)=O]

The title compound was synthesized in a manner similar to that described in Example 66. MS found for C17H19F3N6O3 as (M+H)+ 413.5. UV: λ=255.3, 305.1.

Example 148

(R)-5-(1-amino-3-methyl-1-oxobutan-2-ylamino)-3-(4-(morpholinomethyl)phenylamino)pyrazine-2-carboxamide

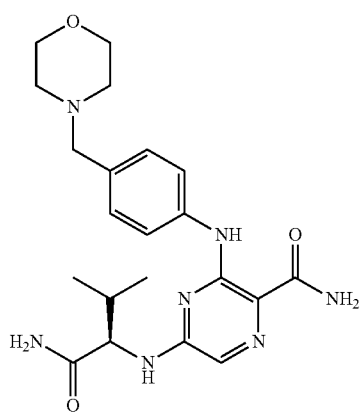 [SMILES: CC(C)[C@@H](Nc1cnc(C(N)=O)c(Nc2ccc(CN3CCOCC3)cc2)n1)C(N)=O]

The title compound was synthesized in a manner similar to that described in Example 66. MS found for C21H29N7O3 as (M+H)+ 428.6. UV: λ=259.0, 310.0.

Example 149

(R)-3-(4-(1H-imidazol-1-yl)phenylamino)-5-(1-amino-3-methyl-1-oxobutan-2-ylamino)pyrazine-2-carboxamide

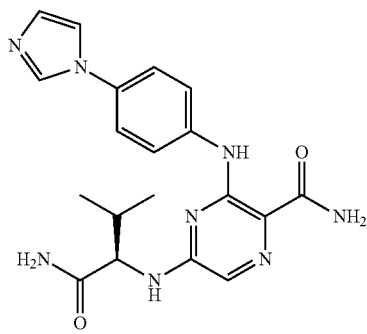 [SMILES: CC(C)[C@@H](Nc1cnc(C(N)=O)c(Nc2ccc(-n3ccnc3)cc2)n1)C(N)=O]

The title compound was synthesized in a manner similar to that described in Example 66. MS found for C19H22N8O2 as (M+H)⁺ 395.4. UV: λ=264.1, 314.0.

Example 150

(R)-5-(1-amino-3-methyl-1-oxobutan-2-ylamino)-3-(4-(methylsulfonylmethyl)phenylamino)pyrazine-2-carboxamide

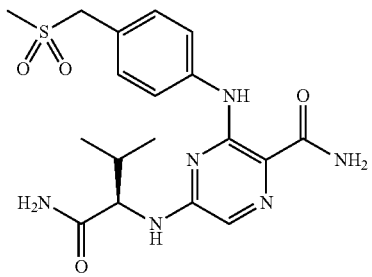 [SMILES: CC(C)[C@@H](Nc1cnc(C(N)=O)c(Nc2ccc(CS(C)(=O)=O)cc2)n1)C(N)=O]

The title compound was synthesized in a manner similar to that described in Example 66. MS found for C18H24N6O4S as (M+H)⁺ 421.3. UV: λ=259.0, 310.0.

Example 151

(R)-5-(1-amino-1-oxobutan-2-ylamino)-3-(3,4-dimethoxyphenylamino)pyrazine-2-carboxamide

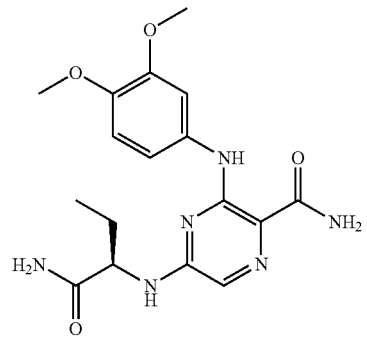 [SMILES: CC[C@@H](Nc1cnc(C(N)=O)c(Nc2ccc(OC)c(OC)c2)n1)C(N)=O]

The title compound was synthesized in a manner similar to that described in Example 66. MS found for C17H22N6O4 as (M+H)⁺ 375.5. UV: λ=258.4, 305.1.

Example 152

(R)-5-(1-amino-1-oxobutan-2-ylamino)-3-(p-tolylamino)pyrazine-2-carboxamide

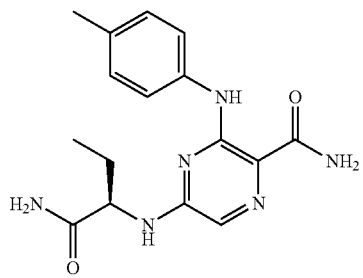 [SMILES: CC[C@@H](Nc1cnc(C(N)=O)c(Nc2ccc(C)cc2)n1)C(N)=O]

The title compound was synthesized in a manner similar to that described in Example 66. MS found for C16H20N6O2 as (M+H)⁺ 329.2. UV: λ=253.4, 303.3.

Example 153

5-((1R,2S)-2-aminocyclohexylamino)-3-(4-(methylsulfonyl)phenylamino)pyrazine-2-carboxamide

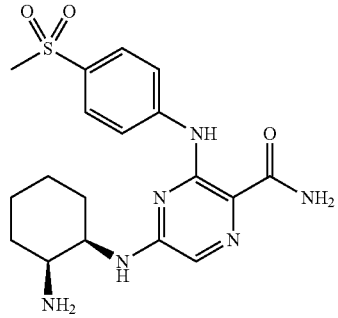 [SMILES: CS(=O)(=O)c1ccc(Nc2nc(N[C@@H]3CCCC[C@@H]3N)cnc2C(N)=O)cc1]

The title compound was synthesized in a manner similar to that described in Example 78. MS found for C18H24N6O3S as (M+H)⁺ 405.4. UV: λ=266.6, 317.7.

Example 154

5-((1R,2S)-2-aminocyclohexylamino)-3-(3-(methylsulfonyl)phenylamino)pyrazine-2-carboxamide

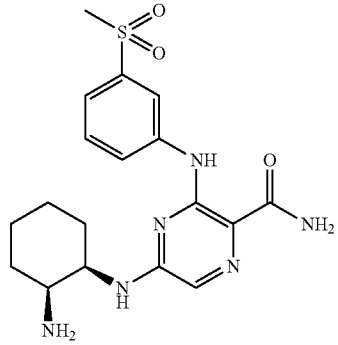 [SMILES: CS(=O)(=O)c1cccc(Nc2nc(N[C@@H]3CCCC[C@@H]3N)cnc2C(N)=O)c1]

The title compound was synthesized in a manner similar to that described in Example 78. MS found for C18H24N6O3S as (M+H)⁺ 405.3. UV: λ=258.0, 306.0.

Example 155

(R)-5-(1-amino-3-methyl-1-oxobutan-2-ylamino)-3-(p-tolylamino)pyrazine-2-carboxamide

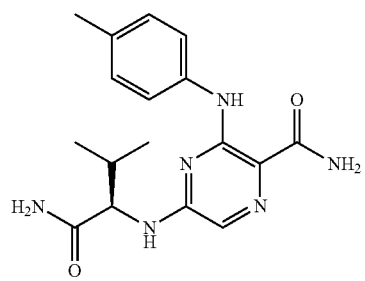 [SMILES: Cc1ccc(Nc2nc(N[C@@H](C(N)=O)C(C)C)cnc2C(N)=O)cc1]

The title compound was synthesized in a manner similar to that described in Example 66. MS found for C17H22N6O2 as (M+H)⁺ 343.4. UV: λ=254.3, 302.9.

Example 156

(R)-5-(1-amino-3-methyl-1-oxobutan-2-ylamino)-3-(4-(N,N-dimethylsulfamoyl)phenylamino)pyrazine-2-carboxamide

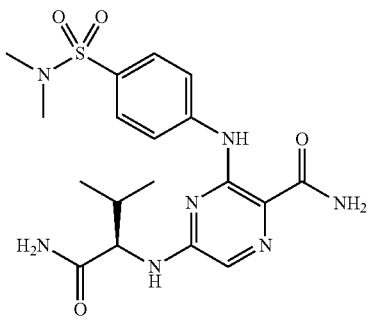 [SMILES: CC(C)[C@@H](Nc1cnc(C(N)=O)c(Nc2ccc(S(=O)(=O)N(C)C)cc2)n1)C(N)=O]

The title compound was synthesized in a manner similar to that described in Example 66. MS found for C18H25N7O4S as (M+H)⁺ 436.3. UV: λ=266.5, 317.6.

Example 157

(R)-5-(1-amino-3-methyl-1-oxobutan-2-ylamino)-3-(4-(N-methylacetamido)phenylamino)pyrazine-2-carboxamide

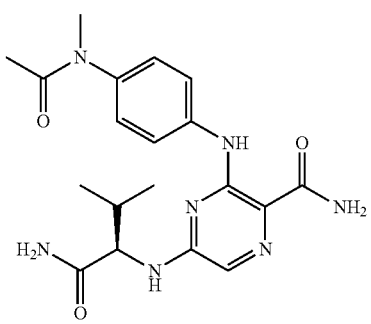 [SMILES: CC(=O)N(C)c1ccc(Nc2nc(N[C@@H](C(N)=O)C(C)C)cnc2C(N)=O)cc1]

The title compound was synthesized in a manner similar to that described in Example 66. MS found for C19H25N7O3 as (M+H)⁺ 400.3. UV: λ=257.0, 305.6.

Example 158

(R)-5-(1-amino-1-oxobutan-2-ylamino)-3-(3,5-dimethoxyphenylamino)pyrazine-2-carboxamide

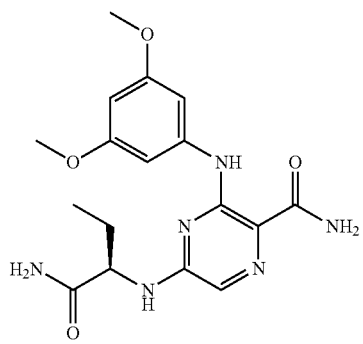 [SMILES: CC[C@@H](Nc1cnc(C(N)=O)c(Nc2cc(OC)cc(OC)c2)n1)C(N)=O]

The title compound was synthesized in a manner similar to that described in Example 66. MS found for C17H22N6O4 as (M+H)⁺ 375.3. UV: λ=257.1, 295.2.

Example 159

(R)-5-(1-amino-1-oxobutan-2-ylamino)-3-(4-(methylsulfonyl)phenylamino)pyrazine-2-carboxamide

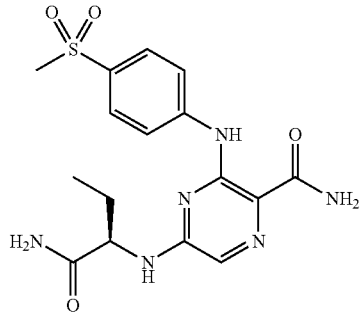 [SMILES: CC[C@@H](Nc1cnc(C(N)=O)c(Nc2ccc(S(C)(=O)=O)cc2)n1)C(N)=O]

The title compound was synthesized in a manner similar to that described in Example 66. MS found for C16H20N6O4S as (M+H)⁺ 393.2. UV: λ=266.5, 311.6.

Example 160

(R)-5-(1-amino-3-methyl-1-oxobutan-2-ylamino)-3-(4-(methylsulfonyl)phenylamino)pyrazine-2-carboxamide

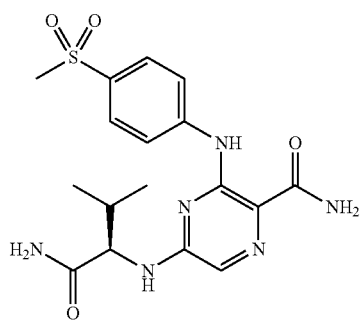 [SMILES: CC(C)[C@@H](Nc1cnc(C(N)=O)c(Nc2ccc(S(C)(=O)=O)cc2)n1)C(N)=O]

The title compound was synthesized in a manner similar to that described in Example 66. MS found for C17H22N6O4S as (M+H)+ 407.3. UV: λ=266.5, 317.6.

Example 161

(R)-5-(1-amino-1-oxobutan-2-ylamino)-3-(4-(N-methylacetamido)phenylamino)pyrazine-2-carboxamide

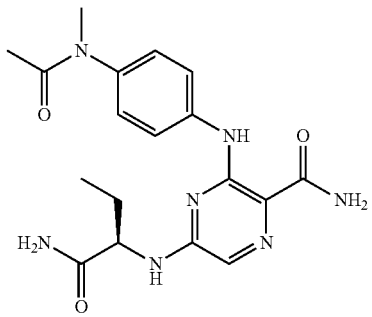 [SMILES: CC[C@@H](Nc1cnc(C(N)=O)c(Nc2ccc(N(C)C(C)=O)cc2)n1)C(N)=O]

The title compound was synthesized in a manner similar to that described in Example 66. MS found for C18H23N7O3 as (M+H)+ 386.3. UV: λ=258.4, 308.8.

Example 162

(R)-5-(1-amino-3-methyl-1-oxobutan-2-ylamino)-3-(3,4-dimethylphenylamino)pyrazine-2-carboxamide

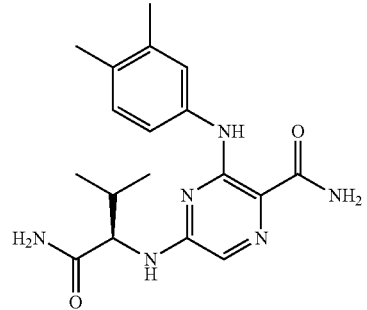 [SMILES: Cc1ccc(Nc2nc(N[C@@H](C(N)=O)C(C)C)cnc2C(N)=O)cc1C]

The title compound was synthesized in a manner similar to that described in Example 66. MS found for C18H24N6O2 as (M+H)+ 357.3. UV: λ=255.8, 303.3.

Example 163

(R)-5-(1-amino-3-methyl-1-oxobutan-2-ylamino)-3-(3,5-dimethylphenylamino)pyrazine-2-carboxamide

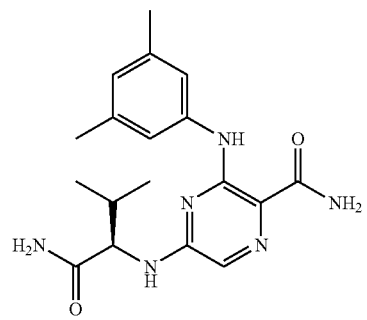 [SMILES: Cc1cc(C)cc(Nc2nc(N[C@@H](C(N)=O)C(C)C)cnc2C(N)=O)c1]

The title compound was synthesized in a manner similar to that described in Example 66. MS found for C18H24N6O2 as (M+H)+ 357.3. UV: λ=254.6, 304.5.

Example 164

(R)-5-(1-amino-3-cyclopropyl-1-oxopropan-2-ylamino)-3-(3,5-dimethoxyphenylamino)pyrazine-2-carboxamide

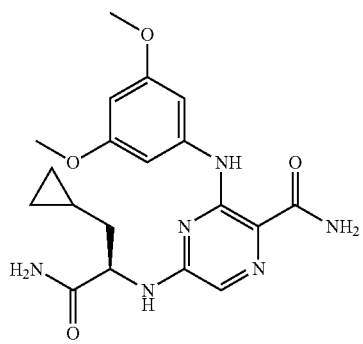 [SMILES: COc1cc(Nc2nc(N[C@H](CC3CC3)C(N)=O)cnc2C(N)=O)cc(OC)c1]

The title compound was synthesized in a manner similar to that described in Example 66. MS found for C19H24N6O4 as (M+H)+ 401.3. UV: λ=255.5, 305.4.

Example 165

5-((1R,2R)-2-amino-3,3-difluorocyclohexylamino)-3-(3,4-dimethoxyphenylamino)pyrazine-2-carboxamide

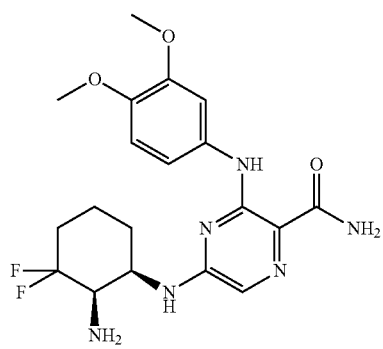 [SMILES: COc1ccc(Nc2nc(N[C@@H]3CCCC(F)(F)[C@@H]3N)cnc2C(N)=O)cc1OC]

The title compound was synthesized in a manner similar to that described in Example 78. MS found for C19H24F2N6O3 as (M+H)+ 423.4. UV: λ=254.9, 302.3.

Example 166

(R)-5-(1-amino-3-cyclopropyl-1-oxopropan-2-ylamino)-3-(4-(methylsulfonyl)phenylamino)pyrazine-2-carboxamide

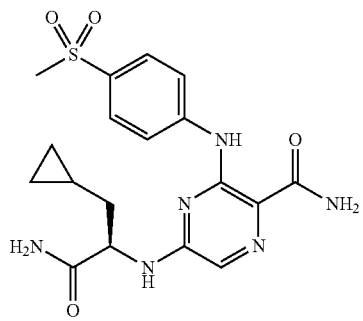 [SMILES: CS(=O)(=O)c1ccc(Nc2nc(N[C@H](CC3CC3)C(N)=O)cnc2C(N)=O)cc1]

The title compound was synthesized in a manner similar to that described in Example 66. MS found for C18H22N6O4S as (M+H)⁺ 419.3. UV: λ=266.3, 318.0.

Example 167

5-((1R,2R)-2-amino-3,3-difluorocyclohexylamino)-3-(4-(methylsulfonyl)phenylamino)pyrazine-2-carboxamide

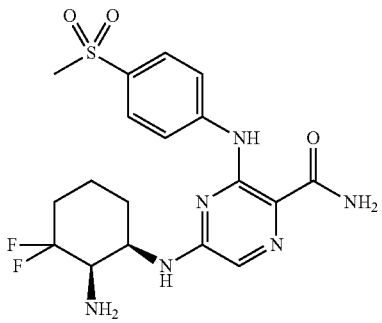 [SMILES: CS(=O)(=O)c1ccc(Nc2nc(N[C@@H]3CCCC(F)(F)[C@@H]3N)cnc2C(N)=O)cc1]

The title compound was synthesized in a manner similar to that described in Example 78. MS found for C18H22F2N6O3S as (M+H)⁺ 441.3. UV: λ=263.3, 317.4.

Example 168

5-((1R,2R)-2-amino-3,3-difluorocyclohexylamino)-3-(3,5-dimethoxyphenylamino)pyrazine-2-carboxamide

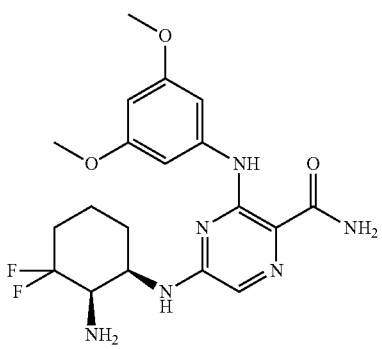 [SMILES: COc1cc(Nc2nc(N[C@@H]3CCCC(F)(F)[C@@H]3N)cnc2C(N)=O)cc(OC)c1]

The title compound was synthesized in a manner similar to that described in Example 78. MS found for C19H24F2N6O3 as (M+H)⁺ 423.3. UV: λ=302.1.

Example 169

5-((1R,2R)-2-amino-3,3-difluorocyclohexylamino)-3-(3,4-dimethylphenylamino)pyrazine-2-carboxamide

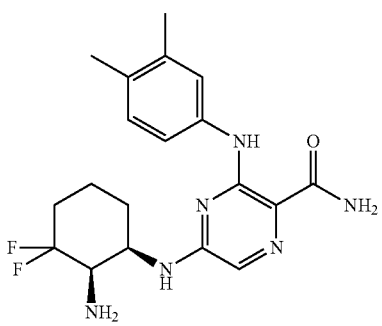 [SMILES: Cc1ccc(Nc2nc(N[C@@H]3CCCC(F)(F)[C@@H]3N)cnc2C(N)=O)cc1C]

The title compound was synthesized in a manner similar to that described in Example 78. MS found for C19H24F2N6O as (M+H)⁺ 391.3. UV: λ=251.0, 302.6.

Example 170

(R)-5-(1-amino-1-oxobutan-2-ylamino)-3-(4-(N,N-dimethylsulfamoyl)phenylamino)pyrazine-2-carboxamide

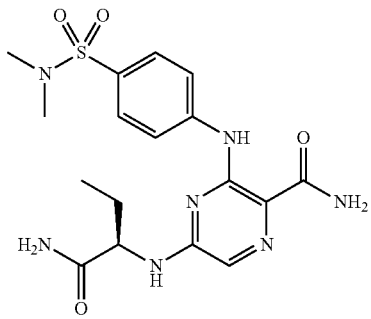 [SMILES: CC[C@@H](Nc1cnc(C(N)=O)c(Nc2ccc(S(=O)(=O)N(C)C)cc2)n1)C(N)=O]

The title compound was synthesized in a manner similar to that described in Example 66. MS found for C17H23N7O4S as (M+H)⁺ 422.4. UV: λ=266.5, 317.6.

Example 171

(R)-5-(1-amino-3-cyclopropyl-1-oxopropan-2-ylamino)-3-(3,4-dimethoxyphenylamino)pyrazine-2-carboxamide

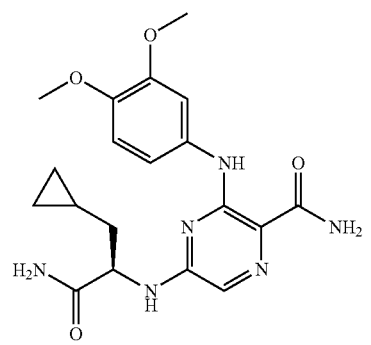 [SMILES: COc1ccc(Nc2nc(N[C@H](CC3CC3)C(N)=O)cnc2C(N)=O)cc1OC]

The title compound was synthesized in a manner similar to that described in Example 66. MS found for C19H24N6O4 as (M+H)⁺ 401.3. UV: λ=259.2, 306.6.

Example 172

(R)-5-(1-amino-3-cyclopropyl-1-oxopropan-2-ylamino)-3-(3,4-dimethylphenylamino)pyrazine-2-carboxamide

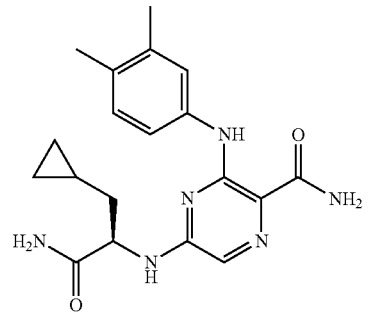 [SMILES: Cc1ccc(Nc2nc(N[C@H](CC3CC3)C(N)=O)cnc2C(N)=O)cc1C]

The title compound was synthesized in a manner similar to that described in Example 66. MS found for C19H24N6O2 as (M+H)+ 369.4. UV: λ=254.6, 304.5.

Example 173

(R)-5-(1-amino-1-oxobutan-2-ylamino)-3-(1-phenyl-1H-pyrazol-4-ylamino)pyrazine-2-carboxamide

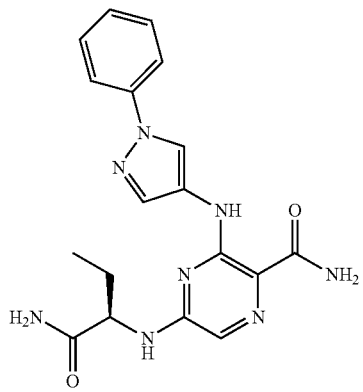 [SMILES: CC[C@@H](Nc1cnc(C(N)=O)c(Nc2cnn(-c3ccccc3)c2)n1)C(N)=O]

The title compound was synthesized in a manner similar to that described in Example 66. MS found for C18H20N8O2 as (M+H)+ 381.3. UV: λ=241.2, 305.1.

Example 174

(R)-5-(1-amino-3-cyclopropyl-1-oxopropan-2-ylamino)-3-(p-tolylamino)pyrazine-2-carboxamide

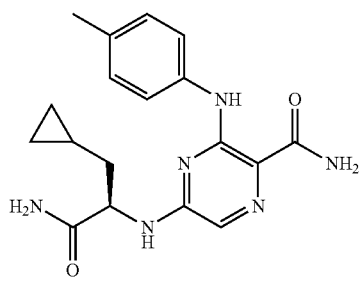 [SMILES: Cc1ccc(Nc2nc(N[C@H](CC3CC3)C(N)=O)cnc2C(N)=O)cc1]

The title compound was synthesized in a manner similar to that described in Example 66. MS found for C18H22N6O2 as (M+H)+ 355.3. UV: λ=253.5, 302.6.

Example 175

5-(1-carbamoylcyclopropylamino)-3-(6-fluoroquinolin-3-ylamino)pyrazine-2-carboxamide

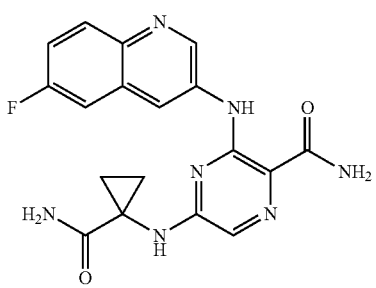 [SMILES: NC(=O)c1ncc(NC2(C(N)=O)CC2)nc1Nc1cnc2ccc(F)cc2c1]

The title compound was synthesized in a manner similar to that described in Example 66. MS found for C18H16FN7O2 as (M+H)+ 382.3. UV: λ=245.7, 295.5.

Example 176

(S)-5-(2-amino-4,4-difluorobutylamino)-3-(3-(pyrimidin-2-yl)phenylamino)pyrazine-2-carboxamide

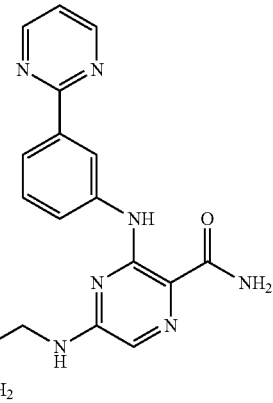

The title compound was synthesized in a manner similar to that described in Example 66. MS found for C19H20F2N8O as (M+H)+ 415.3. UV: λ=207.5, 249.9, 302.1.

Example 177

(R)-5-(1-amino-1-oxobutan-2-ylamino)-3-(5-methylpyridin-3-ylamino)pyrazine-2-carboxamide

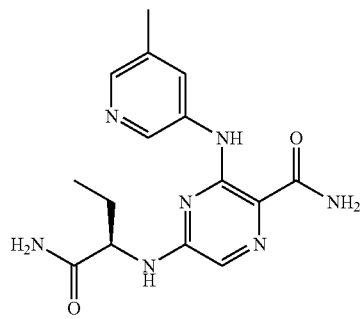 [SMILES: CC[C@@H](Nc1cnc(C(N)=O)c(Nc2cncc(C)c2)n1)C(N)=O]

The title compound was synthesized in a manner similar to that described in Example 66. MS found for C15H19N7O2 as (M+H)+ 330.2. UV: λ=234.5, 261.7, 303.3.

Example 178

(R)-5-(1-amino-1-oxobutan-2-ylamino)-3-(2-methylpyridin-4-ylamino)pyrazine-2-carboxamide

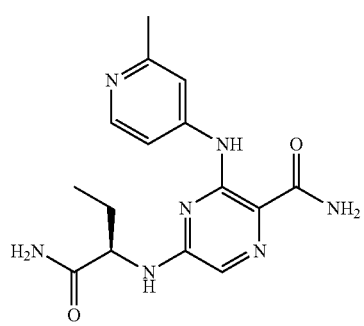 [SMILES: CC[C@@H](Nc1cnc(C(N)=O)c(Nc2ccnc(C)c2)n1)C(N)=O]

The title compound was synthesized in a manner similar to that described in Example 66. MS found for C15H19N7O2 as (M+H)+ 330.2. UV: λ=273.6, 319.9.

Example 179

(R)-5-(1-amino-1-oxobutan-2-ylamino)-3-(2,6-dimethylpyridin-4-ylamino)pyrazine-2-carboxamide

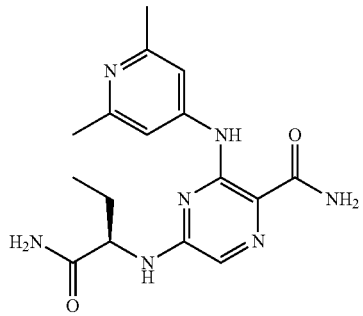 [SMILES: CC[C@@H](Nc1cnc(C(N)=O)c(Nc2cc(C)nc(C)c2)n1)C(N)=O]

The title compound was synthesized in a manner similar to that described in Example 66. MS found for C16H21N7O2 as (M+H)+ 344.2. UV: λ=273.6, 319.9.

Example 180

(R)-5-(1-amino-4-methyl-1-oxopentan-2-ylamino)-3-(1-methyl-1H-pyrazol-3-ylamino)pyrazine-2-carboxamide

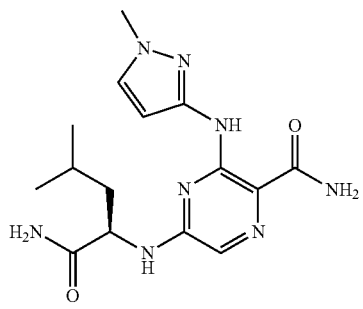 [SMILES: CC(C)C[C@@H](Nc1cnc(C(N)=O)c(Nc2ccn(C)n2)n1)C(N)=O]

The title compound was synthesized in a manner similar to that described in Example 66. MS found for C15H22N8O2 as (M+H)+ 347.2. UV: λ=249.9, 297.3.

Example 181

(R)-5-(1-amino-1-oxobutan-2-ylamino)-3-(pyridin-3-ylamino)pyrazine-2-carboxamide

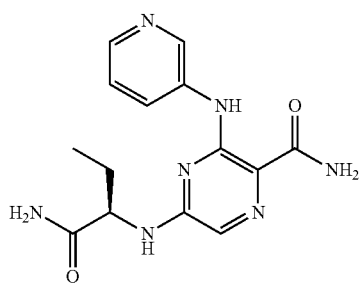 [SMILES: CC[C@@H](Nc1cnc(C(N)=O)c(Nc2cccnc2)n1)C(N)=O]

The title compound was synthesized in a manner similar to that described in Example 66. MS found for C14H17N7O2 as (M+H)+ 316.2. UV: λ=259.4, 302.1.

Example 182

(R)-5-(1-amino-1-oxobutan-2-ylamino)-3-(5-fluoropyridin-3-ylamino)pyrazine-2-carboxamide

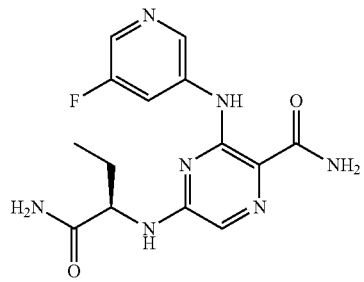

The title compound was synthesized in a manner similar to that described in Example 66. MS found for C14H16FN7O2 as (M+H)+ 334.2. UV: λ=259.4, 299.7.

Example 183

5-((1s,4s)-4-aminocyclohexylamino)-3-(m-tolylamino)pyrazine-2-carboxamide

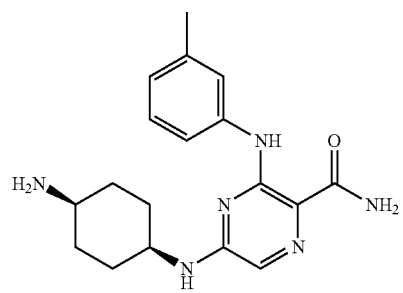 [SMILES: Cc1cccc(Nc2nc(N[C@H]3CC[C@@H](N)CC3)cnc2C(N)=O)c1]

The title compound was synthesized in a manner similar to that described in Example 78. MS found for C18H24N6O as (M+H)+ 341.3. UV: λ=258.2, 304.5.

Example 184

5-((1s,4s)-4-aminocyclohexylamino)-3-(3-(pyrimidin-2-yl)phenylamino)pyrazine-2-carboxamide

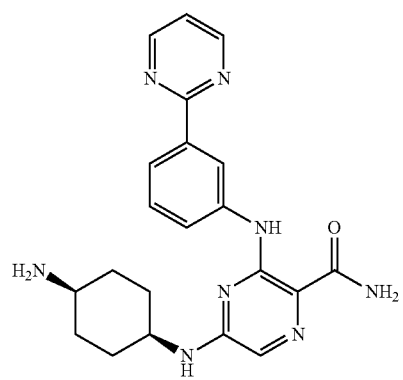 [SMILES: NC(=O)c1ncc(N[C@H]2CC[C@@H](N)CC2)nc1Nc1cccc(-c2ncccn2)c1]

The title compound was synthesized in a manner similar to that described in Example 78. MS found for C21H24N8O as (M+H)+ 405.3. UV: λ=258.2, 304.5.

Example 185

5-((1s,4s)-4-aminocyclohexylamino)-3-(quinolin-3-ylamino)pyrazine-2-carboxamide

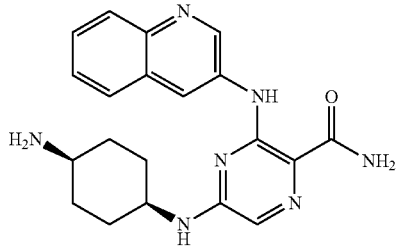 [SMILES: NC(=O)c1ncc(N[C@H]2CC[C@@H](N)CC2)nc1Nc1cnc2ccccc2c1]

The title compound was synthesized in a manner similar to that described in Example 78. MS found for C20H23N7O as (M+H)+ 378.2. UV: λ=249.1, 296.6.

Example 186

5-((1R,2S)-2-aminocyclohexylamino)-3-(1-methyl-1H-pyrazol-4-ylamino)pyrazine-2-carboxamide

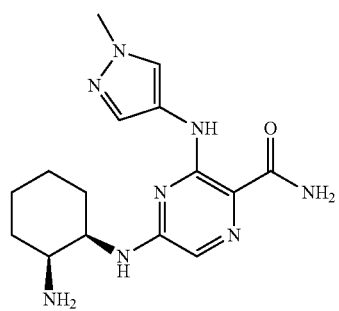 [SMILES: Cn1cc(Nc2nc(N[C@@H]3CCCC[C@@H]3N)cnc2C(N)=O)cn1]

The title compound was synthesized in a manner similar to that described in Example 78. MS found for C15H22N8O as (M+H)+ 331.2. UV: λ=244.0, 292.6.

Example 187

5-((1s,4s)-4-aminocyclohexylamino)-3-(quinolin-6-ylamino)pyrazine-2-carboxamide

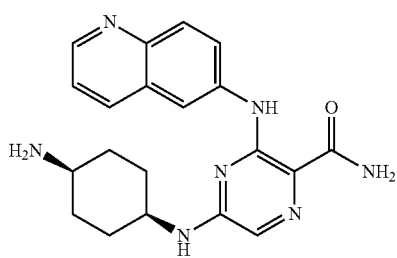 [SMILES: NC(=O)c1ncc(N[C@H]2CC[C@@H](N)CC2)nc1Nc1ccc2ncccc2c1]

The title compound was synthesized in a manner similar to that described in Example 78. MS found for C20H23N7O as (M+H)+ 378.2. UV: λ=268.1, 301.3.

Example 188

3-(3-(2H-1,2,3-triazol-2-yl)phenylamino)-5-((1r,4r)-4-aminocyclohexylamino)pyrazine-2-carboxamide

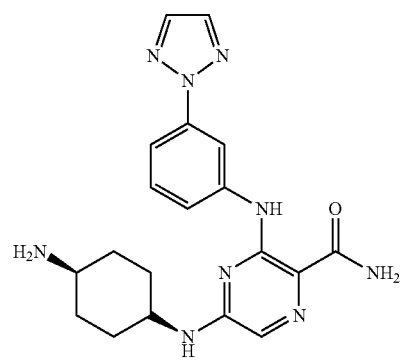

The title compound was synthesized in a manner similar to that described in Example 78. MS found for C19H23N9O as (M+H)+ 394.3. UV: λ=262.9, 305.6.

Example 189

(R)-5-(1-amino-3-methyl-1-oxobutan-2-ylamino)-3-(isoquinolin-6-ylamino)pyrazine-2-carboxamide

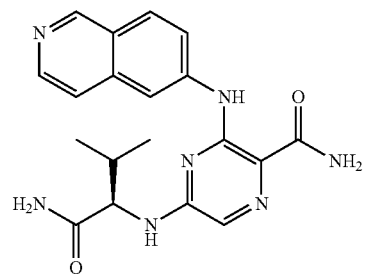 [SMILES: CC(C)[C@@H](Nc1cnc(C(N)=O)c(Nc2ccc3cnccc3c2)n1)C(N)=O]

The title compound was synthesized in a manner similar to that described in Example 66. MS found for C19H21N7O2 as (M+H)+ 380.3. UV: λ=255.8, 284.2.

Example 190

(R)-5-(2-amino-1-cyclopropyl-2-oxoethylamino)-3-(isoquinolin-6-ylamino)pyrazine-2-carboxamide

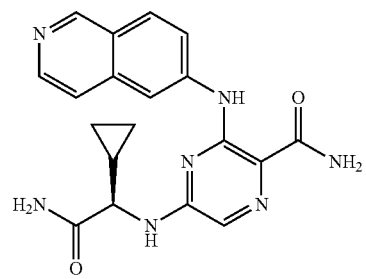 [SMILES: NC(=O)c1ncc(N[C@@H](C(N)=O)C2CC2)nc1Nc1ccc2cnccc2c1]

The title compound was synthesized in a manner similar to that described in Example 66. MS found for C19H19N7O2 as (M+H)+ 378.2. UV: λ=222.8, 255.8, 279.5.

Example 191

(R)-5-(1-amino-3,3-dimethyl-1-oxobutan-2-ylamino)-3-(quinolin-3-ylamino)pyrazine-2-carboxamide

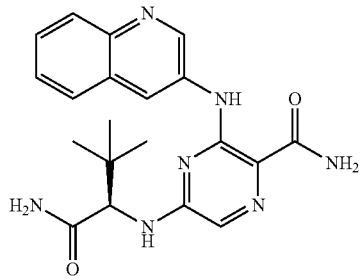

The title compound was synthesized in a manner similar to that described in Example 66. MS found for C20H23N7O2 as (M+H)+ 394.2. UV: λ=247.5, 304.5.

Example 192

(R)-5-(1-amino-3,3-dimethyl-1-oxobutan-2-ylamino)-3-(quinolin-6-ylamino)pyrazine-2-carboxamide

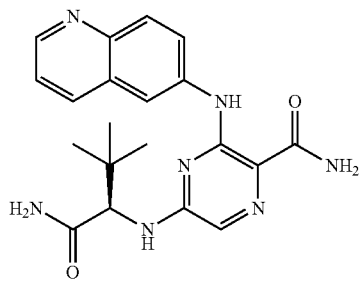 [SMILES: CC(C)(C)[C@@H](Nc1cnc(C(N)=O)c(Nc2ccc3ncccc3c2)n1)C(N)=O]

The title compound was synthesized in a manner similar to that described in Example 66. MS found for C20H23N7O2 as (M+H)+ 394.3. UV: λ=216.9, 265.3, 293.8.

Example 193

(R)-3-(1,5-naphthyridin-3-ylamino)-5-(1-amino-3-methyl-1-oxobutan-2-ylamino)pyrazine-2-carboxamide

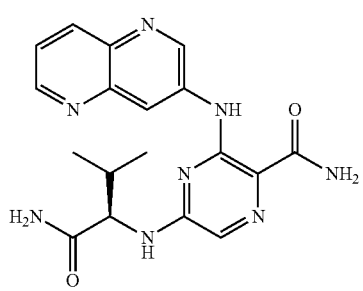 [SMILES: CC(C)[C@@H](Nc1cnc(C(N)=O)c(Nc2cnc3cccnc3c2)n1)C(N)=O]

The title compound was synthesized in a manner similar to that described in Example 66. MS found for C18H20N8O2 as (M+H)+ 381.1. UV: λ=206.3, 252.3, 304.5.

Example 194

(R)-3-(1,6-naphthyridin-3-ylamino)-5-(1-amino-3-methyl-1-oxobutan-2-ylamino)pyrazine-2-carboxamide

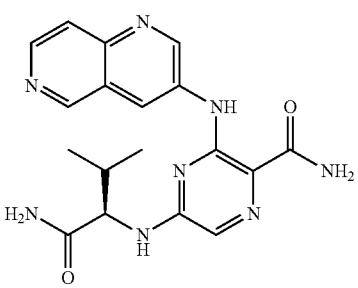 [SMILES: CC(C)[C@@H](Nc1cnc(C(N)=O)c(Nc2cnc3ccncc3c2)n1)C(N)=O]

The title compound was synthesized in a manner similar to that described in Example 66. MS found for C18H20N8O2 as (M+H)+ 381.3. UV: λ=260.5, 314.0.

Example 195

(R)-5-(1-amino-3-methyl-1-oxobutan-2-ylamino)-3-(isoquinolin-7-ylamino)pyrazine-2-carboxamide

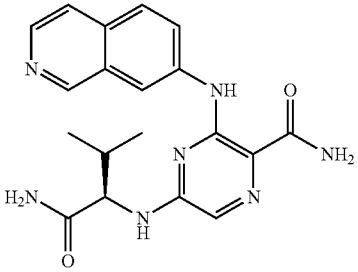 [SMILES: CC(C)[C@@H](Nc1cnc(C(N)=O)c(Nc2ccc3ccncc3c2)n1)C(N)=O]

The title compound was synthesized in a manner similar to that described in Example 66. MS found for C19H21N7O2 as (M+H)+ 380.3. UV: λ=262.9, 312.8.

Example 196

(R)-5-(1-amino-4-methyl-1-oxopentan-2-ylamino)-3-(5-(trifluoromethyl)pyridin-3-ylamino)pyrazine-2-carboxamide

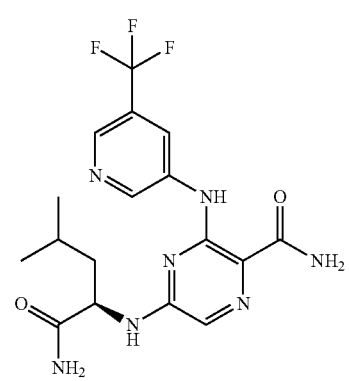 [SMILES: CC(C)C[C@@H](Nc1cnc(C(N)=O)c(Nc2cncc(C(F)(F)F)c2)n1)C(N)=O]

The title compound was synthesized in a manner similar to that described in Example 66. MS found for C17H20F3N7O2 as (M+H)+ 412.3. UV: λ=261.7, 299.7.

Example 197

5-((1R,2S)-2-aminocyclohexylamino)-3-(5-(trifluoromethyl)pyridin-3-ylamino)pyrazine-2-carboxamide

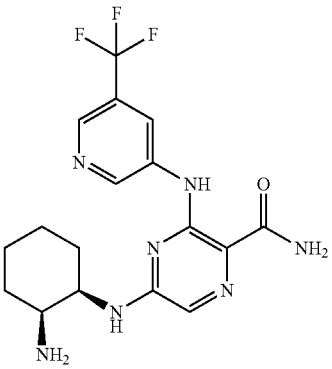 [SMILES: NC(=O)c1ncc(N[C@@H]2CCCC[C@@H]2N)nc1Nc1cncc(C(F)(F)F)c1]

The title compound was synthesized in a manner similar to that described in Example 78. MS found for C17H20F3N7O as (M+H)+ 396.3. UV: λ=260.5, 302.1.

Example 198

5-((1R,2S)-2-aminocyclohexylamino)-3-(6-fluoroquinolin-3-ylamino)pyrazine-2-carboxamide

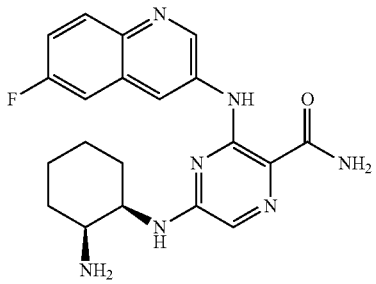 [SMILES: NC(=O)c1ncc(N[C@@H]2CCCC[C@@H]2N)nc1Nc1cnc2ccc(F)cc2c1]

The title compound was synthesized in a manner similar to that described in Example 78. MS found for C20H22FN7O as (M+H)+ 396.3. UV: λ=245.2, 302.1.

Example 199

5-((1R,2S)-2-aminocyclohexylamino)-3-(3-(trifluoromethyl)phenylamino)pyrazine-2-carboxamide

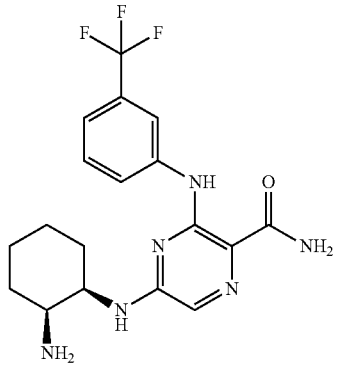 [SMILES: NC(=O)c1ncc(N[C@@H]2CCCC[C@@H]2N)nc1Nc1cccc(C(F)(F)F)c1]

The title compound was synthesized in a manner similar to that described in Example 78. MS found for C18H21F3N6O as (M+H)+ 395.3. UV: λ=255.8, 303.3.

Example 200

(R)-5-(1-amino-3-methyl-1-oxobutan-2-ylamino)-3-(6-fluoroquinolin-3-ylamino)pyrazine-2-carboxamide

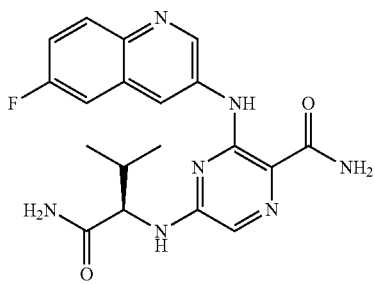 [SMILES: CC(C)[C@@H](Nc1cnc(C(N)=O)c(Nc2cnc3ccc(F)cc3c2)n1)C(N)=O]

The title compound was synthesized in a manner similar to that described in Example 66. MS found for C19H20FN7O2 as (M+H)+ 398.3. UV: λ=246.3, 294.9.

Example 201

5-((1R,2S)-2-aminocyclohexylamino)-3-(7-fluoroquinolin-3-ylamino)pyrazine-2-carboxamide

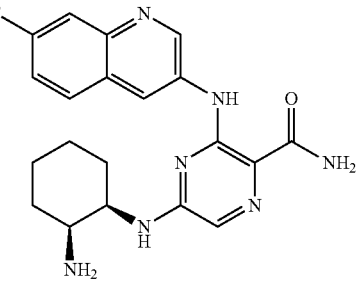

The title compound was synthesized in a manner similar to that described in Example 78. MS found for C20H22FN7O as (M+H)+ 396.5. UV: λ=251.1, 292.6.

Example 202

5-((1R,2S)-2-aminocyclohexylamino)-3-(8-fluoroquinolin-3-ylamino)pyrazine-2-carboxamide

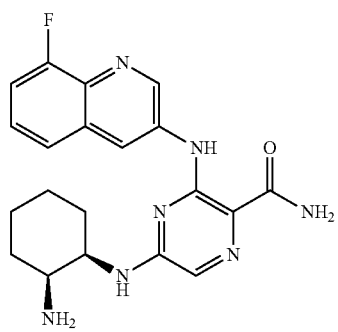 [SMILES: NC(=O)c1ncc(N[C@@H]2CCCC[C@@H]2N)nc1Nc1cnc2c(F)cccc2c1]

The title compound was synthesized in a manner similar to that described in Example 78. MS found for C20H22FN7O as (M+H)+ 396.4. UV: λ=254.6, 302.1.

Example 203

(R)-5-(1-amino-3-methyl-1-oxobutan-2-ylamino)-3-(7-fluoroquinolin-3-ylamino)pyrazine-2-carboxamide

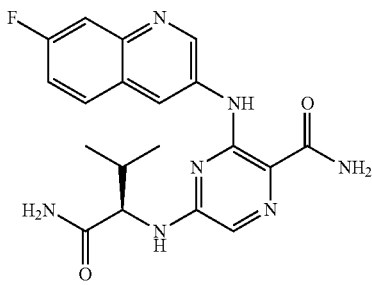 [SMILES: CC(C)[C@@H](Nc1cnc(C(N)=O)c(Nc2cnc3cc(F)ccc3c2)n1)C(N)=O]

The title compound was synthesized in a manner similar to that described in Example 78. MS found for C19H20FN7O2 as (M+H)+ 398.4. UV: λ=251.1, 292.6.

Example 204

(R)-5-(1-amino-3-methyl-1-oxobutan-2-ylamino)-3-(8-fluoroquinolin-3-ylamino)pyrazine-2-carboxamide

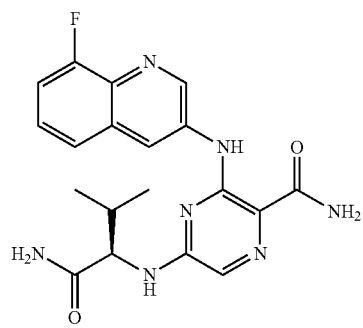 [SMILES: CC(C)[C@@H](Nc1cnc(C(N)=O)c(Nc2cnc3c(F)cccc3c2)n1)C(N)=O]

The title compound was synthesized in a manner similar to that described in Example 66. MS found for C19H20FN7O2 as (M+H)+ 398.4. UV: λ=247.5, 293.8.

Example 205

5-((1R,2S)-2-aminocyclohexylamino)-3-(8-fluoroquinolin-6-ylamino)pyrazine-2-carboxamide

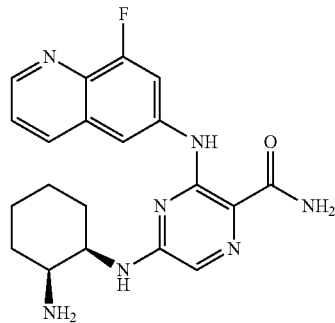 [SMILES: NC(=O)c1ncc(N[C@@H]2CCCC[C@@H]2N)nc1Nc1cc(F)c2ncccc2c1]

The title compound was synthesized in a manner similar to that described in Example 78. MS found for C20H22FN7O as (M+H)+ 396.4. UV: λ=267.6, 299.7.

Example 206

(R)-5-(1-amino-3-methyl-1-oxobutan-2-ylamino)-3-(8-fluoroquinolin-6-ylamino)pyrazine-2-carboxamide

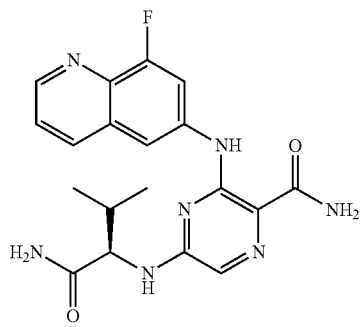 [SMILES: CC(C)[C@@H](Nc1cnc(C(N)=O)c(Nc2cc(F)c3ncccc3c2)n1)C(N)=O]

The title compound was synthesized in a manner similar to that described in Example 66. MS found for C19H20FN7O2 as (M+H)+ 398.3. UV: λ=261.7, 292.6.

Example 207

5-((1R,2S)-2-aminocyclohexylamino)-3-(4-methyl-3-oxo-3,4-dihydro-2H-benzo[b][1,4]oxazin-6-ylamino)pyrazine-2-carboxamide

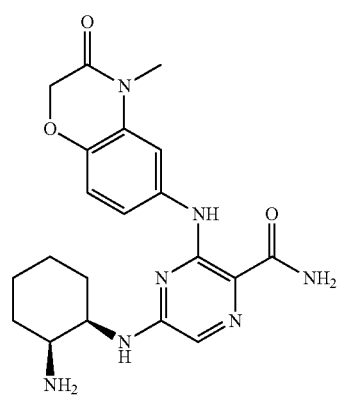 [SMILES: CN1C(=O)COc2ccc(Nc3nc(N[C@@H]4CCCC[C@@H]4N)cnc3C(N)=O)cc21]

The title compound was synthesized in a manner similar to that described in Example 78. MS found for C20H25N7O3 as (M+H)+ 412.3. UV: λ=239.3, 302.1.

Example 208

(R)-5-(1-amino-1-oxobutan-2-ylamino)-3-(8-fluoroquinolin-6-ylamino)pyrazine-2-carboxamide

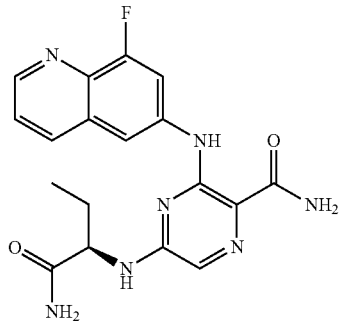 [SMILES: CC[C@@H](Nc1cnc(C(N)=O)c(Nc2cc(F)c3ncccc3c2)n1)C(N)=O]

The title compound was synthesized in a manner similar to that described in Example 66. MS found for C18H18FN7O2 as (M+H)⁺ 384.3. UV: λ=265.3, 308.0.

Example 209

(R)-5-(1-amino-3-methyl-1-oxobutan-2-ylamino)-3-(4-(pyridin-2-yl)phenylamino)pyrazine-2-carboxamide

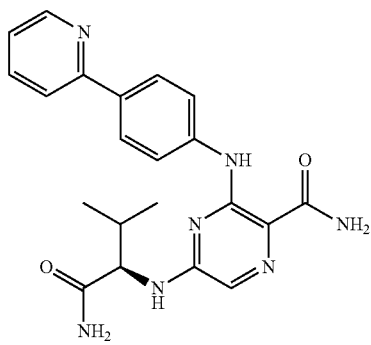 [SMILES: CC(C)[C@@H](Nc1cnc(C(N)=O)c(Nc2ccc(-c3ccccn3)cc2)n1)C(N)=O]

The title compound was synthesized in a manner similar to that described in Example 66. MS found for C21H23N7O2 as (M+H)⁺ 406.4. UV: λ=209.8, 279.5, 330.0.

Example 210

5-((1R,2R)-2-amino-3,3-difluorocyclohexylamino)-3-(8-fluoroquinolin-6-ylamino)pyrazine-2-carboxamide

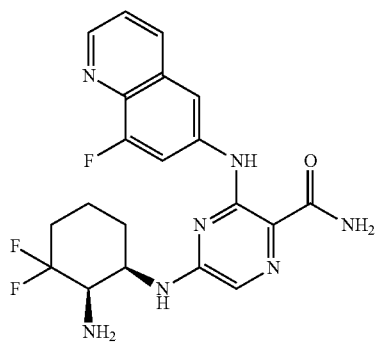 [SMILES: NC(=O)c1ncc(N[C@@H]2CCCC(F)(F)[C@@H]2N)nc1Nc1cc(F)c2ncccc2c1]

The title compound was synthesized in a manner similar to that described in Example 14. MS found for C20H20F3N7O as (M+H)⁺ 432.4. UV: λ=214.5, 266.5, 298.5.

Example 211

(R)-5-(1-amino-1-oxobutan-2-ylamino)-3-(1-methyl-1H-pyrazol-4-ylamino)pyrazine-2-carboxamide

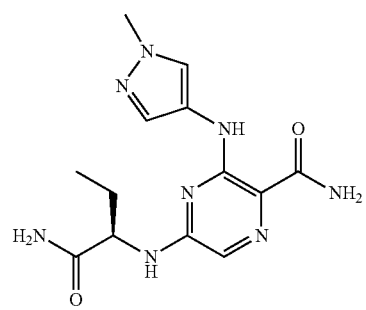 [SMILES: CC[C@@H](Nc1cnc(C(N)=O)c(Nc2cnn(C)c2)n1)C(N)=O]

The title compound was synthesized in a manner similar to that described in Example 66. MS found for C13H18N8O2 as (M+H)⁺ 319.3. UV: λ=242.8, 293.8.

Example 212

(R)-5-(1-amino-3-methyl-1-oxobutan-2-ylamino)-3-(3-methylisothiazol-5-ylamino)pyrazine-2-carboxamide

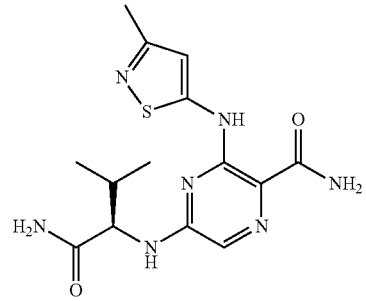 [SMILES: Cc1cc(Nc2nc(N[C@@H](C(N)=O)C(C)C)cnc2C(N)=O)sn1]

The title compound was synthesized in a manner similar to that described in Example 66. MS found for C14H19N7O2S as (M+H)⁺ 350.3. UV: λ=274.8, 316.4.

Example 213

5-((1R,2S)-2-aminocyclohexylamino)-3-(pyridazin-4-ylamino)pyrazine-2-carboxamide

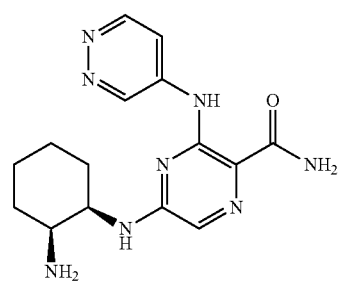 [SMILES: NC(=O)c1ncc(N[C@@H]2CCCC[C@@H]2N)nc1Nc1ccnnc1]

The title compound was synthesized in a manner similar to that described in Example 78. MS found for C15H20N8O as (M+H)+ 329.3. UV: λ=257.0, 292.6, 325.9.

Example 214

(R)-5-(1-amino-3,3-dimethyl-1-oxobutan-2-ylamino)-3-(3-methylisothiazol-5-ylamino)pyrazine-2-carboxamide

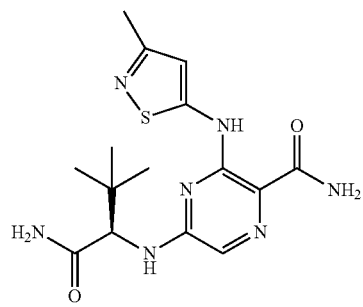 [SMILES: Cc1cc(Nc2nc(N[C@@H](C(N)=O)C(C)(C)C)cnc2C(N)=O)sn1]

The title compound was synthesized in a manner similar to that described in Example 66. MS found for C15H21N7O2S as (M+H)+ 364.4. UV: λ=277.1, 314.0.

Example 215

(R)-5-(1-amino-1-oxopropan-2-ylamino)-3-(3-methylisothiazol-5-ylamino)pyrazine-2-carboxamide

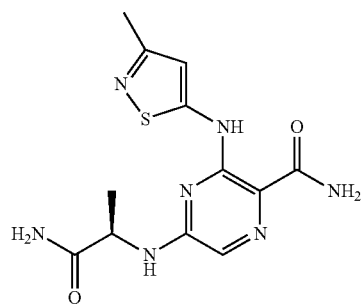 [SMILES: Cc1cc(Nc2nc(N[C@H](C)C(N)=O)cnc2C(N)=O)sn1]

The title compound was synthesized in a manner similar to that described in Example 66. MS found for C12H15N7O2S as (M+H)+ 322.4. UV: λ=274.8, 322.3.

Example 216

(R)-5-(1-amino-4-methyl-1-oxopentan-2-ylamino)-3-(5-chloropyridin-3-ylamino)pyrazine-2-carboxamide

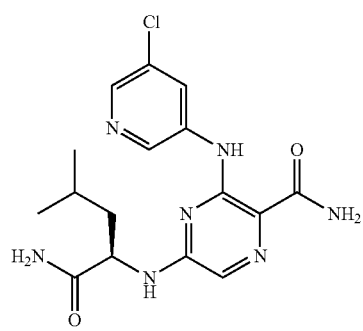

The title compound was synthesized in a manner similar to that described in Example 66. MS found for C16H20ClN7O2 as (M+H)+ 378.3, 380.3. UV: λ=211.0, 262.9, 304.5.

Example 217

5-(((1R,2S)-2-aminocyclohexylamino)-3-(5-chloropyridin-3-ylamino)pyrazine-2-carboxamide

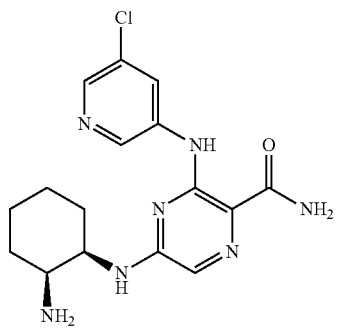 [SMILES: NC(=O)c1ncc(N[C@@H]2CCCC[C@@H]2N)nc1Nc1cncc(Cl)c1]

The title compound was synthesized in a manner similar to that described in Example 78. MS found for C16H20ClN7O as (M+H)+ 362.3, 364.3. UV: λ=262.9, 304.5.

Example 218

(R)-5-(1-amino-1-oxobutan-2-ylamino)-3-(1-(cyclopropylmethyl)-1H-pyrazol-4-ylamino)pyrazine-2-carboxamide

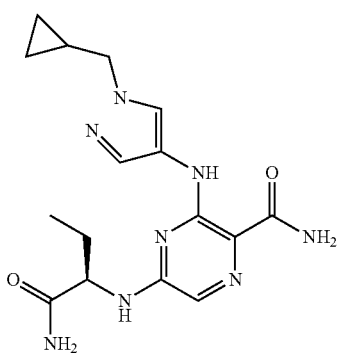 [SMILES: CC[C@@H](Nc1cnc(C(N)=O)c(N/C(C=N)=C/NCC2CC2)n1)C(N)=O]

The title compound was synthesized in a manner similar to that described in Example 66. MS found for C16H22N8O2 as (M+H)+ 359.4. UV: λ=244.0, 292.6.

Example 219

5-((1R,2S)-2-aminocyclohexylamino)-3-(1-(cyclo-propylmethyl)-1H-pyrazol-4-ylamino)pyrazine-2-carboxamide

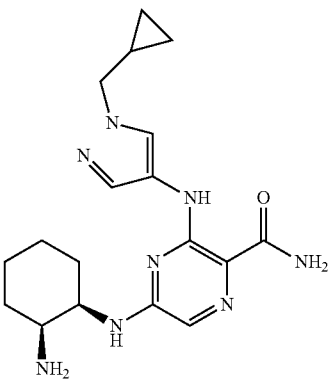 [SMILES: N=C/C(=C\NCC1CC1)Nc1nc(N[C@@H]2CCCC[C@@H]2N)cnc1C(N)=O]

The title compound was synthesized in a manner similar to that described in Example 78. MS found for Cl8H26N8O as (M+H)⁺ 371.4. UV: λ=244.0, 291.4.

Example 220

5-(1-carbamoylcyclopropylamino)-3-(3-methyl-isothiazol-5-ylamino)pyrazine-2-carboxamide

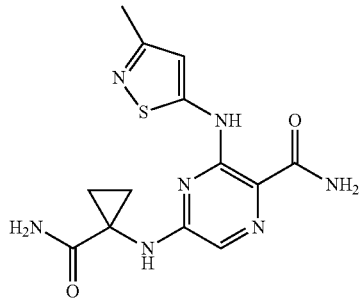 [SMILES: Cc1cc(Nc2nc(NC3(C(N)=O)CC3)cnc2C(N)=O)sn1]

The title compound was synthesized in a manner similar to that described in Example 66. MS found for C13H15N7O2S as (M+H)⁺ 334.3. UV: λ=245.2, 273.6, 324.7.

Example 221

(R)-5-(1-amino-1-oxobutan-2-ylamino)-3-(3-ethyl-isothiazol-5-ylamino)pyrazine-2-carboxamide

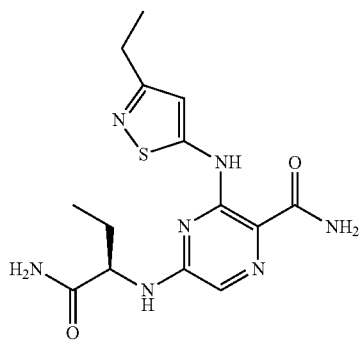 [SMILES: CCc1cc(Nc2nc(N[C@H](CC)C(N)=O)cnc2C(N)=O)sn1]

The title compound was synthesized in a manner similar to that described in Example 66. MS found for C14H19N7O2S as (M+H)⁺ 350.3. UV: λ=212.2, 275.9, 315.2.

Example 222

(R)-5-(1-amino-3-methyl-1-oxobutan-2-ylamino)-3-(5-chloropyridin-3-ylamino)pyrazine-2-carboxamide

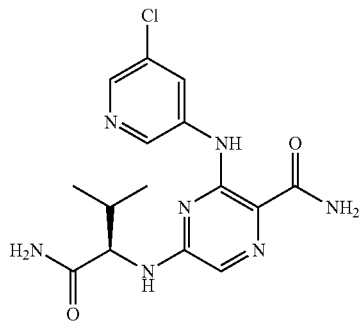 [SMILES: CC(C)[C@@H](Nc1cnc(C(N)=O)c(Nc2cncc(Cl)c2)n1)C(N)=O]

The title compound was synthesized in a manner similar to that described in Example 66. MS found for C15H18ClN7O2 as (M+H)⁺ 364.3, 366.3. UV: λ=264.1, 306.8.

Example 223

(R)-5-(1-amino-1-oxobutan-2-ylamino)-3-(5-chloro-pyridin-3-ylamino)pyrazine-2-carboxamide

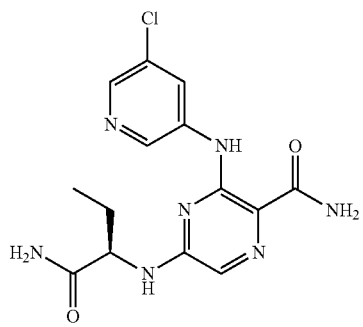 [SMILES: CC[C@@H](Nc1cnc(C(N)=O)c(Nc2cncc(Cl)c2)n1)C(N)=O]

The title compound was synthesized in a manner similar to that described in Example 66. MS found for C14H16ClN7O2 as (M+H)⁺ 350.3, 352.3. UV: λ=262.9, 306.8.

Example 224

(R)-5-(1-amino-3-methyl-1-oxobutan-2-ylamino)-3-(3-ethylisothiazol-5-ylamino)pyrazine-2-carboxamide

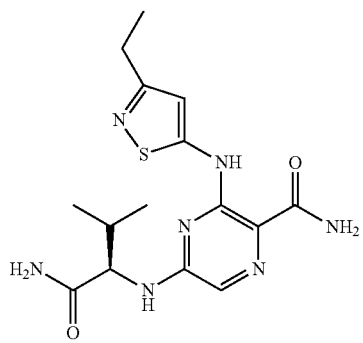 [SMILES: CCc1cc(Nc2nc(N[C@@H](C(N)=O)C(C)C)cnc2C(N)=O)sn1]

The title compound was synthesized in a manner similar to that described in Example 66. MS found for C15H21N7O2S as (M+H)+ 364.2. UV: λ=209.8, 275.9, 323.5.

Example 225

(R)-5-(1-amino-3-cyclopropyl-1-oxopropan-2-ylamino)-3-(3-ethylisothiazol-5-ylamino)pyrazine-2-carboxamide

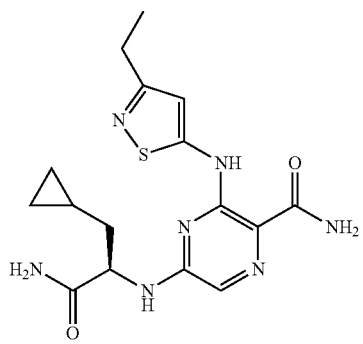 [SMILES: CCc1cc(Nc2nc(N[C@H](CC3CC3)C(N)=O)cnc2C(N)=O)sn1]

The title compound was synthesized in a manner similar to that described in Example 66. MS found for C16H21N7O2S as (M+H)+ 376.2. UV: λ=212.2, 274.8, 316.4.

Example 226

5-((1R,2R)-2-amino-3,3-difluorocyclohexylamino)-3-(3-ethylisothiazol-5-ylamino)pyrazine-2-carboxamide

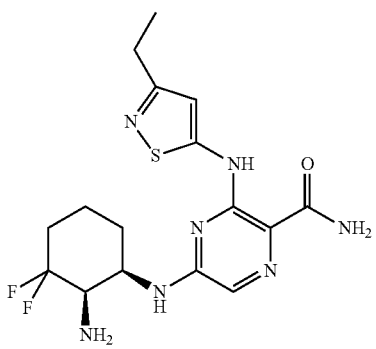 [SMILES: CCc1cc(Nc2nc(N[C@@H]3CCCC(F)(F)[C@@H]3N)cnc2C(N)=O)sn1]

The title compound was synthesized in a manner similar to that described in Example 23. MS found for C16H21F2N7OS as (M+H)+ 398.3. UV: λ=209.8, 271.2, 319.9.

Example 227

5-((1R,2R)-2-amino-3,3-difluorocyclohexylamino)-3-(7-fluoroquinolin-3-ylamino)pyrazine-2-carboxamide

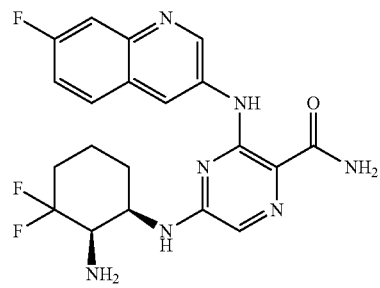 [SMILES: NC(=O)c1ncc(N[C@@H]2CCCC(F)(F)[C@@H]2N)nc1Nc1cnc2cc(F)ccc2c1]

The title compound was synthesized in a manner similar to that described in Example 14. MS found for C20H20F3N7O as (M+H)+ 432.2. UV: λ=215.7, 246.3, 291.4.

Example 228

(R)-5-(1-amino-1-oxobutan-2-ylamino)-3-(3-tert-butylisothiazol-5-ylamino)pyrazine-2-carboxamide

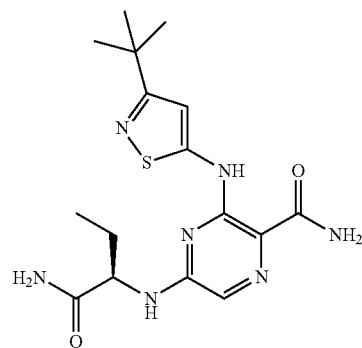 [SMILES: CC[C@@H](Nc1cnc(C(N)=O)c(Nc2cc(C(C)(C)C)ns2)n1)C(N)=O]

The title compound was synthesized in a manner similar to that described in Example 66. MS found for C16H23N7O2S as (M+H)+ 378.2. UV: λ=212.2, 275.9, 327.1.

Example 229

(R)-5-(1-amino-3-cyclopropyl-1-oxopropan-2-ylamino)-3-(3-tert-butylisothiazol-5-ylamino)pyrazine-2-carboxamide

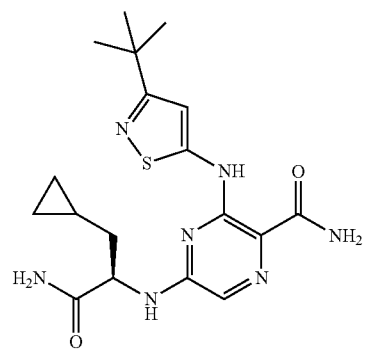 [SMILES: CC(C)(C)c1cc(Nc2nc(N[C@H](CC3CC3)C(N)=O)cnc2C(N)=O)sn1]

The title compound was synthesized in a manner similar to that described in Example 66. MS found for C18H25N7O2S as (M+H)+ 404.3. UV: λ=211.0, 275.9, 324.7.

Example 230

5-((1R,2R)-2-amino-3,3-difluorocyclohexylamino)-3-(4-methyl-3-oxo-3,4-dihydro-2H-benzo[b][1,4]oxazin-6-ylamino)pyrazine-2-carboxamide

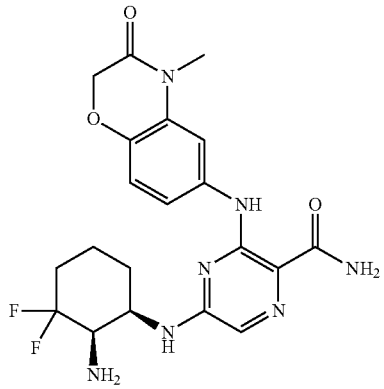 [SMILES: CN1C(=O)COc2ccc(Nc3nc(N[C@@H]4CCCC(F)(F)[C@@H]4N)cnc3C(N)=O)cc21]

The title compound was synthesized in a manner similar to that described in Example 14. MS found for C20H23F2N7O3 as (M+H)+ 448.4. UV: λ=238.1, 300.9.

Example 231

5-((1R,2S)-2-aminocyclohexylamino)-3-(3-cyclopropylisoxazol-5-ylamino)pyrazine-2-carboxamide

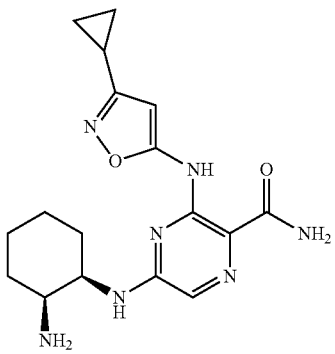 [SMILES: NC(=O)c1ncc(N[C@@H]2CCCC[C@@H]2N)nc1Nc1cc(C2CC2)no1]

The title compound was synthesized in a manner similar to that described in Example 78. MS found for C17H23N7O2 as (M+H)+ 358.3. UV: λ=255.8, 297.3.

Example 232

(R)-5-(1-amino-1-oxobutan-2-ylamino)-3-(6-fluoroquinolin-3-ylamino)pyrazine-2-carboxamide

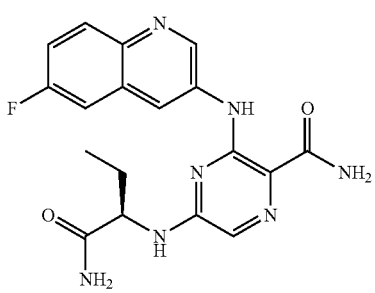 [SMILES: CC[C@@H](Nc1cnc(C(N)=O)c(Nc2cnc3ccc(F)cc3c2)n1)C(N)=O]

The title compound was synthesized in a manner similar to that described in Example 66. MS found for C18H18FN7O2 as (M+H)+ 384.3. UV: λ=226.3, 244.0, 294.9.

Example 233

(R)-5-(1-amino-1-oxobutan-2-ylamino)-3-(7-fluoroquinolin-3-ylamino)pyrazine-2-carboxamide

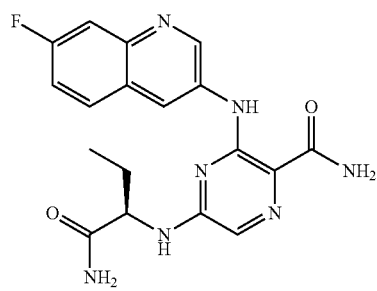 [SMILES: CC[C@@H](Nc1cnc(C(N)=O)c(Nc2cnc3cc(F)ccc3c2)n1)C(N)=O]

The title compound was synthesized in a manner similar to that described in Example 66. MS found for C18H18FN7O2 as (M+H)+ 384.3. UV: λ=251.1, 293.8.

Example 234

(R)-5-(1-amino-3,3-dimethyl-1-oxobutan-2-ylamino)-3-(6-fluoroquinolin-3-ylamino)pyrazine-2-carboxamide

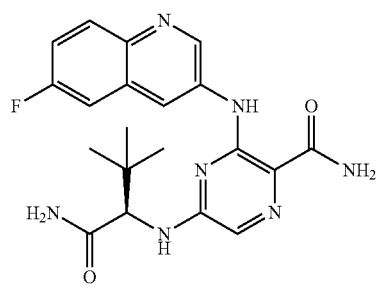

The title compound was synthesized in a manner similar to that described in Example 66. MS found for C20H22FN7O2 as (M+H)+ 412.4. UV: λ=247.5, 296.1.

Example 235

(R)-5-(1-amino-3,3-dimethyl-1-oxobutan-2-ylamino)-3-(quinolin-7-ylamino)pyrazine-2-carboxamide

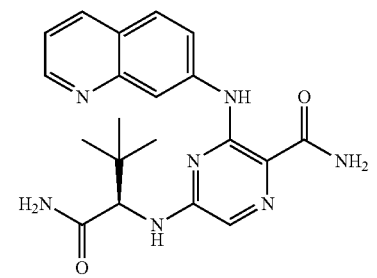 [SMILES: CC(C)(C)[C@@H](Nc1cnc(C(N)=O)c(Nc2ccc3cccnc3c2)n1)C(N)=O]

The title compound was synthesized in a manner similar to that described in Example 66. MS found for C20H23N7O2 as (M+H)+ 394.4. UV: λ=262.9, 292.6.

Example 236

(R)-5-(1-amino-3,3-dimethyl-1-oxobutan-2-ylamino)-3-(3-ethylisothiazol-5-ylamino)pyrazine-2-carboxamide

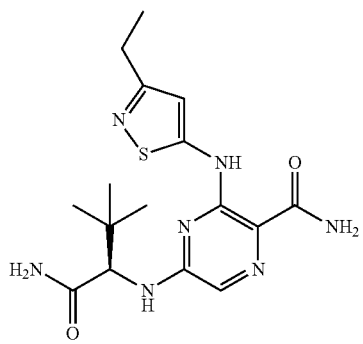 [SMILES: CCc1cc(Nc2nc(N[C@@H](C(N)=O)C(C)(C)C)cnc2C(N)=O)sn1]

The title compound was synthesized in a manner similar to that described in Example 66. MS found for C16H23N7O2S as (M+H)+ 378.3. UV: λ=275.9, 327.1.

Example 237

(R)-3-(1,5-naphthyridin-3-ylamino)-5-(1-amino-3,3-dimethyl-1-oxobutan-2-ylamino)pyrazine-2-carboxamide

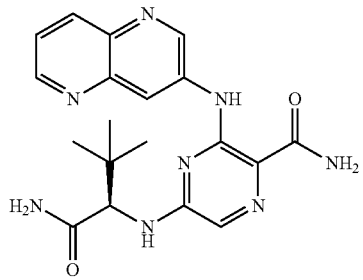 [SMILES: CC(C)(C)[C@@H](Nc1cnc(C(N)=O)c(Nc2cnc3cccnc3c2)n1)C(N)=O]

The title compound was synthesized in a manner similar to that described in Example 66. MS found for C19H22N8O2 as (M+H)+ 395.4. UV: λ=252.3, 305.6.

Example 238

(R)-5-(1-amino-1-oxobutan-2-ylamino)-3-(3-cyclopropylisothiazol-5-ylamino)pyrazine-2-carboxamide

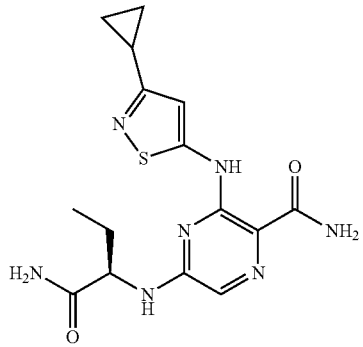 [SMILES: CC[C@@H](Nc1cnc(C(N)=O)c(Nc2cc(C3CC3)ns2)n1)C(N)=O]

The title compound was synthesized in a manner similar to that described in Example 66. MS found for C15H19N7O2S as (M+H)+ 362.3. UV: λ=278.3, 325.9.

Example 239

(R)-5-(1-amino-1-oxopropan-2-ylamino)-3-(3-cyclopropylisothiazol-5-ylamino)pyrazine-2-carboxamide

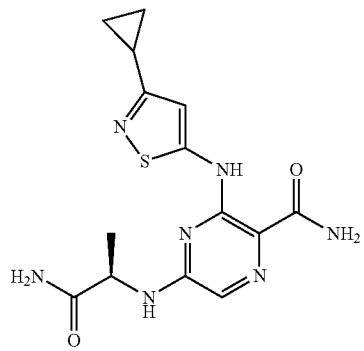 [SMILES: C[C@@H](Nc1cnc(C(N)=O)c(Nc2cc(C3CC3)ns2)n1)C(N)=O]

The title compound was synthesized in a manner similar to that described in Example 66. MS found for C14H17N7O2S as (M+H)+ 348.3. UV: λ=275.9, 325.9.

Example 240

(R)-5-(1-amino-1-oxobutan-2-ylamino)-3-(3-isopropylisothiazol-5-ylamino)pyrazine-2-carboxamide

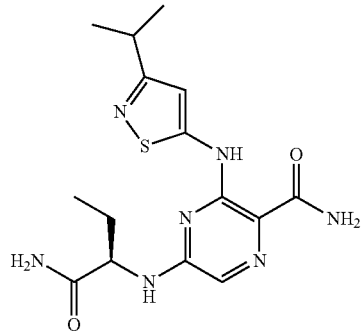 [SMILES: CC[C@@H](Nc1cnc(C(N)=O)c(Nc2cc(C(C)C)ns2)n1)C(N)=O]

The title compound was synthesized in a manner similar to that described in Example 66. MS found for C15H21N7O2S as (M+H)+ 364.3. UV: λ=275.9, 316.4.

Example 241

(R)-5-(1-amino-1-oxopropan-2-ylamino)-3-(3-isopropylisothiazol-5-ylamino)pyrazine-2-carboxamide

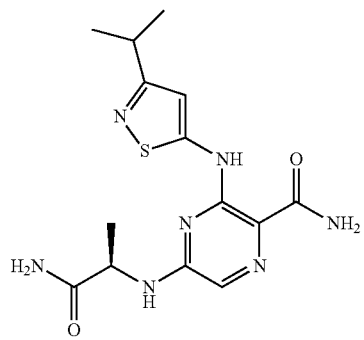 [SMILES: CC(C)c1cc(Nc2nc(N[C@H](C)C(N)=O)cnc2C(N)=O)sn1]

The title compound was synthesized in a manner similar to that described in Example 66. MS found for C14H19N7O2S as (M+H)+ 350.3. UV: λ=274.8, 322.3.

Example 242

5-((1R,2R)-2-amino-3,3-difluorocyclohexylamino)-3-(3-cyclopropylisothiazol-5-ylamino)pyrazine-2-carboxamide

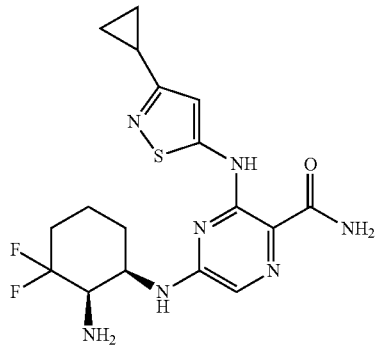 [SMILES: NC(=O)c1ncc(N[C@@H]2CCCC(F)(F)[C@@H]2N)nc1Nc1cc(C2CC2)ns1]

The title compound was synthesized in a manner similar to that described in Example 23. MS found for C17H21F2N7OS as (M+H)+ 410.4. UV: λ=271.2, 318.8.

Example 243

(R)-5-(1-amino-1-oxopropan-2-ylamino)-3-(6-fluoroquinolin-3-ylamino)pyrazine-2-carboxamide

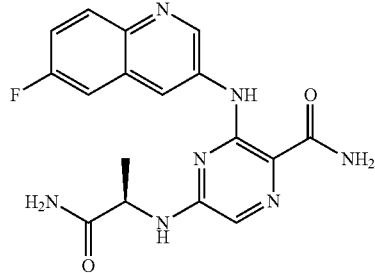 [SMILES: C[C@@H](Nc1cnc(C(N)=O)c(Nc2cnc3ccc(F)cc3c2)n1)C(N)=O]

The title compound was synthesized in a manner similar to that described in Example 66. MS found for C17H16FN7O2 as (M+H)+ 370.3. UV: A=296.1.

Example 244

(R)-5-(1-amino-3,3-dimethyl-1-oxobutan-2-ylamino)-3-(3-cyclopropylisothiazol-5-ylamino)pyrazine-2-carboxamide

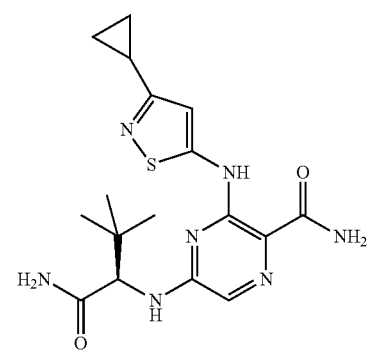 [SMILES: CC(C)(C)[C@@H](Nc1cnc(C(N)=O)c(Nc2cc(C3CC3)ns2)n1)C(N)=O]

The title compound was synthesized in a manner similar to that described in Example 66. MS found for C17H23N7O2S as (M+H)+ 390.3. UV: A=277.1, 324.7.

Example 245

(R)-5-(1-amino-4,4-dimethyl-1-oxopentan-2-ylamino)-3-(quinolin-7-ylamino)pyrazine-2-carboxamide

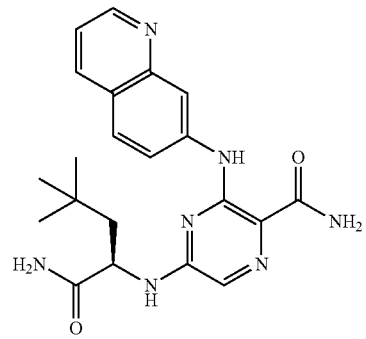 [SMILES: CC(C)(C)C[C@@H](Nc1cnc(C(N)=O)c(Nc2ccc3cccnc3c2)n1)C(N)=O]

The title compound was synthesized in a manner similar to that described in Example 66. MS found for C21H25N7O2 as (M+H)+ 408.4. UV: A=262.9, 293.8.

Example 246

(R)-3-(1,5-naphthyridin-3-ylamino)-5-(1-amino-4,4-dimethyl-1-oxopentan-2-ylamino)pyrazine-2-carboxamide

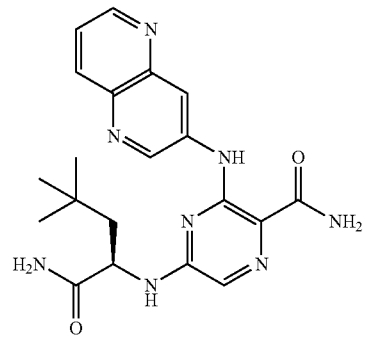 [SMILES: CC(C)(C)C[C@@H](Nc1cnc(C(N)=O)c(Nc2cnc3cccnc3c2)n1)C(N)=O]

The title compound was synthesized in a manner similar to that described in Example 66. MS found for C20H24N8O2 as (M+H)+ 409.4. UV: λ=252.3, 303.3.

Example 247

(R)-5-(1-amino-4,4-dimethyl-1-oxopentan-2-ylamino)-3-(5-fluoropyridin-3-ylamino)pyrazine-2-carboxamide

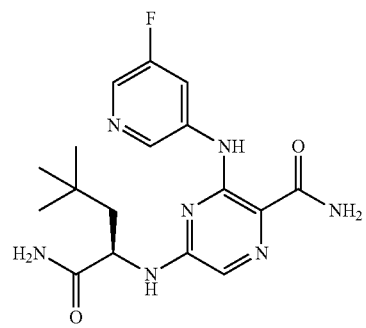 [SMILES: CC(C)(C)C[C@@H](Nc1cnc(C(N)=O)c(Nc2cncc(F)c2)n1)C(N)=O]

The title compound was synthesized in a manner similar to that described in Example 66. MS found for C17H22FN7O2 as (M+H)+ 376.3. UV: λ=233.4, 259.4, 302.1.

Example 248

5-(6-((1R,2S)-2-aminocyclohexylamino)-3-carbamoylpyrazin-2-ylamino)-N,N-dimethylisothiazole-3-carboxamide

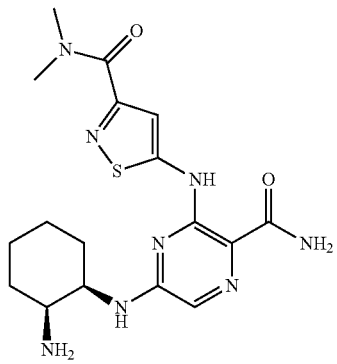 [SMILES: CN(C)C(=O)c1cc(Nc2nc(N[C@@H]3CCCC[C@@H]3N)cnc2C(N)=O)sn1]

The title compound was synthesized in a manner similar to that described in Example 78. MS found for Cl7H24N8O2S as (M+H)+ 405.4. UV: λ=268.8, 318.8.

Example 249

(R)-5-(6-(1-amino-1-oxobutan-2-ylamino)-3-carbamoylpyrazin-2-ylamino)-N,N-dimethylisothiazole-3-carboxamide

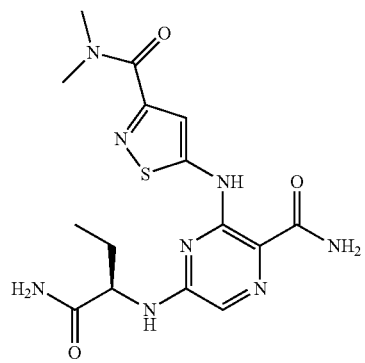 [SMILES: CC[C@@H](Nc1cnc(C(N)=O)c(Nc2cc(C(=O)N(C)C)ns2)n1)C(N)=O]

The title compound was synthesized in a manner similar to that described in Example 66. MS found for C15H20N8O3S as (M+H)+ 393.3. UV: λ=268.8, 317.6.

Example 250

5-((1R,2S)-2-aminocyclohexylamino)-3-(3-(hydroxymethyl)isothiazol-5-ylamino)pyrazine-2-carboxamide

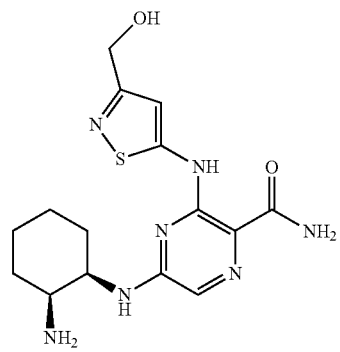 [SMILES: NC(=O)c1ncc(N[C@@H]2CCCC[C@@H]2N)nc1Nc1cc(CO)ns1]

The title compound was synthesized in a manner similar to that described in Example 78. MS found for C15H21N7O2S as (M+H)+ 364.3. UV: λ=268.8, 315.2.

Example 251

(R)-5-(1-amino-1-oxobutan-2-ylamino)-3-(3-(hydroxymethyl)isothiazol-5-ylamino)pyrazine-2-carboxamide

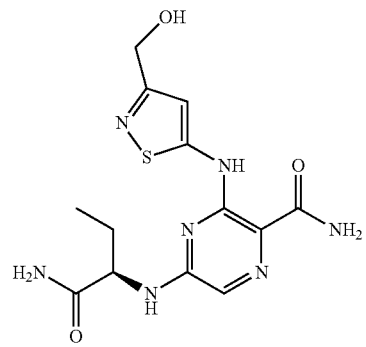 [SMILES: CC[C@@H](Nc1cnc(C(N)=O)c(Nc2cc(CO)ns2)n1)C(N)=O]

The title compound was synthesized in a manner similar to that described in Example 66. MS found for C13H17N7O3S as (M+H)+ 352.3. UV: λ=213.3, 270.8, 321.3.

Example 252

5-((1R,2S)-2-aminocyclohexylamino)-3-(thieno[2,3-c]isothiazol-3-ylamino)pyrazine-2-carboxamide

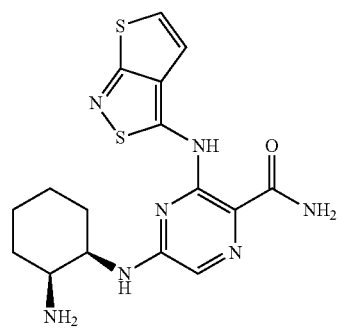 [SMILES: NC(=O)c1ncc(N[C@@H]2CCCC[C@@H]2N)nc1Nc1snc2sccc12]

The title compound was synthesized in a manner similar to that described in Example 78. MS found for C16H19N7O S2 as (M+H)+ 390.2. UV: λ=246.9, 279.4, 350.7.

Example 253

(R)-5-(1-amino-4,4-dimethyl-1-oxopentan-2-ylamino)-3-(5-methoxypyridin-3-ylamino)pyrazine-2-carboxamide

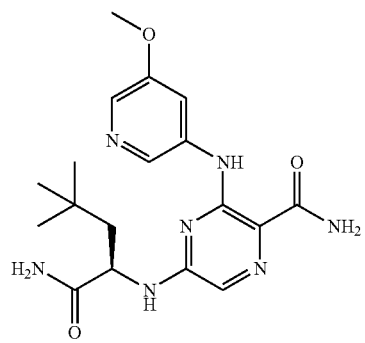 [SMILES: COc1cncc(Nc2nc(N[C@H](CC(C)(C)C)C(N)=O)cnc2C(N)=O)c1]

The title compound was synthesized in a manner similar to that described in Example 66. MS found for C18H25N7O3 as (M+H)+ 388.4. UV: λ=274.5, 310.8.

Example 254

(R)-5-(1-amino-1-oxobutan-2-ylamino)-3-(3-(morpholinomethyl)isothiazol-5-ylamino)pyrazine-2-carboxamide

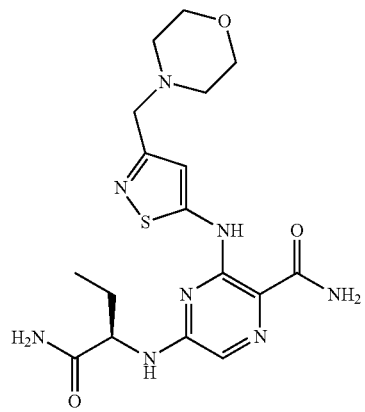 [SMILES: CC[C@@H](Nc1cnc(C(N)=O)c(Nc2cc(CN3CCOCC3)ns2)n1)C(N)=O]

The title compound was synthesized in a manner similar to that described in Example 66. MS found for C17H24N8O3S as (M+H)+ 421.4. UV: λ=271.2, 315.2.

Example 255

5-((1R,2S)-2-aminocyclohexylamino)-3-(3-(morpholinomethyl)isothiazol-5-ylamino)pyrazine-2-carboxamide

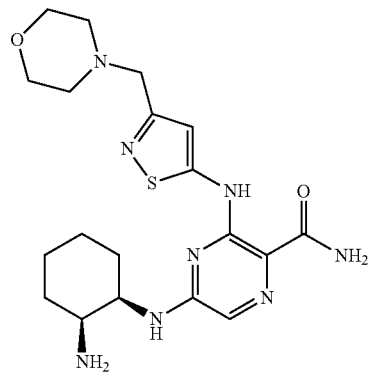 [SMILES: NC(=O)c1ncc(N[C@@H]2CCCC[C@@H]2N)nc1Nc1cc(CN2CCOCC2)ns1]

The title compound was synthesized in a manner similar to that described in Example 78. MS found for C19H28N8O2S as (M+H)+ 433.4. UV: λ=271.4, 316.4.

Example 256

(R)-5-(1-amino-4,4-dimethyl-1-oxopentan-2-ylamino)-3-(2-methoxypyridin-4-ylamino)pyrazine-2-carboxamide

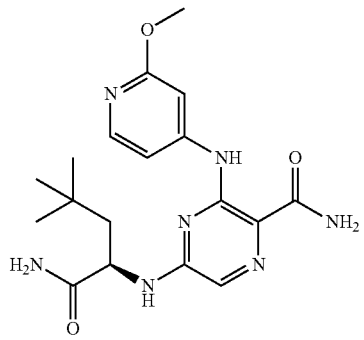 [SMILES: COc1cc(Nc2nc(N[C@H](CC(C)(C)C)C(N)=O)cnc2C(N)=O)ccn1]

The title compound was synthesized in a manner similar to that described in Example 66. MS found for C18H25N7O3 as (M+H)+ 388.3. UV: λ=274.5, 319.5.

Example 257

(R)-5-(1-amino-1-oxobutan-2-ylamino)-3-(3-(methoxymethyl)isothiazol-5-ylamino)pyrazine-2-carboxamide

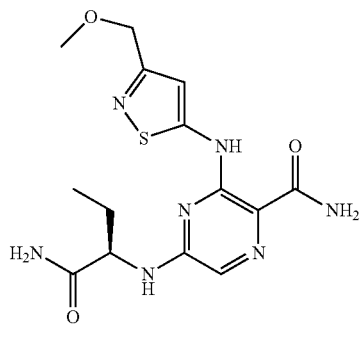 [SMILES: CC[C@@H](Nc1cnc(C(N)=O)c(Nc2cc(COC)ns2)n1)C(N)=O]

The title compound was synthesized in a manner similar to that described in Example 66. MS found for C14H19N7O3S as (M+H)+ 366.3. UV: λ=268.8, 316.4.

Example 258

5-((1R,2S)-2-aminocyclohexylamino)-3-(1-cyclopropyl-1H-pyrazol-4-ylamino)pyrazine-2-carboxamide

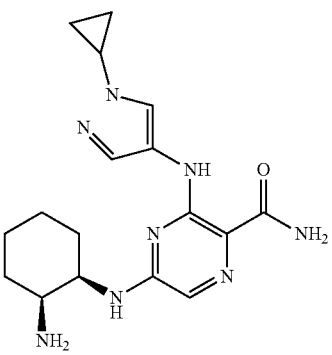 [SMILES: N=C/C(=C\NC1CC1)Nc1nc(N[C@@H]2CCCC[C@@H]2N)cnc1C(N)=O]

The title compound was synthesized in a manner similar to that described in Example 78. MS found for C17H24N8O as (M+H)+ 357.4. UV: λ=244.0, 293.8.

Example 259

(R)-5-(1-amino-4,4-dimethyl-1-oxopentan-2-ylamino)-3-(1-cyclopropyl-1H-pyrazol-4-ylamino)pyrazine-2-carboxamide

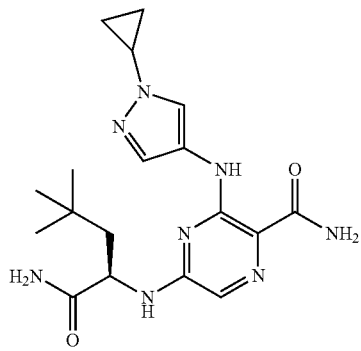 [SMILES: CC(C)(C)C[C@@H](Nc1cnc(C(N)=O)c(Nc2cnn(C3CC3)c2)n1)C(N)=O]

The title compound was synthesized in a manner similar to that described in Example 66. MS found for C18H26N8O2 as (M+H)+ 387.4. UV: λ=245.2, 294.9.

Example 260

(R)-5-(1-amino-1-oxobutan-2-ylamino)-3-(1-cyclopropyl-1H-pyrazol-4-ylamino)pyrazine-2-carboxamide

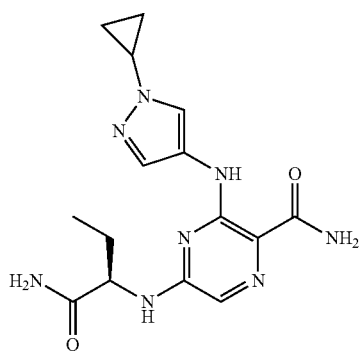 [SMILES: CC[C@@H](Nc1cnc(C(N)=O)c(Nc2cnn(C3CC3)c2)n1)C(N)=O]

The title compound was synthesized in a manner similar to that described in Example 66. MS found for C15H20N8O2 as (M+H)+ 345.3. UV: λ=243.8, 295.4.

Example 261

(R)-5-(1-amino-4,4-dimethyl-1-oxopentan-2-ylamino)-3-(thieno[2,3-c]isothiazol-3-ylamino)pyrazine-2-carboxamide

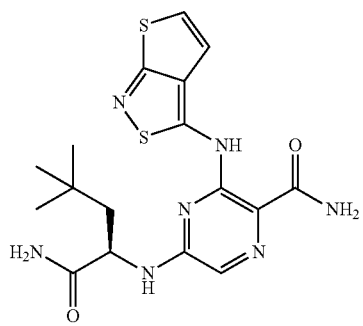 [SMILES: CC(C)(C)C[C@@H](Nc1cnc(C(N)=O)c(Nc2snc3sccc23)n1)C(N)=O]

The title compound was synthesized in a manner similar to that described in Example 66. MS found for C17H21N7O2S2 as (M+H)+ 420.3. UV: λ=247.5, 279.5, 354.3.

Example 262

5-((1R,2S)-2-aminocyclohexylamino)-3-(1-phenyl-1H-pyrazol-4-ylamino)pyrazine-2-carboxamide

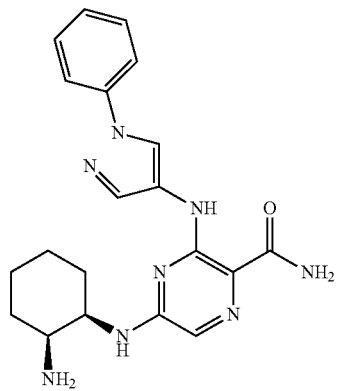 [SMILES: N=C/C(=C\Nc1ccccc1)Nc1nc(N[C@@H]2CCCC[C@@H]2N)cnc1C(N)=O]

The title compound was synthesized in a manner similar to that described in Example 78. MS found for C20H24N8O as (M+H)+ 393.4. UV: λ=241.6, 302.1.

Example 263

5-((1R,2S)-2-aminocyclohexylamino)-3-(2-fluoropyridin-4-ylamino)pyrazine-2-carboxamide

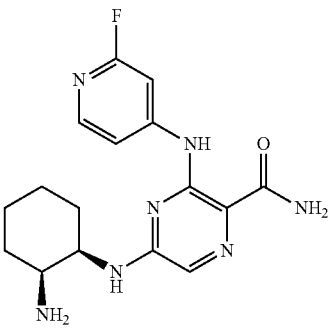 [SMILES: NC(=O)c1ncc(N[C@@H]2CCCC[C@@H]2N)nc1Nc1ccnc(F)c1]

The title compound was synthesized in a manner similar to that described in Example 78. MS found for C16H20FN7O as (M+H)+ 346.3. UV: λ=257.0, 303.3.

Example 264

(R)-5-(1-amino-1-oxobutan-2-ylamino)-3-(2-fluoropyridin-4-ylamino)pyrazine-2-carboxamide

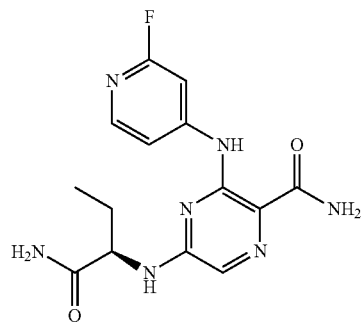 [SMILES: CC[C@@H](Nc1cnc(C(N)=O)c(Nc2ccnc(F)c2)n1)C(N)=O]

The title compound was synthesized in a manner similar to that described in Example 66. MS found for C14H16FN7O2 as (M+H)+ 334.3. UV: λ=211.0, 258.2, 308.0.

Example 265

(R)-5-(1-amino-4,4-dimethyl-1-oxopentan-2-ylamino)-3-(2-fluoropyridin-4-ylamino)pyrazine-2-carboxamide

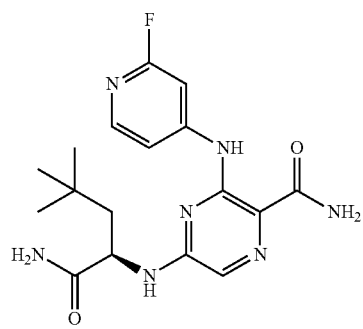 [SMILES: CC(C)(C)C[C@@H](Nc1cnc(C(N)=O)c(Nc2ccnc(F)c2)n1)C(N)=O]

The title compound was synthesized in a manner similar to that described in Example 66. MS found for C17H22FN7O2 as (M+H)+ 376.3. UV: λ=258.2, 299.7.

Example 266

(R)-5-(1-amino-4,4-dimethyl-1-oxopentan-2-ylamino)-3-(3-methylisothiazol-5-ylamino)pyrazine-2-carboxamide

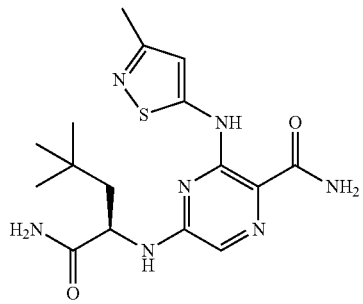 [SMILES: Cc1cc(Nc2nc(N[C@H](CC(C)(C)C)C(N)=O)cnc2C(N)=O)sn1]

The title compound was synthesized in a manner similar to that described in Example 66. MS found for C16H23N7O2S as (M+H)+ 378.3. UV: λ=275.9, 322.3.

Example 267

5-((1R,2S)-2-aminocyclohexylamino)-3-(thieno[3,2-c]isothiazol-3-ylamino)pyrazine-2-carboxamide

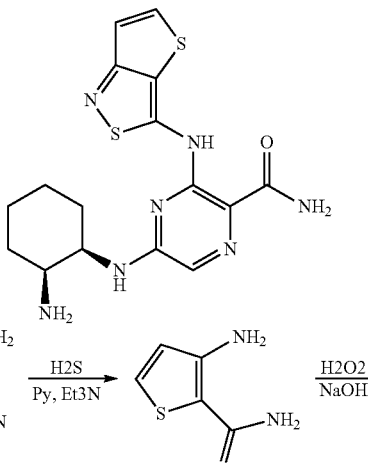

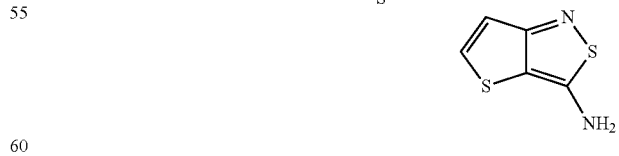

Synthesis of thieno[3,2-c]isothiazol-3-amine

Step 1: To a solution of 3-aminothiophene-2-carbonitrile (400 mg, 3.22 mmol) in pyridine (5 mL) was added Et3N (0.5 mL) and then the solution was bubbled with H2S gas for 5 min. After stirring at room temperature for 15 h, the solution was concentrated to give crude 3-aminothiophene-2-carbothioamide.

Step 2: To a solution of crude 3-aminothiophene-2-carbothioamide in MeOH (5 mL) was added H2O2 (30%, 0.6 mL), after stirring at room temperature for 15 min, it was concentrated to remove most of MeOH, and then diluted with EtOAC, organic layer was washed with brine, concentrated to give crude pdt, purification by column chromatography (DCM/EtOAC=3:1) gave thieno[3,2-c]isothiazol-3-amine (334 mg).

With thieno[3,2-c]isothiazol-3-amine, the title compound was synthesized in a manner similar to that described in Example 78. MS found for C16H19N7O S2 as (M+H)+ 390.2. UV: λ=265.3.

Example 268

(R)-5-(1-amino-1-oxobutan-2-ylamino)-3-(thieno[3,2-c]isothiazol-3-ylamino)pyrazine-2-carboxamide

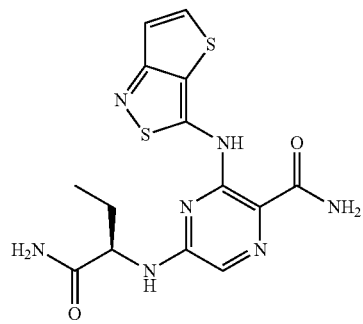 [SMILES: CC[C@@H](Nc1cnc(C(N)=O)c(Nc2snc3ccsc23)n1)C(N)=O]

The title compound was synthesized in a manner similar to that described in Example 66. MS found for C14H15N7O2S2 as (M+H)+ 378.2. UV: λ=265.9, 351.8.

Example 269

(R)-5-(1-amino-1-oxobutan-2-ylamino)-3-(benzo[c]isothiazol-3-ylamino)pyrazine-2-carboxamide

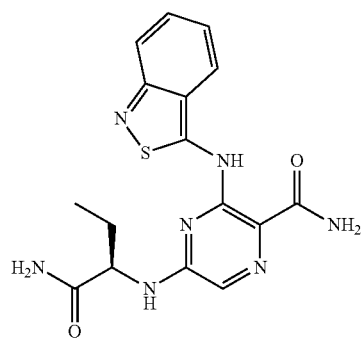 [SMILES: CC[C@@H](Nc1cnc(C(N)=O)c(Nc2snc3ccccc23)n1)C(N)=O]

The title compound was synthesized in a manner similar to that described in Example 66. MS found for C16H17N7O2S as (M+H)+ 372.3. UV: λ=231.0, 273.6.

Example 270

5-((1R,2S)-2-aminocyclohexylamino)-3-(benzo[c]isothiazol-3-ylamino)pyrazine-2-carboxamide

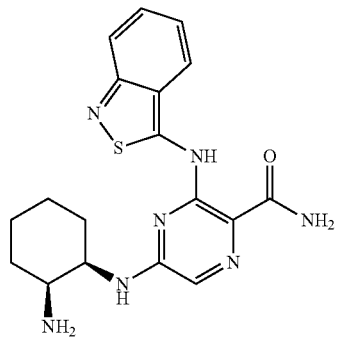 [SMILES: NC(=O)c1ncc(N[C@@H]2CCCC[C@@H]2N)nc1Nc1snc2ccccc12]

The title compound was synthesized in a manner similar to that described in Example 267. MS found for C18H21N7OS as (M+H)+ 384.3. UV: λ=231.0, 274.8.

Example 271

(R)-5-(1-amino-1-oxobutan-2-ylamino)-3-(thieno[2,3-c]isothiazol-3-ylamino)pyrazine-2-carboxamide

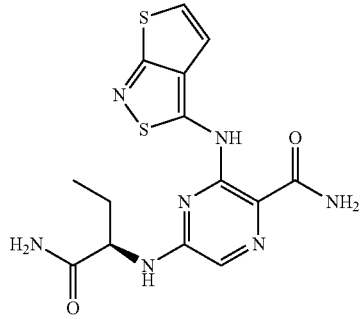 [SMILES: CC[C@@H](Nc1cnc(C(N)=O)c(Nc2snc3sccc23)n1)C(N)=O]

The title compound was synthesized in a manner similar to that described in Example 66. MS found for C14H15N7O2S2 as (M+H)+ 378.3. UV: λ=246.3, 279.5, 346.8.

Example 272

5-((3R,4R)-3-aminotetrahydro-2H-pyran-4-ylamino)-3-(thieno[3,2-c]isothiazol-3-ylamino)pyrazine-2-carboxamide

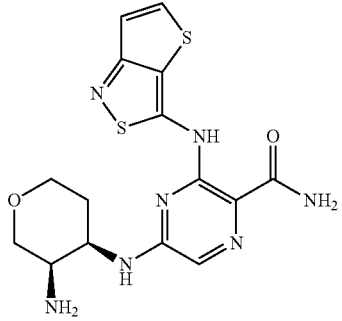 [SMILES: NC(=O)c1ncc(N[C@@H]2CCOC[C@@H]2N)nc1Nc1snc2ccsc12]

The title compound was synthesized in a manner similar to that described in Example 267. MS found for C15H17N7O2S2 as (M+H)+ 392.3. UV: λ=264.1.

Example 273

5-((3R,4R)-3-aminotetrahydro-2H-pyran-4-ylamino)-3-(thieno[2,3-c]isothiazol-3-ylamino)pyrazine-2-carboxamide

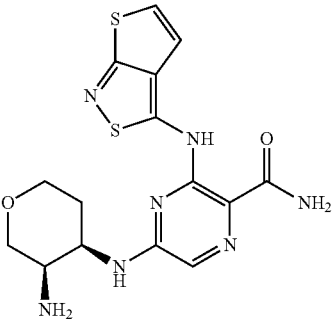 [SMILES: NC(=O)c1ncc(N[C@@H]2CCOC[C@@H]2N)nc1Nc1snc2sccc12]

The title compound was synthesized in a manner similar to that described in Example 267. MS found for C15H17N7O2S2 as (M+H)+ 392.3. UV: λ=246.3, 278.8, 348.0.

Example 274

5-((1R,2S)-2-aminocyclohexylamino)-3-(isothiazolo[4,3-b]pyrazin-3-ylamino)pyrazine-2-carboxamide

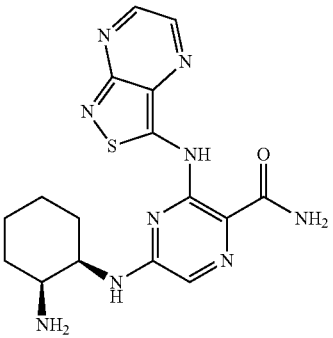 [SMILES: NC(=O)c1ncc(N[C@@H]2CCCC[C@@H]2N)nc1Nc1snc2nccnc12]

The title compound was synthesized in a manner similar to that described in Example 267. MS found for C16H19N9OS as (M+H)+ 386.4. UV: λ=242.8, 297.3.

Example 275

5-((1R,2S)-2-aminocyclohexylamino)-3-(m-tolylamino)pyrazine-2-carboxamide

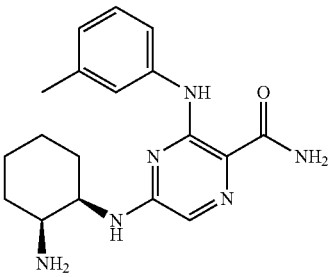 [SMILES: Cc1cccc(Nc2nc(N[C@@H]3CCCC[C@@H]3N)cnc2C(N)=O)c1]

The title compound was synthesized in a manner similar to that described in Scheme 1 using tert-butyl (1S,2R)-2-aminocyclohexylcarbamate in place of leucinamide in Step 1 and 4M HCl/dioxane for deprotection of the Boc amine as a final step before purification. MS found for C18H24N6O as (M+H)+ 341.6. UV: λ=208, 253, 303.

Example 276

3-(4-(1H-pyrazol-1-yl)phenylamino)-5-((1R,2S)-2-aminocyclohexylamino)pyrazine-2-carboxamide

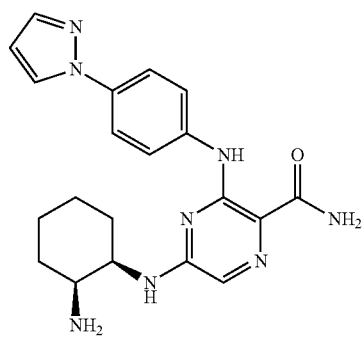 [SMILES: NC(=O)c1ncc(N[C@@H]2CCCC[C@@H]2N)nc1Nc1ccc(-n2cccn2)cc1]

The title compound was synthesized in a manner similar to that described in Example 275. MS found for C20H24N8O as (M+H)+ 393.6. UV: λ=204, 314.

Example 277

5-((1R,2S)-2-aminocyclohexylamino)-3-(4-(dimethylcarbamoyl)phenylamino)pyrazine-2-carboxamide

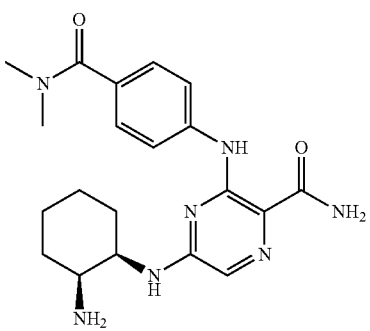 [SMILES: CN(C)C(=O)c1ccc(Nc2nc(N[C@@H]3CCCC[C@@H]3N)cnc2C(N)=O)cc1]

The title compound was synthesized in a manner similar to that described in Example 275. MS found for C20H27N7O2 as (M+H)+ 398.5. UV: λ=214, 266, 315. 1H NMR: (CD3OD)

δ 7.72 (d, 1H), 7.53 (s, 1H), 7.44 (d, 1H), 4.42 (m, 1H), 3.83 (m, 1H), 3.08 (s, 6H), 1.57-1.96 (m, 8H).

Example 278

5-((1R,2S)-2-aminocyclohexylamino)-3-(6-(dimethylcarbamoyl)pyridin-3-ylamino)pyrazine-2-carboxamide

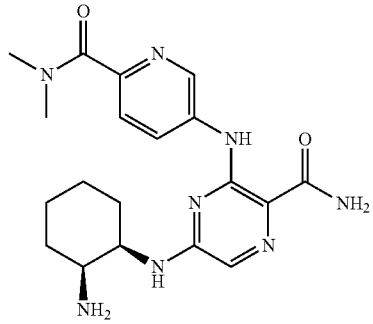 [SMILES: CN(C)C(=O)c1ccc(Nc2nc(N[C@@H]3CCCC[C@@H]3N)cnc2C(N)=O)cn1]

The title compound was synthesized in a manner similar to that described in Example 275. MS found for C19H26N8O2 as (M+H)+ 399.5. UV: λ=204, 265, 315. $^1$H NMR: (CD$_3$OD) δ 8.96 (s, 1H), 8.18 (dd, 1H, 2.4 Hz, 8.4 Hz), 7.62 (d, 1H, 8.4 Hz), 7.61 (s, 1H), 4.46 (m, 1H), 3.73 (m, 1H), 3.13 (s, 3H), 3.11 (s, 3H), 1.60-1.92 (m, 8H).

Example 279

5-((1R,2S)-2-aminocyclohexylamino)-3-(3-chloro-4-(dimethylcarbamoyl)phenylamino)pyrazine-2-carboxamide

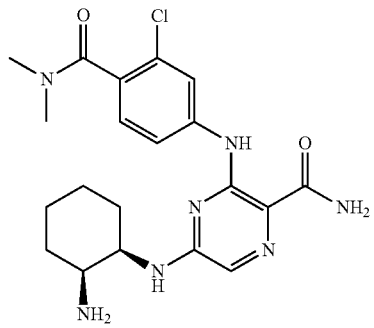

The title compound was synthesized in a manner similar to that described in Example 275. MS found for C20H26ClN7O2 as (M+H)+ 432.5, 434.5. UV: λ=219, 261, 313. $^1$H NMR: (CD$_3$OD) δ 8.18 (broad s, 1H0, 7.56 (s, 1H), 7.38 (broad m, 1H), 7.27 (d, 1H, 8 Hz), 4.40 (m, 1H), 3.81 (m, 1H), 3.25 (s, 3H), 2.93 (s, 3H), 1.63-1.96 (m, 8H).

Example 280

5-((1R,2S)-2-aminocyclohexylamino)-3-(6-(azetidine-1-carbonyl)pyridin-3-ylamino)pyrazine-2-carboxamide

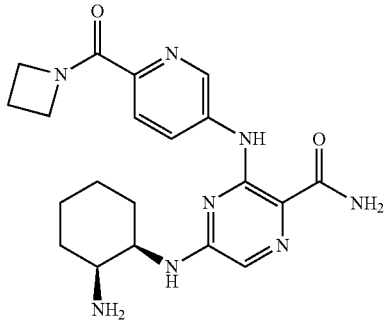 [SMILES: NC(=O)c1ncc(N[C@@H]2CCCC[C@@H]2N)nc1Nc1ccc(C(=O)N2CCC2)nc1]

The title compound was synthesized in a manner similar to that described in Example 275. MS found for C20H26N8O2 as (M+H)+ 411.6. UV: λ=211, 269, 326. $^1$H NMR: (CD$_3$OD) δ 8.81 (d, 1H, 2 Hz), 8.29 (dd, 1H, 2.8 Hz, 9 Hz), 7.96 (d, 1H, 9 Hz), 7.60 (s, 1H), 4.77 (m, 1H), 4.22 (m, 1H), 4.22 (t, 2H, 8 Hz), 3.79 (m, 1H), 2.39 (m, 8 Hz), 1.62-1.91 (m, 8H).

Example 281

(R)-5-(1-amino-4-methyl-1-oxopentan-2-ylamino)-3-(4-(dimethylcarbamoyl)phenylamino)pyrazine-2-carboxamide

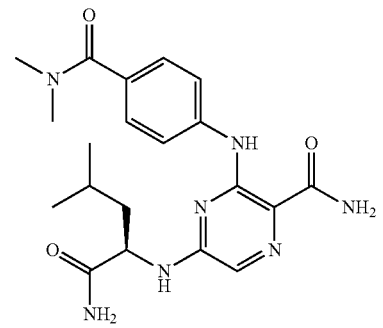 [SMILES: CC(C)C[C@@H](Nc1cnc(C(N)=O)c(Nc2ccc(C(=O)N(C)C)cc2)n1)C(N)=O]

The title compound was synthesized in a manner similar to that described in Example 275. MS found for C20H27N7O3 as (M+H)+ 414.6. UV: λ=204, 265, 314. $^1$H NMR: (CD$_3$OD) δ 7.74 (d, 2H, 8 Hz), 7.49 (s, 1H), 7.41 (d, 2H, 8 Hz), 4.44 (dd, 1H, 4.4 Hz, 10 Hz), 3.09 (s, 6H), 1.83 (m, 1H), 1.74 (m, 1H), 1.01 (d, 3H, 7 Hz), 0.93 (d, 3H, 6 Hz).

Example 282

(R)-5-(1-amino-4-methyl-1-oxopentan-2-ylamino)-3-(6-(azetidine-1-carbonyl)pyridin-3-ylamino)pyrazine-2-carboxamide

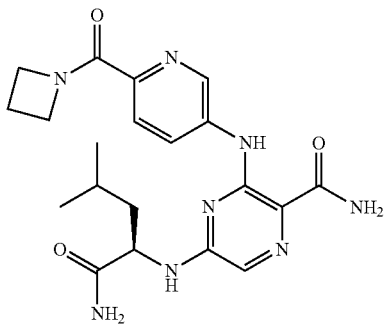 [SMILES: CC(C)C[C@@H](Nc1cnc(C(N)=O)c(Nc2ccc(C(=O)N3CCC3)nc2)n1)C(N)=O]

The title compound was synthesized in a manner similar to that described in Example 275. MS found for C20H26N8O3 as (M+H)+ 427.5. UV: λ=203, 269, 326. $^1$H NMR: (CD$_3$OD) δ 8.71 (s, 1H), 8.45 (d, 1H, 9 Hz), 7.96 (d, 1H, 9 Hz), 7.56 (s, 1H), 4.74 (t, 2H, 8 Hz), 4.42 (dd, 1H, 4 Hz, 15 Hz), 4.22 (t, 2H, 7 Hz), 2.39 (m, 2H, 8 Hz), 1.86 (m, 1H), 1.75 (m, 1H), 1.01 (d, 3H, 6 Hz), 0.94 (d, 3H, 6 Hz).

Example 283

5-((1R,2S)-2-aminocyclohexylamino)-3-(3-(dimethylcarbamoyl)phenylamino)pyrazine-2-carboxamide

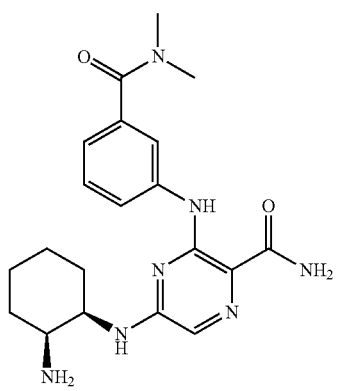 [SMILES: CN(C)C(=O)c1cccc(Nc2nc(N[C@@H]3CCCC[C@@H]3N)cnc2C(N)=O)c1]

The title compound was synthesized in a manner similar to that described in Example 275. MS found for C20H27N7O2 as (M+H)+ 398.5. UV: λ=207, 254, 295. $^1$H NMR: (CD$_3$OD) δ 8.11 (s, 1H), 7.53 (s, 1H), 7.39 (m, 2H), 7.08 (m, 1H), 4.44 (m, 1H), 3.71 (m, 1H), 3.12 (s, 3H), 3.06 (s, 3H), 1.58-1.86 (m, 8H).

Example 284

5-((1R,2S)-2-aminocyclohexylamino)-3-(3-(dimethylcarbamoyl)-4-fluorophenylamino)pyrazine-2-carboxamide

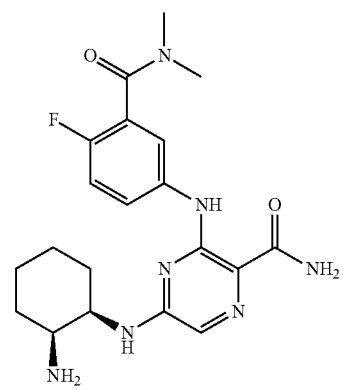 [SMILES: CN(C)C(=O)c1cc(Nc2nc(N[C@@H]3CCCC[C@@H]3N)cnc2C(N)=O)ccc1F]

The title compound was synthesized in a manner similar to that described in Example 275. MS found for C20H26FN7O2 as (M+H)+ 416.5. UV: λ=205, 251, 293 nm. $^1$H NMR: (CD$_3$OD) δ 8.02 (s, 1H), 7.52 (s, 1H), 7.40 (m, 1H), 7.18 (t, 1H, 9 Hz), 4.15 (m, 1H), 3.68 (m, 1H), 3.13 (s, 3H), 3.01 (s, 3H), 1.56-1.85 (m, 8H).

Example 285

5-((1R,2S)-2-aminocyclohexylamino)-3-(4-(pyrrolidin-1-yl)-3-(pyrrolidine-1-carbonyl)phenylamino)pyrazine-2-carboxamide

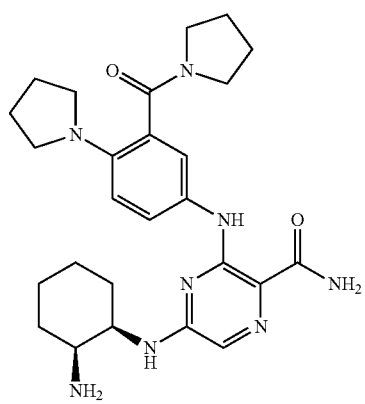 [SMILES: NC(=O)c1ncc(N[C@@H]2CCCC[C@@H]2N)nc1Nc1ccc(N2CCCC2)c(C(=O)N2CCCC2)c1]

207

The title compound was synthesized in a manner similar to that described in Example 275. MS found for C26H36N8O2 as (M+H)+ 493.6. UV: λ=205, 261, 313, 354 nm.

Example 286

5-((1R,2S)-2-aminocyclohexylamino)-3-(3-(dimethylcarbamoyl)-4-methoxyphenylamino)pyrazine-2-carboxamide

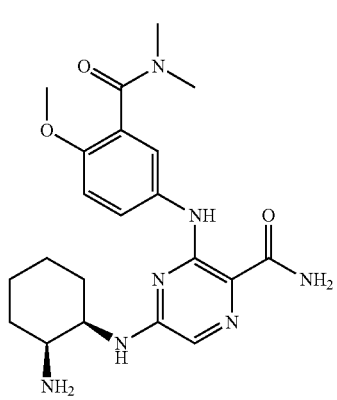 [SMILES: COc1ccc(Nc2nc(N[C@@H]3CCCC[C@@H]3N)cnc2C(N)=O)cc1C(=O)N(C)C]

The title compound was synthesized in a manner similar to that described in Example 275. MS found for C21H29N7O3 as (M+H)+ 428.5. UV: λ=205, 254, 295 nm.

Example 287

5-((1R,2S)-2-aminocyclohexylamino)-3-(3-(pyrrolidine-1-carbonyl)phenylamino)pyrazine-2-carboxamide

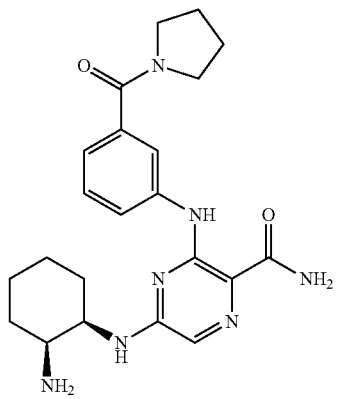 [SMILES: NC(=O)c1ncc(N[C@@H]2CCCC[C@@H]2N)nc1Nc1cccc(C(=O)N2CCCC2)c1]

208

The title compound was synthesized in a manner similar to that described in Example 275. MS found for C22H29N7O2 as (M+H)+ 424.5. UV: λ=205, 256, 293 nm.

Example 288

5-((1R,2S)-2-aminocyclohexylamino)-3-(5-(dimethylcarbamoyl)-2-fluorophenylamino)pyrazine-2-carboxamide

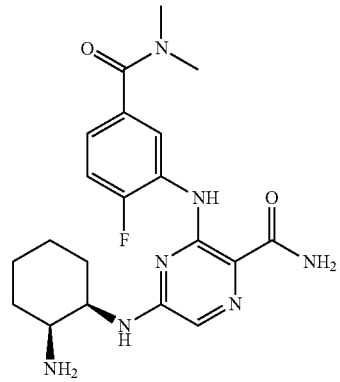 [SMILES: CN(C)C(=O)c1ccc(F)c(Nc2nc(N[C@@H]3CCCC[C@@H]3N)cnc2C(N)=O)c1]

The title compound was synthesized in a manner similar to that described in Example 275. MS found for C20H26FN7O2 as (M+H)+ 416.5. UV: λ=. 205, 254, 298, 352 nm. $^1$H NMR: (CD$_3$OD) δ 8.67 (dd, 1H, 2 Hz, 8 Hz), 7.59 (s, 1H), 7.38 (d, 1H, 8 Hz), 7.25 (dd, 1H, 8 Hz, 11 Hz), 7.10 (ddd, 1H, 2 Hz, 4.8 Hz), 8 Hz), 4.48 (m, 1H), 3.69 (m, 1H), 3.12 (s, 3H), 3.08 (s, 3H), 1.68-1.85 (m, 6H), 1.61 (m, 2H).

Example 289

5-((1R,2S)-2-aminocyclohexylamino)-3-(2-fluoro-5-(pyrrolidine-1-carbonyl)phenylamino)pyrazine-2-carboxamide

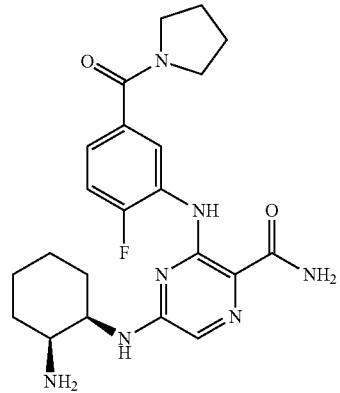 [SMILES: NC(=O)c1ncc(N[C@@H]2CCCC[C@@H]2N)nc1Nc1cc(C(=O)N2CCCC2)ccc1F]

The title compound was synthesized in a manner similar to that described in Example 275. MS found for C22H28FN7O2 as (M+H)+ 442.5. UV: λ=207, 251, 288, 349 nm.

Example 290

5-((1R,2S)-2-aminocyclohexylamino)-3-(5-(dimethylcarbamoyl)-2-methoxyphenylamino)pyrazine-2-carboxamide

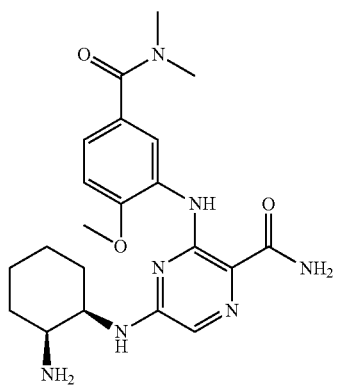 [SMILES: COc1ccc(C(=O)N(C)C)cc1Nc1nc(N[C@@H]2CCCC[C@@H]2N)cnc1C(N)=O]

The title compound was synthesized in a manner similar to that described in Example 275. MS found for C21H29N7O3 as (M+H)+ 428.5. UV: λ=202, 261, 317. $^1$H NMR: (CD$_3$OD) δ 8.71 (d, 1H), 7.54 (s, 1H), 7.09 (dd, 1H), 7.04 (d, 1H), 4.54 (m, 1H), 3.97 (s, 3H), 3.71 (m, 1H), 3.12 (s, 6H), 1.70-1.92 (m, 6H), 1.64 (m, 2H).

Example 291

5-((1R,2S)-2-aminocyclohexylamino)-3-(2-methoxypyridin-4-ylamino)pyrazine-2-carboxamide

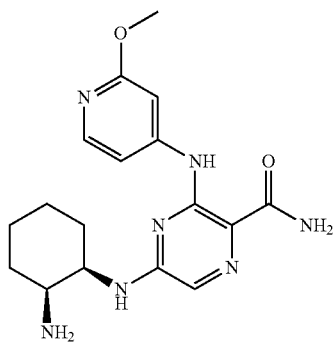 [SMILES: COc1cc(Nc2nc(N[C@@H]3CCCC[C@@H]3N)cnc2C(N)=O)ccn1]

The title compound was synthesized in a manner similar to that described in Example 275. MS found for C17H23N7O2 as (M+H)+ 358.5. UV: λ=205, 271, 308, 347. $^1$H NMR: (CD$_3$OD) δ 8.00 (d, 1H, 7 Hz), 7.73 (s, 1H), 7.60 (s, 1H), 7.33 (m, 1H), 4.52 (m, 1H), 4.05 (s, 3H), 3.76 (m, 1H), 1.71-1.98 (m, 6H), 1.62 (m, 2H).

Example 292

(R)-5-(1-amino-4-methyl-1-oxopentan-2-ylamino)-3-(3-(dimethylcarbamoyl)phenylamino)pyrazine-2-carboxamide

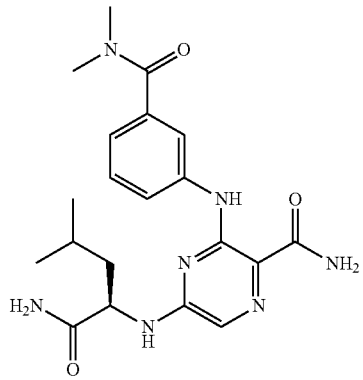 [SMILES: CC(C)C[C@@H](Nc1cnc(C(N)=O)c(Nc2cccc(C(=O)N(C)C)c2)n1)C(N)=O]

The title compound was synthesized in a manner similar to that described in Example 275. MS found for C20H27N7O3 as (M+H)+ 414.5. UV: λ=212, 154, 303 nm. $^1$H NMR: (CD$_3$OD) δ 8.04 (s, 1H), 7.50 (d, 1H, 8 Hz), 7.45 (s, 1H), 7.37 (t, 1H, 8 Hz), 7.02 (d, 1H, 8 Hz), 4.52 (dd, 1H, 5 Hz, 9 Hz), 3.11 (s, 3H), 3.04 (s, 3H), 1.81 (m, 1H), 1.72 (m, 2H), 1.01 (d, 3H, 7 Hz), 0.93 (d, 3H, 6 Hz).

Example 293

(R)-5-(1-amino-4-methyl-1-oxopentan-2-ylamino)-3-(4-(azetidine-1-carbonyl)phenylamino)pyrazine-2-carboxamide

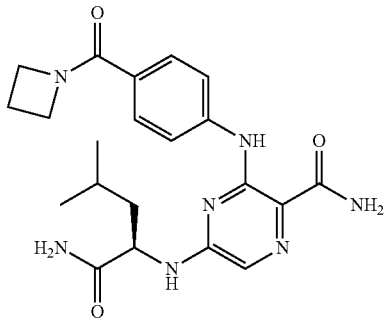 [SMILES: CC(C)C[C@@H](Nc1cnc(C(N)=O)c(Nc2ccc(C(=O)N3CCC3)cc2)n1)C(N)=O]

The title compound was synthesized in a manner similar to that described in Example 275. MS found for C21H27N7O3 as (M+H)+ 426.5. UV: λ=205, 268, 320. $^1$H NMR: (CD$_3$OD) δ 7.34 (d, 2H, 9 Hz), 7.62 (d, 2H, 9 Hz), 7.50 (s, 1H), 4.44 (m, 4H), 4.19 (t, 2H, 8 Hz), 2.38 (m, 2H, 8 Hz), 1.82 (m, 1H), 1.74 (m, 2H), 1.01 (d, 3H, 7 Hz), 0.94 (d, 3H, 6 Hz).

Example 294

(R)-5-(6-(1-amino-4-methyl-1-oxopentan-2-ylamino)-3-carbamoylpyrazin-2-ylamino)picolinic acid

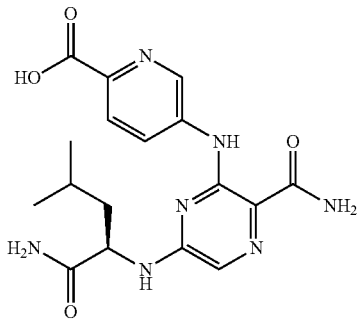 [SMILES: CC(C)C[C@@H](Nc1cnc(C(N)=O)c(Nc2ccc(C(=O)O)nc2)n1)C(N)=O]

The title compound was synthesized in a manner similar to that described in Example 275. MS found for C17H21N7O4 as (M+H)+ 388.5. UV: λ=205, 278, 325 nm. ¹H NMR: (CD₃OD) δ 9.04 (d, 1H, 2 Hz), 8.44 (dd, 1H, 2 Hz, 9 Hz), 8.19 (d, 1H, 8 Hz), 7.62 (s, 1H), 4.41 (dd, 1H, 5 Hz, 11 Hz), 1.84 (m, 1H), 1.78 (m, 1H), 1.72 (m, 1H), 1.02 (d, 3H, 6 Hz), 0.95 (d, 3H, 7 Hz).

Example 295

5-((1R,2S)-2-aminocyclohexylamino)-3-(4-(azetidine-1-carbonyl)phenylamino)pyrazine-2-carboxamide

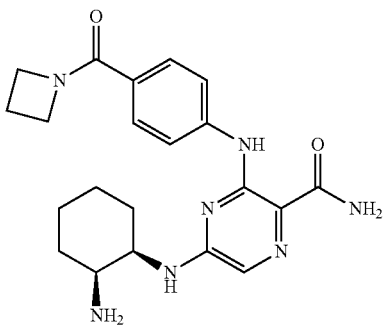 [SMILES: NC(=O)c1ncc(N[C@@H]2CCCC[C@@H]2N)nc1Nc1ccc(C(=O)N2CCC2)cc1]

The title compound was synthesized in a manner similar to that described in Example 275. MS found for C21H27N7O2 as (M+H)+ 410.5. UV: λ=207, 268, 320 nm. ¹H NMR: (CD₃OD) δ 7.72 (d, 2H, 8 Hz), 7.63 (d, 2H, 9 Hz), 7.55 (s, 1H), 4.44 (distorted t, 3H, 6 Hz), 4.20 (2H, 8 Hz), 3.81 (m, 1H), 2.39 (m, 2H, 8 Hz), 1.84 (m, 5H), 1.64 (m, 3H).

Example 296

5-((1R,2S)-2-aminocyclohexylamino)-3-(6-methoxy-pyridin-3-ylamino)pyrazine-2-carboxamide

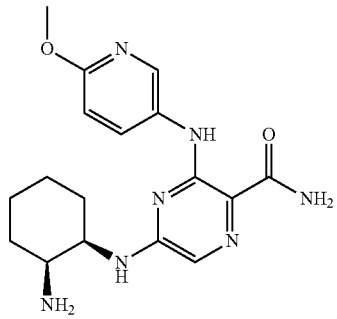 [SMILES: COc1ccc(Nc2nc(N[C@@H]3CCCC[C@@H]3N)cnc2C(N)=O)cn1]

The title compound was synthesized in a manner similar to that described in Example 275. MS found for C17H23N7O2 as (M+H)+ 358.5. UV: λ=205, 256, 298 nm. ¹H NMR: (CD₃OD) δ 8.43 (d, 1H, 2 Hz), 7.83 (dd, 1H, 3 Hz, 9 Hz), 7.48 (s, 1H), 6.83 (d, 1H, 9 Hz), 4.32 (m, 1H), 3.90 (s, 3H), 3.69 (m, 1H), 1.55-1.85 (m, 8H).

Example 297

5-((1R,2S)-2-aminocyclohexylamino)-3-(6-(3,3-difluoroazetidine-1-carbonyl)pyridin-3-ylamino)pyrazine-2-carboxamide

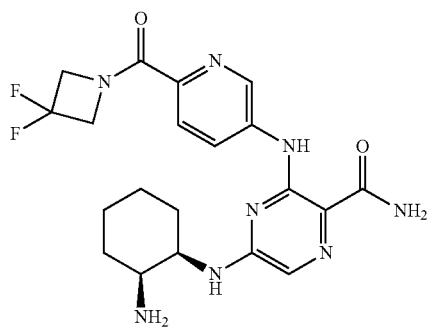 [SMILES: NC(=O)c1ncc(N[C@@H]2CCCC[C@@H]2N)nc1Nc1ccc(C(=O)N2CC(F)(F)C2)nc1]

The title compound was synthesized in a manner similar to that described in Example 275. MS found for C20H24F2N8O2 as (M+H)+ 447.5. UV: λ=212, 268, 325.

Example 298

5-((1R,2S)-2-aminocyclohexylamino)-3-(4-(methyl (2,2,2-trifluoroethyl)carbamoyl)phenylamino)pyrazine-2-carboxamide

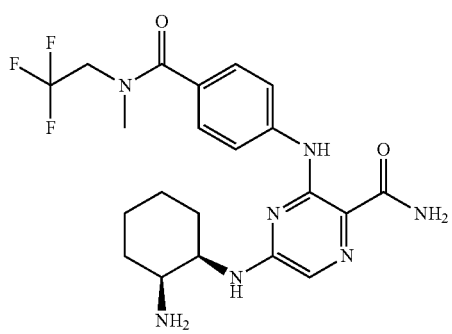 [SMILES: CN(CC(F)(F)F)C(=O)c1ccc(Nc2nc(N[C@@H]3CCCC[C@@H]3N)cnc2C(N)=O)cc1]

The title compound was synthesized in a manner similar to that described in Example 275. MS found for C21H26F3N7O2 as (M+H)+ 466.5. UV: λ=207, 266, 315 nm. ¹H NMR: (CD₃OD) δ 7.75 (d, 2H, 9 Hz), 7.55 (s, 1H), 7.45 (d, 2H, 8 Hz), 4.30 (m, 1H), 3.81 (m, 1H), 3.19 (s, 3H), 1.59-1.94 (m, 8H).

Example 299

(R)-5-(1-amino-1-oxobutan-2-ylamino)-3-(4-(dimethylcarbamoyl)phenylamino)pyrazine-2-carboxamide

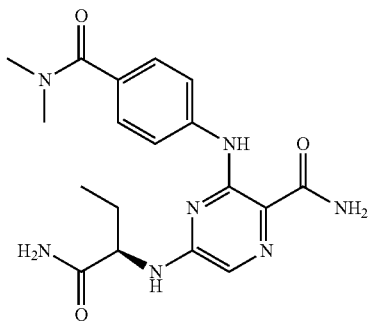 [SMILES: CC[C@@H](Nc1cnc(C(N)=O)c(Nc2ccc(C(=O)N(C)C)cc2)n1)C(N)=O]

The title compound was synthesized in a manner similar to that described in Example 275. MS found for C18H23N7O3 as (M+H)+ 386.5. UV: λ=210, 266, 315 nm.

Example 300

(R)-5-(1-amino-1-oxobutan-2-ylamino)-3-(6-(azetidine-1-carbonyl)pyridin-3-ylamino)pyrazine-2-carboxamide

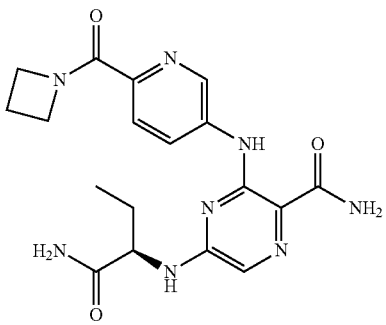 [SMILES: CC[C@@H](Nc1cnc(C(N)=O)c(Nc2ccc(C(=O)N3CCC3)nc2)n1)C(N)=O]

The title compound was synthesized in a manner similar to that described in Example 275. MS found for C18H22N8O3 as (M+H)+ 399.5. UV: λ=205, 236, 271, 325 nm. ¹H NMR: (CD₃OD) δ 8.73 (d, 1H), 8.47 (dd, 1H), 7.98 (d, 1H), 7.58 (s, 1H), 4.23 (t, 4H), 2.39 (m, 2H), 1.99 (m, 1H), 1.89 (m, 1H), 1.08 (t, 3H).

Example 301

(R)-5-(1-amino-1-oxobutan-2-ylamino)-3-(6-(3,3-difluoroazetidine-1-carbonyl)pyridin-3-ylamino)pyrazine-2-carboxamide

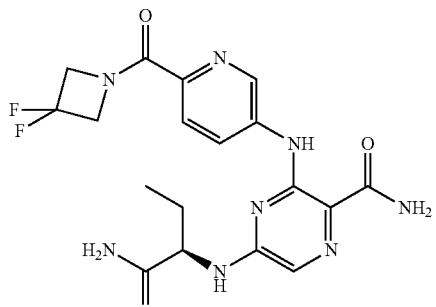

The title compound was synthesized in a manner similar to that described in Example 275. MS found for C18H20F2N8O3 as (M+H)+ 435.5. UV: λ=212, 271, 330 nm. ¹H NMR: (CD₃OD) δ 8.78 (d, 1H), 8.43 (dd, 1H), 8.03 (d, 1H), 7.59 (s, 1H), 4.23 (dd, 1H), 2.03 (m, 1H), 1.88 (m, 1H), 1.08 (t, 3H).

Example 302

(R)-5-(1-amino-1-oxobutan-2-ylamino)-3-(2-methoxypyridin-4-ylamino)pyrazine-2-carboxamide

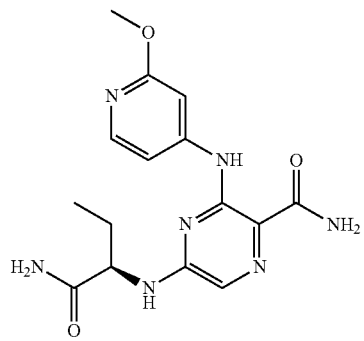 [SMILES: CC[C@@H](Nc1cnc(C(N)=O)c(Nc2ccnc(OC)c2)n1)C(N)=O]

The title compound was synthesized in a manner similar to that described in Example 275. MS found for C15H19N7O3 as (M+H)+ 346.4. UV: λ=205, 271, 320 nm. ¹H NMR: (CD₃OD) δ 7.98 (d, 1H, 7 Hz), 7.77 (s, 1H), 7.70 (d, 1H), 7.49 (s, 1H), 4.27 (dd, 1H, 5.2 Hz, 8 Hz), 4.16 (s, 3H), 2.00 (m, 1H), 1.92 (m, 1H), 1.09 (t, 3H, 8 Hz).

Example 303

5-((1R,2S)-2-aminocyclohexylamino)-3-(pyrimidin-5-ylamino)pyrazine-2-carboxamide

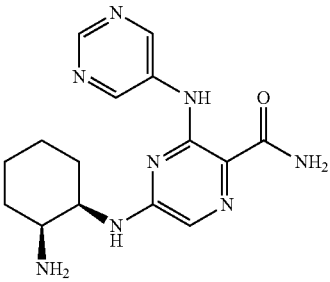 [SMILES: NC(=O)c1ncc(N[C@@H]2CCCC[C@@H]2N)nc1Nc1cncnc1]

The title compound was synthesized in a manner similar to that described in Example 275. MS found for C15H20N8O as (M+H)+ 329.5. UV: λ=202, 258, 303, 352. ¹H NMR: (CD₃OD) δ 9.14 (s, 2H), 8.79 (s, 1H), 7.62 (s, 1H), 4.44 (m, 1H), 3.70 (m, 1H), 1.88 (m, 4H), 1.73 (m, 2H), 1.60 (m, 2H).

Example 304

5-((1R,2S)-2-aminocyclohexylamino)-3-(6-fluoropyridin-3-ylamino)pyrazine-2-carboxamide

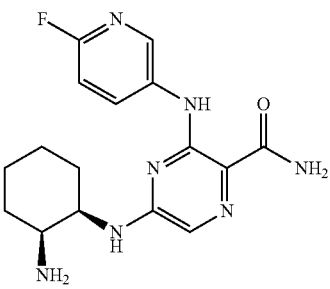

The title compound was synthesized in a manner similar to that described in Example 275. MS found for C16H20FN7O as (M+H)+ 346.5. UV: λ=251, 278, 305, 351 nm. ¹H NMR: (CD₃OD) δ 8.58 (m, 1 Hz, 3 Hz), 8.07 (m, 1H), 7.54 (s, 1H), 7.07 (dd, 1H, 3 Hz, 9 Hz), 4.36 (m, 1H), 3.69 (m, 1H), 1.55-1.88 (m, 8H).

Example 305

5-((1R,2S)-2-aminocyclohexylamino)-3-(2-methoxypyrimidin-5-ylamino)pyrazine-2-carboxamide

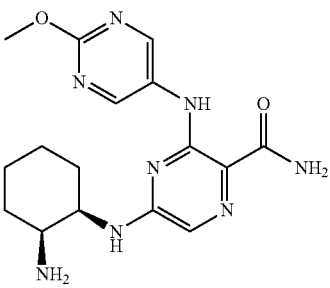 [SMILES: COc1ncc(Nc2nc(N[C@@H]3CCCC[C@@H]3N)cnc2C(N)=O)cn1]

The title compound was synthesized in a manner similar to that described in Example 275. MS found for C16H22N8O2 as (M+H)+ 359.5. UV: λ=205, 293 nm. ¹H NMR: (CD₃OD) δ 8.82 (s, 2H), 7.54 (s, 1H), 4.33 (m, 1H), 4.00 (s, 3H), 3.66 (m, 1H), 1.52-1.87 (m, 8H).

Example 306

5-((1R,2S)-2-aminocyclohexylamino)-3-(6-methoxy-5-methylpyridin-3-ylamino)pyrazine-2-carboxamide

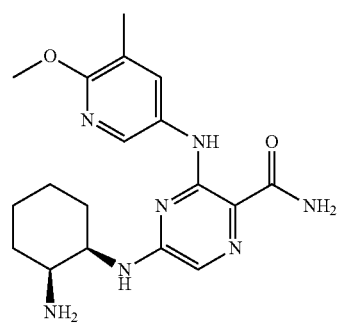 [SMILES: COc1ncc(Nc2nc(N[C@@H]3CCCC[C@@H]3N)cnc2C(N)=O)cc1C]

The title compound was synthesized in a manner similar to that described in Example 275. MS found for C18H25N7O2 as (M+H)+ 372.5. UV: λ=210, 254, 298 nm. ¹H NMR: (CD₃OD) δ 8.28 (d, 1H, 2 Hz), 7.64 (m, 1H), 7.47 (s, 1H), 4.34 (m, 1H), 3.92 (s, 3H), 3.69 (m, 1H), 2.20 (s, 3H), 1.55-1.83 (m, 8H).

Example 307

5-((1R,2S)-2-aminocyclohexylamino)-3-(3-(azetidine-1-carbonyl)phenylamino)pyrazine-2-carboxamide

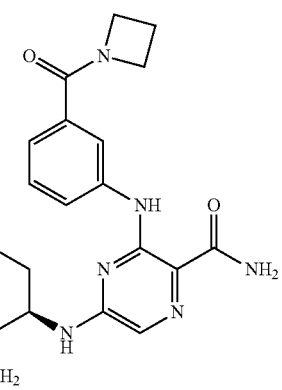

The title compound was synthesized in a manner similar to that described in Example 275. MS found for C21H27N7O2 as (M+H)+ 410.5. UV: λ=224, 251, 303 nm. ¹H NMR: (CD₃OD) δ 8.43 (s, 1H), 7.55 (s, 1H), 7.39 (m, 2H), 7.24 (m, 1H), 4.55 (m, 1H), 4.42 (m, 2H, 8 Hz), 4.22 (m, 2H, 6 Hz), 3.74 (m, 4 Hz), 2.39 (m, 2H, 8 Hz), 1.56-1.95 (m, 8H).

Example 308

5-((1R,2S)-2-aminocyclohexylamino)-3-(6-ethoxy-pyridin-3-ylamino)pyrazine-2-carboxamide

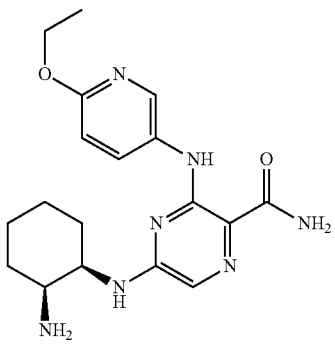 [SMILES: CCOc1ccc(Nc2nc(N[C@@H]3CCCC[C@@H]3N)cnc2C(N)=O)cn1]

The title compound was synthesized in a manner similar to that described in Example 275. MS found for C18H25N7O2 as (M+H)+ 372.5. UV: λ=214, 263, 305, 354 nm. ¹H NMR: (CD₃OD) δ 8.41 (d, 1H, 3 Hz), 7.83 (dd, 1H, 3 Hz, 9 Hz), 7.48 (s, 1H), 6.81 (d, 1H, 9 Hz), 4.31 (m, 1H), 4.29 (q, 2H, 7 Hz), 3.70 (m, 1H), 1.55-1.85 (m, 8H), 1.38 (t, 3H, 7 Hz).

Example 309

5-((1R,2S)-2-aminocyclohexylamino)-3-(5-methoxy-pyridin-3-ylamino)pyrazine-2-carboxamide

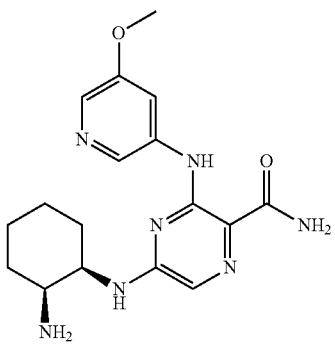 [SMILES: COc1cncc(Nc2nc(N[C@@H]3CCCC[C@@H]3N)cnc2C(N)=O)c1]

The title compound was synthesized in a manner similar to that described in Example 275. MS found for C17H23N7O2 as (M+H)+ 358.5. UV: λ=224, 281, 347 nm. ¹H NMR: (CD₃OD) δ 8.76 (d, 1H, 2 Hz), 8.04 (m, 2H), 7.64 (s, 1H), 4.48 (m, 1H), 3.98 (s, 3H), 3.72 (m, 1H), 1.55-1.93 (m, 8H).

Example 310

(R)-5-(1-amino-1-oxobutan-2-ylamino)-3-(6-(dimethylamino)pyridin-3-ylamino)pyrazine-2-carboxamide

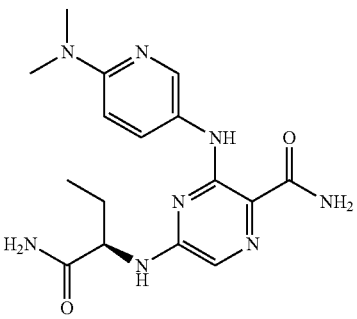 [SMILES: CC[C@@H](Nc1cnc(C(N)=O)c(Nc2ccc(N(C)C)nc2)n1)C(N)=O]

The title compound was synthesized in a manner similar to that described in Example 275. MS found for C16H22N8O2 as (M+H)+ 359.5. UV: λ=217, 305 nm. ¹H NMR: (CD₃OD) δ 8.55 (d, 1H, 3 Hz), 8.01 (dd, 1H, 3 Hz, 10 Hz), 7.56 (s, 1H), 7.24 (d, 1H, 10 Hz), 4.11 (dd, 1H, 5 Hz, 8 Hz), 3.29 (s, 6H), 1.98 (m, 1H), 1.89 (m, 1H), 1.13 (t, 3H, 8 Hz).

Example 311

(R)-5-(1-amino-1-oxobutan-2-ylamino)-3-(6-methoxy-5-methylpyridin-3-ylamino)pyrazine-2-carboxamide

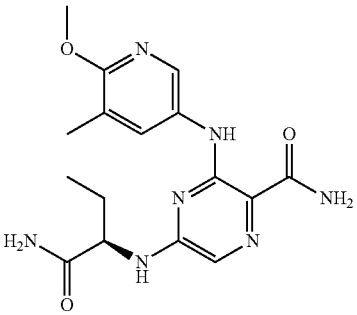 [SMILES: CC[C@@H](Nc1cnc(C(N)=O)c(Nc2cnc(OC)c(C)c2)n1)C(N)=O]

The title compound was synthesized in a manner similar to that described in Example 275. MS found for C16H21N7O3 as (M+H)+ 360.5. UV: λ=207, 256, 300 nm. ¹H NMR: (CD₃OD) δ 8.35 (d, 1H, 3 Hz), 7.73 (d, 1H, 2 Hz), 7.45 (s, 1H), 4.31 (dd, 1H, 5 Hz, 8 Hz), 2.66 (s, 3H), 2.22 (s, 3H), 1.95 (m, 1H), 1.84 (m, 1H), 1.06 (t, 3H, 7 Hz).

Example 312

(R)-5-(1-amino-4-methyl-1-oxopentan-2-ylamino)-3-(6-methoxypyridin-3-ylamino)pyrazine-2-carboxamide

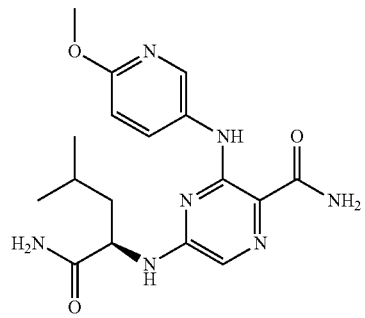 [SMILES: COc1ccc(Nc2nc(N[C@H](CC(C)C)C(N)=O)cnc2C(N)=O)cn1]

The title compound was synthesized in a manner similar to that described in Example 275. MS found for C17H23N7O3 as (M+H)+ 18A. UV: λ=202, 256, 300 nm. ¹H NMR: (CD₃OD) δ 8.48 (d, 1H, 2 Hz), 8.11 (dd, 1H, 3 Hz, 9 Hz), 7.47 (s, 1H), 6.98 (d, 1H, 9 Hz), 4.35 (dd, 1H, 5 Hz, 10 Hz), 3.93 (s, 3H), 2.66 (s, 3H), 1.67-1.82 (m, 3H), 0.99 (d, 3H, 7 Hz), 0.91 (d, 3H, 7 Hz).

Example 313

(R)-5-(1-amino-4-methyl-1-oxopentan-2-ylamino)-3-(6-(dimethylamino)pyridin-3-ylamino)pyrazine-2-carboxamide

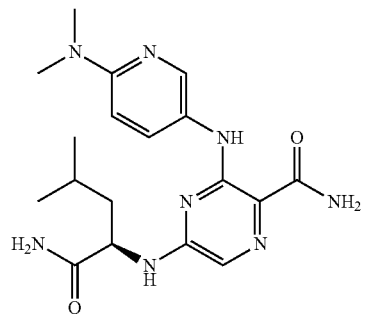 [SMILES: CC(C)C[C@@H](Nc1cnc(C(N)=O)c(Nc2ccc(N(C)C)nc2)n1)C(N)=O]

The title compound was synthesized in a manner similar to that described in Example 275. MS found for C18H26N8O2 as (M+H)+ 387.5. UV: λ=202, 261, 305 nm. ¹H NMR: (CD₃OD) δ 8.54 (d, 1H, 2 Hz), 8.00 (dd, 1H, 3 Hz, 10 Hz), 7.55 (s, 1H), 7.24 (d, 1H, 10 Hz), 4.23 (dd, 1H, 4 Hz), 10 Hz), 1.70-1.88 (m, 3H), 1.02 (d, 3H, 6 Hz), 0.94 (d, 3H, 6 Hz).

Example 314

(R)-5-(1-amino-1-oxobutan-2-ylamino)-3-(6-(dimethylamino)-5-methylpyridin-3-ylamino)pyrazine-2-carboxamide

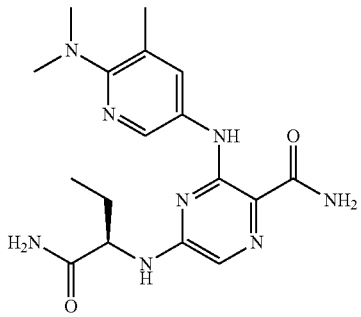 [SMILES: CC[C@@H](Nc1cnc(C(N)=O)c(Nc2cnc(N(C)C)c(C)c2)n1)C(N)=O]

The title compound was synthesized in a manner similar to that described in Example 275. MS found for C17H24N8O2 as (M+H)+ 373.2. UV: λ=221, 310 nm.

Example 315

(R)-5-(1-amino-3-methyl-1-oxobutan-2-ylamino)-3-(2-methoxypyridin-4-ylamino)pyrazine-2-carboxamide

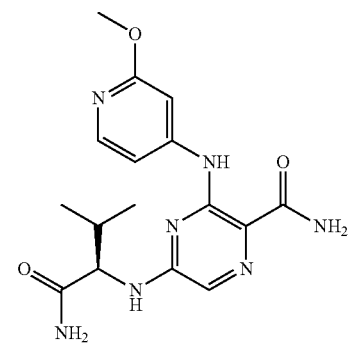 [SMILES: COc1cc(Nc2nc(N[C@@H](C(N)=O)C(C)C)cnc2C(N)=O)ccn1]

The title compound was synthesized in a manner similar to that described in Example 275. MS found for C16H21N7O3 as (M+H)+ 360.3. UV: λ=205, 273, 319 nm. ¹H NMR: (CD₃OD) δ 7.99 (d, 1H, 7 Hz), 7.83 (s, 1H), 7.69 (m, 1H), 7.53 (m, 1H), 4.25 (d, 1H, 5 Hz), 4.16 (s, 3H), 2.31 (m, 1H, 6 Hz), 1.11 (m, 6H).

Example 316

(R)-5-(1-amino-1-oxobutan-2-ylamino)-3-(6-(2,2,2-trifluoroethoxy)pyridin-3-ylamino)pyrazine-2-carboxamide

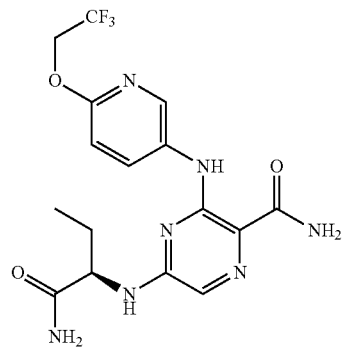 [SMILES: CC[C@@H](Nc1cnc(C(N)=O)c(Nc2ccc(OCC(F)(F)F)nc2)n1)C(N)=O]

The title compound was synthesized in a manner similar to that described in Example 275. MS found for C16H18F3N7O3 as (M+H)+ 414.3. UV: λ=203, 252, 298, 359 nm. $^1$H NMR: (CD$_3$OD) δ 8.31 (d, 1H, 6 Hz), 8.12 (dd, 1H, 3 Hz, 9 Hz), 7.47 (s, 1H), 6.89 (d, 1H, 9 Hz), 4.82 (q, 8 Hz), 4.23 (dd, 1H, 5 Hz, 8 Hz), 1.95 (m, 1H), 1.84 (m, 1H), 1.07 (t, 3H, 8 Hz).

Example 317

(R)-5-(1-amino-1-oxobutan-2-ylamino)-3-(6-methoxypyridin-3-ylamino)pyrazine-2-carboxamide

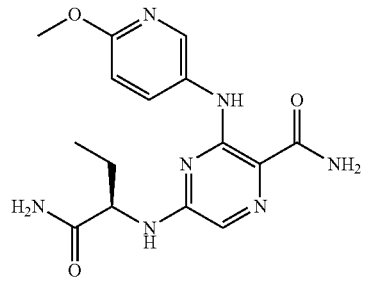 [SMILES: CC[C@@H](Nc1cnc(C(N)=O)c(Nc2ccc(OC)nc2)n1)C(N)=O]

The title compound was synthesized in a manner similar to that described in Example 275. MS found for C15H19N7O3 as (M+H)+ 346.3. $^1$H NMR: (CD$_3$OD) δ 8.53 (d, 1H, 3 Hz), 8.19 (dd, 1H, 3 Hz, 9 Hz), 7.51 (s, 1H), 7.07 (d, 1H, 9 Hz), 4.20 (dd, 1H, 5 Hz, 8 Hz), 1.94 (m, 1H), 1.84 (m, 1H), 1.08 (t, 3H, 8 Hz).

Example 318

(R)-5-(1-amino-1-oxobutan-2-ylamino)-3-(2-(dimethylamino)benzo[d]oxazol-6-ylamino)pyrazine-2-carboxamide

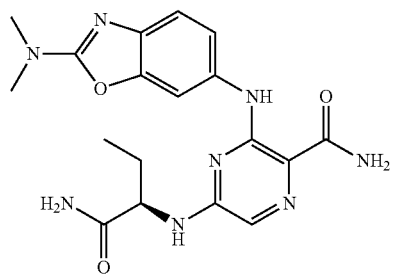 [SMILES: CC[C@@H](Nc1cnc(C(N)=O)c(Nc2ccc3nc(N(C)C)oc3c2)n1)C(N)=O]

The title compound was synthesized in a manner similar to that described in Example 275. MS found for Cl8H22N8O3 as (M+H)+ 399.3. UV: λ=209, 260, 317 nm. $^1$H NMR: (CD$_3$OD) δ 8.11 (s, 1H), 7.48 (s, 1H), 7.29 (d, 1H, 9 Hz), 7.24 (d, 1H, 9 Hz), 4.25 (dd, 1H, 5 Hz, 9 Hz), 1.98 (m, 1H), 1.87 (m, 1H), 1.10 (t, 3H, 7 Hz).

Example 319

(R)-5-(1-amino-1-oxobutan-2-ylamino)-3-(6-(azetidin-1-yl)pyridin-3-ylamino)pyrazine-2-carboxamide

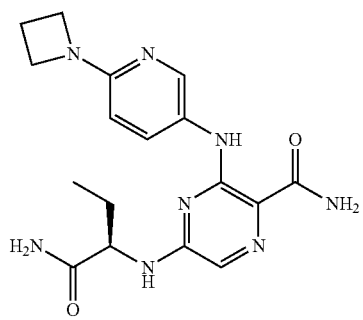 [SMILES: CC[C@@H](Nc1cnc(C(N)=O)c(Nc2ccc(N3CCC3)nc2)n1)C(N)=O]

The title compound was synthesized in a manner similar to that described in Example 275. MS found for C17H22N8O2 as (M+H)+ 371.3. UV: λ=217, 261, 305 nm. $^1$H NMR: (CD$_3$OD) δ 8.47 (s, 1H), 7.96 (dd, 1H, 2 Hz, 9 Hz), 7.54 (s, 1H), 6.83 (d, 1H, 10 Hz), 4.33 (t, 4H, 7 Hz), 4.08 (dd, 1H, 6 Hz, 9 Hz), 2.59 (m, 2H, 8 Hz), 1.96 (m, 1H), 1.89 (m, 1H), 1.11 (t, 3H, 7 Hz).

Example 320

(R)-5-(1-amino-1-oxobutan-2-ylamino)-3-(4-methylpyridin-2-ylamino)pyrazine-2-carboxamide

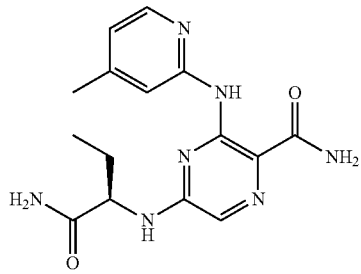 [SMILES: CC[C@@H](Nc1cnc(C(N)=O)c(Nc2cc(C)ccn2)n1)C(N)=O]

The title compound was synthesized in a manner similar to that described in Example 275. MS found for C15H19N7O2 as (M+H)+ 330.3. UV: λ=213, 270, 329 nm.

Example 321

(R)-5-(1-amino-4-methyl-1-oxopentan-2-ylamino)-3-(6-(3-cyanoazetidine-1-carbonyl)pyridin-3-ylamino)pyrazine-2-carboxamide

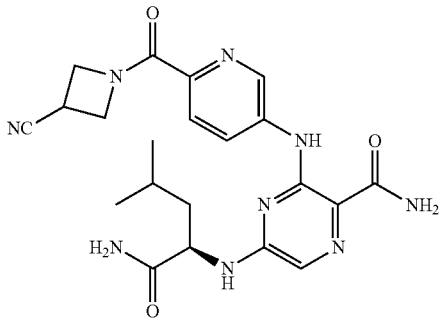 [SMILES: CC(C)C[C@@H](Nc1cnc(C(N)=O)c(Nc2ccc(C(=O)N3CC(C#N)C3)nc2)n1)C(N)=O]

The title compound was synthesized in a manner similar to that described in Example 275. MS found for C21H25N9O3 as (M+H)+ 452.4. UV: λ=211, 269, 329 nm. $^1$H NMR: (CD$_3$OD) δ 8.73 (dd, 1H, 2 Hz, 10 Hz), 8.43 (m, 1H), 8.01 (d, 1H, 9 Hz), 7.57 (s, 1H), 4.48 (t, 1H, 5 Hz), 4.42 (m, 1H), 4.33 (m, 1H), 3.78 (m, 1H), 1.84 (m, 2H), 1.74 (m, 2H), 1.01 (d, 3H, 6 Hz), 0.94 (d, 3H, 6 Hz).

Example 322

(R)-5-(1-amino-1-oxobutan-2-ylamino)-3-(5-methoxypyridin-3-ylamino)pyrazine-2-carboxamide

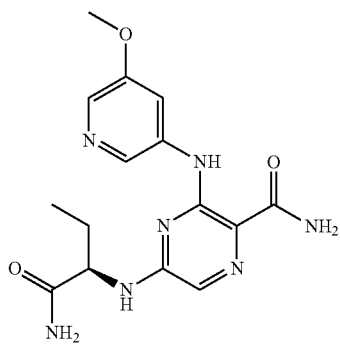 [SMILES: CC[C@@H](Nc1cnc(C(N)=O)c(Nc2cncc(OC)c2)n1)C(N)=O]

The title compound was synthesized in a manner similar to that described in Example 275. MS found for C15H19N7O3 as (M+H)+ 346.3. UV: λ=224, 284, 301, 350. $^1$H NMR: (CD$_3$OD) δ 9.03 (2 Hz), 8.11 (d, 1H, 2 Hz), 8.00 (t, 1H, 2 Hz), 7.66 (s, 1H), 4.20 (dd, 1H, 6 Hz), 8 Hz), 1.99 (m, 1H), 1.88 (m, 1H), 1.11 (t, 3H, 8 Hz).

Example 323

(R)-5-(1-amino-4-methyl-1-oxopentan-2-ylamino)-3-(5-methoxypyridin-3-ylamino)pyrazine-2-carboxamide

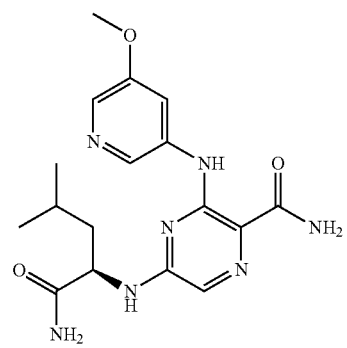 [SMILES: COc1cncc(Nc2nc(N[C@H](CC(C)C)C(N)=O)cnc2C(N)=O)c1]

The title compound was synthesized in a manner similar to that described in Example 275. MS found for C17H23N7O3 as (M+H)+ 374.3. UV: λ=201, 224, 285 nm. $^1$H NMR: (CD$_3$OD) δ 9.04 (d, 1H, 2 Hz), 8.11 (d, 1H, 2 Hz), 8.02 (t, 1H, 2 Hz), 7.65 (s, 1H), 4.30 (dd, 1H, 5 Hz), 10 Hz), 4.03 (s, 3H), 1.73-1.92 (m, 3H), 1.02 (d, 3H, 6 Hz), 0.94 (d, 3H, 6 Hz).

Example 324

5-((1R,2S)-2-aminocyclohexylamino)-3-(1-methyl-2-oxoindolin-5-ylamino)pyrazine-2-carboxamide

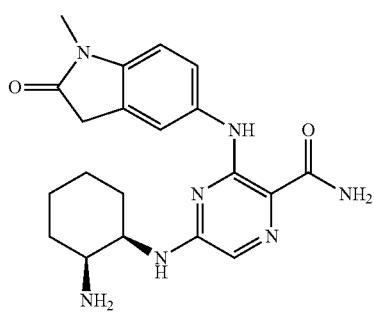 [SMILES: CN1C(=O)Cc2cc(Nc3nc(N[C@@H]4CCCC[C@@H]4N)cnc3C(N)=O)ccc21]

The title compound was synthesized in a manner similar to that described in Example 275. MS found for C20H25N7O2 as (M+H)+ 396.4. UV: λ=205, 306 nm. $^1$H NMR: (CD$_3$OD) δ 7.06 (s, 1H), 7.47 (d, 1H), 7.45 (s, 1H), 6.96 (d, 1H, 9 Hz), 4.31 (m, 1H), 3.74 (m, 1H), 3.58 (s, 2H), 3.22 (s, 3H), 1.58-1.84 (m, 8H).

Example 325

5-((1R,2S)-2-aminocyclohexylamino)-3-(2-(dimethylamino)benzo[d]oxazol-6-ylamino)pyrazine-2-carboxamide

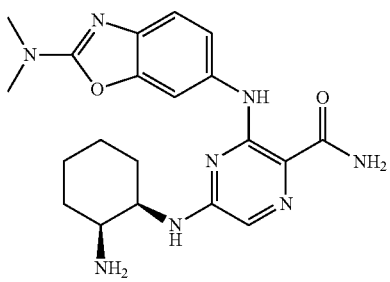 [SMILES: CN(C)c1nc2ccc(Nc3nc(N[C@@H]4CCCC[C@@H]4N)cnc3C(N)=O)cc2o1]

The title compound was synthesized in a manner similar to that described in Example 275. MS found for C20H26N8O2 as (M+H)+ 411.4. UV: λ=206, 260, 316. $^1$H NMR: (CD$_3$OD) δ 7.87 (d, 1H, 2 Hz), 7.47 (s, 1H), 7.25 (m, 2H), 4.32 (m, 1H), 3.82 (m, 1H), 3.22 (s, 6H), 1.54-1.90 (m, 8H).

Example 326

(R)-5-(1-amino-3-methyl-1-oxobutan-2-ylamino)-3-(6-methoxypyridin-3-ylamino)pyrazine-2-carboxamide

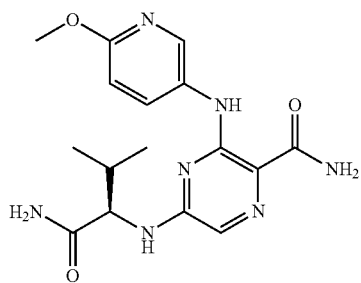 [SMILES: COc1ccc(Nc2nc(N[C@@H](C(N)=O)C(C)C)cnc2C(N)=O)cn1]

The title compound was synthesized in a manner similar to that described in Example 275. MS found for C16H21N7O3 as (M+H)+ 360.3. UV: λ=203, 256, 300, 355 nm. $^1$H NMR: (CD$_3$OD) δ 8.55 (d, 1H, 2 Hz), 8.13 (dd, 1H, 2 Hz, 9 Hz), 7.56 (s, 1H), 7.04 (d, 1H, 9 Hz), 4.21 (d, 1H, 6 Hz), 3.98 (s, 3H), 2.23 (m, 1H, 6 Hz), 1.09 (d, 6H, 7 Hz).

Example 327

(R)-5-(1-amino-3-methyl-1-oxobutan-2-ylamino)-3-(6-(2,2,2-trifluoroethoxy)pyridin-3-ylamino)pyrazine-2-carboxamide

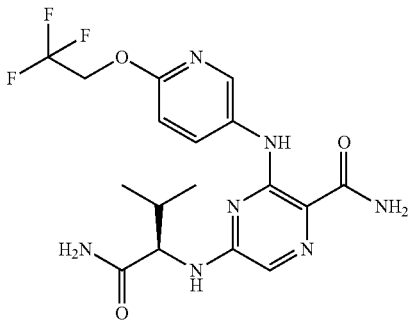 [SMILES: CC(C)[C@@H](Nc1cnc(C(N)=O)c(Nc2ccc(OCC(F)(F)F)nc2)n1)C(N)=O]

The title compound was synthesized in a manner similar to that described in Example 275. MS found for C17H20F3N7O3 as (M+H)+ 428.3. UV: λ=203, 253, 298, 360 nm. $^1$H NMR: (CD$_3$OD) δ 8.33 (d, 1H, 3 Hz), 8.11 (dd, 1H, 3 Hz, 8 Hz), 7.53 (s, 1H), 6.91 (d, 1H, 9 Hz), 4.81 (q, 2H, 9 Hz), 4.24 (d, 1H, 5 Hz), 2.24 (m, 1H), 1.06 (d, 6H, 6 Hz).

Example 328

5-((1R,2S)-2-aminocyclohexylamino)-3-(3-methylisothiazol-5-ylamino)pyrazine-2-carboxamide

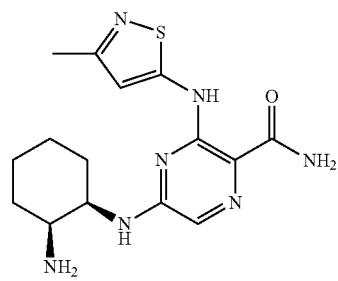 [SMILES: Cc1cc(Nc2nc(N[C@@H]3CCCC[C@@H]3N)cnc2C(N)=O)sn1]

The title compound was synthesized in a manner similar to that described in Example 275. MS found for C15H21N7OS as (M+H)+ 348.3. UV: λ=209, 275, 322 nm. $^1$H NMR: (CD$_3$OD) δ 7.62 (s, 1H), 6.78 (s, 1H), 4.68 (m, 1H), 3.91 (m, 1H), 2.38 (s, 3H), 2.00 (m, 2H), 1.89 (m, 2H), 1.81 (m, 1H), 1.69 (m, 3H).

Example 329

(R)-5-(1-amino-1-oxobutan-2-ylamino)-3-(6-(3-cyanoazetidine-1-carbonyl)pyridin-3-ylamino)pyrazine-2-carboxamide

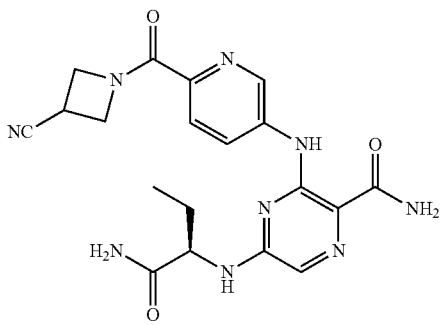 [SMILES: CC[C@@H](Nc1cnc(C(N)=O)c(Nc2ccc(C(=O)N3CC(C#N)C3)nc2)n1)C(N)=O]

The title compound was synthesized in a manner similar to that described in Example 275. MS found for C19H21N9O3 as (M+H)+ 424.3. UV: λ=211, 269, 329 nm. $^1$H NMR:

(CD₃OD) δ 8.74 (d, 1H), 8.43 (m, 1H), 8.01 (d, 1H), 7.59 (s, 1H), 4.47 (t, 2H), 4.31 (m, 3H), 2.01 (m, 1H), 1.88 (m, 1H), 1.12 (t, 3H).

Example 330

5-((1R,2R)-2-amino-3,3-difluorocyclohexylamino)-3-(6-methoxypyridin-3-ylamino)pyrazine-2-carboxamide

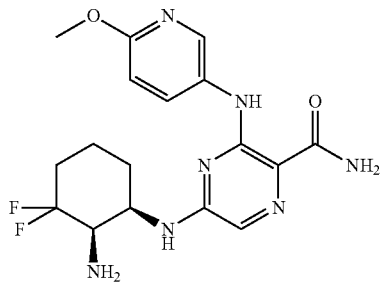 [SMILES: COc1ccc(Nc2nc(N[C@@H]3CCCC(F)(F)[C@@H]3N)cnc2C(N)=O)cn1]

The title compound was synthesized in a manner similar to that described in Example 275. MS found for C17H21F2N7O2 as (M+H)⁺ 394.3. UV: λ=202, 253, 295, 355 nm. ¹H NMR: (CD₃OD) δ 8.32 (d, 1H, 3 Hz), 7.91 (dd, 1H, 3 Hz, m 9 Hz), 7.51 (s, 1H), 6.80 (d, 1H, 9 Hz), 4.62 (m, 1H), 4.10 (m, 1H), 3.89 (s, 3H), 2.13 (m, 2H), 1.84 (m, 4H).

Example 331

5-((1R,2R)-2-amino-3,3-difluorocyclohexylamino)-3-(2-methoxypyridin-4-ylamino)pyrazine-2-carboxamide

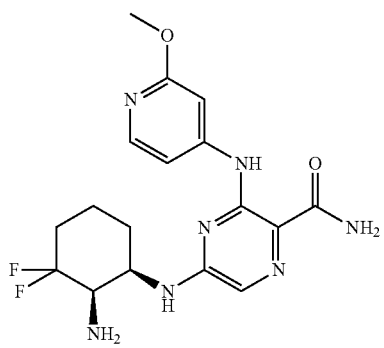 [SMILES: COc1cc(Nc2nc(N[C@@H]3CCCC(F)(F)[C@@H]3N)cnc2C(N)=O)ccn1]

The title compound was synthesized in a manner similar to that described in Example 275. MS found for C17H21F2N7O2 as (M+H)⁺ 394.3. UV: λ=207, 271, 317 nm. ¹H NMR: (CD₃OD) δ 7.98 (d, 1H, 6 Hz), 7.79 (s, 1H), 7.56 (broad m, 1H), 7.42 (broad m, 1H), 4.84 (m, 1H), 4.18 (m, 1H), 4.07 (s, 3H), 1.91-2.27 (m, 5H), 1.84 (m, 1H).

Example 332

5-((1R,2R)-2-amino-3,3-difluorocyclohexylamino)-3-(6-methoxy-5-methylpyridin-3-ylamino)pyrazine-2-carboxamide

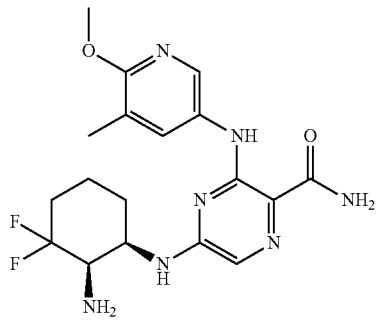 [SMILES: COc1ncc(Nc2nc(N[C@@H]3CCCC(F)(F)[C@@H]3N)cnc2C(N)=O)cc1C]

The title compound was synthesized in a manner similar to that described in Example 275. MS found for C18H23F2N7O2 as (M+H)⁺ 408.3. UV: λ=207, 250, 295 nm. ¹H NMR: (CD₃OD) δ 8.19 (s, 1H), 7.64 (s, 1H), 7.49 (s, 1H), 4.64 (s, 1H), 4.07 (m, 1H), 3.92 (s, 3H), 2.19 (s, 3H), 2.17-1.72 (m, 6H).

Example 333

5-((1R,2R)-2-amino-3,3-difluorocyclohexylamino)-3-(5-methoxypyridin-3-ylamino)pyrazine-2-carboxamide

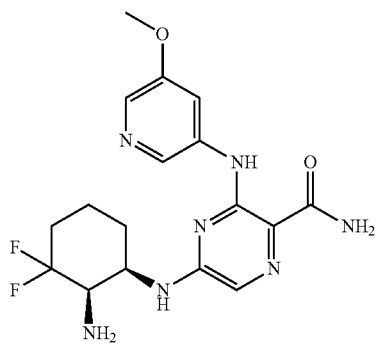 [SMILES: COc1cncc(Nc2nc(N[C@@H]3CCCC(F)(F)[C@@H]3N)cnc2C(N)=O)c1]

The title compound was synthesized in a manner similar to that described in Example 275. MS found for C17H21F2N7O2 as (M+H)⁺ 394.3. UV: λ=223, 281, 349 nm. ¹H NMR: (CD₃OD) δ 8.71 (d, 1H, 2 Hz), 8.04 (d, 1H, 3 Hz), 7.92 (distorted t, 1H, 2 Hz), 7.67 (s, 1H), 4.11 (m, 1H), 3.95 (s, 3H), 1.89-2.33 (m, 5H), 1.83 (m, 1H).

Example 334

(R)-5-(1-amino-4-methyl-1-oxopentan-2-ylamino)-3-(6-(azetidin-1-yl)pyridin-3-ylamino)pyrazine-2-carboxamide

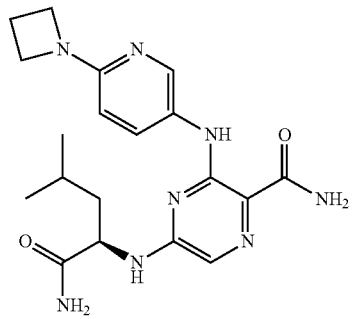 [SMILES: CC(C)C[C@@H](Nc1cnc(C(N)=O)c(Nc2ccc(N3CCC3)nc2)n1)C(N)=O]

The title compound was synthesized in a manner similar to that described in Example 275. MS found for C19H26N8O2 as (M+H)+ 399.3. UV: λ=202, 262, 306, 357 nm. $^1$H NMR: (CD$_3$OD) δ 8.47 (d, 1H, 2 Hz), 7.95 (dd, 1H, 2 Hz, 10 Hz), 7.53 (s, 1H), 6.83 (d, 1H, 10 Hz), 4.33 (t, 4H, 8 Hz), 4.18 (dd, 1H, 4 Hz, 6 Hz), 2.59 (m, 2H, 8 Hz), 1.70-1.83 (m, 3H), 1.02 (d, 3H, 6 Hz), 0.93 (d, 3H, 6 Hz).

Example 335

(R)-5-(1-amino-4-methyl-1-oxopentan-2-ylamino)-3-(2-(dimethylamino)pyridin-4-ylamino)pyrazine-2-carboxamide

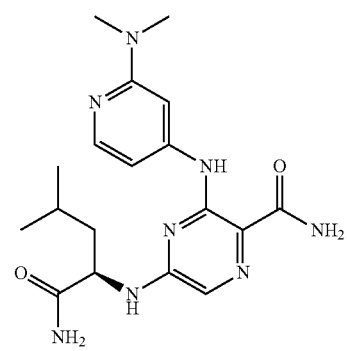 [SMILES: CC(C)C[C@@H](Nc1cnc(C(N)=O)c(Nc2ccnc(N(C)C)c2)n1)C(N)=O]

The title compound was synthesized in a manner similar to that described in Example 275. MS found for C18H26N8O2 as (M+H)+ 387.3. UV: λ=202, 255, 316 nm. $^1$H NMR: (CD$_3$OD) δ 7.72 (s, 1H), 7.70 (d, 1H, 7 Hz), 7.31 (d, 1H, 2 Hz), 7.24 (dd, 1H, 2 Hz, 8 Hz), 4.38 (dd, 1H, 5 Hz, 9 Hz), 3.26 (s, 6H), 1.75-1.84 (m, 3H), 1.01 (d, 3H, 6 Hz), 0.93 (d, 3H, 6 Hz).

Example 336

5-((1R,2R)-2-amino-3,3-difluorocyclohexylamino)-3-(2-(dimethylamino)benzo[d]oxazol-6-ylamino)pyrazine-2-carboxamide

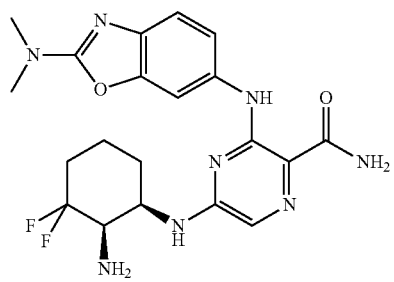 [SMILES: CN(C)c1nc2ccc(Nc3nc(N[C@@H]4CCCC(F)(F)[C@@H]4N)cnc3C(N)=O)cc2o1]

The title compound was synthesized in a manner similar to that described in Example 275. MS found for C20H24F2N8O2 as (M+H)+ 447.4. UV: λ=207, 256, 316 nm. $^1$H NMR: (CD$_3$OD) δ 7.81 (d, 1H, 2 Hz), 7.47 (s, 1H), 7.28 (dd, 1H, 2 Hz, 9 Hz), 7.22 (d, 1H, 8 Hz), 4.58 (m, 1H), 4.22 (m, 1H), 3.21 (s, 6H), 2.13 (m, 2H), 1.95 (m, 2H), 1.79 (m, 2H).

Example 337

5-((1R,2R)-2-amino-3,3-difluorocyclohexylamino)-3-(2-(azetidin-1-yl)benzo[d]oxazol-6-ylamino)pyrazine-2-carboxamide

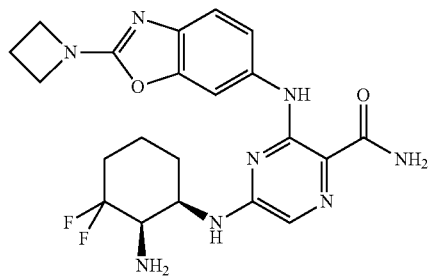 [SMILES: NC(=O)c1ncc(N[C@@H]2CCCC(F)(F)[C@@H]2N)nc1Nc1ccc2nc(N3CCC3)oc2c1]

The title compound was synthesized in a manner similar to that described in Example 275. MS found for C21H24F2N8O2 as (M+H)+ 459.4. UV: λ=207, 254, 317 nm. $^1$H NMR: (CD$_3$OD) δ 7.77 (d, 1H, 2 Hz), 7.48 (s, 1H), 7.30 (dd, 1H, 2 Hz, 8 Hz), 7.23 (d, 1H, 8 Hz), 4.60 (m, 1H), 4.31 (t, 4H, 8 Hz), 4.19 (m, 1H), 2.55 (m, 2H, 7 Hz), 2.12 (m, 2H), 1.95 (m, 2H), 1.80 (m, 2H).

Example 338

5-((1R,2S)-2-aminocyclohexylamino)-3-(6-cyanopyridin-3-ylamino)pyrazine-2-carboxamide

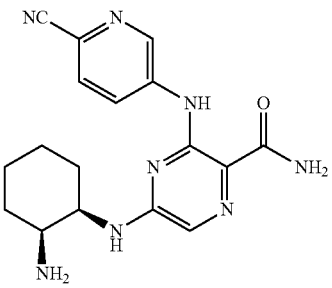 [SMILES: N#Cc1ccc(Nc2nc(N[C@@H]3CCCC[C@@H]3N)cnc2C(N)=O)cn1]

The title compound was synthesized in a manner similar to that described in Example 275. MS found for C17H20N8O as (M+H)+ 353.3. UV: λ=211, 271, 330 nm. ¹H NMR: (CD₃OD) δ 9.10 (d, 1H, 2 Hz), 8.20 (dd, 1H, 3 Hz, 9 Hz), 7.81 (d, 1H, 8 Hz), 7.66 (s, 1H), 4.74 (m, 1H), 3.74 (m, 1H), 1.90 (m, 2H), 1.86 (m, 2H), 1.75 (m, 2H), 1.64 (m, 2H).

Example 339

5-((1R,2S)-2-aminocyclohexylamino)-3-(2-methyl-1-oxoisoindolin-5-ylamino)pyrazine-2-carboxamide

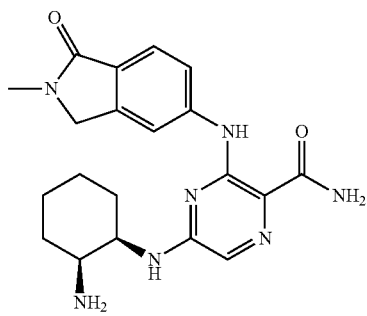 [SMILES: CN1Cc2cc(Nc3nc(N[C@@H]4CCCC[C@@H]4N)cnc3C(N)=O)ccc2C1=O]

The title compound was synthesized in a manner similar to that described in Example 275. MS found for C20H25N7O2 as (M+H)+ 396.4. UV: λ=203, 237, 270, 322 nm. ¹H NMR: (CD₃OD) δ 7.85 (s, 1H), 7.79 (d, 1H, 9 Hz), 7.68 (d, 1H, 8 Hz), 7.54 (s, 1H), 4.48 (s, 2H), 4.39 (m, 1H), 3.74 (m, 1H), 3.18 (s, 3H), 1.61-1.89 (m, 8H).

Example 340

(R)-5-(1-amino-1-oxobutan-2-ylamino)-3-(6-ethylpyridin-3-ylamino)pyrazine-2-carboxamide

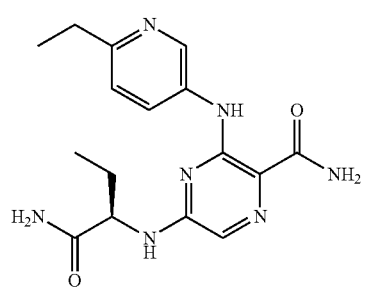 [SMILES: CCc1ccc(Nc2nc(N[C@H](CC)C(N)=O)cnc2C(N)=O)cn1]

The title compound was synthesized in a manner similar to that described in Example 275. MS found for C16H21N7O2 as (M+H)+ 344.3. UV: λ=203, 233, 260, 303, 350 nm. ¹H NMR: (CD₃OD) δ 9.23 (d, 1H, 2.8 Hz), 8.47 (dd, 1H, 3 Hz, 9 Hz), 7.78 (d, 1H, 9 Hz), 7.66 (s, 1H), 4.14 (dd, 1H, 5 Hz, 8 Hz), 3.00 (q, 2H, 8 Hz), 1.99 (m, 1H), 1.92 (m, 1H), 1.40 (t, 3H, 8 Hz), 1.27 (t, 3H, 8 Hz).

Example 341

(R)-5-(1-amino-1-oxobutan-2-ylamino)-3-(6-cyclopropylpyridin-3-ylamino)pyrazine-2-carboxamide

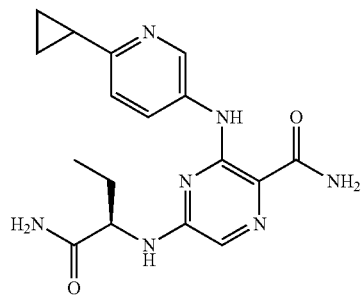 [SMILES: CC[C@@H](Nc1cnc(C(N)=O)c(Nc2ccc(C3CC3)nc2)n1)C(N)=O]

The title compound was synthesized in a manner similar to that described in Example 275. MS found for C17H21N7O2 as (M+H)+ 356.3. UV: λ=203, 239, 263, 305, 353 nm. ¹H NMR: (CD₃OD) δ 9.15 (s, 1H), 8.37 (dd, 1H, 2 Hz, 9 Hz), 7.65 (s, 1H), 7.50 (d, 1H, 9 Hz), 4.14 (dd, 1H, 5 Hz, 8 Hz), 2.28 (m, 1H), 1.99 (m, 1H), 1.90 (m, 1H), 1.36 (m, 2H), 1.13 (m, 5H).

Example 342

(R)-5-(1-amino-1-oxobutan-2-ylamino)-3-(2-cyclopropylpyridin-4-ylamino)pyrazine-2-carboxamide

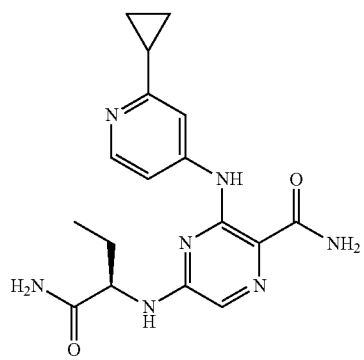 [SMILES: CC[C@@H](Nc1cnc(C(N)=O)c(Nc2ccnc(C3CC3)c2)n1)C(N)=O]

The title compound was synthesized in a manner similar to that described in Example 275. MS found for C17H21N7O2 as (M+H)+ 356.3. UV: λ=214, 276, 321 nm. ¹H NMR: (CD₃OD) δ 8.23 (d, 1H, 6 Hz), 8.17 (d, 1H, 7 Hz), 7.80 (s, 1H), 7.56 (s, 1H), 4.21 (dd, 1H, 5 Hz, 8 Hz), 2.29 (m, 1H), 2.02 (m, 1H), 1.93 (m, 1H), 1.35 (m, 2H), 1.17 (m, 2H), 1.13 (t, 3H, 8 Hz).

Example 343

5-((1R,2R)-2-amino-3,3-difluorocyclohexylamino)-3-(6-ethylpyridin-3-ylamino)pyrazine-2-carboxamide

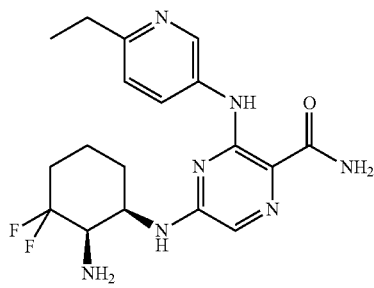 [SMILES: CCc1ccc(Nc2nc(N[C@@H]3CCCC(F)(F)[C@@H]3N)cnc2C(N)=O)cn1]

The title compound was synthesized in a manner similar to that described in Example 275. MS found for C18H23F2N7O as (M+H)+ 392.3. UV: λ=203, 231, 257, 303, 349 nm. ¹H NMR: (CD₃OD) δ 9.10 (s, 1H), 8.49 (dd, 1H, 2 Hz, 9 Hz), 7.12 (d, 1H, 8 Hz), 7.69 (s, 1H), 4.78 (m, 1H), 4.10 (m, 1H), 2.98 (q, 2H, 8 Hz), 2.40 (m, 2H), 1.82-1.02 (m, 4H), 1.38 (t, 3H, 8 Hz).

Example 344

(R)-5-(1-amino-4-methyl-1-oxopentan-2-ylamino)-3-(2-cyclopropylpyridin-4-ylamino)pyrazine-2-carboxamide

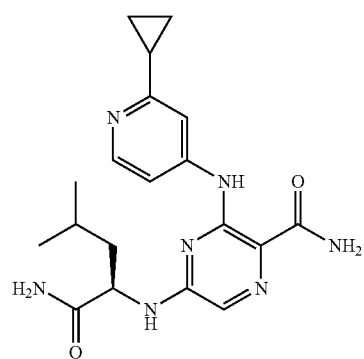 [SMILES: CC(C)C[C@@H](Nc1cnc(C(N)=O)c(Nc2ccnc(C3CC3)c2)n1)C(N)=O]

The title compound was synthesized in a manner similar to that described in Example 275. MS found for C19H25N7O2 as (M+H)+ 384.4. UV: λ=214, 276, 321 nm. ¹H NMR: (CD₃OD) δ 8.18 (m, 2H), 7.79 (s, 1H), 7.61 (s, 1H), 4.31 (dd, 1H, 5 Hz, 10 Hz), 2.30 (m, 1H), 1.76-1.86 (m, 3H), 1.36 (m, 2H), 1.16 (m, 2H), 1.03 (d, 3H, 6 Hz), 0.95 (d, 3H, 6 Hz).

Example 345

5-((1R,2R)-2-amino-3,3-difluorocyclohexylamino)-3-(6-cyclopropylpyridin-3-ylamino)pyrazine-2-carboxamide

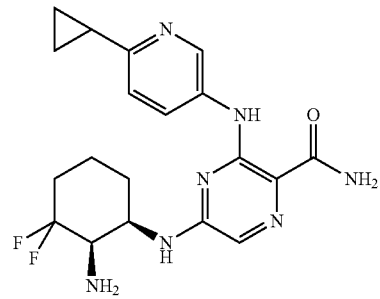 [SMILES: NC(=O)c1ncc(N[C@@H]2CCCC(F)(F)[C@@H]2N)nc1Nc1ccc(C2CC2)nc1]

The title compound was synthesized in a manner similar to that described in Example 275. MS found for C19H23F2N7O as (M+H)+ 404.4. UV: λ=207, 235, 260, 303, 350 nm.

Example 346

5-((1R,2R)-2-amino-3,3-difluorocyclohexylamino)-3-(2-cyclopropylpyridin-4-ylamino)pyrazine-2-carboxamide

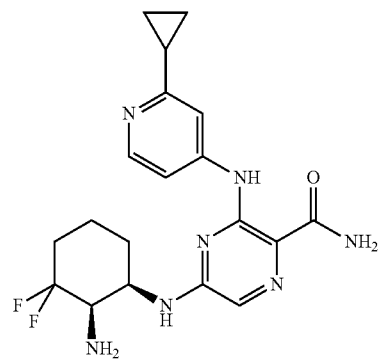 [SMILES: NC(=O)c1ncc(N[C@@H]2CCCC(F)(F)[C@@H]2N)nc1Nc1ccnc(C2CC2)c1]

The title compound was synthesized in a manner similar to that described in Example 275. MS found for C19H23F2N7O as (M+H)+ 404.4. UV: λ=214, 273, 321 nm. ¹H NMR: (CD₃OD) δ 8.19 (d, 1H, 7 Hz), 8.13 (d, 1H, 5 Hz), 7.85 (s, 1H), 7.61 (s, 1H), 4.79 (m, 1H), 4.18 (m, 1H), 2.22 (m, 3H), 1.97 (m, 3H), 1.85 (m, 1H), 1.37 (m, 2H), 1.16 (m, 2H).

Example 347

(R)-5-(1-amino-4-methyl-1-oxopentan-2-ylamino)-3-(6-ethylpyridin-3-ylamino)pyrazine-2-carboxamide

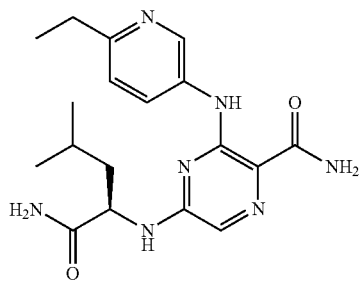 [SMILES: CCc1ccc(Nc2nc(N[C@H](CC(C)C)C(N)=O)cnc2C(N)=O)cn1]

The title compound was synthesized in a manner similar to that described in Example 275. MS found for C18H25N7O2 as (M+H)+ 372.3. UV: λ=207, 235, 260, 303, 353 nm. $^1$H NMR: (CD$_3$OD) δ 9.25 (d, 1H, 2 Hz), 8.45 (dd, 1H, 2 Hz, 9 Hz), 7.80 (d, 1H, 9 Hz), 7.65 (s, 1H), 4.24 (dd, 1H, 5 Hz, 10 Hz), 3.00 (q, 2H, 8 Hz), 1.73-1.89 (m, 3H), 1.41 (t, 3H, 8 Hz), 1.03 (d, 3H, 6 Hz), 0.95 (d, 3H, 7 Hz).

Example 348

(R)-5-(1-amino-4-methyl-1-oxopentan-2-ylamino)-3-(6-cyclopropylpyridin-3-ylamino)pyrazine-2-carboxamide

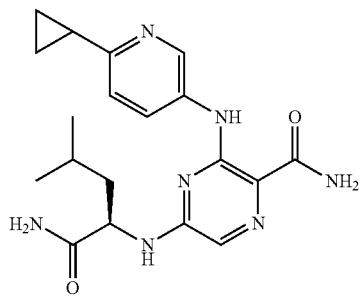 [SMILES: CC(C)C[C@@H](Nc1cnc(C(N)=O)c(Nc2ccc(C3CC3)nc2)n1)C(N)=O]

The title compound was synthesized in a manner similar to that described in Example 275. MS found for C19H25N7O2 as (M+H)+ 384.3. UV: λ=204, 263, 305, 353 nm. $^1$H NMR: (CD$_3$OD) δ 9.19 (s, 1H), 8.37 (d, 1H, 9 Hz), 7.65 (d, 1H, 4 Hz), 7.52 (dd, 1H, 4 Hz, 9 Hz), 4.24 (m, 1H), 2.29 (m, 1H), 1.73-1.87 (m, 3H), 1.37 (m, 2H), 1.14 (m, 2H), 1.03 (m, 3H), 0.95 (m, 3H).

Example 349

(R)-5-(1-amino-1-oxobutan-2-ylamino)-3-(2-(trifluoromethyl)pyridin-4-ylamino)pyrazine-2-carboxamide

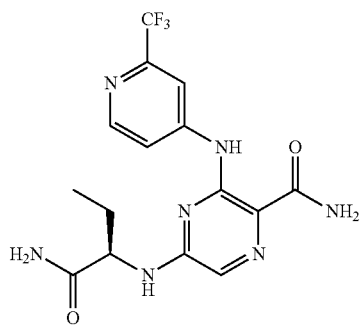 [SMILES: CC[C@@H](Nc1cnc(C(N)=O)c(Nc2ccnc(C(F)(F)F)c2)n1)C(N)=O]

The title compound was synthesized in a manner similar to that described in Example 275. MS found for C15H16F3N7O2 as (M+H)+ 384.3. UV: λ=204, 263, 313 nm.

Example 350

5-((1R,2S)-2-aminocyclohexylamino)-3-(6-ethylpyridin-3-ylamino)pyrazine-2-carboxamide

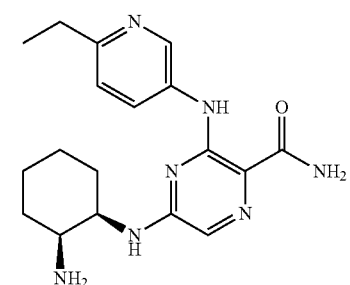

The title compound was synthesized in a manner similar to that described in Example 275. MS found for C18H25N7O as (M+H)+ 356.3. UV: λ=204, 260, 303, 350 nm. $^1$H NMR: (CD$_3$OD) δ 9.28 (s, 1H), 8.41 (s, 1H), 7.79 (d, 1H, 9 Hz), 7.68 (s, 1H), 4.52 (m, 1H), 3.66 (m, 1H), 3.00 (q, 2H, 8 Hz), 1.75-1.92 (m, 6H), 1.60 (m, 2H), 1.40 (t, 3H, 8 Hz).

Example 351

5-((1R,2S)-2-aminocyclohexylamino)-3-(6-cyclopropylpyridin-3-ylamino)pyrazine-2-carboxamide

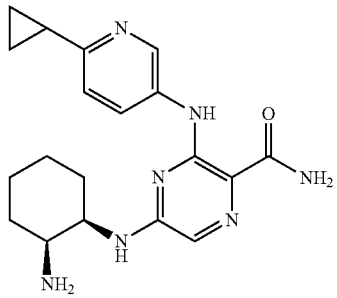 [SMILES: NC(=O)c1ncc(N[C@@H]2CCCC[C@@H]2N)nc1Nc1ccc(C2CC2)nc1]

The title compound was synthesized in a manner similar to that described in Example 275. MS found for C19H25N7O as (M+H)+ 368.4. UV: λ=205, 238, 263, 306, 350 nm.

Example 352

5-((1R,2S)-2-aminocyclohexylamino)-3-(2-cyclopropylpyridin-4-ylamino)pyrazine-2-carboxamide

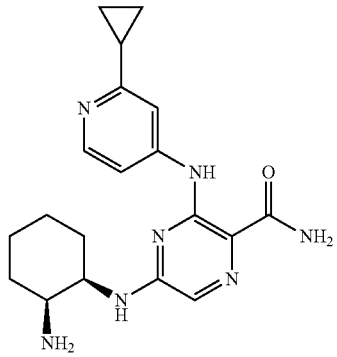 [SMILES: NC(=O)c1ncc(N[C@@H]2CCCC[C@@H]2N)nc1Nc1ccnc(C2CC2)c1]

The title compound was synthesized in a manner similar to that described in Example 275. MS found for C19H25N7O as (M+H)1 368.4. UV: λ=214, 276, 321 nm.

Example 353

(R)-5-(1-amino-1-oxobutan-2-ylamino)-3-(2-(dimethylamino)pyridin-4-ylamino)pyrazine-2-carboxamide

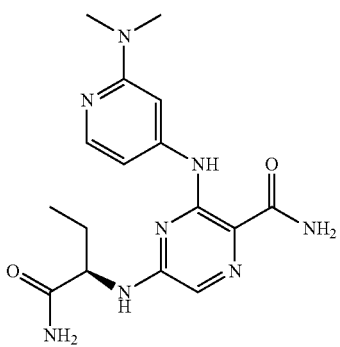 [SMILES: CC[C@@H](Nc1cnc(C(N)=O)c(Nc2ccnc(N(C)C)c2)n1)C(N)=O]

The title compound was synthesized in a manner similar to that described in Example 275. MS found for C16H22N8O2 as (M+H)1 359.3. UV: λ=256, 314 nm. 1H NMR: (CD3OD) δ 7.73 (s, 1H), 7.70 (d, 1H, 7 Hz), 7.36 (dd, 1H, 2 Hz, 7 Hz), 7.22 (s, 1H), 4.27 (dd, 1H, 5 Hz, 8 Hz), 3.25 (s, 6H), 2.01 (m, 1H), 1.89 (m, 1H), 1.09 (t, 3H, 7 Hz).

Example 354

(R)-5-(1-amino-1-oxobutan-2-ylamino)-3-(2-cyclobutoxypyridin-4-ylamino)pyrazine-2-carboxamide

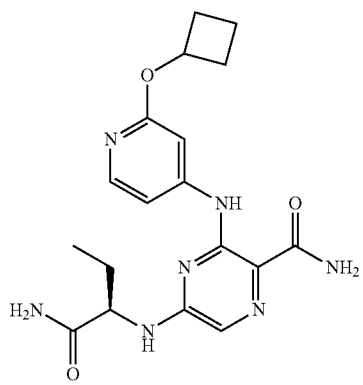 [SMILES: CC[C@@H](Nc1cnc(C(N)=O)c(Nc2ccnc(OC3CCC3)c2)n1)C(N)=O]

The title compound was synthesized in a manner similar to that described in Example 275. MS found for C18H23N7O3 as (M+H)+ 386.3. UV: λ=208, 273, 319 nm. 1H NMR: (CD3OD) δ 7.99 (d, 1H, 7 Hz), 7.93 (broad s, 1H), 7.81 (s, 1H), 7.22 (broad s, 1H), 5.27 (m, 1H), 4.23 (dd, 1H, 5 Hz, 12 Hz), 2.60 (m, 2H), 2.29 (m, 2H), 2.02 (m, 1H), 1.81-1.94 (m, 3H), 1.13 (t, 3H, 8 Hz).

Example 355

5-((1R,2R)-2-amino-3,3-difluorocyclohexylamino)-3-(2-ethylpyridin-4-ylamino)pyrazine-2-carboxamide

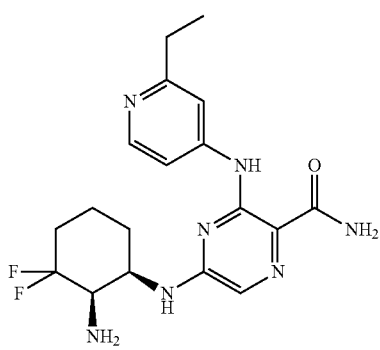 [SMILES: CCc1cc(Nc2nc(N[C@@H]3CCCC(F)(F)[C@@H]3N)cnc2C(N)=O)ccn1]

The title compound was synthesized in a manner similar to that described in Example 275. MS found for C18H23F2N7O as (M+H)+ 392.4. UV: λ=205, 271, 319 nm. 1H NMR: (CD3OD) δ 8.31 (d, 1H, 7 Hz), 8.18 (d, 1H, 6 Hz), 7.87 (d, 1H, 2 Hz), 7.86 (s, 1H), 4.80 (m, 1H), 4.22 (m, 1H), 2.95 (q, 2H, 8 Hz), 2.20 (m, 2H), 1.99 (3H), 1.84 (m, 1H), 1.40 (t, 3H, 8 Hz).

Example 356

5-((1R,2R)-2-amino-3,3-difluorocyclohexylamino)-3-(2-cyclobutoxypyridin-4-ylamino)pyrazine-2-carboxamide

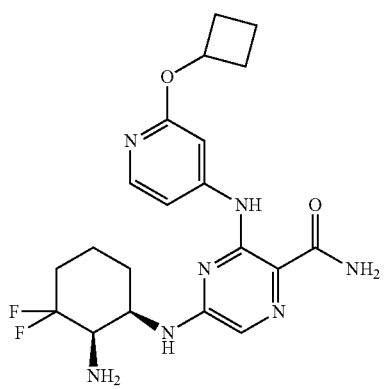 [SMILES: NC(=O)c1ncc(N[C@@H]2CCCC(F)(F)[C@@H]2N)nc1Nc1ccnc(OC2CCC2)c1]

The title compound was synthesized in a manner similar to that described in Example 275. MS found for C20H25F2N7O2 as (M+H)+ 434.4. UV: λ=210, 271, 317 nm.

Example 357

5-((3R,4R)-3-aminotetrahydro-2H-pyran-4-ylamino)-3-(2-methoxypyridin-4-ylamino)pyrazine-2-carboxamide

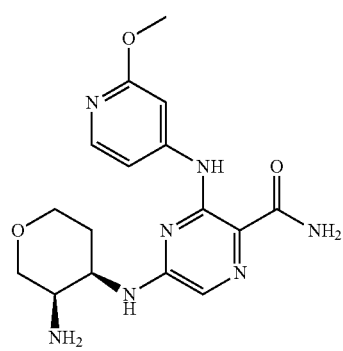 [SMILES: COc1cc(Nc2nc(N[C@@H]3CCOC[C@@H]3N)cnc2C(N)=O)ccn1]

The title compound was synthesized in a manner similar to that described in Example 275. MS found for C16H21N7O3 as (M+H)+ 360.3. UV: λ=210, 261, 307, 357 nm. $^1$H NMR: (CD$_3$OD) δ 8.00 (d, 1H, 2 Hz), 7.64 (s, 1H), 7.47 (d, 1H, 2 Hz), 7.26 (broad d, 1H), 4.41 (m, 1H), 4.14 (m, 1H), 3.92-4.08 (m, 5H), 3.88 (d, 1H, 13 Hz), 3.71 (dt, 1H, 3 Hz, 12 Hz), 2.10 (m, 1H), 1.93 (m, 1H).

Example 358

5-((3R,4R)-3-aminotetrahydro-2H-pyran-4-ylamino)-3-(5-methoxypyridin-3-ylamino)pyrazine-2-carboxamide

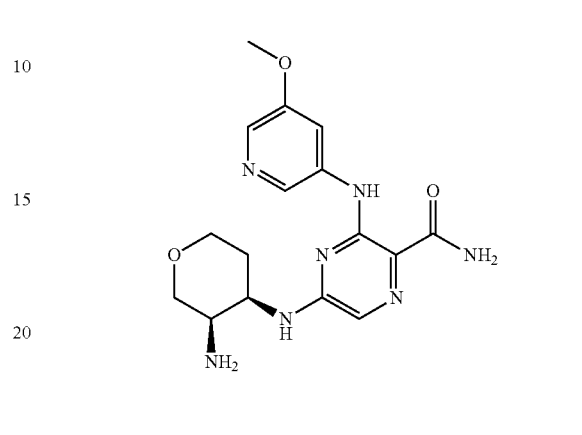

The title compound was synthesized in a manner similar to that described in Example 275. MS found for C16H21N7O3 as (M+H)+ 360.3. UV: λ=201, 224, 281, 346 nm. $^1$H NMR: (CD$_3$OD) δ 8.64 (d, 1H), 8.04 (d, 1H, 2 Hz), 7.94 (distorted t, 1H), 7.57 (s, 1H), 4.36 (dt, 1H, 5 Hz, 11 Hz), 4.12 (dd, 1H, 4 Hz, 12 Hz), 3.99 (d, 1H, 14 Hz), 3.96 (s, 3H), 3.86 (m, 2H), 3.68 (dt, 3 hz, 12 Hz), 2.07 (m, 1H), 1.90 (m, 1H).

Example 359

(R)-5-(1-amino-1-oxobutan-2-ylamino)-3-(4-(1-methyl-1H-pyrazol-4-yl)phenylamino)pyrazine-2-carboxamide

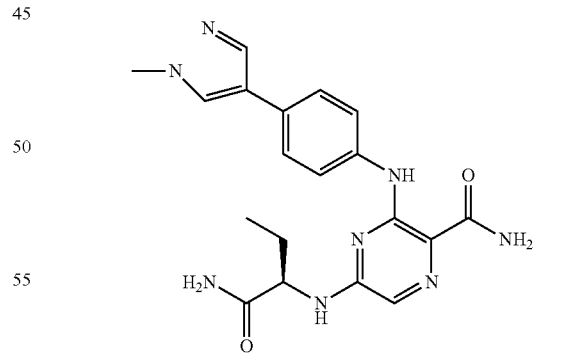

The title compound was synthesized in a manner similar to that described in Example 27. MS found for C19H22N8O2 as (M+H)+ MS 395.3; UV 207.2, 268.3, 322.5 nm; t 0.535 min.

Example 360

(R)-5-(1-amino-3-methoxy-1-oxopropan-2-ylamino)-3-(quinolin-6-ylamino)pyrazine-2-carboxamide

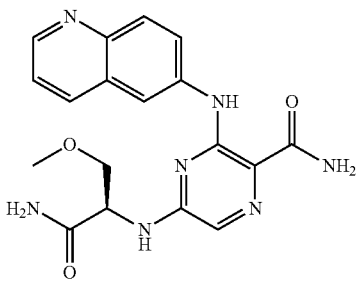 [SMILES: COC[C@@H](Nc1cnc(C(N)=O)c(Nc2ccc3ncccc3c2)n1)C(N)=O]

The title compound was synthesized in a manner similar to that described in Example 1. MS found for C18H19N7O3 as (M+H)+ MS 382.2; UV 202.9, 264.6, 297.2 nm; t 0.382 min.

Example 361

(R)-5-(1-amino-1-oxo-3-(pyridin-4-yl)propan-2-ylamino)-3-(quinolin-6-ylamino)pyrazine-2-carboxamide

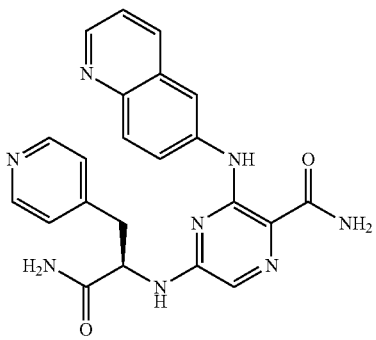 [SMILES: NC(=O)c1ncc(N[C@H](Cc2ccncc2)C(N)=O)nc1Nc1ccc2ncccc2c1]

The title compound was synthesized in a manner similar to that described in Example 1. MS found for C22H20N8O2 as (M+H)+ MS 429.2; UV 201.7, 260.3, 296.6, 359.2 nm; t 0.265 min. $^1$H NMR: (CD$_3$OD) δ 9.10 (d, 1H), 8.90 (dd, 1H), 8.82 (d, 1H), 8.66 (d, 2H), 8.10 (d, 1H), 7.97 (dd, 1H), 7.91-7.84 (m, 3H), 7.57 (s, 1H), 4.88 (dd, 1H), 3.69 (dd, 1H), 3.49 (dd, 1H).

Example 362

5-(1-carbamoylcyclopropylamino)-3-(quinolin-3-ylamino)pyrazine-2-carboxamide

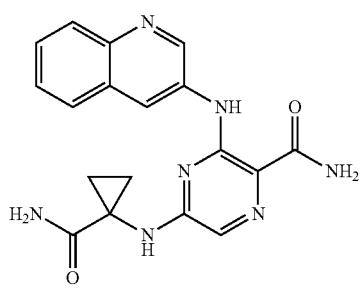 [SMILES: NC(=O)c1ncc(NC2(C(N)=O)CC2)nc1Nc1cnc2ccccc2c1]

The title compound was synthesized in a manner similar to that described in Example 1. MS found for C18H17N7O2 as (M+H)+ MS 364.1; UV 202.3, 223.0, 246.2, 294.1, 351.7 nm; t 0.390 min.

Example 363

5-((1R,2R)-2-amino-3,3-difluorocyclohexylamino)-3-(isoquinolin-4-ylamino)pyrazine-2-carboxamide

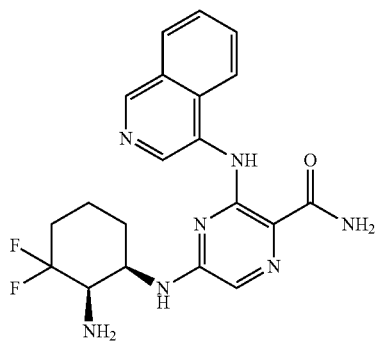

The title compound was synthesized in a manner similar to that described in Example 14. MS found for C20H21F2N7O as (M+H)+ MS 414.2; UV 219.4, 267.1, 284.9, 349.2 nm; t 0.374 min.

Example 364

5-((1R,2R)-2-amino-3,3-difluorocyclohexylamino)-3-(isoquinolin-6-ylamino)pyrazine-2-carboxamide

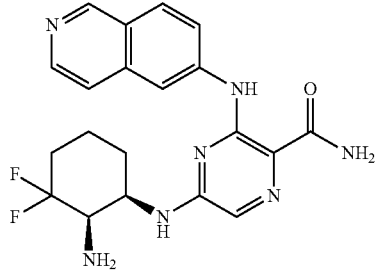

The title compound was synthesized in a manner similar to that described in Example 14. MS found for C20H21F2N7O as (M+H)+ MS 414.2; UV 212.7, 253.6, 282.4, 348.6 nm; t 0.347 min.

Example 365

5-((1R,2R)-2-amino-3,3-difluorocyclohexylamino)-3-(quinoxalin-6-ylamino)pyrazine-2-carboxamide

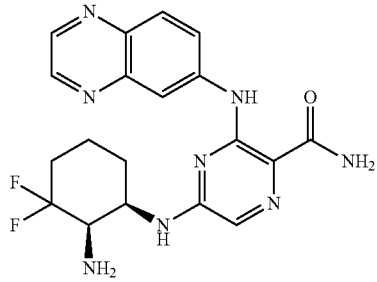 [SMILES: NC(=O)c1ncc(N[C@@H]2CCCC(F)(F)[C@@H]2N)nc1Nc1ccc2nccnc2c1]

The title compound was synthesized in a manner similar to that described in Example 14. MS found for C19H20F2N8O as (M+H)+ MS 415.2; UV 212.7, 257.8, 291.6, 358.5 nm; t 0.421 min.

Example 366

5-((1R,2R)-2-amino-3,3-difluorocyclohexylamino)-3-(quinolin-4-ylamino)pyrazine-2-carboxamide

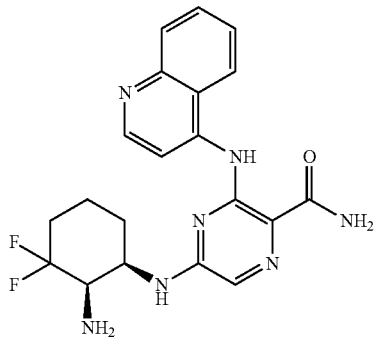 [SMILES: NC(=O)c1ncc(N[C@@H]2CCCC(F)(F)[C@@H]2N)nc1Nc1ccnc2ccccc12]

The title compound was synthesized in a manner similar to that described in Example 14. MS found for C20H21F2N7O as (M+H)+ MS 414.2; UV 235.2, 267.1, 336.7 nm; t 0.374 min.

Example 367

(R)-5-(1-amino-1-oxobutan-2-ylamino)-3-(isoquinolin-4-ylamino)pyrazine-2-carboxamide

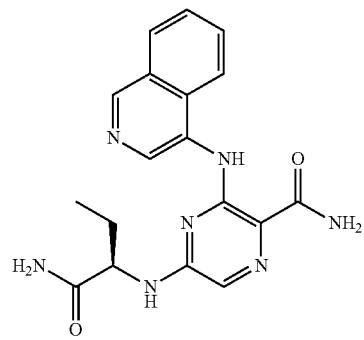 [SMILES: CC[C@@H](Nc1cnc(C(N)=O)c(Nc2cncc3ccccc23)n1)C(N)=O]

The title compound was synthesized in a manner similar to that described in Example 1. MS found for C18H19N7O2 as (M+H)+ MS 366.2; UV 218.7, 268.3, 287.3, 350.5 nm; t 0.402 min.

Example 368

(R)-5-(1-amino-1-oxobutan-2-ylamino)-3-(isoquinolin-6-ylamino)pyrazine-2-carboxamide

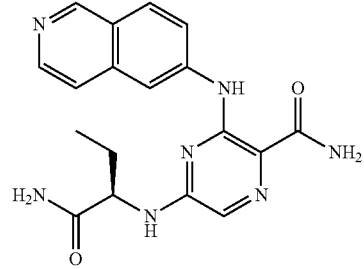 [SMILES: CC[C@@H](Nc1cnc(C(N)=O)c(Nc2ccc3cnccc3c2)n1)C(N)=O]

The title compound was synthesized in a manner similar to that described in Example 1. MS found for C18H19N7O2 as (M+H)+ MS 366.2; UV 213.9, 256.0, 283.0, 349.2 nm; t 0.378 min.

Example 369

(R)-5-(1-amino-1-oxobutan-2-ylamino)-3-(quinoxalin-6-ylamino)pyrazine-2-carboxamide

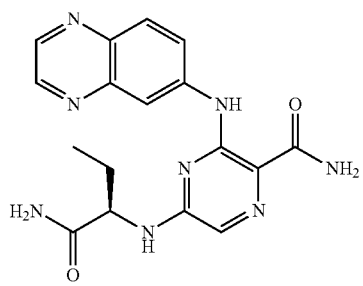 [SMILES: CC[C@@H](Nc1cnc(C(N)=O)c(Nc2ccc3nccnc3c2)n1)C(N)=O]

The title compound was synthesized in a manner similar to that described in Example 1. MS found for C17H18N8O2 as (M+H)+ MS 367.2; UV 200.0, 259.7, 292.9 nm; t 0.437 min.

Example 370

(R)-5-(1-amino-1-oxobutan-2-ylamino)-3-(quinolin-4-ylamino)pyrazine-2-carboxamide

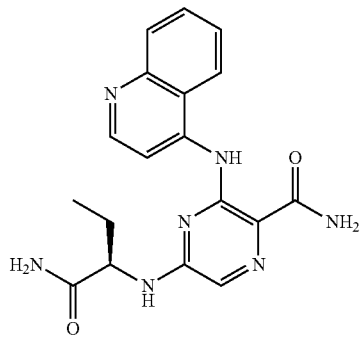 [SMILES: CC[C@@H](Nc1cnc(C(N)=O)c(Nc2ccnc3ccccc23)n1)C(N)=O]

The title compound was synthesized in a manner similar to that described in Example 1. MS found for C18H19N7O2 as (M+H)+ MS 366.2; UV 200.5, 230.3, 268.9, 337.4 nm; t 0.394 min.

Example 371

5-((1R,2R)-2-amino-3,3-difluorocyclohexylamino)-3-(pyridin-3-ylamino)pyrazine-2-carboxamide

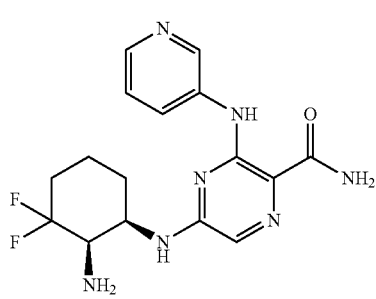 [SMILES: NC(=O)c1ncc(N[C@@H]2CCCC(F)(F)[C@@H]2N)nc1Nc1cccnc1]

The title compound was synthesized in a manner similar to that described in Example 14. MS found for C16H19F2N7O as (M+H)+ MS 364.2; UV 200.5, 228.5, 257.2, 302.1, 347.4 nm.

Example 372

5-((1R,2R)-2-amino-3,3-difluorocyclohexylamino)-3-(3-fluorophenylamino)pyrazine-2-carboxamide

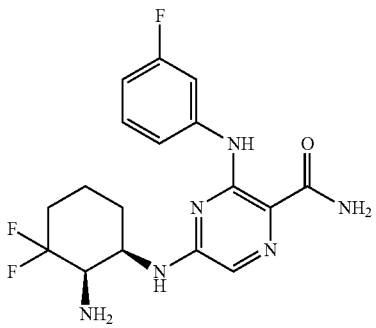 [SMILES: NC(=O)c1ncc(N[C@@H]2CCCC(F)(F)[C@@H]2N)nc1Nc1cccc(F)c1]

The title compound was synthesized in a manner similar to that described in Example 14. MS found for C17H19F3N6O as (M+H)+ MS 381.2; UV 203.6, 249.3, 304.6, 358.5 nm; t 0.496 min.

Example 373

(R)-5-(1-amino-1-oxobutan-2-ylamino)-3-(3-methylisothiazol-5-ylamino)pyrazine-2-carboxamide

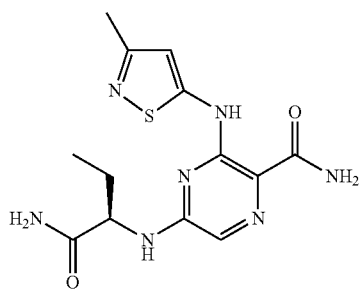 [SMILES: CC[C@@H](Nc1cnc(C(N)=O)c(Nc2cc(C)ns2)n1)C(N)=O]

A mixture of (R)-2-(6-chloro-5-cyanopyrazin-2-ylamino)butanamide (90 mg, 0.375 mmol), 3-methylisothiazol-5-amine hydrochloride (70 mg, 0.464 mmol), K2CO3 (130 mg, 0.942 mmol), BINAP (30 mg, 0.048 mmol) and Pd(OAc)2 (15 mg, 0.066 mmol) in dioxane (2 mL) was degassed with Ar, then was stirred at 110 C for 20 h. EtOAc and H2O were added. Organic phase was separated, dried over Na2SO4, concentrated in vacuo to give (R)-2-(5-cyano-6-(3-methylisothiazol-5-ylamino)pyrazin-2-ylamino)butanamide (106 mg).

The compound (R)-2-(5-cyano-6-(3-methylisothiazol-5-ylamino)pyrazin-2-ylamino)butanamide (106 mg, 0.334 mmol) was dissolved in EtOH (2 mL) and DMSO (1 mL), aq. 1N NaOH (1.0 mL) and aq. H2O2 (30%, 1.0 mL) were added. The mixture was stirred at room temperature for 15 min. HOAc (0.1 mL) was added. The mixture was then concentrated in vacuo. The residue was purified by HPLC to give the titled compound (38 mg). MS found for C13H17N7O2S as (M+H)+ MS 336.2; UV 206.0, 275.0, 323.1 nm; t 0.365 min. 1H NMR: (CD3OD) δ 7.70 (s, 1H), 6.88 (s, 1H), 4.65 (br.s, 1H), 2.45 (s, 3H), 2.18-2.05 (m, 1H), 1.96-1.87 (m, 1H), 1.10 (t, 3H).

Example 374

(R)-5-(1-amino-3-cyclopropyl-1-oxopropan-2-ylamino)-3-(3-methylisothiazol-5-ylamino)pyrazine-2-carboxamide

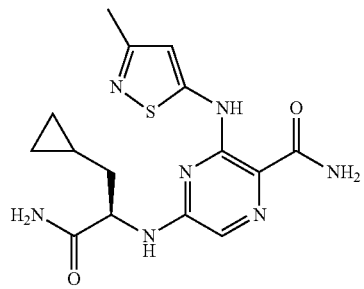 [SMILES: Cc1cc(Nc2nc(N[C@H](CC3CC3)C(N)=O)cnc2C(N)=O)sn1]

A mixture of (R)-2-(6-chloro-5-cyanopyrazin-2-ylamino)-3-cyclopropylpropanamide (86 mg, 0.323 mmol), 3-methylisothiazol-5-amine hydrochloride (70 mg, 0.464 mmol), K2CO3 (130 mg, 0.942 mmol), BINAP (30 mg, 0.048 mmol) and Pd(OAc)2 (15 mg, 0.066 mmol) in dioxane (2 mL) was degassed with Ar, then was stirred at 110 C for 20 h. EtOAc and H2O were added. Organic phase was separated, dried over Na2SO4, concentrated in vacuo to give (R)-2-(5-cyano-6-(3-methylisothiazol-5-ylamino)pyrazin-2-ylamino)-3-cyclopropylpropanamide (143 mg).

The compound (R)-2-(5-cyano-6-(3-methylisothiazol-5-ylamino)pyrazin-2-ylamino)-3-cyclopropylpropanamide (143 mg, 0.323 mmol) was dissolved in EtOH (2 mL) and DMSO (1 mL), aq. 1N NaOH (1.0 mL) and aq. H2O2 (30%, 1.0 mL) were added. The mixture was stirred at room temperature for 15 min. HOAc (0.1 mL) was added. The mixture was then concentrated in vacuo. The residue was purified by HPLC to give the titled compound (39 mg). MS found for C15H19N7O2S as (M+H)+ MS 362.2; UV 205.4, 275.6, 324.4 nm; t 0.418 min. 1H NMR: (CD3OD) δ 7.51 (s, 1H), 6.69 (s, 1H), 4.68-4.60 (m, 1H), 2.28 (s, 3H), 1.84-1.75 (m, 1H), 1.65-1.57 (m, 1H), 0.82-0.72 (m, 1H), 0.40-0.28 (m, 2H), 0.10-0.0 (m, 2H).

Example 375

(R)-5-(1-amino-1-oxobutan-2-ylamino)-3-(quinolin-5-ylamino)pyrazine-2-carboxamide

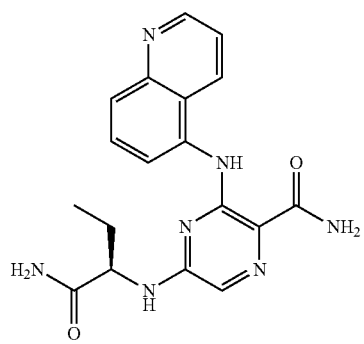 [SMILES: CC[C@@H](Nc1cnc(C(N)=O)c(Nc2cccc3ncccc23)n1)C(N)=O]

The title compound was synthesized in a manner similar to that described in Example 1. MS found for C18H19N7O2 as (M+H)+ MS 366.2; UV 204.2, 237.7, 272.0, 352.9 nm; t 0.356 min.

Example 376

(R)-5-(1-amino-1-oxobutan-2-ylamino)-3-(quinolin-7-ylamino)pyrazine-2-carboxamide

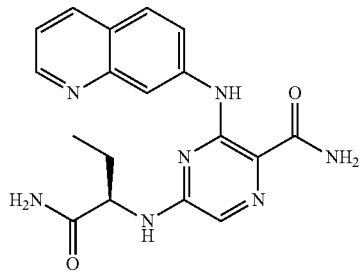 [SMILES: CC[C@@H](Nc1cnc(C(N)=O)c(Nc2ccc3cccnc3c2)n1)C(N)=O]

The title compound was synthesized in a manner similar to that described in Example 1. MS found for C18H19N7O2 as (M+H)+ MS 366.2; UV 262.1, 292.3, 354.8 nm; t 0.401 min.

Example 377

(R)-5-(1-amino-1-oxobutan-2-ylamino)-3-(isoquinolin-8-ylamino)pyrazine-2-carboxamide

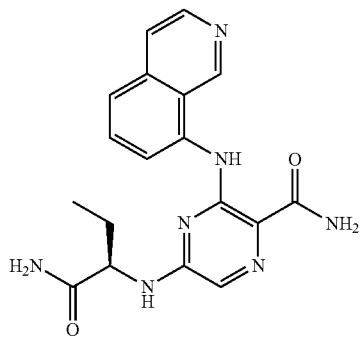 [SMILES: CC[C@@H](Nc1cnc(C(N)=O)c(Nc2cccc3ccncc23)n1)C(N)=O]

The title compound was synthesized in a manner similar to that described in Example 1. MS found for C18H19N7O2 as (M+H)+ MS 366.2; UV 213.3, 283.0, 346.1 nm; t 0.368 min.

Example 378

(R)-5-(1-amino-1-oxobutan-2-ylamino)-3-(isoquinolin-5-ylamino)pyrazine-2-carboxamide

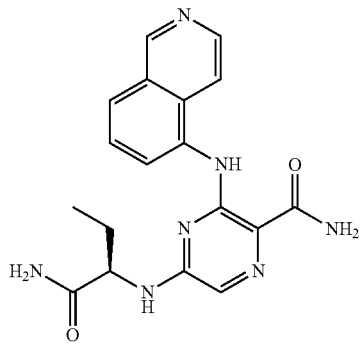 [SMILES: CC[C@@H](Nc1cnc(C(N)=O)c(Nc2cccc3cnccc23)n1)C(N)=O]

The title compound was synthesized in a manner similar to that described in Example 1. MS found for C18H19N7O2 as (M+H)+ MS 366.2; UV 214.5, 250.5, 288.0, 352.9 nm; t 0.362 min.

Example 379

(R)-5-(1-amino-1-oxobutan-2-ylamino)-3-(isoquinolin-7-ylamino)pyrazine-2-carboxamide

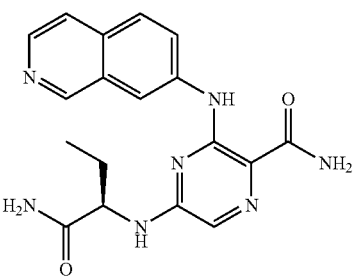 [SMILES: CC[C@@H](Nc1cnc(C(N)=O)c(Nc2ccc3ccncc3c2)n1)C(N)=O]

The title compound was synthesized in a manner similar to that described in Example 1. MS found for C18H19N7O2 as (M+H)+ MS 366.2; UV 208.4, 264.6, 322.5 nm; t 0.381 min.

Example 380

(R)-3-(1,8-naphthyridin-3-ylamino)-5-(1-amino-1-oxobutan-2-ylamino)pyrazine-2-carboxamide

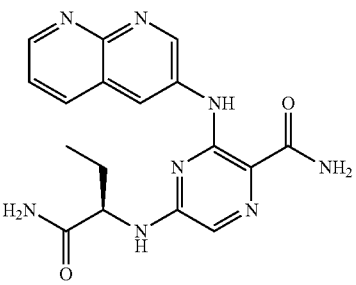 [SMILES: CC[C@@H](Nc1cnc(C(N)=O)c(Nc2cnc3ncccc3c2)n1)C(N)=O]

The title compound was synthesized in a manner similar to that described in Example 1. MS found for C17H18N8O2 as (M+H)+ MS 367.2; UV 204.2, 257.2, 292.3, 354.2 nm; t 0.368 min.

Example 381

(R)-3-(1,6-naphthyridin-3-ylamino)-5-(1-amino-1-oxobutan-2-ylamino)pyrazine-2-carboxamide

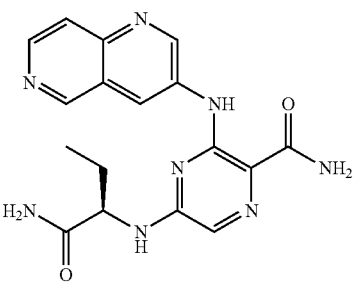 [SMILES: CC[C@@H](Nc1cnc(C(N)=O)c(Nc2cnc3ccncc3c2)n1)C(N)=O]

The title compound was synthesized in a manner similar to that described in Example 1. MS found for C17H18N8O2 as (M+H)+ MS 367.2; UV 209.0, 266.4, 322.5 nm; t 0.363 min.

Example 382

5-(2-amino-2-oxoethylamino)-3-(quinolin-6-ylamino)pyrazine-2-carboxamide

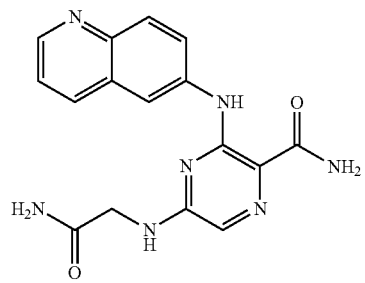 [SMILES: NC(=O)CNc1cnc(C(N)=O)c(Nc2ccc3ncccc3c2)n1]

The title compound was synthesized in a manner similar to that described in Example 1. MS found for C16H15N7O2 as (M+H)[1] MS 338.2; UV 203.6, 264.7, 297.3, 357.5 nm; t 0.330 min.

Example 383

(R)-3-(1,5-naphthyridin-3-ylamino)-5-(1-amino-1-oxobutan-2-ylamino)pyrazine-2-carboxamide

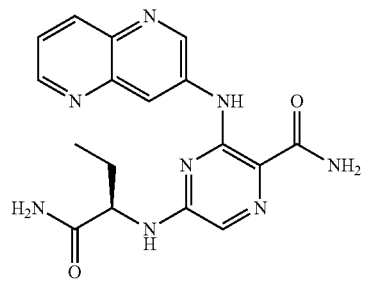

The title compound was synthesized in a manner similar to that described above. MS found for C17H18N8O2 as (M+H)[1] MS 367.2; UV 202.9, 251.1, 303.4, 351.7 nm; t 0.388 min. $^1$H NMR: (CD3OD) δ 9.25 (d, 1H), 9.04 (dd, 1H), 8.97 (d, 1H), 8.74 (d, 1H), 7.85 (dd, 1H), 7.68 (s, 1H), 4.43 (dd, 1H), 2.13-1.90 (m, 2H), 1.16 (t, 3H).

Example 384

5-((1R,2R)-2-amino-3,3-difluorocyclohexylamino)-3-(quinolin-7-ylamino)pyrazine-2-carboxamide

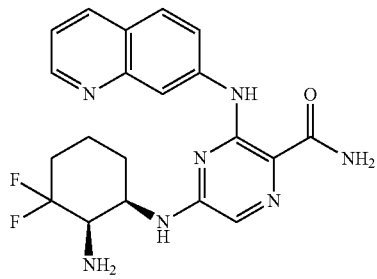 [SMILES: NC(=O)c1ncc(N[C@@H]2CCCC(F)(F)[C@@H]2N)nc1Nc1ccc2cccnc2c1]

The title compound was synthesized in a manner similar to that described in Example 14. MS found for C20H21F2N7O as (M+H)[1] MS 414.3; UV 215.1, 260.3, 291.6, 353.6 nm; t 0.341 min.

Example 385

5-((1R,2R)-2-amino-3,3-difluorocyclohexylamino)-3-(isoquinolin-7-ylamino)pyrazine-2-carboxamide

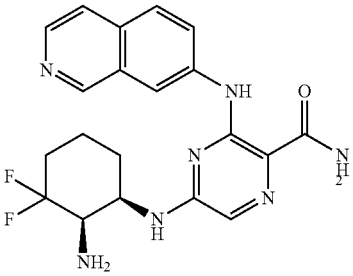 [SMILES: NC(=O)c1ncc(N[C@@H]2CCCC(F)(F)[C@@H]2N)nc1Nc1ccc2ccncc2c1]

The title compound was synthesized in a manner similar to that described in Example 14. MS found for C20H21F2N7O as (M+H)+ MS 414.2; UV 212.7, 260.3, 321.3 nm; t 0.338 min.

Example 386

(R)-3-(1,8-naphthyridin-4-ylamino)-5-(1-amino-1-oxobutan-2-ylamino)pyrazine-2-carboxamide

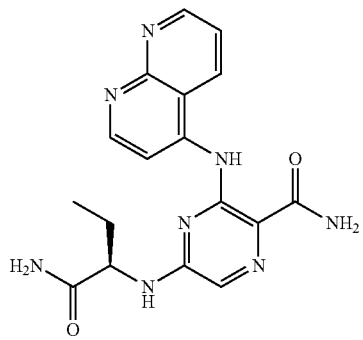 [SMILES: CC[C@@H](Nc1cnc(C(N)=O)c(Nc2ccnc3ncccc23)n1)C(N)=O]

The title compound was synthesized in a manner similar to that described in Example 1. MS found for C17H18N8O2 as (M+H)+ MS 367.2; UV 201.1, 276.3, 339.2 nm; t 0.344 min.

Example 387

5-((1R,2R)-2-amino-3,3-difluorocyclohexylamino)-3-(3-phenylisoxazol-5-ylamino)pyrazine-2-carboxamide

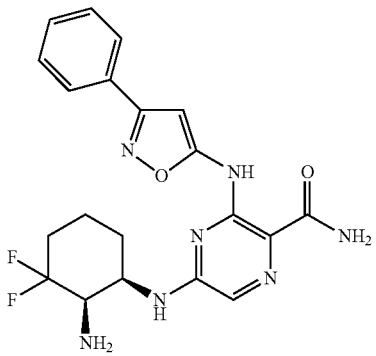 [SMILES: NC(=O)c1ncc(N[C@@H]2CCCC(F)(F)[C@@H]2N)nc1Nc1cc(-c2ccccc2)no1]

The title compound was synthesized in a manner similar to that described in Example 14. MS found for C20H21F2N7O2 as (M+H)+ MS 430.2; UV 201.7, 243.8, 301.5, 348.6 nm; t 0.512 min.

Example 388

(R)-5-(1-amino-3-(1H-indol-3-yl)-1-oxopropan-2-ylamino)-3-(quinolin-6-ylamino)pyrazine-2-carboxamide

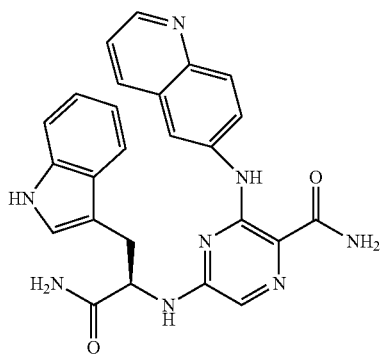 [SMILES: NC(=O)c1ncc(N[C@H](Cc2c[nH]c3ccccc23)C(N)=O)nc1Nc1ccc2ncccc2c1]

The title compound was synthesized in a manner similar to that described in Example 1. MS found for C25H22N8O2 as (M+H)+ MS 467.3; UV 223.0, 295.3, 358.5 nm; t 0.429 min.

Example 389

(R)-5-(1-amino-3-(1H-indol-3-yl)-1-oxopropan-2-ylamino)-3-(3-methylisothiazol-5-ylamino)pyrazine-2-carboxamide

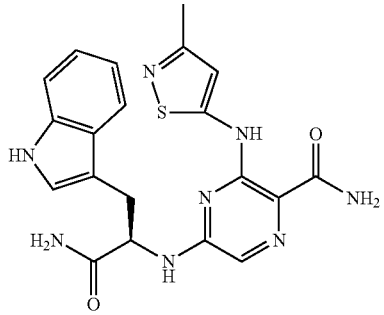 [SMILES: Cc1cc(Nc2nc(N[C@H](Cc3c[nH]c4ccccc34)C(N)=O)cnc2C(N)=O)sn1]

The title compound was synthesized in a manner similar to that described in Example 22. MS found for C20H20N8O2S as (M+H)+ MS 437.2; UV 218.7, 274.4, 323.1 nm; t 0.439 min.

Example 390

(R)-5-(1-amino-3-cyclohexyl-1-oxopropan-2-ylamino)-3-(3-methylisothiazol-5-ylamino)pyrazine-2-carboxamide

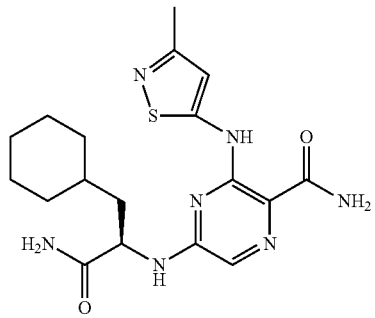 [SMILES: Cc1cc(Nc2nc(N[C@H](CC3CCCCC3)C(N)=O)cnc2C(N)=O)sn1]

The title compound was synthesized in a manner similar to that described in Example 22. MS found for C18H25N7O2S as (M+H)+ MS 404.2; UV 275.0, 323.1 nm; t 0.505 min.

Example 391

5-((1R,2R)-2-amino-3,3-difluorocyclohexylamino)-3-(1-methyl-1H-indol-5-ylamino)pyrazine-2-carboxamide

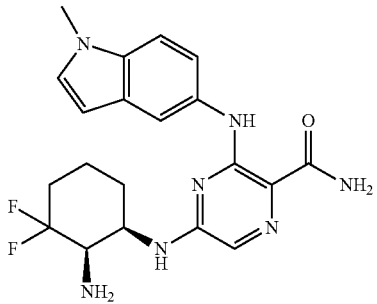 [SMILES: Cn1ccc2cc(Nc3nc(N[C@@H]4CCCC(F)(F)[C@@H]4N)cnc3C(N)=O)ccc21]

The title compound was synthesized in a manner similar to that described in Example 14. MS found for C20H23F2N7O as (M+H)+ MS 416.2; UV 249.9, 288.6 nm; t 0.483 min.

Example 392

5-((1R,2R)-2-amino-3,3-difluorocyclohexylamino)-3-(1-methyl-1H-indol-4-ylamino)pyrazine-2-carboxamide

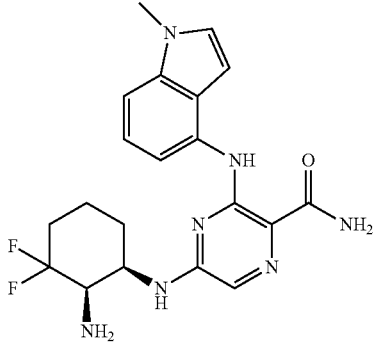 [SMILES: Cn1ccc2c(Nc3nc(N[C@@H]4CCCC(F)(F)[C@@H]4N)cnc3C(N)=O)cccc21]

The title compound was synthesized in a manner similar to that described in Example 14. MS found for C20H23F2N7O as (M+H)$^+$ MS 416.2; UV 200.5, 220.0, 272.0, 322.5 nm; t 0.493 min.

Example 393

(R)-5-(1-amino-1-oxobutan-2-ylamino)-3-(1-methyl-1H-indol-5-ylamino)pyrazine-2-carboxamide

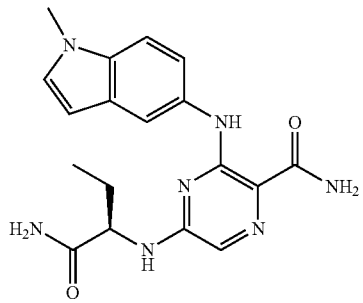 [SMILES: CC[C@@H](Nc1cnc(C(N)=O)c(Nc2ccc3c(ccn3C)c2)n1)C(N)=O]

The title compound was synthesized in a manner similar to that described in Example 1. MS found for C18H21N7O2 as (M+H)$^+$ MS 368.2; UV 205.4, 252.9, 297.8 nm; t 0.549 min.

Example 394

(R)-5-(1-amino-1-oxobutan-2-ylamino)-3-(1-methyl-1H-indol-4-ylamino)pyrazine-2-carboxamide

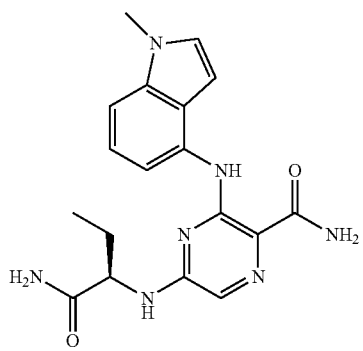 [SMILES: CC[C@@H](Nc1cnc(C(N)=O)c(Nc2cccc3c2ccn3C)n1)C(N)=O]

The title compound was synthesized in a manner similar to that described in Example 1. MS found for C18H21N7O2 as (M+H)$^+$ MS 368.2; UV 201.7, 221.2, 273.2, 325.0 nm; t 0.550 min.

Example 395

(R)-5-(2-amino-2-oxo-1-phenylethylamino)-3-(3-methylisothiazol-5-ylamino)pyrazine-2-carboxamide

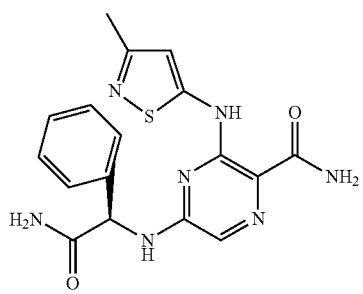 [SMILES: Cc1cc(Nc2nc(N[C@@H](C(N)=O)c3ccccc3)cnc2C(N)=O)sn1]

The title compound was synthesized in a manner similar to that described in Example 22. MS found for C17H17N7O2S as (M+H)$^+$ MS 384.1; UV 210.2, 274.4, 322.5 nm; t 0.420 min.

Example 396

(R)-5-(1-amino-3-cyclopropyl-1-oxopropan-2-ylamino)-3-(1-methyl-1H-indol-5-ylamino)pyrazine-2-carboxamide

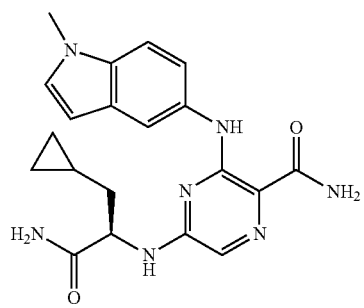 [SMILES: Cn1ccc2cc(Nc3nc(N[C@H](CC4CC4)C(N)=O)cnc3C(N)=O)ccc21]

The title compound was synthesized in a manner similar to that described in Example 1. MS found for C20H23N7O2 as (M+H)$^+$ MS 394.2; UV 205.4, 252.9, 296.0 nm; t 0.595 min.

Example 397

(R)-5-(1-amino-3-cyclopropyl-1-oxopropan-2-ylamino)-3-(1-methyl-1H-indol-4-ylamino)pyrazine-2-carboxamide

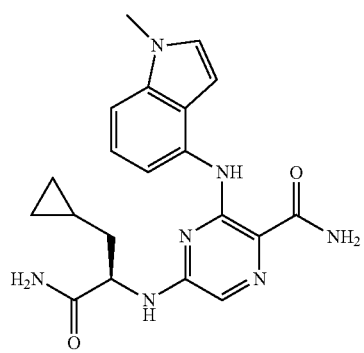 [SMILES: Cn1ccc2c(Nc3nc(N[C@H](CC4CC4)C(N)=O)cnc3C(N)=O)cccc21]

The title compound was synthesized in a manner similar to that described in Example 1. MS found for C20H23N7O2 as (M+H)$^+$ MS 394.2; UV 200.0, 273.2, 324.4 nm; t 0.601 min.

Example 398

(R)-5-(1-amino-4,4,4-trifluoro-1-oxobutan-2-ylamino)-3-(3-methylisothiazol-5-ylamino)pyrazine-2-carboxamide

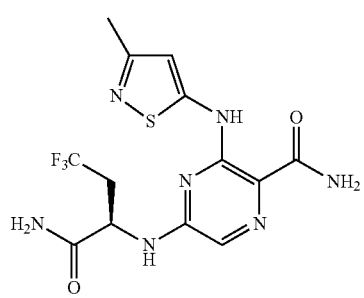 [SMILES: Cc1cc(Nc2nc(N[C@H](CC(F)(F)F)C(N)=O)cnc2C(N)=O)sn1]

The title compound was synthesized in a manner similar to that described in Example 22. MS found for C13H14F3N7O2S as (M+H)+ MS 390.2; UV 207.8, 272.0, 318.8 nm; t 0.417 min.

Example 399

5-((2R)-1-amino-4-(methylsulfinyl)-1-oxobutan-2-ylamino)-3-(3-methylisothiazol-5-ylamino)pyrazine-2-carboxamide

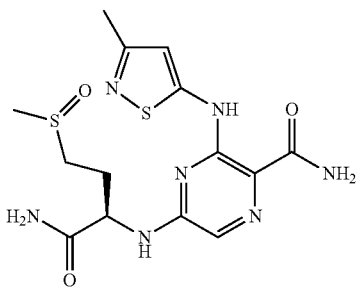 [SMILES: Cc1cc(Nc2nc(N[C@H](CCS(C)=O)C(N)=O)cnc2C(N)=O)sn1]

The title compound was synthesized in a manner similar to that described in Example 22. MS found for C14H19N7O3S2 as (M+H)+ MS 398.2; UV 207.2, 273.2, 321.9 nm; t 0.297 min.

Example 400

(R)-5-(1-amino-4-(methylsulfonyl)-1-oxobutan-2-ylamino)-3-(3-methylisothiazol-5-ylamino)pyrazine-2-carboxamide

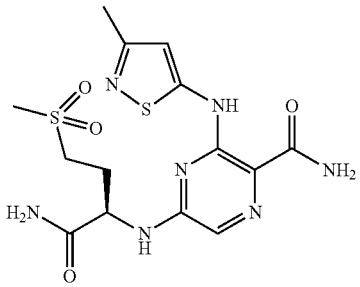 [SMILES: Cc1cc(Nc2nc(N[C@H](CCS(C)(=O)=O)C(N)=O)cnc2C(N)=O)sn1]

The title compound was synthesized in a manner similar to that described in Example 22. MS found for C14H19N7O4S2 as (M+H)+ MS 414.2; UV 205.4, 273.2, 322.5 nm; t 0.314 min.

Example 401

5-(1-carbamoylcyclohexylamino)-3-(3-methyl-isothiazol-5-ylamino)pyrazine-2-carboxamide

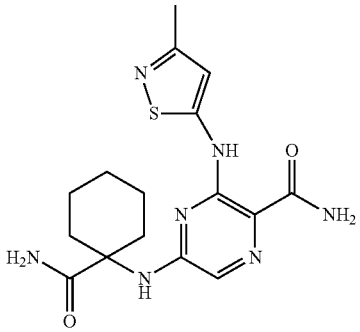 [SMILES: Cc1cc(Nc2nc(NC3(C(N)=O)CCCCC3)cnc2C(N)=O)sn1]

The title compound was synthesized in a manner similar to that described in Example 22. MS found for C16H21N7O2S as (M+H)+ MS 376.3. UV: λ=UV 201.1, 245.0, 277.5, 325.6 nm.

Example 402

(R)-5-(1-amino-3-methoxy-1-oxopropan-2-ylamino)-3-(3-methylisothiazol-5-ylamino)pyrazine-2-carboxamide

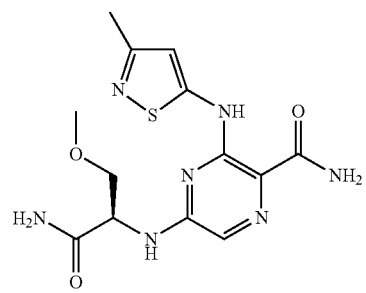

The title compound was synthesized in a manner similar to that described in Example 22. MS found for C13H17N7O3S as (M+H)+ MS 352.2. UV: λ=UV 208.4, 273.8, 323.1 nm.

Example 403

(R)-5-(1-amino-1-oxobutan-2-ylamino)-3-(3-phenyl-isothiazol-5-ylamino)pyrazine-2-carboxamide

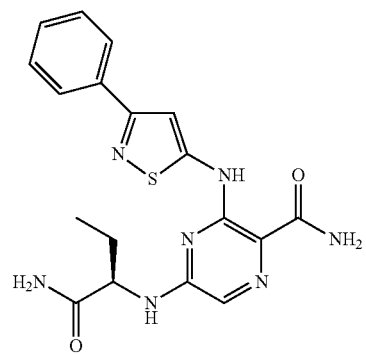 [SMILES: CC[C@@H](Nc1cnc(C(N)=O)c(Nc2cc(-c3ccccc3)ns2)n1)C(N)=O]

A mixture of benzoylacetonitrile (510 mg, 3.51 mmol) and conc. NH4OH (4 mL, 56.0 mmol) in a sealed tube was stirred at 80 C for 20 h. After cooling, solids precipitated out, which were collected by filtration, dried on vacuum to give (Z)-3-amino-3-phenylacrylonitrile (95 mg).

To a solution of (Z)-3-amino-3-phenylacrylonitrile (95 mg, 0.660 mmol) in EtOH (1.0 mL) and THF (1.0 mL) in a sealed tube, H2S gas was bubbled through for 5 min. It was then stirred at 90 C for 20 h. The mixture was concentrated in vacuo. The residue was dissolved in MeOH (2.0 mL), aq. H2O2 (30%, 0.5 mL) was added. After being stirred at room temperature for 2 min, the reaction was completed. The mixture was concentrated in vacuo. The residue was purified by HPLC to give 3-phenylisothiazol-5-amine (22 mg).

A mixture of (R)-2-(6-chloro-5-cyanopyrazin-2-ylamino) butanamide (50 mg, 0.208 mmol), 3-phenylisothiazol-5- amine (22 mg, 0.125 mmol), K$_2$CO$_3$ (100 mg, 0.724 mmol), BINAP (25 mg, 0.040 mmol) and Pd(OAc)2 (15 mg, 0.066 mmol) in dioxane (2 mL) was degassed with Ar, then was stirred at 110 C for 4 h. HOAc (0.2 mL) was added. The mixture was concentrated in vacuo. The residue was purified by HPLC to give (R)-2-(5-cyano-6-(3-phenylisothiazol-5-ylamino)pyrazin-2-ylamino)butanamide (8 mg)

The compound (R)-2-(5-cyano-6-(3-phenylisothiazol-5-ylamino)pyrazin-2-ylamino)butanamide (8 mg, 0.021 mmol) was dissolved in EtOH (1 mL) and DMSO (0.5 mL), aq. 1N NaOH (0.5 mL) and aq. H2O2 (30%, 0.5 mL) were added. The mixture was stirred at room temperature for 20 min. HOAc (0.1 mL) was added. The mixture was then concentrated in vacuo. The residue was purified by HPLC to give the titled compound (5 mg). MS found for C18H19N7O2S as (M+H)$^+$ MS 398.2. UV: λ=UV 201.1, 267.7, 321.9 nm.

Example 404

(R)-5-(1-amino-1-oxobutan-2-ylamino)-3-(quinazolin-6-ylamino)pyrazine-2-carboxamide

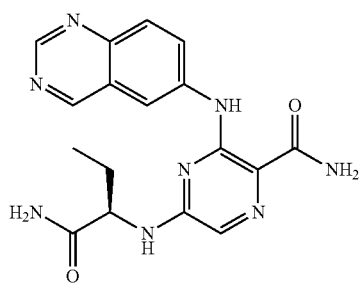 [SMILES: CC[C@@H](Nc1cnc(C(N)=O)c(Nc2ccc3ncncc3c2)n1)C(N)=O]

The title compound was synthesized in a manner similar to that described in Example 1. MS found for C17H18N8O2 as (M+H)$^+$ MS 367.2. UV: 2=UV 206.0, 325.0 nm.

Example 405

5-((1R,2R)-2-amino-3,3-difluorocyclohexylamino)-3-(quinazolin-6-ylamino)pyrazine-2-carboxamide

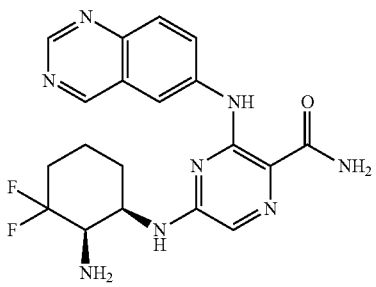

The title compound was synthesized in a manner similar to that described in Example 14. MS found for C19H20F2N8O as (M+H)$^+$ MS 415.3. UV: λ=UV 211.4, 275.6, 321.9 nm.

Example 406

(R)-3-(1,5-naphthyridin-3-ylamino)-5-(1-amino-3-cyclopropyl-1-oxopropan-2-ylamino)pyrazine-2-carboxamide

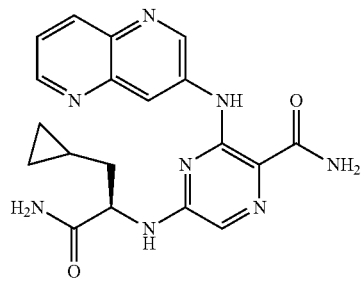 [SMILES: NC(=O)c1ncc(N[C@H](CC2CC2)C(N)=O)nc1Nc1cnc2cccnc2c1]

The title compound was synthesized in a manner similar to that described in Example 1. MS found for C19H20N8O2 as (M+H)$^+$ MS 393.3. UV: λ=UV 203.6, 251.7, 304.6, 352.9 nm.

Example 407

(R)-3-(1,5-naphthyridin-3-ylamino)-5-(1-amino-4-methyl-1-oxopentan-2-ylamino)pyrazine-2-carboxamide

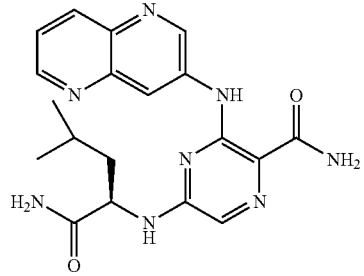 [SMILES: CC(C)C[C@@H](Nc1cnc(C(N)=O)c(Nc2cnc3cccnc3c2)n1)C(N)=O]

The title compound was synthesized in a manner similar to that described in Example 1. MS found for C19H22N8O2 as (M+H)$^+$ MS 395.3. UV: λ=UV 204.2, 251.7, 304.6, 352.3 nm.

Example 408

5-((3R,4R)-3-aminotetrahydro-2H-pyran-4-ylamino)-3-(3-methylisothiazol-5-ylamino)pyrazine-2-carboxamide

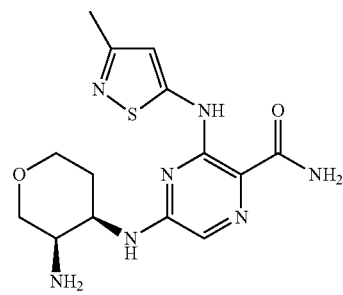 [SMILES: Cc1cc(Nc2nc(N[C@@H]3CCOC[C@@H]3N)cnc2C(N)=O)sn1]

The title compound was synthesized in a manner similar to that described in Example 78. MS found for C14H19N7O2S as (M+H)+ MS 350.2. UV: λ=UV 207.2, 272.0, 322.5 nm.

Example 409

(R)-3-(1,5-naphthyridin-3-ylamino)-5-(1-amino-1-oxo-3-(thiophen-2-yl)propan-2-ylamino)pyrazine-2-carboxamide

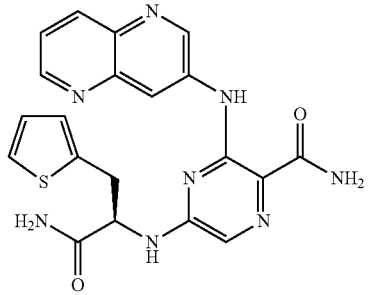 [SMILES: NC(=O)c1ncc(N[C@H](Cc2cccs2)C(N)=O)nc1Nc1cnc2cccnc2c1]

The title compound was synthesized in a manner similar to that described in Example 1. MS found for C20H18N8O2S as (M+H)+ MS 435.2. UV: λ=UV 204.8, 246.8, 305.8, 352.9 nm.

Example 410

(R)-3-(1,5-naphthyridin-3-ylamino)-5-(1-amino-3-methoxy-1-oxopropan-2-ylamino)pyrazine-2-carboxamide

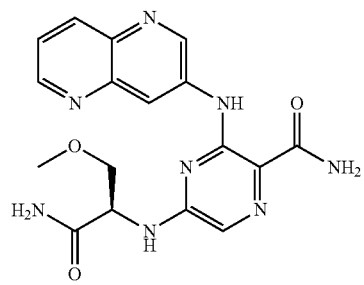 [SMILES: COC[C@@H](Nc1cnc(C(N)=O)c(Nc2cnc3cccnc3c2)n1)C(N)=O]

The title compound was synthesized in a manner similar to that described in Example 1. MS found for C17H18N8O3 as (M+H)+ MS 383.3. UV: λ=UV 204.2, 250.5, 302.7, 351.7 nm.

Example 411

(R)-3-(1,5-naphthyridin-3-ylamino)-5-(2-amino-2-oxo-1-phenylethylamino)pyrazine-2-carboxamide

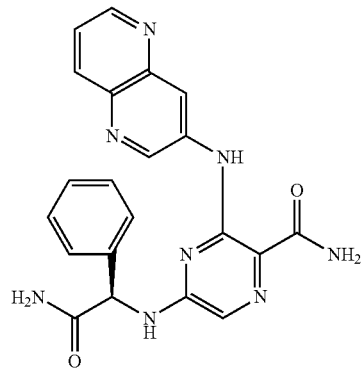 [SMILES: NC(=O)c1ncc(N[C@@H](C(N)=O)c2ccccc2)nc1Nc1cnc2cccnc2c1]

The title compound was synthesized in a manner similar to that described in Example 1. MS found for C21H18N8O2 as (M+H)+ MS 415.3. UV: λ=UV 202.9, 251.7, 304.6, 352.9 nm.

Example 412

5-((1R,2S)-2-aminocyclohexylamino)-3-(isothiazolo[3,4-b]pyridin-3-ylamino)pyrazine-2-carboxamide

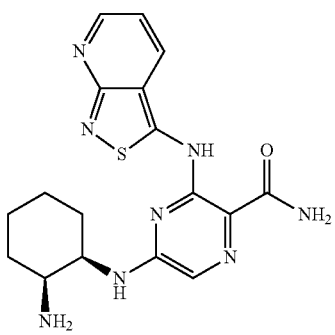 [SMILES: NC(=O)c1ncc(N[C@@H]2CCCC[C@@H]2N)nc1Nc1snc2ncccc12]

To a solution of 2-amino-3-cyanopyridine (1.00 g, 8.40 mmol) in pyridine (8 mL) and TEA (0.8 mL) in a sealed tube, H2S gas was bubbled through for 5 min. It was then stirred at room temperature for 20 h. The mixture was concentrated in vacuo to dryness. The residue was dissolved in MeOH (10 mL). To the solution, aq. H2O2 (30%, 3 mL) was added. The mixture was then stirred at room temperature for 5 h, during which time, solids precipitated out. The solids were collected by filtration, dried on vacuum to give isothiazolo[3,4-b]pyridin-3-amine (860 mg).

A mixture of tert-butyl (1S,2R)-2-(6-chloro-5-cyanopyrazin-2-ylamino)cyclohexylcarbamate (53 mg, 0.150 mmol), isothiazolo[3,4-b]pyridin-3-amine (29 mg, 0.0.192 mmol), Cs2CO3 (100 mg, 0.304 mmol), 2'-(dicyclohexylphosphino)-N,N-dimethylbiphenyl-2-amine (DavePhos) (12 mg, 0.030 mmol) and Pd2dba3 (15 mg, 0.016 mmol) in dioxane (1 mL) was degassed with Ar, then was stirred at 110 C for 2 h. The mixture was concentrated in vacuo. The residue was dissolved in TFA (4 mL). After 20 min of stirring, excess of TFA was removed in vacuo. The residue was purified by HPLC to give 5-((1R,2S)-2-aminocyclohexylamino)-3-(isothiazolo[3,4-b]pyridin-3-ylamino)pyrazine-2-carbonitrile (36 mg).

To a solution of 5-((1R,2S)-2-aminocyclohexylamino)-3-(isothiazolo[3,4-b]pyridin-3-ylamino)pyrazine-2-carbonitrile (36 mg) in EtOH (1 mL) and DMSO (0.5 mL), aq. 1N NaOH (1 mL) and aq. H2O2 (30%, 1 mL) were added. The mixture was stirred at room temperature for 20 h. After being neutralized with HOAc (0.3 mL), the mixture was purified by HPLC to give the titled compound (7 mg). MS found for C17H20N8OS as (M+H)+ MS 385.3. UV: λ=UV 207.4, 245.8, 298.6, 343.2 nm. $^1$H NMR: (CD3OD) δ 8.50 (dd, 1H), 8.22 (dd, 1H), 7.73 (s, 1H), 7.05 (dd, 1H), 4.70-4.62 (m, 1H), 4.12-4.05 (m, 1H), 2.14-1.60 (m, 8H).

Example 413

5-(((1R,2S)-2-aminocyclohexyl)amino)-3-(pyrazolo[1,5-a]pyridin-3-ylamino)pyrazine-2-carboxamide

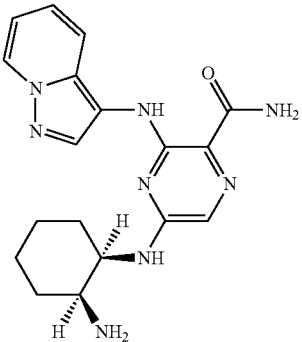 [SMILES: NC(=O)c1ncc(N[C@@H]2CCCC[C@@H]2N)nc1Nc1cnn2ccccc12]

The mixture of tert-tutyl ((1S,2R)-2-((6-chloro-5-cyanopyrazin-2-yl)amino)cyclohexyl)carbamate (100 mg, 0.28 mmol), pyrazolo[1,5-a]pyridin-3-amine dihydrochloride (118 mg, 0.56 mmol), powder cesium carbonate (730 mg, 2.24 mmol), BINAP (62 mg, 0.1 mmol), Pd(OAc)$_2$ (22 mg, 0.1 mmol) in 20 mL dioxane was degassed with argon stream. It was stirred in argon atmosphere at 110° C. for 1 h. The mixture was cooled, diluted with 100 mL EtOAc, vigorously stirred, and filtered through celite. The filtrate was concentrated and subjected to silica flash column with 0-60% EtOAc in hexane to isolate tert-butyl ((1S,2R)-2-((5-carbamoyl-6-(pyrazolo[1,5-a]pyridin-3-ylamino)pyrazin-2-yl)amino)cyclohexyl)carbamate. It was then stirred in 5 mL TFA at RT for 1 h, and concentrated in vacuo till complete dryness. The residue was further diluted with heptane and concentrated to dryness. This residue was dissolved in 10 ml MeOH and 2 mL DMSO. To the solution were added KOH (100 mg) and then 1 mL of H$_2$O$_2$ (50%). The mixture was stirred at RT for 30 m, quenched with acetonitrile and then TFA, concentrated in vacuo and subjected to reverse phase preparative HPLC to isolate the title compound (72 mg). MS found for C18H22N8O as (M+H)$^+$ 367.5. UV: λ=292 nm. $^1$H NMR: (CD$_3$OD) δ 8.47 (1H, m), 8.23 (1H, m), 7.56 (1H, m), 7.45 (1H, m), 7.21 (1H, m), 6.91 (1H, m), 4.18 (1H, m), 3.55 (1H, m), 1.74-1.53 (8H, m) ppm.

Example 415

5-(((1R,2S)-2-aminocyclohexyl)amino)-3-((R)-chroman-3-ylamino)pyrazine-2-carboxamide

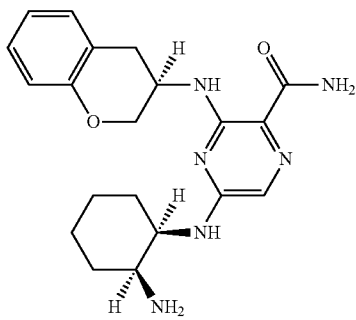 [SMILES: NC(=O)c1ncc(N[C@@H]2CCCC[C@@H]2N)nc1N[C@H]1COc2ccccc2C1]

The title compound was separated from 5-(((1R,2S)-2-aminocyclohexyl)amino)-3-((S)-chroman-3-ylamino)pyrazine-2-carboxamide using reverse phase HPLC of the mixture of Example 42. MS found for C20H26N6O2 as (M+H)$^+$ 383.5. UV: λ=278 nm.

Example 416

5-(((1R,2S)-2-aminocyclohexyl)amino)-3-((S)-chroman-3-ylamino)pyrazine-2-carboxamide

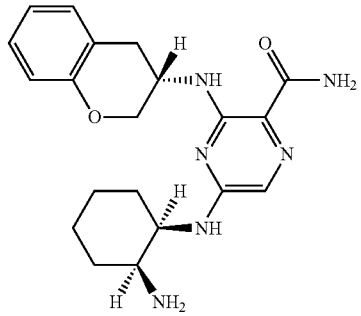 [SMILES: NC(=O)c1ncc(N[C@@H]2CCCC[C@@H]2N)nc1N[C@@H]1COc2ccccc2C1]

The title compound was separated from 5-(((1R,2S)-2-aminocyclohexyl)amino)-3-((R)-chroman-3-ylamino)pyrazine-2-carboxamide using reverse phase HPLC of the mixture of Example 42. MS found for C20H26N6O2 as (M+H)$^+$ 383.5. UV: λ=278 nm.

Example 417

5-(((1R,2S)-2-aminocyclohexyl)amino)-3-(pyridin-3-ylamino)pyrazine-2-carboxamide

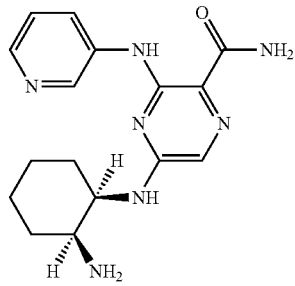 [SMILES: NC(=O)c1ncc(N[C@@H]2CCCC[C@@H]2N)nc1Nc1cccnc1]

The mixture of tert-tutyl ((1S,2R)-2-((6-chloro-5-cyanopyrazin-2-yl)amino)cyclohexyl)carbamate (100 mg, 0.28 mmol), 3-aminopyridine (53 mg, 0.56 mmol), powder cesium carbonate (360 mg, 1.12 mmol), BINAP (37 mg, 0.06 mmol), Pd(OAc)$_2$ (14 mg, 0.06 mmol) in 20 mL dioxane was degassed with argon stream. It was stirred in argon atmosphere at 110° C. for 2 h. The mixture was cooled, diluted with 100 mL EtOAc, vigorously stirred, and filtered through celite. The filtrate was concentrated and subjected to silica flash column with 0-70% EtOAc in hexane to isolate the coupling product. It was then stirred in 6 mL TFA and 1 mL conc. H$_2$SO$_4$ at 80° C. for 30 m. It was cooled in ice bath, diluted with water, filtered, and subjected to reverse phase preparative HPLC to isolate the title compound (103 mg). MS found for C16H21N7O as (M+H)$^+$ 328.5. UV: λ=230, 259, 301 nm. $^1$H NMR: (CD$_3$OD) δ 9.50 (1H, s), 8.56 (1H, d, J=8.8

Hz), 8.42 (1H, d, J=5.6 Hz), 7.95 (1H, dd, J=8.8; 5.6 Hz), 7.75 (1H, s), 4.57 (1H, m), 3.70 (1H, m), 1.95-1.58 (8H, m) ppm.

Example 418

5-(((1R,2S)-2-aminocyclohexyl)amino)-3-((5-fluoro-pyridin-3-yl)amino)pyrazine-2-carboxamide

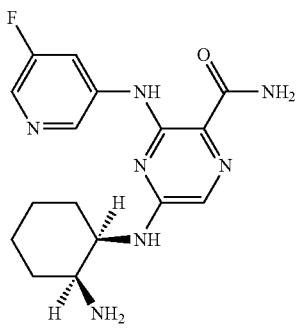 [SMILES: NC(=O)c1ncc(N[C@@H]2CCCC[C@@H]2N)nc1Nc1cncc(F)c1]

The mixture of tert-tutyl ((1S,2R)-2-((6-chloro-5-cyanopyrazin-2-yl)amino)cyclohexyl)carbamate (100 mg, 0.28 mmol), 3-fluoro-5-aminopyridine (60 mg, 0.56 mmol), powder cesium carbonate (360 mg, 1.12 mmol), BINAP (37 mg, 0.06 mmol), Pd(OAc)$_2$ (14 mg, 0.06 mmol) in 20 mL dioxane was degassed with argon stream. It was stirred in argon atmosphere at 110° C. for 2 h. The mixture was cooled, diluted with 100 mL EtOAc, vigorously stirred, and filtered through celite. The filtrate was concentrated and subjected to silica flash column with 0-60% EtOAc in hexane to isolate the coupling product. It was then stirred in 6 mL TFA and 1 mL conc. H$_2$SO$_4$ at 80° C. for 30 m. It was cooled in ice bath, diluted with water, filtered, and subjected to reverse phase preparative HPLC to isolate the title compound (83 mg). MS found for C16H20FN7O as (M+H)$^+$ 346.5. UV: λ=259, 301 nm. $^1$H NMR: (CD$_3$OD) δ 9.04 (1H, m), 8.57 (1H, m), 8.40 (1H, m), 7.73 (1H, s), 4.49 (1H, m), 3.74 (1H, m), 1.96-1.60 (8H, m) ppm.

Example 419

3-((1,5-naphthyridin-3-yl)amino)-5-(((1R,2S)-2-aminocyclohexyl)amino)pyrazine-2-carboxamide

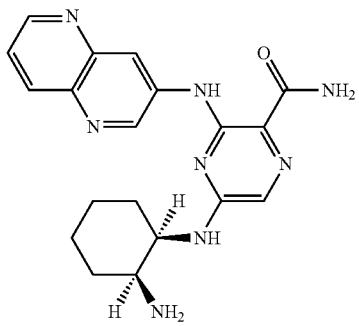 [SMILES: NC(=O)c1ncc(N[C@@H]2CCCC[C@@H]2N)nc1Nc1cnc2cccnc2c1]

The title compound was synthesized in a manner similar to that described in Example 5-(((1R,2S)-2-aminocyclohexyl)amino)-3-(pyridin-3-ylamino)pyrazine-2-carboxamide. MS found for C19H22N8O as (M+H)$^+$ 379.5. UV: λ=254, 306 nm. $^1$H NMR: (CD$_3$OD) δ 9.03 (1H, s), 9.02 (1H, m), 8.95 (1H, dd, J=4.8; 1.6 Hz), 8.49 (1H, d, J=8.4 Hz), 7.72 (1H, m), 7.70 (1H, s), 4.70 (1H, m), 3.79 (1H, m), 2.00-1.61 (8H, m) ppm.

Example 420

3-((1,8-naphthyridin-3-yl)amino)-5-(((1R,2S)-2-aminocyclohexyl)amino)pyrazine-2-carboxamide

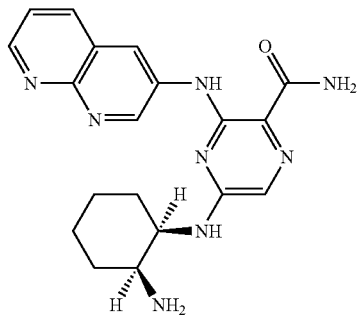 [SMILES: NC(=O)c1ncc(N[C@@H]2CCCC[C@@H]2N)nc1Nc1cnc2ncccc2c1]

The title compound was synthesized in a manner similar to that described in Example 5-(((1R,2S)-2-aminocyclohexyl)amino)-3-(pyridin-3-ylamino)pyrazine-2-carboxamide. MS found for C19H22N8O as (M+H)$^+$ 379.5. UV: λ=258, 292, 354 nm. $^1$H NMR: (CD$_3$OD) δ 9.33 (1H, d, J=2.4 Hz), 8.93 (1H, m), 8.68 (1H, d, J=2.4 Hz), 8.45 (1H, dd, J=8.4; 2.0 Hz), 7.67 (1H, dd, J=8.0; 4.0 Hz), 7.65 (1H, s), 4.53 (1H, m), 3.76 (1H, m), 1.90-1.63 (8H, m) ppm.

Example 421

(R)-5-((l-amino-1-oxobutan-2-yl)amino)-3-(pyrazolo[1,5-a]pyridin-3-ylamino)pyrazine-2-carboxamide

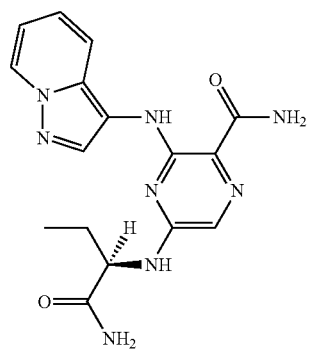 [SMILES: CC[C@@H](Nc1cnc(C(N)=O)c(Nc2cnn3ccccc23)n1)C(N)=O]

The mixture of (R)-2-((6-chloro-5-cyanopyrazin-2-yl)amino)butanamide (65 mg, 0.27 mmol), pyrazolo[1,5-a]pyridin-3-amine dihydrochloride (56 mg, 0.27 mmol), powder cesium carbonate (360 mg, 1.08 mmol), BINAP (31 mg, 0.05 mmol), Pd(OAc)$_2$ (11 mg, 0.05 mmol) in 15 mL dioxane was degassed with argon stream. It was stirred in argon atmosphere at 115° C. for 16 h. The mixture was cooled, diluted with 100 mL EtOAc, vigorously stirred, and filtered through celite. The filtrate was concentrated and subjected to silica flash column with 0-8% MeOH in DCM to isolate the coupling product. It was dissolved in 8 mL MeOH and 2 mL DMSO. To the solution were added KOH (100 mg) and then 1 mL of H$_2$O$_2$ (50%). The mixture was stirred at RT for 30 m, quenched with acetonitrile and then TFA, concentrated in vacuo and subjected to reverse phase preparative HPLC to isolate the title compound (9 mg). MS found for C16H18N8O2 as (M+H)$^+$ 355.4. UV: λ=297 nm. $^1$H NMR: (CD$_3$OD) δ 8.33 (2H, m), 7.46 (1H, d, J=9.2 Hz), 7.32 (1H, s), 7.09 (1H, dd, J=8.8; 6.8 Hz), 6.78 (1H, t, J=7.2 Hz), 4.18 (1H, m), 1.83 (1H, m), 1.68 (1H, m), 0.92 (3H, t, J=7.2 Hz) ppm.

Example 422

5-(((1R,2S)-2-aminocyclohexyl)amino)-3-((5-(pyrimidin-2-yl)pyridin-3-yl)amino)pyrazine-2-carboxamide

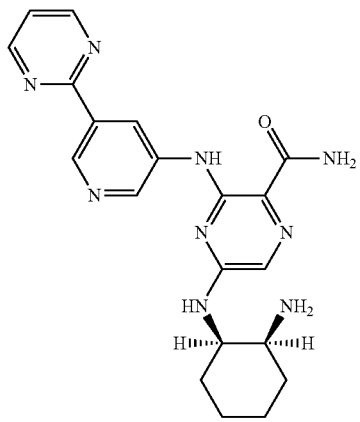 [SMILES: NC(=O)c1ncc(N[C@@H]2CCCC[C@@H]2N)nc1Nc1cncc(-c2ncccn2)c1]

The mixture of 2-bromopyrimidine (0.76 g, 4.80 mmol), (5-aminopyridin-3-yl)boronic acid hydrochloride (1.00 g, 5.75 mmol), Pd(Ph$_3$P)$_2$Cl$_2$ (0.73 g, 0.96 mmol) and K$_2$CO$_3$ (2.78 g, 20.2 mmol) in dioxane (40 mL) and water (10 mL) was degassed with argon stream. It was stirred at 95° C. in argon atmosphere for overnight. The mixture was concentrated in vacuo to dryness. The solid was triturated with dioxane and EtOAc. The organic solutions were combined, filtered, concentrated and subjected to flash column (0-8% MeOH in DCM) to isolate 5-(pyrimidin-2-yl)pyridin-3-amine (0.24 g).

The mixture of tert-tutyl ((1S,2R)-2-((6-chloro-5-cyanopyrazin-2-yl)amino)cyclohexyl)carbamate (100 mg, 0.28 mmol), 5-(pyrimidin-2-yl)pyridin-3-amine (100 mg, 0.58 mmol), powder cesium carbonate (380 mg, 1.16 mmol), BINAP (37 mg, 0.06 mmol), Pd(OAc)$_2$ (14 mg, 0.06 mmol) in 15 mL dioxane was degassed with argon stream. It was stirred in argon atmosphere at 110° C. for overnight. The mixture was cooled, diluted with 100 mL EtOAc, vigorously stirred, and filtered through celite. The filtrate was concentrated and subjected to silica flash column with 20-100% EtOAc in DCM to isolate the coupling product. It was then stirred in 5 mL TFA and 1 mL conc. H$_2$SO$_4$ at 80° C. for 30 m. It was cooled in ice bath, diluted with water, filtered, and subjected to reverse phase preparative HPLC to isolate the title compound (35 mg). MS found for C20H23N9O as (M+H)$^+$ 406.5. UV: λ=259, 306 nm. $^1$H NMR: (CD$_3$OD) δ 9.63 (1H, s), 9.24 (1H, s), 9.02 91H, s), 8.98 (2H, d, J=4.4 Hz), 7.70 (1H, s), 7.53 (1H, t, J=4.8 Hz), 4.74 (1H, m), 3.69 (1H, m), 1.92-1.56 (8H, m) ppm.

Example 423

5-(((1R,2S)-2-aminocyclohexyl)amino)-3-((3,5-di(pyrimidin-2-yl)phenyl)amino)pyrazine-2-carboxamide

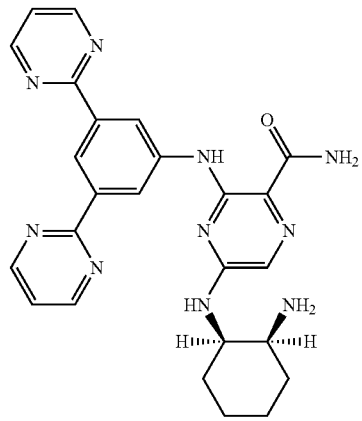 [SMILES: NC(=O)c1ncc(N[C@@H]2CCCC[C@@H]2N)nc1Nc1cc(-c2ncccn2)cc(-c2ncccn2)c1]

The mixture of 3,5-dibromoaniline (1.05 g, 4.2 mmol), 2-tributylstannylpyrimidine (5.00 g, 13.6 mmol), Pd(Ph$_3$P)$_4$ (0.97 g, 0.84 mmol) in 60 mL toluene was degassed with argon stream and stirred at 110° C. in argon atmosphere for three days. It was cooled to RT, diluted with EtOAc, filtered through celite, concentrated in vacuo, and subjected to silica flash column to isolate 3,5-di(pyrimidin-2-yl)aniline and 3-bromo-5-(pyrimidin-2-yl)aniline.

The mixture of 3-bromo-5-(pyrimidin-2-yl)aniline (140 mg, 0.56 mmol),), 2-tributylstannylpyrimidine (420 mg, 1.12 mmol), Pd(Ph$_3$P)$_4$ (65 mg, 0.056 mmol) in 20 mL toluene and 5 mL dioxane was degassed with argon stream and stirred at 110° C. in argon atmosphere for two days. It was cooled to RT, diluted with EtOAc, filtered through celite, concentrated in vacuo, and subjected to silica flash column to isolate 3,5-di(pyrimidin-2-yl)aniline.

The mixture of tert-tutyl ((1S,2R)-2-((6-chloro-5-cyanopyrazin-2-yl)amino)cyclohexyl)carbamate (60 mg, 0.24 mmol), 3,5-di(pyrimidin-2-yl)aniline (85 mg, 0.24 mmol), powder cesium carbonate (326 mg, 1.00 mmol), BINAP (31 mg, 0.05 mmol), Pd(OAc)$_2$ (12 mg, 0.05 mmol) in 15 mL dioxane was degassed with argon stream. It was stirred in argon atmosphere at 110° C. for 2.5 h. The mixture was cooled, diluted with 100 mL EtOAc, vigorously stirred, and filtered through celite. The filtrate was concentrated and subjected to silica flash column with 0-90% EtOAc in hexane to isolate the coupling product. It was then stirred in 5 mL TFA and 1 mL conc. H$_2$SO$_4$ at 80° C. for 30 m. It was cooled in ice bath, diluted with water, filtered, and subjected to reverse phase preparative HPLC to isolate the title compound (68 mg). MS found for C25H26N10O as (M+H)$^+$ 483.5. UV: λ=254, 315 nm. $^1$H NMR: (CD$_3$OD) δ 9.05 (1H, t, J=1.6 Hz), 8.83 (4H, d, J=5.2 Hz), 8.75 (2H, d, J=1.6 Hz), 7.48 (1H, s), 7.35 (2H, t, J=4.8 Hz), 4.71 (1H, m), 3.60 (1H, m), 1.82-1.39 (8H, m) ppm.

Example 424

5-(((1R,2S)-2-aminocyclohexyl)amino)-3-((3,5-di (2H-1,2,3-triazol-2-yl)phenyl)amino)pyrazine-2-carboxamide

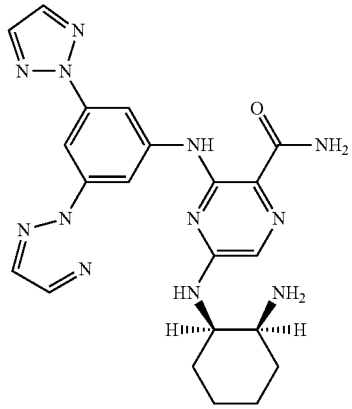 [SMILES: N=C/C=N\Nc1cc(Nc2nc(N[C@@H]3CCCC[C@@H]3N)cnc2C(N)=O)cc(-n2nccn2)c1]

The mixture of 3,5-dibromoaniline (2.00 g, 8.00 mmol), 1,2,3-triazole (3.70 mL, 64.0 mmol), $K_3PO_4$ (8.48 g, 40.0 mmol), CuI (0.77 g, 4.00 mmol), 1,2-ethylenediamine (0.27 mL, 4.00 mmol) in 40 mL dioxane and 4 mL DMSO was stirred at 120° C. in a sealed tube for four days. It was diluted with dioxane and EtOAc, filtered through celite, concentrated and subjected to flash column with 0-5% MeOH in DCM to isolate 3-bromo-5-(2H-1,2,3-triazol-2-yl)aniline (273 mg), 3,5-di(2H-1,2,3-triazol-2-yl)aniline (559 mg), 3-(1H-1,2,3-triazol-1-yl)-5-(2H-1,2,3-triazol-2-yl)aniline (636 mg), and 3,5-di(1H-1,2,3-triazol-1-yl)aniline (100 mg).

The mixture of tert-tutyl ((1S,2R)-2-((6-chloro-5-cyanopyrazin-2-yl)amino)cyclohexyl)carbamate (90 mg, 0.26 mmol), 3,5-di(2H-1,2,3-triazol-2-yl)aniline (88 mg, 0.39 mmol), powder cesium carbonate (340 mg, 1.04 mmol), BINAP (31 mg, 0.05 mmol), $Pd(OAc)_2$ (12 mg, 0.05 mmol) in 15 mL dioxane was degassed with argon stream. It was stirred in argon atmosphere at 110° C. for 16 h. The mixture was cooled, diluted with 100 mL EtOAc, vigorously stirred, and filtered through celite. The filtrate was concentrated and subjected to silica flash column with 0-55% EtOAc in hexane to isolate the coupling product. It was then stirred in 5 mL TFA and 1 mL conc. $H_2SO_4$ at 80° C. for 20 m. It was cooled in ice bath, diluted with water, filtered, and subjected to reverse phase preparative HPLC to isolate the title compound (18 mg). MS found for C21H24N12O as $(M+H)^+$ 461.5. UV: λ=259, 311 nm. $^1$H NMR: (CD$_3$OD) δ 8.52 (2H, d, J=1.6 Hz), 8.43 (1H, t, J=1.6 Hz), 8.01 (4H, s), 7.61 (2H, s), 4.83 (1H, m), 3.76 (1H, m), 1.93-1.55 (8H, m) ppm.

Example 425

5-(((1R,2S)-2-aminocyclohexyl)amino)-3-(imidazo [1,2-a]pyridin-6-ylamino)pyrazine-2-carboxamide

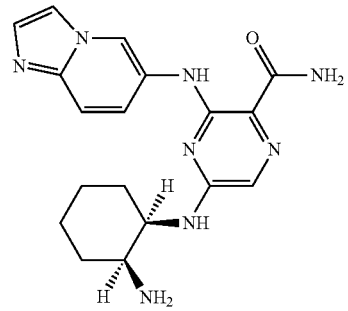 [SMILES: NC(=O)c1ncc(N[C@@H]2CCCC[C@@H]2N)nc1Nc1ccc2nccn2c1]

The title compound was synthesized in a manner similar to that described in Example 5-(((1R,2S)-2-aminocyclohexyl) amino)-3-(pyridin-3-ylamino)pyrazine-2-carboxamide. MS found for C18H22N8O as $(M+H)^+$ 367.5. UV: λ=249, 296 nm. $^1$H NMR: (CD$_3$OD) δ 9.50 (1H, s), 8.23 (1H, d, J=1.6 Hz), 8.01 (1H, d, J=2.0 Hz), 7.99 (1H, m), 7.88 (1H, d, J=10.0 Hz), 7.66 (1H, s), 4.55 (1H, m), 3.72 (1H, m), 1.94-1.58 (8H, m) ppm.

Example 426

(R)-5-((l-amino-1-oxobutan-2-yl)amino)-3-(imidazo [1,2-a]pyridin-6-ylamino)pyrazine-2-carboxamide

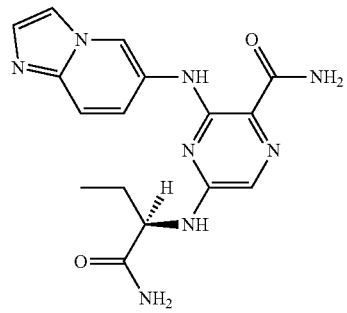 [SMILES: CC[C@@H](Nc1cnc(C(N)=O)c(Nc2ccc3nccn3c2)n1)C(N)=O]

The title compound was synthesized in a manner similar to that described in Example (R)-5-((l-amino-1-oxobutan-2-yl) amino)-3-(pyrazolo[1,5-a]pyridin-3-ylamino)pyrazine-2-carboxamide. MS found for C16H18N8O2 as $(M+H)^+$ 355.4. UV: λ=254, 297, 354 nm. $^1$H NMR: (CD$_3$OD) δ 9.60 (1H, s), 8.27 (1H, d, J=1.6 Hz), 7.83 (1H, d, J=2.0 Hz), 7.70 (1H, d, J=10.0 Hz), 7.66 (1H, dd, J=9.2; 2.0 Hz), 7.54 (1H, s), 4.03 (1H, m), 1.94-1.84 (2H, m), 1.05 (3H, t, J=7.2 Hz) ppm.

Example 427

5-(((1R,2S)-2-aminocyclohexyl)amino)-3-(imidazo [1,2-a]pyridin-7-ylamino)pyrazine-2-carboxamide

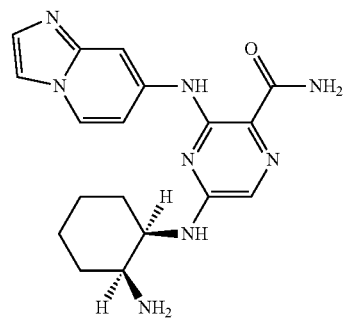 [SMILES: NC(=O)c1ncc(N[C@@H]2CCCC[C@@H]2N)nc1Nc1ccn2ccnc2c1]

The title compound was synthesized in a manner similar to that described in Example 5-(((1R,2S)-2-aminocyclohexyl) amino)-3-(pyridin-3-ylamino)pyrazine-2-carboxamide. MS found for C18H22N8O as $(M+H)^+$ 367.5. UV: λ=240, 292, 327 nm. $^1$H NMR: (CD$_3$OD) δ 8.59 (1H, d, J=7.6 Hz), 8.52 (1H, s), 7.97 (1H, dd, J=2.0; 0.8 Hz), 7.82 (1H, d, J=2.0 Hz), 7.78 (1H, s), 7.41 (1H, dd, J=7.6; 2.0 Hz), 4.69 (1H, m), 3.77 (1H, m), 1.98-1.57 (8H, m) ppm.

Example 428

5-(((1R,2S)-2-aminocyclohexyl)amino)-3-(thieno[2,3-b]pyridin-3-ylamino)pyrazine-2-carboxamide

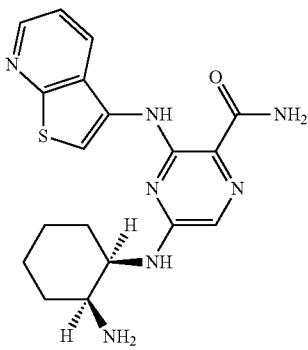 [SMILES: NC(=O)c1ncc(N[C@@H]2CCCC[C@@H]2N)nc1Nc1csc2ncccc12]

The title compound was synthesized in a manner similar to that described in Example 5-(((1R,2S)-2-aminocyclohexyl)amino)-3-(pyridin-3-ylamino)pyrazine-2-carboxamide. MS found for C18H21N7OS as (M+H)$^+$ 384.4. UV: λ=226, 263, 292 nm. $^1$H NMR: (CD$_3$OD) δ 8.63 (1H, dd, J=5.2; 1.6 Hz), 8.27 (1H, dd, =8.0; 1.6 Hz), 7.96 (1H, s), 7.59 (1H, s), 7.57 (1H, dd, J=8.4; 5.2 Hz), 4.48 (1H, m), 3.73 (1H, m), 1.89-1.60 (8H, m) ppm.

Example 429

3-((3-(1H-1,2,3-triazol-1-yl)-5-(2H-1,2,3-triazol-2-yl)phenyl)amino)-5-(((1R,2S)-2-aminocyclohexyl)amino)pyrazine-2-carboxamide

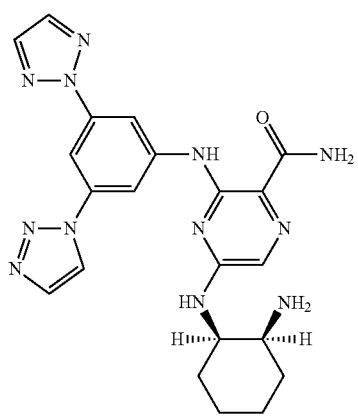 [SMILES: NC(=O)c1ncc(N[C@@H]2CCCC[C@@H]2N)nc1Nc1cc(-n2ccnn2)cc(-n2nccn2)c1]

The title compound was synthesized in a manner similar to that described in Example 5-(((1R,2S)-2-aminocyclohexyl)amino)-3-((3,5-di(2H-1,2,3-triazol-2-yl)phenyl)amino)pyrazine-2-carboxamide. MS found for C21H24N12O as (M+H)$^+$ 461.5. UV: λ=254, 311 nm. $^1$H NMR: (CD$_3$OD) δ 8.72 (1H, m), 8.55 (1H, m), 8.48 (1H, m), 8.14 (1H, m), 8.02 (2H, s), 7.97 (1H, m), 7.62 (1H, m), 4.38 (1H, m), 3.77 (1H, m), 1.88-1.56 (8H, m) ppm.

Example 430

5-(((1R,2S)-2-aminocyclohexyl)amino)-3-(isothiazol-4-ylamino)pyrazine-2-carboxamide

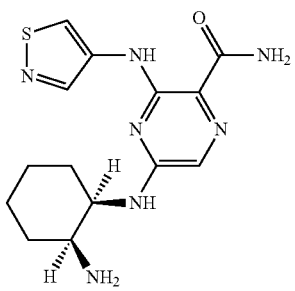 [SMILES: NC(=O)c1ncc(N[C@@H]2CCCC[C@@H]2N)nc1Nc1cnsc1]

The title compound was synthesized in a manner similar to that described in Example 5-(((1R,2S)-2-aminocyclohexyl)amino)-3-(pyridin-3-ylamino)pyrazine-2-carboxamide. MS found for C14H19N7OS as (M+H)$^+$ 334.4. UV: λ=230, 249, 306 nm. $^1$H NMR: (CD$_3$OD) δ 8.70 (1H, s), 8.60 (1H, s), 7.45 (1H, s), 4.38 (1H, m), 3.62 (1H, m), 1.80-1.50 (8H, m) ppm.

Example 431

5-(((1R,2S)-2-aminocyclohexyl)amino)-3-((3-morpholino-5-(1H-pyrazol-1-yl)phenyl)amino)pyrazine-2-carboxamide

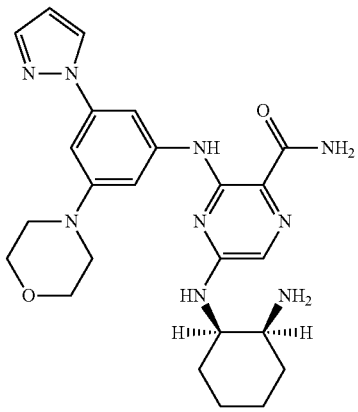 [SMILES: NC(=O)c1ncc(N[C@@H]2CCCC[C@@H]2N)nc1Nc1cc(N2CCOCC2)cc(-n2cccn2)c1]

The mixture of 3,5-dibromoaniline (1.16 g, 4.6 mmol), pyrazole (0.47 g, 6.9 mmol), Fe(acac)$_3$ (0.35 g, 1.0 mmol), Cu(OAc)$_2$.H$_2$O (0.18 g, 1.0 mmol) and cesium carbonate (3.00 g, 9.2 mmol) in 20 mL DMF was stirred at 135° C. in a sealed tube for 3 days. The mixture was diluted with EtOAc, stirred vigorously, filtered through celite, concentrated in vacuo, subjected to silica flash column to isolate 3,5-di(1H-pyrazol-1-yl)aniline and 3-bromo-5-(1H-pyrazol-1-yl)aniline (0.52 g).

The mixture of 3-bromo-5-(1H-pyrazol-1-yl)aniline (200 mg, 0.84 mmol), morphoine (0.22 mL, 2.52 mmol), proline (39 mg, 0.34 mmol), CuI (33 mg, 0.17 mmol) and K$_3$PO$_4$ (540 mg, 2.52 mmol) in 10 mL DMSO was stirred at 120° C. in a sealed tube for 4 days. It was diluted with dioxane, filtered through celite, concentrated in vacuo and subjected to reverse phase preparative HPLC to isolate 3-morpholino-5-(1H-pyrazol-1-yl)aniline (124 mg).

The mixture of tert-tutyl ((1S,2R)-2-(((6-chloro-5-cyan-opyrazin-2-yl)amino)cyclohexyl)carbamate (120 mg, 0.34 mmol), isolate 3-morpholino-5-(1H-pyrazol-1-yl)aniline (124 mg, 0.39 mmol), powder cesium carbonate (670 mg, 2.0 mmol), BINAP (44 mg, 0.07 mmol), Pd(OAc)$_2$ (16 mg, 0.07 mmol) in 20 mL dioxane was degassed with argon stream. It was stirred in argon atmosphere at 115° C. for 3 h. The mixture was cooled, diluted with 100 mL EtOAc, vigorously stirred, and filtered through celite. The filtrate was concentrated and subjected to silica flash column with 0-80% EtOAc in hexane to isolate the coupling product. It was then stirred in 5 mL TFA at RT for 30 m, and concentrated in vacuo till complete dryness. The residue was further diluted with heptane and concentrated to dryness. This residue was dissolved in 10 mL MeOH and 2 mL DMSO. To the solution were added KOH (100 mg) and then 1 mL of H$_2$O$_2$ (50%). The mixture was stirred at RT for 30 m, quenched with acetonitrile and then TFA, concentrated in vacuo and subjected to reverse phase preparative HPLC to isolate the title compound (36 mg). MS found for C24H31N9O2 as (M+H)$^+$ 478.6. UV: λ=254, 306 nm. $^1$H NMR: (CD$_3$OD) δ 8.30 (1H, d, J=2.4 Hz), 8.27 (1H, t, J=1.6 Hz), 7.78 (1H, d, J=2.0 Hz), 7.55 (1H, s), 7.03 (1H, s), 6.81 (1H, s), 6.56 (1H, m), 4.61 (1H, m), 3.89 (4H, m), 3.67 (1H, m), 1.82-1.52 (8H, m) ppm.

Example 432

5-(((1R,2S)-2-aminocyclohexyl)amino)-3-((3,5-di(1H-1,2,3-triazol-1-yl)phenyl)amino)pyrazine-2-carboxamide

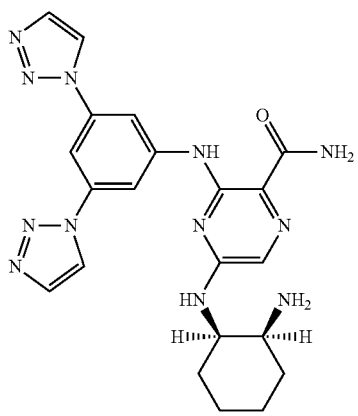 [SMILES: NC(=O)c1ncc(N[C@@H]2CCCC[C@@H]2N)nc1Nc1cc(-n2ccnn2)cc(-n2ccnn2)c1]

The title compound was synthesized in a manner similar to that described in Example 5-(((1R,2S)-2-aminocyclohexyl)amino)-3-((3,5-di(2H-1,2,3-triazol-2-yl)phenyl)amino)pyrazine-2-carboxamide. MS found for C21H24N12O as (M+H)$^+$ 461.5. UV: λ=244, 311 nm. $^1$H NMR: (CD$_3$OD) δ 8.73 (2H, d, J=1.2 Hz), 8.53 (2H, d, J=2.0 Hz), 7.80 (2H, d, J=0.8 Hz), 7.94 (1H, m), 7.64 (1H, s), 4.51 (1H, m), 3.80 (1H, m), 1.87-1.57 (8H, m) ppm Example 433

3-((1,6-naphthyridin-3-yl)amino)-5-(((1R,2S)-2-aminocyclohexyl)amino)pyrazine-2-carboxamide

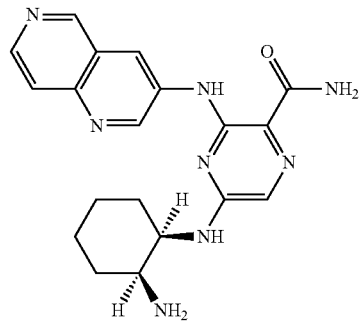

The title compound was synthesized in a manner similar to that described in Example 5-(((1R,2S)-2-aminocyclohexyl)amino)-3-(pyridin-3-ylamino)pyrazine-2-carboxamide. MS found for C19H22N8O as (M+H)$^+$ 379.5. UV: λ=268, 320 nm. $^1$H NMR: (CD$_3$OD) δ 9.63 (1H, m), 9.55 (1H, m), 9.06 (1H, m), 8.67 (1H, m), 8.31 (1H, m), 7.73 (1H, s), 4.62 (1H, m), 3.76 (1H, m), 1.93-1.63 (8H, m) ppm.

Example 434

5-(((1R,2S)-2-aminocyclohexyl)amino)-3-(thiazolo[5,4-b]pyridin-6-ylamino)pyrazine-2-carboxamide

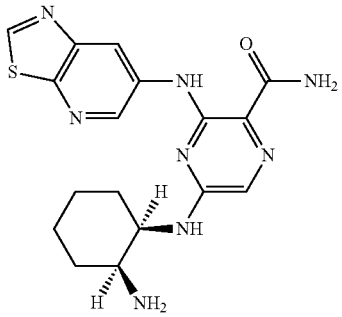 [SMILES: NC(=O)c1ncc(N[C@@H]2CCCC[C@@H]2N)nc1Nc1cnc2scnc2c1]

The title compound was synthesized in a manner similar to that described in Example 5-(((1R,2S)-2-aminocyclohexyl)amino)-3-(pyridin-3-ylamino)pyrazine-2-carboxamide. MS found for C17H20N8OS as (M+H)$^+$ 385.4. UV: λ=244, 301, 352 nm. $^1$H NMR: (CD$_3$OD) δ 9.39 (1H, s), 9.02 (1H, d, J=2.8

Hz), 8.73 (1H, d, J=2.4 Hz), 7.60 (1H, s), 4.49 (1H, m), 3.78 (1H, m), 1.87-1.60 (8H, m) ppm.

Example 435

5-(((1R,2S)-2-aminocyclohexyl)amino)-3-(quinolin-7-ylamino)pyrazine-2-carboxamide

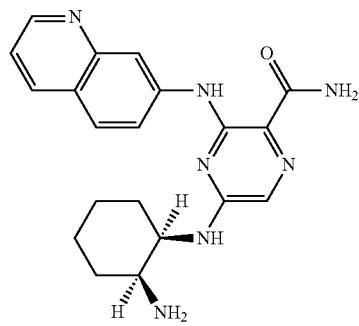 [SMILES: NC(=O)c1ncc(N[C@@H]2CCCC[C@@H]2N)nc1Nc1ccc2cccnc2c1]

The title compound was synthesized in a manner similar to that described in Example 5-(((1R,2S)-2-aminocyclohexyl)amino)-3-(pyridin-3-ylamino)pyrazine-2-carboxamide. MS found for C20H23N7O as (M+H)⁺ 378.5. UV: λ=263, 297, 354 nm. ¹H NMR: (CD₃OD) δ 8.90 (1H, dd, J=5.6; 1.2 Hz), 8.76 (2H, m), 8.09 (1H, d, J=9.2 Hz), 7.76 (1H, m), 7.73 (1H, s), 7.66 (1H, m), 4.80 (1H, m), 3.82 (1H, m), 1.95-1.58 (8H, m) ppm.

Example 436

5-(((1R,2S)-2-aminocyclohexyl)amino)-3-(quinolin-5-ylamino)pyrazine-2-carboxamide

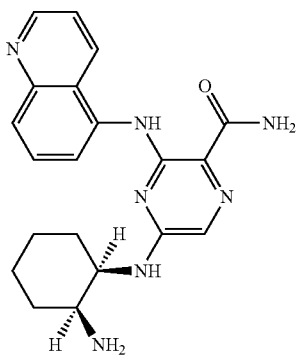 [SMILES: NC(=O)c1ncc(N[C@@H]2CCCC[C@@H]2N)nc1Nc1cccc2ncccc12]

The title compound was synthesized in a manner similar to that described in Example 5-(((1R,2S)-2-aminocyclohexyl)amino)-3-(pyridin-3-ylamino)pyrazine-2-carboxamide. MS found for C20H23N7O as (M+H)⁺ 378.5. UV: λ=240, 273, 352 nm. ¹H NMR: (CD₃OD) δ 9.18 (1H, d, J=8.4 Hz), 9.12 (1H, dd, J=5.2; 1.6 Hz), 8.67 (1H, d, J=8.0 Hz), 8.08 (1H, t, J=8.0 Hz), 7.97 (1H, dd, J=8.0; 5.2 Hz), 7.85 (1H, d, J=8.4 Hz), 7.66 (1H, s), 4.33 (1H, m), 3.66 (1H, m), 1.88-1.58 (8H, m) ppm.

Example 437

3-((1,8-naphthyridin-4-yl)amino)-5-(((1R,2S)-2-aminocyclohexyl)amino)pyrazine-2-carboxamide

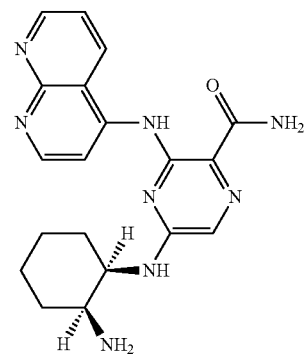 [SMILES: NC(=O)c1ncc(N[C@@H]2CCCC[C@@H]2N)nc1Nc1ccnc2ncccc12]

The title compound was synthesized in a manner similar to that described in Example 5-(((1R,2S)-2-aminocyclohexyl)amino)-3-(pyridin-3-ylamino)pyrazine-2-carboxamide. MS found for C19H22N8O as (M+H)⁺ 379.5. UV: λ=278, 332 nm. ¹H NMR: (CD₃OD) δ 9.18 (1H, dd, J=4.0; 1.6 Hz), 9.02 (1H, d, J=7.6 Hz), 8.96-8.93 (2H, m), 7.97 (1H, s), 7.93 (1H, dd, J=8.4; 4.8 Hz), 4.65 (1H, m), 3.78 (1H, m), 1.98-1.66 (8H, m) ppm.

Example 438

5-(((1R,2S)-2-aminocyclohexyl)amino)-3-((4-(1-propionylpiperidin-4-yl)phenyl)amino)pyrazine-2-carboxamide

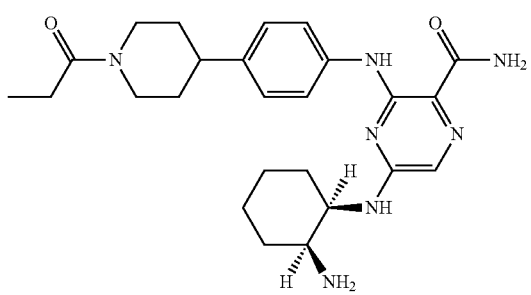 [SMILES: CCC(=O)N1CCC(c2ccc(Nc3nc(N[C@@H]4CCCC[C@@H]4N)cnc3C(N)=O)cc2)CC1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C25H35N7O2 as (M+H)⁺ 466.5. UV: λ=254, 305 nm. ¹H NMR: (CD₃OD) δ 7.53 (2H, m), 7.46 (1H, s), 7.21 (2H, m), 4.68 (1H, m), 4.33 (1H, m), 4.08 (1H, m), 3.82 (1H, m), 3.21 (1H, m), 2.80 (1H, m), 2.71 (1H, m), 2.46 (2H, q, J=7.6 Hz), 1.93-1.54 (12H, m), 1.14 (3H, t, J=8.4 Hz) ppm.

Example 439

5-(((1R,2S)-2-aminocyclohexyl)amino)-3-((3-fluoro-4-morpholinophenyl)amino)pyrazine-2-carboxamide

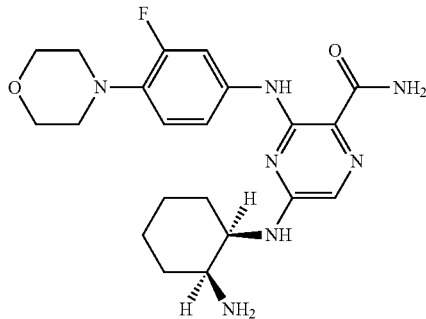 [SMILES: NC(=O)c1ncc(N[C@@H]2CCCC[C@@H]2N)nc1Nc1ccc(N2CCOCC2)c(F)c1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C21H28FN7O2 as (M+H)+ 430.5. UV: λ=259, 311 nm. $^1$H NMR: (CD$_3$OD) δ 7.98 (1H, m), 7.57 (1H, s), 7.44 (1H, m), 7.28 (1H, m), 4.39 (1H, m), 4.00 (4H, m), 3.84 (1H, m), 3.46 (4H, m), 1.94-1.63 (8H, m) ppm.

Example 440

5-(((1R,2S)-2-aminocyclohexyl)amino)-3-((4-(2-oxopyridin-1(2H)-yl)phenyl)amino)pyrazine-2-carboxamide

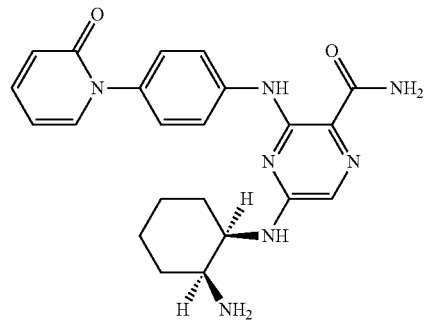 [SMILES: NC(=O)c1ncc(N[C@@H]2CCCC[C@@H]2N)nc1Nc1ccc(-n2ccccc2=O)cc1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C22H25N7O2 as (M+H)+ 420.5. UV: λ=259, 306 nm. $^1$H NMR: (CD$_3$OD) δ 7.77 (2H, m), 7.67-7.63 (2H, m), 7.55 (1H, s), 7.37 (2H, m), 6.65 (1H, m), 6.51 (1H, m), 4.40 (1H, m), 3.79 (1H, m), 1.89-1.59 (8H, m) ppm.

Example 441

5-(((1R,2S)-2-aminocyclohexyl)amino)-3-((4-(2-oxopiperidin-1-yl)phenyl)amino)pyrazine-2-carboxamide

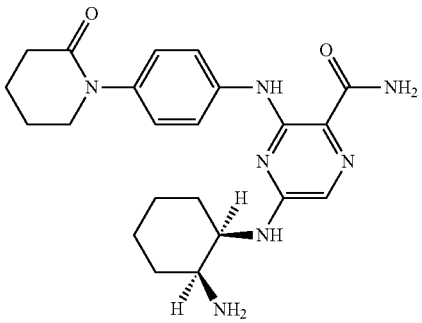 [SMILES: NC(=O)c1ncc(N[C@@H]2CCCC[C@@H]2N)nc1Nc1ccc(N2CCCCC2=O)cc1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C22H29N7O2 as (M+H)+ 424.6. UV: λ=259, 306 nm. $^1$H NMR: (CD$_3$OD) δ 7.64 (2H, m), 7.50 (1H, s), 7.24 (2H, m), 4.33 (1H, m), 3.74 (1H, m), 3.68 (2H, m), 2.52 (2H, m), 1.97 (4H, m), 1.83-1.59 (8H, m) ppm.

Example 442

5-(((1R,2S)-2-aminocyclohexyl)amino)-3-((4-(3-oxomorpholino)phenyl)amino)pyrazine-2-carboxamide

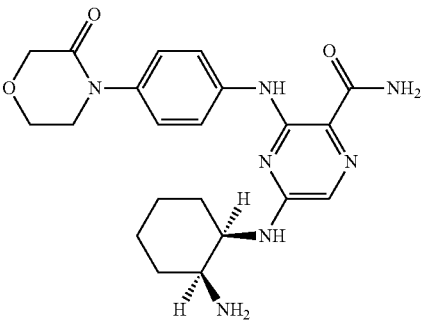 [SMILES: NC(=O)c1ncc(N[C@@H]2CCCC[C@@H]2N)nc1Nc1ccc(N2CCOCC2=O)cc1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C21H27N7O3 as (M+H)+ 426.5. UV: λ=259, 311 nm. $^1$H NMR: (CD$_3$OD) δ 7.67 (2H, m), 7.51

(1H, s), 7.32 (2H, m), 4.36 (1H, m), 4.29 (2H, s), 4.05 (2H, m), 3.77 (3H, m), 1.86-1.59 (8H, m) ppm.

Example 443

5-(((1R,2S)-2-aminocyclohexyl)amino)-3-((3-fluoro-4-(3-oxomorpholino)phenyl)amino)pyrazine-2-carboxamide

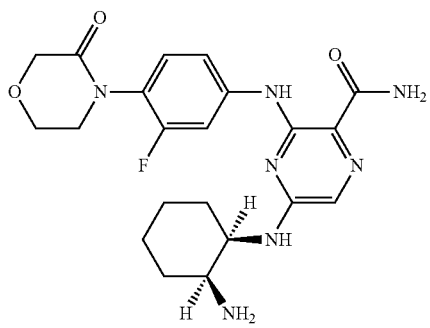 [SMILES: NC(=O)c1ncc(N[C@@H]2CCCC[C@@H]2N)nc1Nc1ccc(N2CCOCC2=O)c(F)c1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C21H26FN7O3 as (M+H)+ 444.5. UV: λ=259, 311 nm. $^1$H NMR: (CD$_3$OD) δ 7.96 (1H, dd, J=13.2; 2.0 Hz), 7.54 (1H, s), 7.32 (1H, t, J=8.4 Hz), 7.22 (1H, dd, J=8.8; 2.4 Hz), 4.39 (1H, m), 4.30 (2H, s), 4.05 (2H, m), 3.85 (1H, m), 3.72 (2H, m), 1.93-1.63 (8H, m) ppm.

Example 444

5-(((1R,2S)-2-aminocyclohexyl)amino)-3-((3-(oxazol-2-yl)phenyl)amino)pyrazine-2-carboxamide

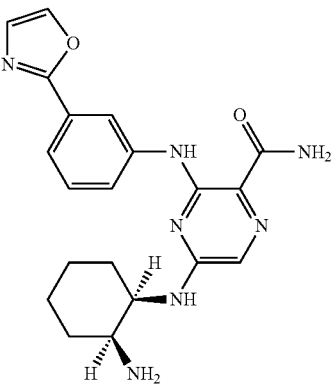 [SMILES: NC(=O)c1ncc(N[C@@H]2CCCC[C@@H]2N)nc1Nc1cccc(-c2ncco2)c1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C20H23N7O2 as (M+H)+ 394.6. UV: λ=263, 301 nm. $^1$H NMR: (CD$_3$OD) δ 8.80 (1H, m), 8.04 (1H, s), 7.66 (1H, m), 7.56 (1H, s), 7.46 (1H, t, J=8.0 Hz), 7.40 (1H, m), 7.35 (1H, d, J=1.6 Hz), 4.61 (1H, m), 3.72 (1H, m), 1.85-1.55 (8H, m) ppm.

Example 445

5-(((1R,2S)-2-aminocyclohexyl)amino)-3-((4-(oxazol-2-yl)phenyl)amino)pyrazine-2-carboxamide

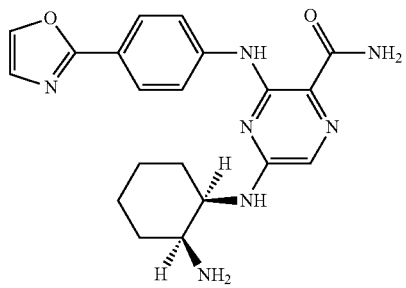 [SMILES: NC(=O)c1ncc(N[C@@H]2CCCC[C@@H]2N)nc1Nc1ccc(-c2ncco2)cc1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C20H23N7O2 as (M+H)+ 394.6. UV: λ=278, 330 nm. $^1$H NMR: (CD$_3$OD) δ 7.99 (3H, m), 7.81 (2H, m), 7.56 (1H, s), 7.32 (1H, m), 4.45 (1H, m), 3.85 (1H, m), 1.93-1.65 (8H, m) ppm.

Example 446

(R)-5-((1-amino-1-oxobutan-2-yl)amino)-3-((4-(oxazol-2-yl)phenyl)amino)pyrazine-2-carboxamide

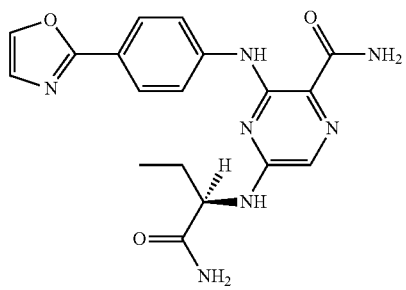 [SMILES: CC[C@@H](Nc1cnc(C(N)=O)c(Nc2ccc(-c3ncco3)cc2)n1)C(N)=O]

The title compound was synthesized in a manner similar to that described in Example (R)-5-((1-amino-1-oxobutan-2-yl)amino)-3-(pyrazolo[1,5-a]pyridin-3-ylamino)pyrazine-2-carboxamide. MS found for C18H19N7O3 as (M+H)+ 382.5. UV: λ=276, 332 nm. $^1$H NMR: (CD$_3$OD) δ 8.05 (1H, s), 7.98 (2H, m), 7.86 (2H, m), 7.55 (1H, s), 7.43 (1H, s), 4.32 (1H, m), 2.00 (1H, m), 1.91 (1H, m), 1.11 (3H, t, J=7.6 Hz) ppm.

Example 447

5-(((1R,2R)-2-amino-3,3-difluorocyclohexyl)amino)-3-(pyrazolo[1,5-a]pyridin-3-ylamino)pyrazine-2-carboxamide

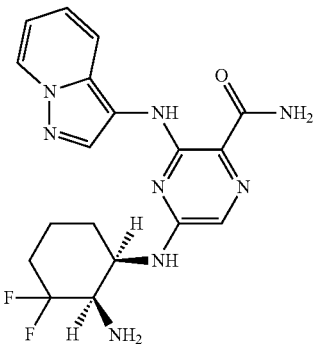 [SMILES: NC(=O)c1ncc(N[C@@H]2CCCC(F)(F)[C@@H]2N)nc1Nc1cnn2ccccc12]

The mixture of 5-(((1R,2R)-2-amino-3,3-difluorocyclohexyl)amino)-3-chloropyrazine-2-carbonitrile (115 mg, 0.40 mmol), pyrazolo[1,5-a]pyridin-3-amine dihydrochloride (247 mg, 1.20 mmol), powder cesium carbonate (1.04 g, 3.20 mmol), BINAP (50 mg, 0.08 mmol), Pd(OAc)$_2$ (18 mg, 0.08 mmol) in 20 mL dioxane was degassed with argon stream. It was stirred in argon atmosphere at 115° C. for overnight. The mixture was cooled, diluted with 100 mL EtOAc, vigorously stirred, and filtered through celite. The filtrate was concentrated and subjected to silica flash column with 0-9% MeOH in DCM to isolate the coupling product. It was dissolved in 10 mL MeOH and 2 mL DMSO. To the solution were added KOH (100 mg) and then 1 mL of H$_2$O$_2$ (50%). The mixture was stirred at RT for 30 m, quenched with acetonitrile and then TFA, concentrated in vacuo and subjected to reverse phase preparative HPLC to isolate the title compound (23 mg). MS found for C18H20F2N8O as (M+H)$^+$ 403.6. UV: λ=289, 355 nm. $^1$H NMR: (CD$_3$OD) δ 8.45 (1H, d, J=7.6 Hz), 8.23 (1H, s), 7.53 (1H, d, J=8.8 Hz), 7.47 (1H, s), 7.21 (1H, m), 6.89 (1H, t, J=6.8 Hz), 4.47 (1H, m), 3.93 (1H, m), 2.07-1.69 (6H, m) ppm.

Example 448

5-(((1R,2R)-2-amino-3,3-difluorocyclohexyl)amino)-3-(thieno[2,3-b]pyridin-3-ylamino)pyrazine-2-carboxamide

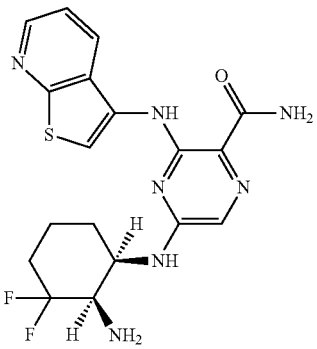 [SMILES: NC(=O)c1ncc(N[C@@H]2CCCC(F)(F)[C@@H]2N)nc1Nc1csc2ncccc12]

The title compound was synthesized in a manner similar to that described in Example 5-(((1R,2R)-2-amino-3,3-difluorocyclohexyl)amino)-3-(pyrazolo[1,5-a]pyridin-3-ylamino)pyrazine-2-carboxamide. MS found for C18H19F2N7OS as (M+H)$^+$ 420.5. UV: λ=226, 263, 292 nm. $^1$H NMR: (CD$_3$OD) δ 8.69 (1H, dd, J=5.2; 1.6 Hz), 8.37 (1H, dd, J=8.4; 1.2 Hz), 8.00 (1H, s), 7.66 (1H, dd, J=8.4; 1.2 Hz), 7.61 (1H, s), 4.73 (1H, m), 4.20 (1H, m), 2.21-1.81 (6H, m) ppm.

Example 449

5-(((1R,2S)-2-aminocyclohexyl)amino)-3-(thiazol-5-ylamino)pyrazine-2-carboxamide

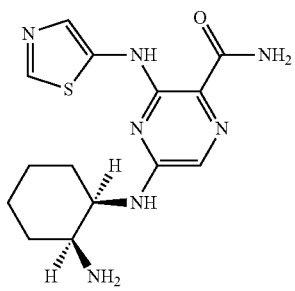 [SMILES: NC(=O)c1ncc(N[C@@H]2CCCC[C@@H]2N)nc1Nc1cncs1]

The title compound was synthesized in a manner similar to that described in Example 5-(((1R,2S)-2-aminocyclohexyl)amino)-3-(pyrazolo[1,5-a]pyridin-3-ylamino)pyrazine-2-carboxamide. MS found for C14H19N7OS as (M+H)$^+$ 334.3. UV: λ=231, 286, 334 nm.

Example 450

(R)-5-((1-amino-1-oxobutan-2-yl)amino)-3-43-(oxazol-2-yl)phenyl)amino)pyrazine-2-carboxamide

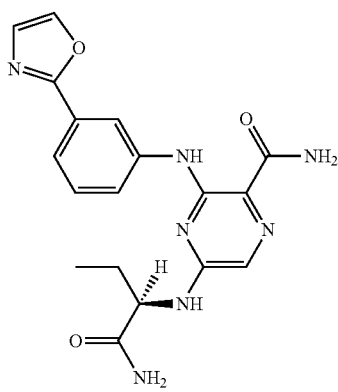 [SMILES: CC[C@@H](Nc1cnc(C(N)=O)c(Nc2cccc(-c3ncco3)c2)n1)C(N)=O]

The title compound was synthesized in a manner similar to that described in Example (R)-5-((1-amino-1-oxobutan-2-yl)

amino)-3-(pyrazolo[1,5-a]pyridin-3-ylamino)pyrazine-2-carboxamide. MS found for C18H19N7O3 as (M+H)+ 382.3. UV: λ=264, 303, 360 nm.

Example 451

5-(((1R,2R)-2-amino-3,3-difluorocyclohexyl)amino)-3-(isochroman-7-ylamino)pyrazine-2-carboxamide

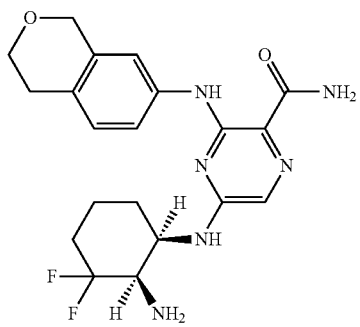 [SMILES: NC(=O)c1ncc(N[C@@H]2CCCC(F)(F)[C@@H]2N)nc1Nc1ccc2c(c1)COCC2]

The title compound was synthesized in a manner similar to that described in Example 5-(((1R,2R)-2-amino-3,3-difluorocyclohexyl)amino)-3-(pyrazolo[1,5-a]pyridin-3-ylamino)pyrazine-2-carboxamide. MS found for C20H24F2N6O2 as (M+H)+ 419.4. UV: λ=250, 303 nm.

Example 452

5-(((1R,2R)-2-amino-3,3-difluorocyclohexyl)amino)-3-((1,3-dihydroisobenzofuran-5-yl)amino)pyrazine-2-carboxamide

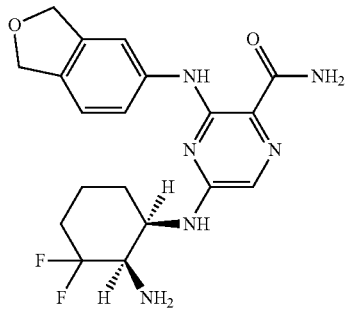 [SMILES: NC(=O)c1ncc(N[C@@H]2CCCC(F)(F)[C@@H]2N)nc1Nc1ccc2c(c1)COC2]

The title compound was synthesized in a manner similar to that described in Example 5-(((1R,2R)-2-amino-3,3-difluorocyclohexyl)amino)-3-(pyrazolo[1,5-a]pyridin-3-ylamino)pyrazine-2-carboxamide. MS found for C19H22F2N6O2 as (M+H)+ 405.3. UV: λ=251, 303 nm.

Example 453

5-(((1R,2R)-2-amino-3,3-difluorocyclohexyl)amino)-3-(isochroman-6-ylamino)pyrazine-2-carboxamide

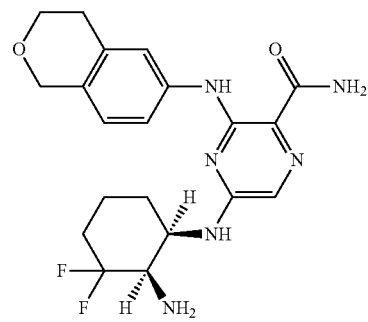 [SMILES: NC(=O)c1ncc(N[C@@H]2CCCC(F)(F)[C@@H]2N)nc1Nc1ccc2c(c1)CCOC2]

The title compound was synthesized in a manner similar to that described in Example 5-(((1R,2R)-2-amino-3,3-difluorocyclohexyl)amino)-3-(pyrazolo[1,5-a]pyridin-3-ylamino)pyrazine-2-carboxamide. MS found for C20H24F2N6O2 as (M+H)+ 419.3. UV: λ=251, 303 nm.

Example 454

5-(((1R,2R)-2-amino-3,3-difluorocyclohexyl)amino)-3-((2,3-dihydro-1H-inden-5-yl)amino)pyrazine-2-carboxamide

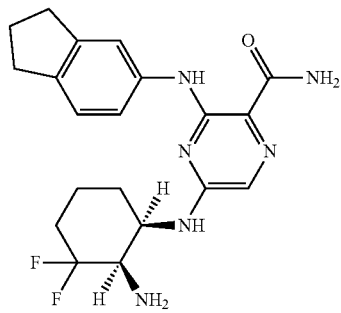 [SMILES: NC(=O)c1ncc(N[C@@H]2CCCC(F)(F)[C@@H]2N)nc1Nc1ccc2c(c1)CCC2]

The title compound was synthesized in a manner similar to that described in Example 5-(((1R,2R)-2-amino-3,3-difluorocyclohexyl)amino)-3-(pyrazolo[1,5-a]pyridin-3-ylamino)pyrazine-2-carboxamide. MS found for C20H24F2N6O as (M+H)+ 403.3. UV: λ=250, 303 nm.

The in vitro and in vivo human Syk activities of the inventive compounds can be determined by various procedures known in the art, such as a test for their ability to inhibit the activity of human plasma Syk. The potent affinities for human Syk inhibition exhibited by the inventive compounds can be measured by an IC$_{50}$ value (in nM). The IC$_{50}$ value is the concentration (in nM) of the compound required to provide 50% inhibition of human Syk proteolytic activity. The smaller the IC$_{50}$ value, the more active (potent) is a compound for inhibiting Syk activity.

An in vitro assay for detecting and measuring inhibition activity against Syk is as follows:

Inhibition of Syk Tyrosine Phosphorylation Activity

Potency of candidate molecules for inhibiting Syk tyrosine phosphorylation activity is assessed by measuring the ability of a test compound to inhibit Syk-mediated tyrosine phosphorylation of a Syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction and which comprises of a candidate molecule, full length active recombinant SYK enzyme (Millipore, Calif.) and biotin-labeled SYK-specific substrate biotin-DEEDYESP-OH. The second reaction involves termination of the kinase reaction and the simultaneous addition of the detection reagents-europium-labeled anti-phosphotyrosine reagent (Eu-W1024-PY100, Perkin Elmer, Boston, Mass.) and Streptavidin-Allophycocyanin detection reagent (SA-APC, Prozyme, Calif.). The kinase reaction is performed in a black U-bottom 96-well microtitre plate. The final reaction volume is 50 µL and contains a final concentration of 1 nM active SYK enzyme, 550 nM SYK-substrate, and 100 µM ATP diluted in a buffer containing 50 mM Tris pH 7.5, 5 mM $MgCl_2$, and 1 mM DTT. The reaction is allowed to proceed for 1 hour at room temperature. The quench buffer contains 100 mM Tris pH 7.5, 300 mM $NaCl_2$, 20 mM EDTA, 0.02% Brij35, and 0.5% BSA. The detection reagents are added to the reaction mixture at the following dilutions-1:500 for Eu-W1024-PY100 and 1:250 for SA-APC. The kinase reaction is terminated by the addition of 50 µL quench buffer containing the detection reagents. The detection is allowed to proceed for 1 hr at room temperature. Detection of the phosphorlated substrate in the absence and presence of inhibitors is measured in the TR-FRET instrument, Analyst HT (Molecular Probes, Sunnyvale, Calif.) and the condition for measurements are set up using CriterionHost Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$s were derived by non-linear regression analysis.

Intracellular phospho-flow cytometry can be used to test compound inhibition of Syk activity in the non-Hodgkin's lymphoma cell line Ramos. $1 \times 10^6$ cells in log phase growth were aliqoted; Syk kinase is activated by incubating cells for 10 minutes with 3 µg/ml antibody specific to the B cell receptor. Directly following, cells are fixed in 1% paraformaldehyde for 5 minutes at room temperature, washed in phosphate buffered saline, and then permeablized by incubation for 2 hours in ice cold methanol. Cells are again washed in phosphate buffered saline, then incubated for 30 minutes with antibody specific for phosphorylated Erk (Y204), which are indicators of Syk kinase activity. All antibodies used are purchased from BD Pharmingen (San Jose, Calif.). After incubation with antibodies, cells are again washed and subjected to flow cytometry.

Syk has been implicated experimentally in B cell development, proliferation, and survival. Moreover, Syk is implicated as an oncogene. Expression of constitutively active Syk in adoptively transferred bone marrow cells induces leukemia in mice, and over-activity of Syk is associated with a variety of lymphomas in humans Given the role of Syk in B cell biology, its selective inhibition may be sufficient to provide clinical benefit in B cell proliferative disorders, while reducing toxicities that may arise due to suppression of other off-target kinases.

The anti-proliferative effects of compounds on non-Hodgkin's lymphoma B cell lines SUDHL-4, SUDHL-6, and Toledo can also assessed. SUDHL-4 and SUDHL-6 require B cell receptor signaling for growth and survival, while the Toledo cell line (serving here as a negative control) does not. Cells are aliquoted into each well of a 96-well plate and incubated with increasing concentrations of compound for 72 hours, after which cell survival and proliferation is determined using the MTT assay (Chemicon International, Inc., Temecula, Calif.) following protocols supplied by the manufacturer.

Induction of apoptosis in non-Hodgkin's lymphoma B cell lines SUDHL-4, SUDHL-6, and Toledo is assessed by measuring the apoptotis marker Caspase 3. Cells were incubated with 1, 3, or 10 µM compound for 24, 48, and 72 hours. At the conclusion of each time point, cells were processed for flow cytometry analysis using the Monoclonal Rabbit Anti-Active Caspase-3 Antibody Kit and related protocols (BD Pharmingen). Data from two independent experiments are presented in Table 1, representing the percent of total cells undergoing apoptosis following incubation with compounds under the indicated conditions.

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Primary mouse B cells isolated from spleen can be aliquoted and incubated with increasing concentrations of compound (0.05 to 2 µM) in the presence of goat anti-mouse IgD (eBiosciences, Inc., San Diego, Calif.) for 20 hours to cross-link the B cell receptor. Cells are washed and incubated for 30 minutes on ice with antibodies specific for the CD80, CD86, and CD69 B cell activation markers. B cells are identified from the pooled population by staining with the B cell marker CD45RO. All antibodies are purchased from BD Pharmingen.

In the table below, activity in the Syk assays is provided as follows: +++++=$IC_{50}$<0.0010 µM; ++++=0.0010 µM<$IC_{50}$<0.010 µM, +++=0.010 µM<$IC_{50}$<0.10 µM, ++=0.10 µM<$IC_{50}$<1 µM, +=$IC_{50}$>1 µM.

TABLE 1

| Example No. | Syk IC50 |
|---|---|
| 1 | ++++ |
| 2 | ++++ |
| 3 | ++++ |
| 4 | ++++ |
| 5 | ++++ |
| 6 | ++++ |
| 7 | ++++ |
| 8 | ++++ |
| 9 | ++++ |
| 10 | ++++ |
| 11 | ++++ |
| 12 | ++++ |
| 13 | ++++ |
| 14 | ++++ |
| 15 | +++ |
| 16 | ++ |
| 17 | +++ |
| 18 | +++ |
| 19 | +++ |
| 20 | ++++ |
| 21 | ++++ |
| 22 | ++++ |
| 23 | +++ |
| 24 | +++ |
| 25 | ++++ |
| 26 | +++ |
| 27 | +++ |
| 28 | ++++ |
| 29 | ++++ |
| 30 | ++++ |
| 31 | ++++ |
| 32 | +++++ |
| 33 | ++++ |
| 34 | ++++ |
| 35 | + |
| 36 | + |
| 37 | +++ |
| 38 | ++ |
| 39 | ++ |
| 44 | ++++ |
| 45 | ++++ |
| 54 | +++++ |
| 55 | ++++ |
| 56 | ++++ |
| 57 | ++ |
| 58 | +++ |
| 59 | ++ |
| 60 | + |
| 61 | ++ |
| 62 | ++ |
| 63 | +++ |
| 64 | +++ |
| 65 | +++ |
| 66 | ++++ |
| 67 | ++++ |
| 68 | ++++ |
| 69 | +++ |
| 70 | +++ |
| 71 | +++ |
| 72 | ++++ |
| 73 | ++++ |
| 74 | ++++ |
| 75 | ++++ |
| 76 | ++++ |
| 77 | ++++ |
| 78 | ++++ |
| 79 | ++++ |
| 80 | ++++ |
| 81 | +++++ |
| 82 | ++++ |
| 83 | ++++ |
| 84 | ++++ |
| 85 | +++ |
| 86 | +++ |
| 87 | ++++ |
| 88 | ++++ |
| 89 | ++++ |
| 90 | ++++ |
| 93 | ++++ |
| 95 | + |
| 96 | +++ |
| 97 | + |
| 98 | +++ |
| 99 | ++++ |
| 100 | +++ |
| 101 | ++++ |
| 102 | +++ |
| 103 | +++ |
| 104 |  |
| 105 | ++++ |
| 106 | ++++ |
| 107 | +++ |
| 108 | +++ |
| 109 | + |
| 110 | + |
| 111 | + |
| 112 | +++ |
| 113 | +++ |
| 114 | ++++ |
| 115 | ++ |
| 116 | ++++ |
| 117 | +++ |
| 118 | ++ |
| 119 | ++++ |
| 120 | +++ |
| 121 | ++ |
| 122 | +++++ |
| 123 | ++++ |
| 125 | + |
| 126 | ++++ |
| 127 | ++++ |
| 128 | ++++ |
| 129 | ++++ |
| 130 | ++++ |
| 131 | +++++ |
| 132 | +++ |
| 133 | +++ |
| 134 | ++ |
| 135 | +++ |
| 136 | +++ |
| 137 | +++ |
| 138 | ++++ |
| 139 | +++ |
| 140 | ++++ |
| 141 | +++ |
| 142 | ++++ |
| 143 | ++++ |
| 144 | ++ |
| 145 | +++ |
| 146 | ++ |
| 147 | ++ |
| 148 | ++ |
| 149 | +++ |
| 150 | ++ |
| 151 | +++ |
| 152 | +++ |
| 153 | ++++ |
| 154 | +++ |
| 155 | +++ |
| 156 | +++ |
| 157 | ++ |
| 158 | +++ |
| 159 | +++ |
| 160 | +++ |
| 161 | ++ |
| 162 | +++ |
| 163 | +++ |
| 164 | ++++ |
| 165 | ++++ |
| 166 | ++++ |
| 167 | +++ |
| 168 | +++ |
| 169 | ++++ |
| 170 | +++ |

TABLE 1-continued

| Example No. | Syk IC50 |
|---|---|
| 171 | ++++ |
| 172 | ++++ |
| 173 | +++ |
| 174 | +++ |
| 175 | ++++ |
| 176 | +++ |
| 177 | +++ |
| 178 | +++ |
| 179 | +++ |
| 180 | + |
| 181 | +++ |
| 182 | +++ |
| 183 | +++ |
| 184 | ++++ |
| 185 | +++ |
| 186 | +++ |
| 187 | ++++ |
| 188 | ++++ |
| 189 | ++++ |
| 190 | ++++ |
| 191 | ++++ |
| 192 | ++++ |
| 193 | +++ |
| 194 | ++++ |
| 195 | ++++ |
| 196 | +++ |
| 197 | ++++ |
| 198 | ++++ |
| 199 | ++++ |
| 200 | ++++ |
| 201 | ++++ |
| 202 | ++++ |
| 203 | ++++ |
| 204 | ++++ |
| 205 | +++++ |
| 206 | ++++ |
| 207 | ++++ |
| 208 | ++++ |
| 209 | +++ |
| 210 | ++++ |
| 211 | ++ |
| 212 | ++++ |
| 213 | +++ |
| 214 | +++ |
| 215 | +++ |
| 216 | ++++ |
| 217 | ++++ |
| 218 | ++ |
| 219 | +++ |
| 220 | ++++ |
| 221 | ++++ |
| 222 | +++ |
| 223 | +++ |
| 224 | ++++ |
| 225 | ++++ |
| 226 | +++ |
| 227 | +++ |
| 228 | +++ |
| 229 | +++ |
| 230 | +++ |
| 231 | +++ |
| 232 | ++++ |
| 233 | ++++ |
| 234 | ++++ |
| 235 | +++ |
| 236 | +++ |
| 237 | +++ |
| 238 | ++++ |
| 239 | ++++ |
| 240 | +++ |
| 241 | ++++ |
| 242 | ++++ |
| 243 | ++++ |
| 244 | ++++ |
| 246 | ++++ |
| 247 | ++++ |
| 248 | ++++ |

TABLE 1-continued

| Example No. | Syk IC50 |
|---|---|
| 249 | ++ |
| 250 | ++++ |
| 251 | +++ |
| 252 | +++++ |
| 253 | ++++ |
| 254 | ++ |
| 255 | +++ |
| 256 | ++++ |
| 257 | +++ |
| 258 | +++ |
| 259 | +++ |
| 260 | ++ |
| 261 | ++++ |
| 262 | +++++ |
| 263 | ++++ |
| 264 | +++ |
| 265 | ++++ |
| 266 | +++ |
| 267 | ++++ |
| 268 | ++++ |
| 269 | +++++ |
| 270 | +++++ |
| 271 | +++++ |
| 275 | +++++ |
| 276 | ++++ |
| 277 | +++ |
| 278 | ++ |
| 279 | +++ |
| 280 | +++ |
| 281 | +++ |
| 282 | ++++ |
| 283 | +++ |
| 284 | ++ |
| 285 | ++ |
| 286 | ++ |
| 287 | +++ |
| 288 | ++ |
| 289 | +++ |
| 290 | ++ |
| 291 | ++++ |
| 292 | ++ |
| 293 | ++++ |
| 294 | ++ |
| 295 | ++++ |
| 296 | ++++ |
| 297 | ++++ |
| 298 | +++ |
| 299 | ++ |
| 300 | +++ |
| 301 | +++ |
| 302 | +++ |
| 303 | +++ |
| 304 | +++ |
| 305 | +++ |
| 306 | ++++ |
| 307 | +++ |
| 308 | ++++ |
| 309 | ++++ |
| 310 | +++ |
| 311 | +++ |
| 312 | ++++ |
| 313 | +++ |
| 314 | ++ |
| 315 | +++ |
| 316 | +++ |
| 317 | +++ |
| 318 | +++ |
| 319 | +++ |
| 320 | + |
| 321 | ++++ |
| 322 | ++ |
| 323 | ++++ |
| 324 | ++++ |
| 325 | ++++ |
| 326 | +++ |
| 327 | ++ |
| 328 | +++++ |

TABLE 1-continued

| Example No. | Syk IC50 |
|---|---|
| 329 | ++++ |
| 330 | ++ |
| 331 | +++ |
| 332 | +++ |
| 333 | ++ |
| 334 | +++ |
| 335 | ++++ |
| 336 | ++++ |
| 337 | +++ |
| 338 | +++ |
| 339 | +++++ |
| 340 | +++ |
| 341 | +++ |
| 342 | +++++ |
| 343 | ++ |
| 344 | +++++ |
| 345 | +++ |
| 346 | ++++ |
| 347 | ++++ |
| 348 | ++++ |
| 349 | +++ |
| 350 | ++++ |
| 351 | ++++ |
| 352 | +++++ |
| 353 | ++++ |
| 354 | ++++ |
| 355 | +++ |
| 356 | +++ |
| 357 | ++++ |
| 358 | ++++ |
| 359 | ++++ |
| 360 | +++ |
| 361 | +++ |
| 362 | +++ |
| 363 | +++ |
| 364 | ++++ |
| 365 | +++ |
| 366 | +++ |
| 367 | ++++ |
| 368 | ++++ |
| 369 | ++++ |
| 370 | ++++ |
| 371 | +++ |
| 372 | +++ |
| 373 | ++++ |
| 374 | ++++ |
| 375 | ++++ |
| 376 | ++++ |
| 377 | ++ |
| 378 | +++ |
| 379 | ++++ |
| 380 | ++++ |
| 381 | ++++ |
| 382 | +++ |
| 383 | +++ |
| 384 | +++ |
| 385 | ++++ |
| 386 | ++++ |
| 387 | + |
| 388 | ++++ |
| 389 | ++++ |
| 390 | +++ |
| 391 | ++++ |
| 392 | ++++ |
| 393 | ++++ |
| 394 | ++++ |
| 395 | ++++ |
| 396 | ++++ |
| 397 | ++++ |
| 398 | ++++ |
| 399 | ++ |
| 400 | +++ |
| 401 | +++ |
| 402 | +++ |
| 403 | +++ |
| 404 | +++ |
| 405 | ++++ |
| 406 | ++++ |
| 407 | ++++ |
| 408 | ++++ |
| 409 | ++++ |
| 410 | +++ |
| 411 | +++ |
| 412 | +++++ |
| 413 | +++++ |
| 415 | +++ |
| 416 | ++ |
| 417 | +++++ |
| 418 | ++++ |
| 419 | ++++ |
| 420 | ++++ |
| 421 | ++++ |
| 422 | ++++ |
| 423 | ++++ |
| 424 | ++++ |
| 425 | ++++ |
| 426 | ++++ |
| 427 | ++++ |
| 428 | +++++ |
| 429 | ++++ |
| 430 | +++ |
| 431 | ++++ |
| 432 | ++++ |
| 433 | ++++ |
| 434 | ++++ |
| 435 | ++++ |
| 436 | +++++ |
| 437 | ++++ |
| 438 | ++++ |
| 439 | ++++ |
| 440 | +++ |
| 441 | +++ |
| 442 | +++ |
| 443 | +++ |
| 444 | +++++ |
| 445 | ++++ |
| 446 | ++++ |
| 447 | ++++ |
| 448 | ++++ |
| 449 | + |
| 450 | +++ |
| 451 | ++++ |
| 452 | ++++ |
| 453 | ++++ |
| 454 | +++ |

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of Formula (I):

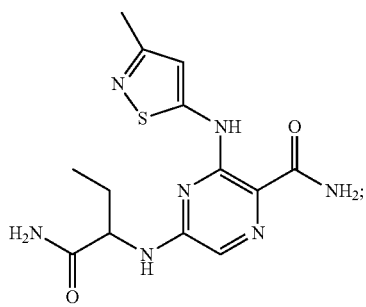 [SMILES: CC[C@@H](Nc1cnc(C(N)=O)c(Nc2cc(C)ns2)n1)C(N)=O]

(I)

or a pharmaceutically acceptable salt thereof.

2. The compound of claim 1 having the formula:

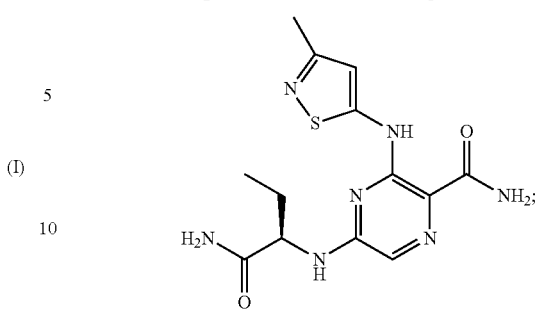

or a pharmaceutically acceptable salt thereof.

3. A pharmaceutical composition comprising the compound of claim 1 or a pharmaceutically acceptable salt thereof, in combination with a pharmaceutically acceptable carrier or diluent.

4. A kit comprising the pharmaceutical composition of claim 3, packaging and instructions for use.

5. A method for modulating spleen tyrosine kinase activity in a subject comprising the step of administering to a subject in need of such treatment a therapeutically effective amount of the pharmaceutical composition of claim 3.

* * * * *